(12) United States Patent
Mao et al.

(10) Patent No.: US 11,730,822 B2
(45) Date of Patent: *Aug. 22, 2023

(54) PROCESS FOR THE PREPARATION OF GLUCURONIDE DRUG-LINKERS AND INTERMEDIATES THEREOF

(71) Applicant: SEAGEN INC., Bothell, WA (US)

(72) Inventors: Yunyu Mao, Everett, WA (US); Philip Moquist, Seattle, WA (US); Anusuya Choudhury, Churchville, PA (US); Wendel Doubleday, Snohomish, WA (US)

(73) Assignee: Seagen Inc., Bothell, WA (US)

( * ) Notice: Subject to any disclaimer, the term of this patent is extended or adjusted under 35 U.S.C. 154(b) by 448 days.

This patent is subject to a terminal disclaimer.

(21) Appl. No.: 16/497,133

(22) PCT Filed: Mar. 23, 2018

(86) PCT No.: PCT/US2018/024191
§ 371 (c)(1),
(2) Date: Sep. 24, 2019

(87) PCT Pub. No.: WO2018/175994
PCT Pub. Date: Sep. 27, 2018

(65) Prior Publication Data
US 2020/0222553 A1 Jul. 16, 2020

Related U.S. Application Data

(60) Provisional application No. 62/476,605, filed on Mar. 24, 2017.

(51) Int. Cl.
*A61K 47/68* (2017.01)
*C07H 15/26* (2006.01)
*C07D 487/04* (2006.01)

(52) U.S. Cl.
CPC ...... *A61K 47/6889* (2017.08); *A61K 47/6809* (2017.08); *C07D 487/04* (2013.01); *C07H 15/26* (2013.01)

(58) Field of Classification Search
CPC ............... A61K 47/64; A61K 47/6889; A61K 47/6803; A61K 47/6809; C07H 15/203; C07H 15/22; C07H 15/26; C07D 487/04
USPC .................................................. 536/6.4
See application file for complete search history.

(56) References Cited

U.S. PATENT DOCUMENTS

| 4,486,414 A | 12/1984 | Pettit |
| 4,816,397 A | 3/1989 | Boss |
| 4,816,444 A | 3/1989 | Pettit |
| 4,816,567 A | 3/1989 | Cabilly |
| 4,879,278 A | 11/1989 | Pettit |
| 4,880,935 A | 11/1989 | Thorpe |
| 4,946,778 A | 8/1990 | Ladner |
| 4,978,744 A | 12/1990 | Pettit |
| 4,986,988 A | 1/1991 | Pettit |
| 5,047,335 A | 9/1991 | Paulson |
| 5,076,973 A | 12/1991 | Pettit |
| 5,122,368 A | 6/1992 | Greenfield |
| 5,138,036 A | 8/1992 | Pettit |
| 5,225,539 A | 7/1993 | Winter |
| 5,278,299 A | 1/1994 | Wong |
| 5,410,024 A | 4/1995 | Pettit |
| 5,504,191 A | 4/1996 | Pettit |
| 5,510,261 A | 4/1996 | Goochee |
| 5,521,284 A | 5/1996 | Pettit |
| 5,530,097 A | 6/1996 | Pettit |
| 5,545,806 A | 8/1996 | Lonberg |
| 5,554,725 A | 9/1996 | Pettit |
| 5,561,119 A | 10/1996 | Jacquesy |
| 5,569,825 A | 10/1996 | Lonberg |
| 5,585,089 A | 12/1996 | Queen |
| 5,591,828 A | 1/1997 | Bosslet |
| 5,599,902 A | 2/1997 | Pettit |
| 5,605,976 A | 2/1997 | Martinez |
| 5,622,929 A | 4/1997 | Willner |
| 5,625,126 A | 4/1997 | Lonberg |
| 5,633,425 A | 5/1997 | Lonberg |
| 5,635,483 A | 6/1997 | Pettit |
| 5,661,016 A | 8/1997 | Lonberg |
| 5,663,149 A | 9/1997 | Pettit |
| 5,665,860 A | 9/1997 | Pettit |
| 5,672,662 A | 9/1997 | Harris |
| 5,681,567 A | 10/1997 | Martinez |
| 5,739,277 A | 4/1998 | Presta |
| 5,756,593 A | 5/1998 | Martinez |
| 5,757,078 A | 5/1998 | Matsuda |

(Continued)

FOREIGN PATENT DOCUMENTS

| EP | 0105360 A1 | 4/1984 |
| EP | 0171496 A2 | 2/1986 |

(Continued)

OTHER PUBLICATIONS

Albin, N. et al. (Aug. 1, 1993). Main Drug-metabolizing Enzyme Systems in Human Breast Tumors and Peritumoral Tissues, Cancer Research 53:3541-3546.
Allen, T.M. (Oct. 2005). "Ligand-Targeted Therapeutics in Anticancer Therapy," Nat Rev Cancer 2(10):750-763.
Alley, S.C. et al. (Mar. 2008, e-pub. Mar. 4, 2008). "Contribution of Linker Stability to the Activities of Anticancer Immunoconjugates," Bioconjugate Chem. 19(3):759-765.
Amsberry, K.L. et al. (1990) "The Lactonizatin of 2'-Hydroxyhydrocinnamic Acid Amides: A Potential Prodrug For Amines," J. Org. Chem. 55(23):5867-5877.
Andrianomenjanahary, S. et al. (1992). "Synthesis of Novel Targeted Pro-Prodrugs of Anthracyclines Potentially Activated by a Monoclonal Antibody Galactosidase Conjugate (Part 1)," Bioorganic & Medicinal Chemistry Letters 2(9):1093-1096.

(Continued)

*Primary Examiner* — Ganapathy Krishnan
(74) *Attorney, Agent, or Firm* — Morrison & Foerster LLP

(57) ABSTRACT

The present invention provides improved processes for the preparation of drug-linkers with a β-glucuronide cleavable unit, as well as intermediates thereof.

48 Claims, No Drawings

(56) References Cited

U.S. PATENT DOCUMENTS

| | | |
|---|---|---|
| 5,770,429 A | 6/1998 | Lonberg et al. |
| 5,780,588 A | 7/1998 | Pettit |
| 5,824,805 A | 10/1998 | King |
| 5,851,527 A | 12/1998 | Hansen |
| 5,919,455 A | 7/1999 | Greenwald |
| 5,939,595 A | 8/1999 | Gehrer |
| 5,965,119 A | 10/1999 | Greenwald |
| 6,034,065 A | 3/2000 | Pettit |
| 6,077,499 A | 6/2000 | Griffiths |
| 6,077,939 A | 6/2000 | Wei |
| 6,113,906 A | 9/2000 | Greenwald |
| 6,124,431 A | 9/2000 | Sakakibara |
| 6,130,237 A | 10/2000 | Denny |
| 6,153,655 A | 11/2000 | Martinez |
| 6,214,330 B1 | 4/2001 | Greenwald |
| 6,214,345 B1 | 4/2001 | Firestone |
| 6,239,104 B1 | 5/2001 | Pettit |
| 6,261,537 B1 | 7/2001 | Klaveness |
| 6,303,569 B1 | 10/2001 | Greenwald |
| 6,323,135 B1 | 11/2001 | Ngo |
| 6,323,322 B1 | 11/2001 | Filpula |
| 6,331,289 B1 | 12/2001 | Klaveness |
| 6,361,774 B1 | 3/2002 | Griffiths |
| 6,395,266 B1 | 5/2002 | Martinez |
| 6,556,506 B2 | 4/2003 | Naven |
| 6,569,834 B1 | 5/2003 | Pettit |
| 6,602,498 B2 | 8/2003 | Shen |
| 6,624,142 B2 | 9/2003 | Greenwald |
| 6,638,499 B2 | 10/2003 | Martinez |
| 6,643,575 B2 | 11/2003 | Ishida |
| 6,680,047 B2 | 1/2004 | Klaveness |
| 6,743,896 B2 | 6/2004 | Filpula |
| 6,743,908 B2 | 6/2004 | Filpula |
| 6,777,387 B2 | 8/2004 | Greenwald |
| 6,824,782 B2 | 11/2004 | Whitlow |
| 6,872,393 B2 | 3/2005 | Whitlow |
| 6,884,869 B2 | 4/2005 | Senter |
| 6,906,182 B2 | 6/2005 | Ts |
| 7,011,812 B1 | 3/2006 | Griffiths |
| 7,026,440 B2 | 4/2006 | Bentley |
| 7,090,843 B1 | 8/2006 | Francisco |
| 7,091,186 B2 | 8/2006 | Senter |
| 7,150,872 B2 | 12/2006 | Whitlow |
| 7,273,845 B2 | 9/2007 | Zhao |
| 7,300,644 B2 | 11/2007 | Griffiths |
| 7,332,164 B2 | 2/2008 | Greenwald |
| 7,374,762 B2 | 5/2008 | Amphlett |
| 7,375,078 B2 | 5/2008 | Feng |
| 7,462,687 B2 | 12/2008 | Greenwald |
| 7,494,649 B2 | 2/2009 | Amphlett |
| 7,498,298 B2 | 3/2009 | Doronina |
| 7,501,120 B2 | 3/2009 | Amphlett |
| 7,514,066 B2 | 4/2009 | Griffiths |
| 7,514,080 B2 | 4/2009 | Amphlett |
| 7,553,816 B2 | 6/2009 | Senter |
| 7,595,304 B2 | 9/2009 | Zhao |
| 7,632,504 B2 | 12/2009 | Whitlow |
| 7,659,241 B2 | 2/2010 | Senter |
| 7,754,681 B2 | 7/2010 | Feng |
| 7,754,885 B2 | 7/2010 | Hoefle |
| 7,767,205 B2 | 8/2010 | Mao |
| 7,785,618 B2 | 8/2010 | Elmaleh |
| 7,872,072 B2 | 1/2011 | Bentley |
| 7,884,869 B2 | 2/2011 | Shurboff |
| 7,888,536 B2 | 2/2011 | Davis |
| 7,931,890 B2 | 4/2011 | Griffiths |
| 7,947,839 B2 | 5/2011 | Gazzard |
| 7,989,434 B2 | 8/2011 | Feng |
| 7,989,598 B2 | 8/2011 | Sleeves |
| 7,994,135 B2 | 8/2011 | Doronina |
| 8,012,485 B2 | 9/2011 | Amphlett |
| 8,012,488 B2 | 9/2011 | Sakanoue |
| 8,039,273 B2 | 10/2011 | Jeffrey |
| 8,088,387 B2 | 1/2012 | Sleeves |
| 8,163,888 B2 | 4/2012 | Sleeves |
| 8,168,605 B2 | 5/2012 | Zhao |
| 8,198,417 B2 | 6/2012 | Sleeves |
| 8,257,706 B2 | 9/2012 | Mcdonagh |
| 8,268,317 B2 | 9/2012 | Govindan |
| 8,273,833 B2 | 9/2012 | Bentley |
| 8,367,065 B2 | 2/2013 | Zhao |
| 8,440,816 B2 | 5/2013 | Bentley |
| 8,455,622 B2 | 6/2013 | Carter |
| 8,563,509 B2 | 10/2013 | Chari |
| 8,568,728 B2 | 10/2013 | Jeffrey |
| 8,609,092 B2 | 12/2013 | Torgov |
| RE45,272 E | 12/2014 | Jeffrey |
| 9,061,074 B2 | 6/2015 | Carter |
| 9,242,013 B2 | 1/2016 | Howard |
| 9,731,030 B2 | 8/2017 | Jeffrey |
| 10,561,739 B2 | 2/2020 | Howard et al. |
| 11,103,593 B2 | 8/2021 | Lyon et al. |
| 2002/0102215 A1 | 8/2002 | Klaveness |
| 2002/0142358 A1 | 10/2002 | Mikayama |
| 2003/0083263 A1 | 5/2003 | Doronina |
| 2003/0211100 A1 | 11/2003 | Bedian |
| 2004/0001820 A1 | 1/2004 | Hahn |
| 2004/0006215 A1 | 1/2004 | Keler |
| 2004/0009166 A1 | 1/2004 | Filpula |
| 2004/0053976 A1 | 3/2004 | Martinez |
| 2004/0141922 A1 | 7/2004 | Klaveness |
| 2005/0002865 A1 | 1/2005 | Klaveness |
| 2005/0009751 A1 | 1/2005 | Senter |
| 2005/0042680 A1 | 2/2005 | Filpula |
| 2005/0238649 A1 | 10/2005 | Doronina |
| 2006/0003412 A1 | 1/2006 | Chamberlain |
| 2006/0008882 A1 | 1/2006 | Wei |
| 2006/0130160 A1 | 6/2006 | Dumas Milne Edwards |
| 2007/0134243 A1 | 6/2007 | Gazzard |
| 2008/0241128 A1 | 10/2008 | Jeffrey |
| 2009/0136526 A1 | 5/2009 | Mcdonagh |
| 2009/0148942 A1 | 6/2009 | Mcdonagh |
| 2009/0202573 A1 | 8/2009 | Zhao |
| 2009/0203706 A1 | 8/2009 | Zhao |
| 2009/0221471 A1 | 9/2009 | Greenwald |
| 2010/0062008 A1 | 3/2010 | Senter |
| 2010/0158909 A1 | 6/2010 | Mcdonagh |
| 2010/0203007 A1 | 8/2010 | Li |
| 2010/0203066 A1 | 8/2010 | Zhao |
| 2010/0260786 A1 | 10/2010 | Doronina |
| 2010/0278842 A1 | 11/2010 | Mao |
| 2011/0014151 A1 | 1/2011 | Nilsson |
| 2011/0206658 A1 | 8/2011 | Crowley |
| 2011/0243880 A1 | 10/2011 | Yurkovetskiy |
| 2011/0245295 A1 | 10/2011 | Chai |
| 2011/0256157 A1 | 10/2011 | Howard |
| 2011/0263650 A1 | 10/2011 | Ellman |
| 2011/0268751 A1 | 11/2011 | Sievers |
| 2011/0281856 A1 | 11/2011 | Chari |
| 2011/0300162 A1 | 12/2011 | Amphlett |
| 2012/0107332 A1 | 5/2012 | Jeffrey |
| 2012/0226025 A1 | 9/2012 | Chari |
| 2012/0252738 A1 | 10/2012 | Richter |
| 2012/0252739 A1 | 10/2012 | Richter |
| 2012/0328555 A1 | 12/2012 | Patil et al. |
| 2013/0217638 A1 | 8/2013 | Wessjohann |
| 2013/0225789 A1 | 8/2013 | Sun |
| 2013/0259860 A1 | 10/2013 | Smith |
| 2013/0295639 A1 | 11/2013 | Bentley |
| 2013/0309223 A1 | 11/2013 | Sutherland |
| 2013/0309256 A1 | 11/2013 | Lyon |
| 2013/0338231 A1 | 12/2013 | Godwin et al. |
| 2014/0086942 A1 | 3/2014 | Carter |
| 2015/0352224 A1 | 12/2015 | Naito |
| 2016/0030594 A1 | 2/2016 | Abrams |
| 2016/0144052 A1 | 5/2016 | Howard et al. |
| 2016/0310612 A1 | 10/2016 | Lyon |
| 2016/0361424 A1 | 12/2016 | Jeffrey |
| 2017/0189540 A9 | 7/2017 | Jeffrey |
| 2017/0189542 A1 | 7/2017 | Jeffrey |
| 2019/0336614 A1 | 11/2019 | Howard et al. |

(56) References Cited

U.S. PATENT DOCUMENTS

| | | |
|---|---|---|
| 2019/0388546 A1 | 12/2019 | Mao |
| 2022/0143209 A1 | 5/2022 | Jeffrey |

FOREIGN PATENT DOCUMENTS

| | | |
|---|---|---|
| EP | 0173494 A2 | 3/1986 |
| EP | 0184187 A2 | 6/1986 |
| EP | 0401384 A1 | 12/1990 |
| EP | 0404097 A2 | 12/1990 |
| EP | 1029551 A2 | 8/2000 |
| EP | 1029551 A3 | 3/2001 |
| JP | 2009501800 A | 1/2009 |
| JP | 2010509315 A | 3/2010 |
| JP | 2015227891 A | 12/2015 |
| SG | 11201807827 A | 10/2018 |
| TW | 201420118 A | 6/2014 |
| WO | 198303679 A1 | 10/1983 |
| WO | 198601533 A1 | 3/1986 |
| WO | 198702671 A1 | 5/1987 |
| WO | 199012874 A2 | 11/1990 |
| WO | 199012874 A3 | 1/1991 |
| WO | 199308829 A1 | 5/1993 |
| WO | 199311161 A1 | 6/1993 |
| WO | 1994004690 A1 | 3/1994 |
| WO | 199734631 A1 | 9/1997 |
| WO | 2002088172 A2 | 11/2002 |
| WO | 2002088172 A3 | 2/2003 |
| WO | 2003026577 A2 | 4/2003 |
| WO | 2003086312 A2 | 10/2003 |
| WO | 2004010957 A2 | 2/2004 |
| WO | 2004010957 A3 | 6/2004 |
| WO | 2003026577 A3 | 9/2004 |
| WO | 2003086312 A3 | 9/2004 |
| WO | 2004085386 A2 | 10/2004 |
| WO | 2004085386 A3 | 12/2004 |
| WO | 2005081711 A2 | 9/2005 |
| WO | 2005082023 A2 | 9/2005 |
| WO | 2005082023 A3 | 9/2005 |
| WO | 2005099768 A2 | 10/2005 |
| WO | 2005112919 A2 | 12/2005 |
| WO | 2006066020 A2 | 6/2006 |
| WO | 2005099768 A3 | 8/2006 |
| WO | 2006066020 A3 | 8/2006 |
| WO | 2005081711 A3 | 11/2006 |
| WO | 2006132670 A2 | 12/2006 |
| WO | 2007001968 A2 | 1/2007 |
| WO | 2007008848 A2 | 1/2007 |
| WO | 2007011968 A2 | 1/2007 |
| WO | 2005112919 A3 | 2/2007 |
| WO | 2006132670 A3 | 7/2007 |
| WO | 2007001968 A3 | 8/2007 |
| WO | 2007085930 A1 | 8/2007 |
| WO | 2007103288 A2 | 9/2007 |
| WO | 2007011968 A3 | 10/2007 |
| WO | 2007103288 A3 | 11/2007 |
| WO | 2008034124 A2 | 3/2008 |
| WO | 2008056346 A2 | 5/2008 |
| WO | 2008070593 A2 | 6/2008 |
| WO | 2008034124 A3 | 8/2008 |
| WO | 2008056346 A3 | 10/2008 |
| WO | 2009002993 A1 | 12/2008 |
| WO | 2009009712 A1 | 1/2009 |
| WO | 2009009716 A1 | 1/2009 |
| WO | 2009025669 A1 | 2/2009 |
| WO | 2007008848 A3 | 4/2009 |
| WO | 2009117531 A1 | 9/2009 |
| WO | 2010048018 A1 | 4/2010 |
| WO | 2010081164 A2 | 7/2010 |
| WO | WO 2010/081163 A1 * | 7/2010 ............... C07H 1/00 |
| WO | 2010091150 A1 | 8/2010 |
| WO | 2010081164 A3 | 11/2010 |
| WO | 2010126551 A1 | 11/2010 |
| WO | 2011023883 A1 | 3/2011 |
| WO | 2011038159 A2 | 3/2011 |
| WO | 2011038159 A3 | 8/2011 |
| WO | 2011109308 A1 | 9/2011 |
| WO | 2011130599 A1 | 10/2011 |
| WO | 2011130613 A1 | 10/2011 |
| WO | 2011130616 A1 | 10/2011 |
| WO | 2012078688 A2 | 6/2012 |
| WO | 2012078688 A3 | 8/2012 |
| WO | 2012112708 A1 | 8/2012 |
| WO | 2012113847 A1 | 8/2012 |
| WO | 2012166560 A1 | 12/2012 |
| WO | 2013033476 A1 | 3/2013 |
| WO | 2013041606 A1 | 3/2013 |
| WO | 2013053873 A1 | 4/2013 |
| WO | 2013055990 A1 | 4/2013 |
| WO | 2013055993 A1 | 4/2013 |
| WO | 2013123152 A2 | 8/2013 |
| WO | 2013170272 A2 | 11/2013 |
| WO | 2013173337 A2 | 11/2013 |
| WO | 2013173391 A1 | 11/2013 |
| WO | 2013173392 A1 | 11/2013 |
| WO | 2013173393 A1 | 11/2013 |
| WO | 2013170272 A3 | 2/2014 |
| WO | 2014061277 A1 | 4/2014 |
| WO | 2014064423 A1 | 5/2014 |
| WO | 2013123152 A3 | 11/2014 |
| WO | 2015057699 A2 | 4/2015 |
| WO | 2013173337 A3 | 6/2015 |
| WO | 2015095755 A1 | 6/2015 |
| WO | 2015057699 A3 | 9/2015 |
| WO | 2016046574 A1 | 3/2016 |
| WO | 2016149535 A1 | 9/2016 |
| WO | 2017165851 A1 | 9/2017 |
| WO | 2018031690 A1 | 2/2018 |

OTHER PUBLICATIONS

Angenault, S. et al. (2003). "Cancer Chemotherapy: A SN-38 (7-Ethyl-10-hydroxycamptothecin) Glucuronide Prodrug for Treatment by a PMT (Prodrug Mono Therapy) Strategy," Bioorganic & Medicinal Chemistry Letters 13:947-950.

Asai, A. et al. (1999). "Synthesis and Antitumor Activity of Water-Soluble Duocarmycin B1 Prodrugs," Bioorganic & Medicinal Chemistry Letters 9:2995-2998.

Azoulay, M. et al. (1995). "Prodrugs Of Anthracycline Antibiotics Suited For Tumor-Specific Activation," Anti-Cancer Drug Design 10:441-450.

Bakina, E. et al. (1997). "Intensely Cytotoxic Anthracycline Prodrugs: Glucuronides," J. Med. Chem. 40(25):4013-4018.

Baldwin, A.D. et al. (Oct. 19, 2011, e-pub. Sep. 26, 2011). "Tunable Degradation of Maleimide—Thiol Adducts in Reducing Environments," Bioconjugate Chem. 22:1946-1953, 8 pages.

Beidler, C.B. et al. (Dec. 1, 1988). "Cloning and High Level Expression Of A Chimeric Antibody With Specificity For Human Carcinoembryonic Antigen," J. Immunol. 141(11):4053-4060.

Better, M. et al. (May 20, 1988). "*Escherichia coli* Secretion of An Active Chimerica Antibody Fragment," Science 240:1041-1043.

Bhattacharya-Chatterjee, M. et al. (Aug. 15, 1988). "Idiotype Vaccines Against Human T Cell Leukemia. II. Generation and Characterization Of A Monoclonal Idiotype Cascade (Ab1, Ab2, and Ab3)," J. Immunol. 141(4):1398-1403.

Bird, R.E. et al. (1988). "Single-Chain Antigen-Binding Proteins," Science 242(4877):423-426.

Boons, G-J. ed. (1998). Carbohydrate Chemistry. Blackie Academics Professional: London, United Kingdom pp. 98-174.

Bosslet, K. et al. (Mar. 15, 1998). "Elucidation of the Mechanism Enabling Tumor Selective Prodrug Monotherapy," Cancer Research 58:1195-1201.

Bouvier et al. (2003). "A New Paclitaxel Prodrug For Use In ADEPT Strategy," Org. Biomol. Chem. 1:3343-3352.

Bouvier et al. (Mar. 1, 2004). "First Enzymatically Activated Taxotere Prodrugs Designed For ADEPT and PMT," Bioorganic & Medicinal Chemistry 12:969-977.

Bowen, M.A. et al. (Dec. 1, 1993). "Functional Effects of CD30 on a Large Granular Lymphoma Cell Line, YT. Inhibition of Cytotoxicity, Regulation of CD28 and IL-2R, and Induction of Homotypic Aggregation," J. Immunol. 151(11):5896-5906.

(56) References Cited

OTHER PUBLICATIONS

Boyd, P.N. et al. (Dec. 1995). "The Effect of the Removal of Sialic Acid, Galactose and Total Carbohydrate on the Functional Activity of Campath-1H," Mol. Immunol. 32(17/18):1311-1318.

Bross, P.F. et al. (Jun. 2001). "Approval Summary: Gemtuzumab Ozogamicln In Relapsed Acute Myeloid Leukemia," Clinical Cancer Research 7:1490-1496.

Bumol, T.F. (Aug. 1988). "Characterization Of The Human Tumor and Normal Tissue Reactivity Of The KS1/4 Monoclonal Antibody," Hybridoma 7(4):407-415.

Burke, P.J. et al. (Jun. 2009). "Design, Synthesis, and Biological Evaluation Of Antibody-Drug Conjugates Comprised Of Potent Camptothecin Analogues," Bioconj. Chem. 20(6):1242-1250.

Caron, P.C. et al. (Oct. 1, 1992). "Engineering Humanized Dimeric Forms of IgG Are More Effective Antibodies," J. Exp Med. 176:1191-1195.

Carter, P. et al. (Feb. 1992). "High Level *Escherichia Coli* Expression and Production of a Bivalent Humanized Antibody Fragment," Bio/Technology 10:163-167.

Carter, P. et al. (Oct. 1995). Toward The Production Of Bispecific Antibody Fragments For Clinical Applications. J. Hematotherapy 4:463-470.

Chari, R.V.J. et al. (Jan. 1, 1992). "Immunoconjugates Containing Novel Maytansinoids: Promising Anticancer Drugs," Cancer Res. 52:127-131.

Chen, X. et al. (Mar. 2003). "Glucuronides in Anti-Cancer Therapy," Curr. Med. Chem. 3(2):139-150.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Cunningham, B.C. et al. (Jun. 2, 1989). "High-Resolution Epitope Mapping of hGH-Receptor Interactions by Alanine-Scanning Mutagenesis," Science 244:1081-1085.

De Graaf, M. et al. (2002). "Beta-Glucuronidase-Mediated Drug Release," Current Pharmaceutical Design 8:1391-1403.

De Graaf, M. et al. (2003). "Cytosolic β-glycosidases For Activation Of Glycoside Prodrugs Of Daunorubicin," Biochemical Pharmacology 65:1875-1881.

De Groot, F.M.H., et al. (2001). "Anticancer Prodrugs for Application in Monotherapy: Targeting Hypoxia, Tumor-Associated Enzymes, and Receptors," Current Medicinal Chemistry 8(9):1093-1122.

Desai, A.A. et al. (2003). "UGT Pharmcogenomics: Implications For Cancer Risk and Cancer Therapeutics," Pharmacogenetics 13(8):517-523.

Desbene, S. et al. (1998). "Doxorubicin Prodrugs With Reduced Cytotoxicity Suited For Tumour Specific Activation," Anti-Cancer Dru Design 13:955-968.

Doronina, S.O. et al. (Jul. 2003). "Development of Potent Monoclonal Antibody Auristatin Conjugates for Cancer Therapy," Nat. Biotechnol. 21(7):778-784.

Doronina, S.O. et al. (Jan. 2006). "Enhanced Activity Of Monomethylauristatin F Through Monoclonal Antibody Delivery: Effects Of Linker Technology On Efficacy And Toxicity," Bioconjug. Chem. 17(1):114-124.

Drueckhammer, D.G. et al. (Jul. 1991). "Enzyme Catalysis in Synthetic Carbohydrate Chemistry," Synthesis pp. 499-525.

Dubowchik, G.M. et al. (Aug. 1999). "Receptor-Mediated and Enzyme-Dependent Targeting of Cytotoxic Anticancer Drugs," Pharm. Therapeutics 83(2):67-123.

Eneyskaya, E.V. et al. (2005). "Chemo-EnzymaticSynthesis Of4-methylumbelliferyl 13-(1-4)-D-2xylooligosides: New Substrates For 13-D-xylanease assaus," Org. Biomol. Chem. 3:146-151.

Estin, C.D. et al. (Mar. 15, 1989). "Transfected Mouse Melanoma Lines That Express Various Levels Of Human Melanoma-Associated Antigen p97," J. Natl. Cancer Instit. 81(6):445-446.

Extended European Search Report, dated Aug. 16, 2017, for European Patent Application No. 14853953.9, 16 pages.

Extended European Search Report, dated May 11, 2017, for European Patent Application No. 06787774.6, 8 pages.

Extended European Search Report, dated Oct. 26, 2017, for European Patent Application No. 17179428.2, 11 pages.

Extended European Search Report, dated Oct. 7, 2019, for European Patent Application No. 17771293.2, 14 pages.

Farquhar, D. et al. (Mar. 12, 1998). "Intensely Potent Doxorubicin Analogues: Structure-Activity Relationship," J. Med. Chem. 41(6):965-972.

Feizi, T. (Mar. 7-13, 1985). "Demonstration By Monoclonal Antibodies That Carbohydrate Structures Of Glycoproteins and Glycolipids Are Onco-Developmental Antigens," Nature 314(6006):53-57.

Florent, J.C. et al. (Sep. 10, 1998, e-pub. Aug. 21, 1998). "Prodrugs of Anthracyclines For Use in Antibody-Directed Enzyme Prodrug Therapy," J. Med. Chem. 41(19):3572-3581.

Foon, K.A. et al. (1994). "Murine Anti-Idiotype Monoclonal Antibody Induces Specific Humoral Responses To Carcinoembryonic Antigen (CEA) In Colorectal Cancer Patients," Proc. Am. Soc. Clin. Oncol. 13:294, Abstract # 957, 2 pages.

Francisco, J.A. et al. (Aug. 15, 2003). "cAC10-vcMMAE, An Anti-CD30-menomethyl auristatin E-Conjugate With Potent and Selective Antitumor Activity," Blood 102(4):1468-1465.

Francisco, J.A. et al. (Jun. 15, 2000). "Agonistic Properties and in Vivo Antitumor Activity of the Anti-CD40 Anibody SGN-14," Cancer Res. 60:3225-3231.

Frankel, A.E. et al. (2000). "Cell Surface Receptor-Targeted Therapy of Acute Myeloid Leukemia: A Review," Cancer Biother. Radiopharm. 15(5):459-476.

Fridkin, M. et al. (1974). "Peptide Synthesis," Ann. Rev. Biochem. 43:419-443.

Fuselier, J.A. et al. (2003). "An Adjustable Refease Rate Linking Strategy for Cytotoxin-Peptide Conjugates," Bioorganic & Medicinal Chemistry Letters 13:799-803.

Gaertner, H.F. et al. (Mar. 11, 1994). "Chemo-Enzymic Backbone Engineering of Proteins," J. Biol. Chem. 269(10):7224-7230.

Gesson, J.-P. et al. (1994). "Prodrugs Of Anthracyclines For Chemotherapy Via Enzyme-Monoclonal Antibody Conjugates," Anti-Cancer Drug Design 9:409-423.

Ghetie, M.A. et al. (Mar. 1, 1994). "Anti-CD19 Inhibits The Growth Of Human B-Cell Tumor Lines In Vitro And Of Daudi Cells In SCID Mice By Inducing Cell Cycle Arrest," Blood 83(5):1329-1336.

Ghosh, N. et al. (2009). "Chemical and Biological Evaluations Of The Family Of CC-1065 and The Duocarmycin Natural Products," Curr. Topics in Med. Chem. 9(16):1494-1524.

Goodson, J. M. (1984). "Chapter 6: Dental Applications," in Medical Applications of Controlled Release 2:115-138.

Goodson, R.J. et al. (Apr. 1990). "Site-Directed Pegylation of Recombinatnt Interleukin-2 At Its Glycosylation Site," Bio/Technology 8:343-346.

Greenwald, R.B. et al. (2003). "Effective Drug Delivery By PEGylated Drug Conjugates," Advanced Drug Delivery Reviews, 55:217-250.

Haisma, H.J. et al. (1992). "A Monoclonal Antibody-β-glucuronidase Conjugate As Activator Of The Prodrug Epirubicin-Glucuronide For Specific Treatment Of Cancer," Br. J. Cancer 66:474-478.

Hamblett, K.J. et al. (Oct. 15, 2004). "Effects of Drug Loading on the Antitumor Activity of a Monoclonal Antibody Drug Conjugate," Clin. Cancer Res. 10:7063-7070.

Han, S.-Y. et al. (2004). "Recent Development Of Peptide Coupling Agents In Organic Synthesis," Tet. 60:2447-2476.

Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMl) for Use With ADEPT and GDEPT," Bioorganic & Medicinal Chemistry Letters 9(15):2237-2242.

Hellström, I. et al (Aug. 1986). "Monoclonal Mouse Antibodies Raised Against Human Lung Carcinoma," Cancer Res. 46(8):3917-3923.

Hellström, I. et al. (May 1985). "Monoclonal Antibodies To Cell Surface Antigens Shared By Chemically Induced Mouse Bladder Carcinomas," Cancer. Res. 45(5):2210-2218.

(56) References Cited

OTHER PUBLICATIONS

Henttu, P. et al. (Apr. 28, 1989). "cDNA Coding For The Entire Human Prostate Specific Antigen Shows High Homologies To The Human Tissue Kallikrein Genes," Biochem. Biophys. Res. Comm. 160(2):903-910.

Herlyn, M. et al. (Apr. 1982). "Monoclonal Antibody Detection Of A Circulating Tumor-Associated Antigen. I. Presence Of Antigen In Sera Of Patients With Colorectal, Gastric, and Pancreatic Carcinoma," J. Clin. Immunol. 2(2):135-140.

Hilkens, J. et al. (Sep. 1992). "Cell Membrane-Associated Mucins and Their Adhesion-Modulating Property," Trends in Bio. Chem. Sci. 17(9):359-363.

Holliger, P. et al. (Jul. 1993). "Diabodies: Small Bivalent And Bispecific Antibody Fragments," Proc. Natl. Acad. Sci. USA 90:6444-6448.

Hoogenboom, H.R. et al. (1992). "By-Passing Immunisation. Human Antibodies From Synthetic Repertoires of Germline VH Gene Segments Rearranged in Vitro," J. Mol. Biol. 227:381-388.

Hoon, D.S.B. et al. (Nov. 1, 1993). "Molecular Cloning of a Human Monoclonal Antibody Reactive to Ganglioside GM3 Antigen on Human Cancers," Cancer Res. 53:5244-5250.

Houba, P.H.J. et al. (1996). "Characterization of Novel Anthracycline Prodrugs Activated by Human β-glucuronidase for Use in Antibody-Directed Enzyme Prodrug Therapy," Biochemical Pharmacology 52(3):455-463.

Hsu, T.-A. et al. (Apr. 4, 1997). "Differential N-Glycan Patterns of Secreted and Intracellular IgG Produced in Trichoplusia ni Cells," J. Biol. Chem. 272(14):9062-9070.

Huang, P.S. et al. (Feb. 2001). "Drug-Targeting Strategies In Cancer Therapy," Current Opinion in Genetics & Development 11(1):104-110.

Huston, J.R. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.

International Preliminary Report on Patentability, dated Apr. 19, 2016, for PCT Application No. PCT/US2014/060477, filed Oct. 14, 2014, 10 pages.

International Preliminary Report on Patentability, dated Jan. 22, 2008, for PCT Application No. PCT/US2006/027925, filed Jul. 18, 2006, 7 pages.

International Preliminary Report on Patentability, dated Sep. 24, 2019, for PCT Application No. PCT/US2018/024191, filed Mar. 23, 2018, 7 pages.

International Preliminary Report on Patentability, dated Sep. 25, 2018, for PCT Application No. PCT/US2017/24148, filed Mar. 24, 2017, 14 pages.

International Search Report and Written Opinion, dated Aug. 8, 2017, for PCT Application No. PCT/US2006/027925, filed Jul. 18, 2006, 8 pages.

International Search Report and Written Opinion, dated Jul. 30, 2015, for PCT Application No. PCT/US2014/060477, filed Oct. 14, 2015, 22 pages.

International Search Report and Written Opinion, dated Jun. 21, 2017, for PCT Application No. PCT/US2017/24148, filed Mar. 24, 2017, 24 pages.

International Search Report and Written Opinion, dated Jun. 6, 2019, for PCT Application No. PCT/US2018/024191, filed Mar. 23, 2018, 14 pages.

International Union of Pure and Applied Chemistry (Nov. 5, 1960). "Definitive Rules for Nomenclature of Organic Chemistry," J. Am. Chem. Soc. 82:5545-5473, 30 pages.

Israeli, R.S. et al. (Jan. 15, 1993). "Molecular Cloning of a Complementary DNA Encoding a Prostate-Specific Membrane Antigen," Cancer Res. 53:227-230.

Jefferis, R. et al. (1997). "Glycosylation Of Antibody Molecules: Structural and Functional Significance," Chem. Immunol. 65:111-128.

Jeffrey, S.C. et al. (May-Jun. 2006, e-pub. May 3, 2006). "Development and Properties of β-Glucuronide Linkers for Monoclonal Antibody-Drug Conjugates," American Chemical Society 17(3):831-840.

Jeffrey, S.C. et al. (Sep. 9, 2010, e-pub. Jun. 14, 2010). "Expanded Utility of the β-Glucuronide Linker: ADCs That Deliver Henolic Cytotoxic Agents," ACS Medicinal Chemistry Letters, 1(6):277-280.

Jeffrey, S.C., et al. (Apr. 15, 2007, e-pub. Jan. 27, 2007). "Minor Groove Binder Antibody Conjugates Employing A Water Soluble β-Glucuronide Linker," Bioorg. Med. Chem. Lett. 17(8):2278-2280.

Jespers, L.S. et al. (Sep. 12. 1994). "Guiding the Selection of Human Antibodies From Phage Display Repertoires to a Single Epitope of an Antigen," Bio/Technology 72:898-903.

Jones, P.T. et al. (May 29, 1986). "Replacing the Complementarity-Determining Regions in a Human Antibody With Those From a Mouse," Nature 321:522-525.

Jongkees, S.A.K. et al. (Apr. 18, 2014). "Mechanistic Investigations of Unsaturated Glucuronyl Hydrolase from Clostridium perfringens." Journal of Biological Chemistry 289(16):11385-11395.

Junutula, J.R. et al. (Oct. 1, 2010, e-pub. Aug. 30, 2010). "Engineered Thio-Trastuzumab-DM1 Conjugate With an Improved Therapeutic Index to Target Human Epidermal Growth Factor Receptor 2-Postitive Breast Cancer," Clinical Cancer Res. 16(19):4769-4778.

Kabat, E.A. et al. (1991). Sequences of Proteins of Immunological Interest, Fifth Edition, National Institute of Health, Bethesda, Md., 10 pages.

Kabat, E.A. et al. (Sep. 1980). "Origins of Antibody Complementarity and Specificity-Hypervariable Regions and the Minigene Hypothesis," J Immunology 125(3):961-969.

Kaneko, T. et al. (May-Jun. 1991). "New Hydrazone Derivatives Of Adriamycin and Their Immunoconjugates—A Correlation Between Acid Stability and Cytotoxicity," Bioconjugate Chem. 2(3):133-141.

Kelly, M.A. et al. (1988). "Preparation Of Some aryl α-L-arabinofuranosides As Substrates For Arabinofuranosides," Carbohydrate Research 181:262-266.

Khandare, J. et al. (2006). "Polymer-Drug Conjugates: Progress In Polymeric Prodrugs," Prog. Polym. Sci. 31:359-397.

King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.

Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," Journal of Medicinal Chemistry 27(11):1447-1451.

Kingston, D.G.I. (Jun. 1994)."Taxol: The Chemistry and Structure-Activity Relationships Of A Novel Anticancer Agent," TIBTECH 12:222-227.

Kirschke, H. (1997). "Lysosomal Cysteine Peptidases and Malignant Tumours," Cellular Peptidases in Immune Functions and Diseases 421:253-257.

Kohler, G. et al. (Aug. 7, 1975) "Continuous Cultures Of Fused Cells Secreting Antibody Of Predefined Specificity," Nature 256:495-497.

Kotarbinski, T. (2014). "Chapter 20—Hematopietic Cancers," in MAK: Primer To The Immune Response pp. 553-585.

Kozbor, D. et al. (1983). "The Production of Monoclonal Antibodies From Human Lymphocytes," Immunology Today 4(3):72-79.

Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.

Langer, R. (Sep. 28, 1990). "New Methods Of Drug Delivery," Science 249(4976):1527-1533.

Leenders, R.G.G. et al. (1995). "Synthesis and Evaluation of Novel Daunomycin-Phosphate-Sulfate-β-Glucuronide and -β-Glucoside Prodrugs for Application in Adept," Bioorganic & Medicinal Chemistry Letters 5(24):2975-2980.

(56) References Cited

OTHER PUBLICATIONS

Leenders, R.G.G. et al. (1995). "β-Glucuronyl Carbamate Based Pro-moieties Designed for Prodrugs in ADEPT," Tetrahedron Letters 36(10):1701-1704.
Leenders, R.G.G. et al. (1999). "Novel Anthracycline-Space-β-glucuronide, -β-glucoside, and -β-galactoside Prodrugs for Application in Selective Chemotherapy," Bioorganic & Medicinal Chemistry 7:1597-1610.
Li, W. et al. (2013, e-pub. Aug. 11, 2012). "Current Drug Research On Pegylation With Small Molecular Agents," Progress in Polymer Science 38:421-444.
Liu, A.Y. et al. (May 1987). "Chimeric Mouse-Human IgG1 Antibody That Can Mediate Lysis of Cancer Cells," Proc. Natl. Acad. Sci. USA 84:3439-3443.
Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.
Livingston, P.O. et al. (May 1994). "Improved Survival In Stage III Melanoma Patients With GM2 Antibodies: A Randomized Trial Of Adjuvant Vaccination With GM2 Ganglioside," J. Clin. Oncol. 12(5):1036-1044.
Lonberg, N. et al. (1995). "Human Antibodies From Transgenic Mice," Intern. Rev. Immunol. 13:65-93.
Lougerstay-Madec, R. et al. (1998). "Synthesis Of Self-Immolative Glucuronide-Based Prodrugs D Of A Phenol Mustard," Anti-Cancer Drug Design 13:995-1007.
Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10): 1059-1062.
Madec-Lougerstay et al. (1999). "Synthesis Of Self-lmmolative Glucuronide Spacers Based On Aminomethylcarbamate. Application To 5-Fluorouracil Prodrugs For Antibody-Directed Enzyme Prodrug Therapy," J. Chem. Soc. Perkin Trans pp. 1369-1375.
Malhotra, R. et al. (Mar. 1995). "Glycosylation Changes Of IgG Associated With Rheumatoid Arthritis Can Activate Complement Via The Mannose-Binding Protein," Nature Med. 1(3):237-243.
Malik, F. et al. (Sep. 1992). "Polyethylene glycol (PEG)-Modified Granulocyte-Macrophage Colony-Stimulating Factor (GM-CSF) With Conserved Biological Activity," Exp. Hematol. 20(8):1028-1035.
Marino, C. et al. (1995). "Synthesis of 4-methylcoumarin-7-yl β-D-galactofuranoside, A Fluorogenic Substrate For Galactofuranosidase," Carbohydrate Research 276:209-213.
Marks, J.D. et al. (1991). "By-Passing Immunization: Human Antibodies FromV-Genen Libraries Displayed on Phage," J. Mol. Biol. 222:581-597.
Merchant, A. M. et al. (Jul. 1998). "An Efficient Route To Human Bispecific IgG," Nature Biotechnology 16:677-681.
Miller, M. et al. (Nov. 2009). "Potent Antigen-Specific Anti-Tumor Activity Observed With Antibody-Drug Conjugates (ADCs) Made Using A New Class Of DNA-crosslinking Agents," Abstract B126, 1 page.
Milstein, C. et al. (Oct. 6, 1983). "Hybrid Hybridomas and Their Use in Immunohistochemistry," Nature 305:537-539.
Minotti, G. et al. (2004). "Anthracyclines: Molecular Advances and Pharmacologic Developments in Antitumor Activity and Cardiotoxicity," Pharmacol. Rev. 56(2):185-229.
Mittelman, A. et al. (1990). Active Specific Immunotherapy in Patients with Melanoma: A Clinical Trial with Mouse Antiidiotypic Monoclonal Antibodies Elicited with Syngeneic Anti-High-Molecular-Weight-Melanoma-Associated Antigen Monoclonal Antibodies J. Clin. Invest. 86:2136-2144.
Molineaux, G. (Apr. 2002)."Pegylation: Engineering Improved Pharmaceuticals For Enhanced Therapy," Cancer Treatment Reviews 28(Suppl. A):13-16.
Morrison, S.L. (Sep. 1985). "Transfectomas Provide Novel Chimeric Antibodies," Science 229(4719):1202-1207.
Murray.J.L. (Dec. 2000). "Monoclonal Antibody Treatment of Solid Tumors: A Coming of Age," Semin. Oncol. 27(Suppl. 1):64-70.

Natali, P.G. et al. (Jan. 1, 1987). "Immunohistochemical Detection Of Antigen In Human Primary and Metastatic Melanomas By The Monoclonal Antibody 140.240 and Its Possible Prognostic Significance," Cancer 59(1):55-63.
Neville, D.M. et al. (Sep. 5, 1989). "Enhancement of Immunotoxin Efficacy by Acid-cleavable Crosslinking Agents Utilizing Diphtheria Toxin and Toxin Mutants," The Journal of Biological Chemistry 264(25):14653-14661.
Nicolaou, K.C. et al. (1994). "Calicheamicin ⊖1 [1]: A Rationally Designed Molecule with Extremely Potent and Selective DNA Cleaving Properties and Apoptosis Inducing Activity," Angew. Chem. Intl. Ed. Engl. 33(2):183-186.
Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.
Oi, V.T. et al. (1986). "Chimeric Antibodies," Bio Techniques 4(3):214-219.
Olsson, L. et al. (1983), "Human-Human Monoclonal Antibody-Producing Hybridomas: Technical Aspects," Meth Enzymol. 92:3-16.
Page, B. et al. (Sep. 1993). "A New Fluorometric Assay For Cytotoxicity Measurements In-Vitro," Intl. J. of Oncology 3(3):473-476.
Papot, S. et al. (Mar. 2002). "Design of Selectively Activated Anticancer Prodrugs: Elimination and Cyclization Strategies," Curr. Med. Chem. Anti-Cancer Agents 2(2):155-185.
Perez, M.S. et al. (May 15, 1989). "Isolation and Characterization of A cDNA Encoding the KS1/4 Epithelial Carcinoma Marker," J. Immunol. 142(10):3662-3667.
Pluckthün, A. (1994) "Antibodies from *Escherichia coli*," The Pharmacology of Monoclonal Antibodies pp. 269-315.
Quan, et al. (2002). "The Rise Of Monoclonal Antibodies As Therapeutics," in Anti-IgE and Allergic Disease, Jardieu and Fick Jr., eds., Marcel Dekker, New York, NY, Chapter 20, pp. 427-469.
Ragnhammar, P. et al. (Mar. 12, 1993). "Effect Of Monoclonal Antibody 17-1A and GM-CSF In Patients With Advanced Colorectal Carcinoma—Long-Lasting, Complete Remissions Can Be Induced," Int. J. Cancer 53(5):751-758.
Reff, M.E. et al. (Jan. 15, 1994). "Depletion of B Cells In Vivo by a Chimeric Mouse Human Monoclonal Antibody to CD20," Blood 83(2):435-445.
Ritter, J.K. (2000) "Roles Of Glucuronidation and UDP-glucuronosyltransferases in Xenobiotic Bioactivation Reactions," Chemico-Biological Interactions 129:171-193.
Robbins, P. et al. (1996) "Human Tumor Antigens Recognized By T Cells," Curr.Opin. Immunol. 8:628-636.
Rodrigues, M.L. et al. (Apr. 1995). "Synthesis and β-Lactamase-Mediated Activation Of A Cephalosporine-Taxol Prodrug," Chem. Biol. 2:223-227.
Rodrigues, M.L. et al. (Dec. 15, 1993). "Engineering Fab' Fragments For Efficient F(ab)2 Formation In *Escherichia coli* and For Improved In Vivo Stability," J. Immunology 151(12):6954-6961.
Rose, K. et al. (May-Jun. 1991). "Preparation Of Well-Defined Protein Conjugates Using Enzyme-Assisted Reverse Proteolysis," Bioconjugate Chem. 2(3):154-159.
Saleh, M.N. et al. (Sep. 15, 1993). "Generation Of A Human Anti-Idiotypic Antibody That Mimics The GD2 Antigen," J. Immunol. 151(6):3390-3398.
Sanderson, R.J. et al. (Jan. 15, 2005). "In vivo Drug-Linker Stability of an Anti-CD30 Dipeptide-Linked Auristatin Immunoconjugate," Clin. Cancer Res. 11:843-852.
Schelté, P. et al. (2000). "Differential Reactivity of Maleimide and Bromoacetyl Functions with Thiols: Application to the Preparation of Liposomal Diepitope Constructs," Bioconjugate Chem. 11:118-123.
Schmidt, F. et al. (2001). "Cancer Chemotherapy: A Paclitaxel Prodrug for ADEPT (Antibody-Directed Enzyme Prodrug Therapy)," Eur. J. Org. Chem. pp. 2129-2134.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwartz, A. et al. (1990). "Enzymatic C-Terminal Biotinylation Of Proteins," Methods Enzymol. 184:160-162.

(56) References Cited

OTHER PUBLICATIONS

Sgouros. G. et al. (Mar. 1993). "Modeling and Dosimetry of Monoclonal Antibody M195 (Anti-CD33) in Acute Myelogenous Leukemia," J. Nucl. Med. 34(3):422-430.
Shaw, D.R. et al. (Dec. 7, 1988). "Mouse/Human Chimeric Antibodies To A Tumor-Associated Antigen: Biologic Activity Of The Four Human IgG Subclasses," J. Natl. Cancer Inst. 80(19):1553-1559.
Shitara, K. et al. (Jun. 1993). "A Mouse/Human Chimeric Anti-(Ganglioside GD3) Antibody With Enhanced Antitumor Activities," Cancer Immunol. Immunother. 36(6):373-380.
Shopes, B. et al. (May 1, 1992). "A Genetically Engineered Human IgG Mutant With Enhanced Cytolytic Activity," J. Imniunol. 148:2918-2922.
Skehan, P. et al. (Jul. 4, 1990). "New Colorimetric Cytotoxicity Assay for Anticancer-Drug Screening," J. Nat'l Cancer Inst. 82(13):1107-1112.
Sperker, B. et al. (Jul. 1997). "The Role of Beta-Glucuronidase in Drug Disposition and Drug Targeting in Humans," Clin. Pharmocokinet, 33(1):18-31.
Stachulski, A.V. et al. (1998). "The Synthesis Of O-glucuronides," Natural Product Reports pp. 173-186.
Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Storm, D.R. et al. (Aug. 9, 1972). "Effect of Small Changes in Orientation on Reaction Rate," Journal of the American Chemical Society 94(16):5815-5825.
Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Sun, M.M.C. et al. (Sep./Oct. 2005). "Reduction-Alkylation Strategies for the Modification of Specific Monoclonal Antibody Disulfides," Bioconjug. Chem. 16(5):1282-1290, 22 pages.
Suresh, M.R. et al. (1986). "Bispecific Monoclonal Antibodies From Hybrid Hybridomas," Methods in Enzymology 121:210-228, 19 pages.
Tailor, P.G. et al. (Aug. 25, 1990). "Nucleotide Sequence Of Human Prostatic Acid Phosphatase Determined From A Full-Length cDNA Clone," Nucl. Acids Res. 18(16):4928, 1 pages.
Teng, N.N.H. et al. (Dec. 1983). "Construction and Testing of Mouse-Human Heteromyelomas For Human Monoclonal Antibody Production," Proc. Natl. Acad. Sci. USA. 80:7308-7312.
Thorpe, P.E. et al. (Nov. 15, 1987). "New Coupling Agents for the Synthesis of Immunotoxins Containing a Hindered Disulfide Bond with Improved Stability in Vivo," Cancer Research 47:5924-5931.
Toki, B.E. et al. (2002, e-pub. Feb. 12, 2002). "Protease-Mediated Fragmentation of p-Amidobenzyl Ethers: A New Strategy for the Activation of Anticancer Prodrugs," J. Org. Chem. 67(6):1866-1872.
Toshima, K. et al. (1993). "Recent Progress in O-Glycosylation Methods and Its Application to Natural Products Synthesis," Chemical Reviews 93(4):1503-1531.
Trail, P.A. et al. (Jan. 1, 1997). "Effects of Linker Variation on the Stability, Potency, and Efficacy of Carcinoma-Reactive BR64-Doxorubicin Immunoconjugates," Cancer Research 57:100-105.
Trail, P.A. et al. (Jul. 9, 1993). "Cure Of Xenografted Human Carcinomas by BR96-Doxorubicin Immunoconjugates," Science 261(5118):212-215.
Translation of Taiwan Patent Office Search Report for Appl. Ser. No. 103135737 dated Feb. 11, 2019.
Traunecker, A. et al. (1991). "Bispecific Single Chain Molecules (Janusins) Target Cytotoxic Lymphocytes on HIV Infected Cells," Embo J. 10(12):3655-3659.
Trauth, B.C. et al. (Jul. 21, 1989). "Monoclonal Antibody-Mediated Tumor Regression by Induction of Apoptosis," Science 245(4915):301-305.
Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.
Venonese, F.M. et al. (Nov. 2005). "PEGylation, Successful Approach to Drug Delivery," Drug Discovery Today 10(21):1451-1458.
Verdier-Pinard, P. et al. (2000). "Sustained Intracellular Retention of Dolastatin 10 Causes Its Potent Antimitotic Activity," Molecular Pharmacology 57:180-187.
Verhoeyan, M. et al. (Mar. 25, 1988). "Reshaping Human Antibodies: Grafting an Antilysozyme Activity," Science 239:1534-1536.
Veronese, F.M. (2001). "Peptide and Protein PEGylation: A Review Of Problems and Solutions," Biomaterials 22:405-417.
Veronese, F.M. et al. (Apr. 1985). "Surface Modification Of Proteins: Activation Of Monomethoxy-Polyethylene Glycols By Phenylchloroformates and Modification Of Ribonuclease and Superoxide Dismutase," Appl. Biochem. Bioechnol 11(2):141-152.
Vijayasardahl, S. et al. (Apr. 1, 1990). "The Melanoma Antigen gp75 Is The Human Homologue Of The Mouse B (Brown) Locus Gene Product," J. Exp. Med. 171(4)1375-1380.
Wald, A.F. et al. (Jul. 1, 2002). "The Anti-CD30 Monoclonal Antibody SGN-30 Promotes Growth Arrest and DNA Fragmentation in Vitro and Affects Antitumor Activity In Models Of Hodgkin's Disease," Cancer Res. 62(13):3736-3742.
Wan, L. et al. (Apr. 24, 2006). "Novel Multi-Component Nanopharmaceuticals Derived From poly (ethylene) glycol, retro-inverso-Tat Nonapeptide and Saquinavir Demostrate Combined Anti-HIV Effects," AIDS Research and Therapy, pp. 1-15.
Ward, E.S. et al. (Oct. 12, 1989). "Binding Activities Of A Repertoire Of Single Immunoglobulin Variable Domains Secreted From *Escherichia coli*," Nature 341:544-554.
Wiels, J. et al. (Feb. 2, 2022). "38.13: A Monoclonal Antibody Directed Against A Burkitt's Lymphoma-Associated Antigen and Its Use as Carrier for Toxins," Laboratoire d'Immuno-Biolgie des Tumeurs, pp. 457-464.
Wilbur, D.S. et al. (2001). "Biotin Reagents for Antibody Pretargeting. 5. Additional Studies of Biotin Conjugate Design To Provide Biotinidase Stability," Bioconjugate Chem. 12:616-623.
Wildman, S.A. et al. (1999, e-pub. Aug. 19, 1999). "Prediction of Physiochemical Parameters by Atomic Contributions," J. Chem. Inf. Comput. Sci. 39(5):868-873.
Wittwer, A.J. et al. (May 1, 1990). "Glycosylation at Asn-184 Inhibits the Conversion of Single-Chain to Two-Chain Tissue-Type Plasminogen Activator by Plasmin," Biochemistry 29(17):4175-4180.
Wolff, E.A. et al. (Jun. 1, 1993). "Monoclonal Antibody Homodimers: Enhanced Antitumor Activity in Nude Mice," Can Res 53:2560-2565.
Wood, C.R. et al. (Apr. 4, 1985). "The Synthesis and in vivo Assembly of Functional Antibodies In Yeast," Nature 314(6010):446-449.
Wright, A. et al. (Jan. 1997). "Effect of Glycosylation on Antibody Function: Implications for Genetics Engineering," Trends Biotechnol. 15:26-32.
Wyss, D.F. et al. (1996). "The Structural Role of Sugars in Glycoproteins," Current Opin. Biotech. 7:409-416.
Yokata, T. et al. (Jun. 15, 1992). "Rapid Tumor Penetration Of A Single-Chain Fvand Comparison With Other Immunoglobulin Forms," Cancer Res. 52(12):3402-3408.
Yokoyama, M. et al. (1989). "Molecular Design for Missile Drug: Synthesis of Adriamycin Conjugate With Immunoglobulin G Using Poly(ethylene glycol)-Block-poly(aspartic acid) As Intermediate Carrier," Makromol. Chem. 190:2041-2054.
Yu, Y.H. et al. (Jan. 15, 1991). "Coexpression Of Different Antigenic Markers On Moieties That Bear CA 125 Determinants," Cancer Res. 51(2):468-475.
Anonymous (1999). "Calculation of SlogP Values," 4 pages.
Banerjee, S.S. et al. (May 7, 2012). "Poly(ethylene glycol)-Prodrug Conjugates: Concepts Design, and Applications," Journal of Drug Delivery 2012(103973):1-17.
Brief Communication (dated Sep. 24, 2021). Reply to Opposition for European Application No. 14853953.9, 322 pages.

(56) References Cited

OTHER PUBLICATIONS

Communication Pursuant to Rule 114(2) EPC (dated Mar. 9, 2022). Third Party Opposition for European Patent Application No. 14853953.9, 49 pages.
Consolidated List for European Opposition for European Application No. EP14853953.9, 1 page.
European Notice of Opposition, dated Apr. 30, 2021, for European Application No. 14853953.9, 76 pages.
European Summons to Attend Oral Proceedings, dated Jan. 4, 2022, for European Application No. 14853953.9, 19 pages.
Extended European Search Report, dated Jun. 10, 2022, for European Patent Application No. 21206543.7, 9 pages.
Extended European Search Report, dated Oct. 20, 2020, for European Patent Application No. 20186727.2, 15 pages.
Grounds for Opposition, dated Apr. 2021, for European Patent No. EP3057585, 66 pages.
Kahn, C.R. et al. (1988)."The Insulin Receptor and the Molecular Mechanism of Insulin Action," Insulin Receptor and Insulin Action 82:1151-1156.
Lyon, R.P. (May 5, 2014). "Novel ADC Chemistry for Improved Stability and Pharmacokinetics," Characterization of Antibody-Drug Conjugates, Seattle Genetics Presentation, PEGS Boston, 25 pages.
Notice of Opposition, dated Apr. 30, 2021, for European Application No. EP14853953.9, 7 pages.
Pfeifer, M. et al. (2015). "Anti-CD22 and Anti-CD79B Antibody Drug Conjugates are Active in Different Molecular Diffuse Large B-cell Lymphoma Subtypes," Leukemia 29:1578-1586.
Proprietors Submission dated Aug. 19, 2019, European Opposition for European Application No. EP14853953.9, 79 pages.
Proprietors Submission dated Jul. 3, 2018, European Opposition for European Application No. EP14853953.9, 40 pages.
Proprietors Submission dated Mar. 12, 2018, European Opposition for European Application No. EP14853953.9, 43 pages.
Proprietors Submission dated Nov. 15, 2019, European Opposition for European Application No. EP14853953.9, 99 pages.
Quiles, S. et al. (2010, e-pub. Dec. 3, 2009). "Synthesis and Preliminary Biological Evaluation of High-Drug-Load Paclitaxel-Antibody Conjugates for Tumor-Targeted Chemotherapy," J. Med. Chem. 53:586-594.
Summons to Attend Oral Proceedings Pursuant to Rule 115(1) EPC (dated Jan. 4, 2022), 59 pages.
U.S. Appl. No. 61/891,320, Provisional Application, filed Oct. 15, 2013, 254 pages.
U.S. Appl. No. 61/941,904, Provisional Application, filed Feb. 19, 2014, 269 pages.
U.S. Appl. No. 61/947,742, Provisional Application, filed Mar. 4, 2014, 279 pages.
U.S. Appl. No. 61/975,318, Provisional Application, filed Apr. 4, 2014, 280 pages.
Zhu, G.D. et al. (2013). "Design of Next Generation Antibody Drug Conjugates," Acta Pharmaceutica Sinica 48(7):1053-1070. With English Abstract, 18 pages. considered only English abstract.

\* cited by examiner

PROCESS FOR THE PREPARATION OF GLUCURONIDE DRUG-LINKERS AND INTERMEDIATES THEREOF

CROSS-REFERENCES TO RELATED APPLICATIONS

This application is a U.S. national stage application under 35 USC § 371 of International Application No. PCT/US2018/024191, filed internationally on Mar. 23, 2018, which claims the benefit of U.S. Provisional Application No. 62/476,605, filed Mar. 24, 2017.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

A great deal of interest has surrounded the use of monoclonal antibodies (mAbs) in the form of an Antibody Drug Conjugate (ADC) for the targeted delivery of cytotoxic drugs to cancer cells. The design of ADCs by conjugation of a cytotoxic drug to an antibody, typically via a linker, involves consideration of a variety of factors. Those factors include the identity and location of the chemical group for conjugation of the cytotoxic drug, the mechanism of drug release, the structural element(s) (if any) providing release of the cytotoxic drug, and structural modification (if any) of the released free drug. In addition, if the cytotoxic drug is to be released after internalization of an ADC compound, the structural elements and mechanism of drug release must be consonant with the intracellular trafficking of the Conjugate compound.

Ligand-Drug Conjugates (LDCs), which includes ADCs, incorporating a β-glucuronide-based linker, which contains a Glucuronide Unit as defined herein, have been used successfully to achieve targeted delivery of therapeutic agents, such as anti-cancer drugs (see e.g., International Publication No WO 2007/011968). The glucuronide-based linker connects a Drug Unit to a Ligand Unit in which its Glucuronide Unit comprises a glycosidase recognition site that in some aspects is cleavable by an enzyme having β-glucuronidase activity thereby releasing free drug. Glucuronide-based linkers improve the solubility of LDCs and exhibit sufficient serum stability to provide targeted delivery of a conjugated drug to a targeted cell.

Literature-reported syntheses of the β-glucuronide-based linkers (Jeffrey, S, C, et al., "Development and properties of β-glucuronide linkers for monoclonal antibody drug conjugates" *Bioconj. Chem.* 17(3): 831-840) involve generation of a series of intermediates that incorporate a protected β-glucuronide carbohydrate moiety. Global deprotection of that carbohydrate moiety by conventional base hydrolysis methods can generate of up to 20-25% of an impurity that has been identified as a product of β-elimination within the carbohydrate moiety of the Glucuronide Unit. That in turn results in loss of material during, and the impurities generated from that loss can be difficult to remove without further reduction in yield. Therefore, there is a need for improved methods for preparing β-glucuronide-based Drug Linker compounds with higher yields and reduced amounts of contaminating impurities.

BRIEF SUMMARY OF THE INVENTION

The invention provides inter alia, improved processes in producing Drug Linker compounds containing a Glucuronide Unit, as well as intermediates thereof.

DESCRIPTION OF THE INVENTION

General

The present invention is based, in part, on the surprising discovery that the method of deprotection of a Glucuronide Unit in the synthesis of certain Drug Linker compounds can have a profound effect on the purity and yield of the desired product. Specifically, the present inventors have discovered that using an alkoxymagnesium halide in a solvent comprising an alcohol for removal of acyl protecting groups in the carbohydrate moiety of the Glucuronide Unit, instead of conventionally used reagents such as LiOH, leads to significant reduction of in an undesirable β-eliminated impurity (to below about 5% from about 20%). In some aspects, the alkoxymagnesium halide reagent is prepared in situ by contacting a Gringard reagent with the alcohol-containing solvent. Thus, the present invention provides improved processes for preparing certain Drug Linkers comprising a Glucuronide Unit.

Definitions

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as used in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, or methods that are, or that consist of, or that consist essentially of those specified components, elements or steps. The term "comprised of" is used interchangeably with the term "comprising" and are stated as equivalent terms. Disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have no or inconsequential material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques, and pharmacology are employed.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, typically by 10% to 0.5%, more typically by 5% to 1%, while still describing the particular property.

"Essentially retains", "essentially retaining" and like terms as used herein refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms as used herein refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property. Thus the phrase "substantially retains" is made in reference to the effect that a physical property or characteristic of a compound or composition has on a physiochemical or pharmacological property or biological activity that is explicitly associated with that physical property or characteristic.

"Negligibly" or "negligible" as used herein is an amount of an impurity below the level of quantification by standard HPLC analysis and if present represents from about 0.5% to about 0.1 w/w % of the composition that it contaminates or is below the limit of quantification. Depending on context, those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount.

"Predominately containing", "predominately having" and like terms as used herein refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

"Electron-withdrawing group" as the term is used herein refers to a functional group or electronegative atom that draws electron density away from an atom to which it is bonded either inductively and/or through resonance, whichever is more dominant (i.e., a functional group or atom may be electron-donating through resonance but may overall be electron withdrawing inductively), and tends to stabilize anions or electron-rich moieties. The electron-withdrawing effect is typically transmitted inductively, albeit in attenuated form, to other atoms attached to the bonded atom that has been made electron-deficient by the electron-withdrawing group (EWG), thus affecting the reactivity of a more remote reactive center.

An electron-withdrawing group (EWG) is typically selected from the group consisting of —C(=O), —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, —PO$_3$H$_2$, —P(=O)(OR')(OR$^{op}$)$_2$, —NO, —NH$_2$, —N(R')(R$^{op}$), —N(R$^{op}$)$_3^+$, and salts thereof, wherein X is —F, —Br, —Cl, or —I, and R$^{op}$ is, at each occurrence, independently selected from a grouping described herein for optional substituents and in some aspects is independently selected from the group consisting of C$_1$-C$_6$alkyl and phenyl, and wherein R' is hydrogen and R$^{op}$ is selected from a grouping as described elsewhere for optional substituents and in some aspects is a C$_1$-C$_{12}$ alkyl, C$_1$-C$_8$ alkyl, C$_1$-C$_6$ alkyl or C$_1$-C$_4$ alkyl. An EWG can also be a substituted aryl (e.g., substituted phenyl) or heteroaryl depending on its substituents and certain electron deficient heteroaryl groups (e.g., pyridine). Thus, in some aspects, an "electron-withdrawing group" further encompasses electron-deficient C$_5$-C$_{24}$ heteroaryls and C$_6$-C$_{24}$ aryls that are further substituted with electron-withdrawing substituents. More typically, an electron-withdrawing group is selected from the group consisting of —C(=O), —CN, —NO$_2$, —CX$_3$, and —X, wherein X is halogen, independently selected typically from the group consisting of —F and —Cl. Depending on its substituents, a substituted alkyl moiety may also be an electron-withdrawing group and thus in such cases aspects would be encompassed by that term.

"Electron-donating group" as the term is used herein refers to a functional group or electropositive atom that increases electron density of an atom to which it is bonded either inductively and/or through resonance, whichever is more dominant (i.e., a functional group or atom may be electron-withdrawing inductively but may overall be electron-donating through resonance), and tends to stabilize cations or electron poor systems. The electron-donating effect is typically transmitted through resonance to other atoms attached to the bonded atom that has been made electron rich by the electron-donating group (EDG) thus affecting the reactivity of a more remote reactive center. Typically, an electron-donating group is selected from the group consisting of —OH, —OR', —NH$_2$, —NHR', and N(R')$_2$, wherein each R' is an independently selected from C$_1$-C$_{12}$ alkyl, typically C$_1$-C$_6$ alkyl. Depending on their substituents, a C$_6$-C$_{24}$ aryl, C$_5$-C$_{24}$ heteroaryl, or unsaturated C$_1$-C$_{12}$ alkyl moiety may also be an electron-donating group and in some aspects such moieties are encompassed by the term for an electron-donating group.

"Moiety" as used herein means a specified segment, fragment, or functional group of a molecule or compound. Chemical moieties are sometimes indicated as chemical entities that are embedded in or appended to (i.e., a substituent or variable group) a molecule, compound or chemical Formula.

Unless indicated otherwise, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms that may be present in the substituents to that base moiety. For esters, carbonates, carbamates, and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, are referred to as carbocyclyls as defined herein.

When referring to an alkyl moiety or group as an alkyl substituent, that alkyl substituent to a Markush structure or another organic moiety with which it is associated is methyl or a chain of contiguous carbon atoms that is covalently attached to the structure or moiety through a $sp^3$ carbon of the alkyl substituent. An alkyl substituent, as used herein, therefore contains at least one saturated moiety and may also contain one or more unsaturated moieties or groups. Thus, an alkyl substituent may additionally contain one, two, three or more independently selected double and/or triple bonds to define an unsaturated alkyl substituent, and may be substituted (i.e., optionally substituted) by other moieties that include optional substituents as described herein. A saturated, unsubstituted alkyl substituent contains saturated carbon atoms (i.e., $sp^3$ carbons) and no $sp^2$ or sp carbon atoms. An unsaturated alkyl substituent contains at least one saturated carbon atom that is monovalent for its site of attachment to the Markush structure or other organic moiety with which it is associated and at least two $sp^2$ or sp carbon atoms that are in conjugation with each other.

Unless otherwise indicated or implied by context, the term "alkyl" will indicate a saturated, non-cyclic hydrocarbon radical, wherein the hydrocarbon radical is methyl or has the indicated number of covalently linked saturated carbon atoms, e.g., "$C_1$-$C_6$ alkyl" or "C1-C6 alkyl" means a saturated alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to a saturated alkyl moiety or group having 1 saturated carbon atom or 2, 3, 4, 5, 6, 7 or 8 contiguous saturated, non-cyclic carbon atoms. The number of saturated carbon atoms in an alkyl moiety or group can vary and typically is 1 to 50, 1 to 30 or 1 to 20, or 1 to 12, and more typically is 1 to 8, 1 to 6 or 1 to 4. In some aspects, alkyl refers to a saturated $C_1$-$C_{12}$ or a $C_1$-$C_8$ alkyl moiety and more typically is a saturated $C_1$-$C_6$ or $C_1$-$C_4$ alkyl moiety with the latter sometimes referred to as lower alkyl. When the number of carbon atoms is not indicated, an alkyl moiety, group or substituent has from 1 to 8 saturated carbon atoms. In some aspects an alkyl moeity, group or substituent is unsubstituted. When an alkyl substituent is unsaturated such moieties typically are unsaturated $C_3$-$C_{12}$ alkyl or $C_3$-$C_8$ moieties, more typically unsaturated $C_3$-$C_6$ alkyl moieties. Unless indicated or otherwise require by context terms such as "$C_1$-$C_{12}$ alkyl", "$C_1$-$C_8$ alkyl" or "$C_1$-$C_6$ alkyl" includes saturated $C_1$-$C_{12}$ alkyl, $C_1$-$C_8$ alkyl or $C_1$-$C_6$ alkyl and unsaturated $C_3$-$C_{12}$ alkyl, $C_3$-$C_8$ alkyl or $C_3$-$C_6$ alkyl.

In some aspects when an alkyl substituent, moiety or group is specified, species are those derived from removing a hydrogen atom from a parent alkane (i.e., is monovalent) and are exemplified by methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, and sec-amyl and in other aspects an alkyl substituent, moiety or group are or are additionally exemplified by other linear and branch chain alkyl moieties.

"Alkylene," as used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more $sp^3$ carbons), of the stated number of carbon atoms, typically 1 to 10 carbon atoms, and having two radical centers (i.e., is divalent) derived by the removal of two hydrogen atoms from the same or two different saturated (i.e., $sp^3$) carbon atoms of a parent alkane. An alkylene moiety in some aspects is an alkyl radical as described herein in which a hydrogen atom has been removed from another of its saturated carbons or from the radical carbon of an alkyl radical to form a diradical. In other aspects, an alkylene moiety is or is further encompassed by a divalent moiety derived from removing a hydrogen atom from a saturated carbon atom of a parent alkyl moiety and are exemplified without limitation by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon containing only $sp^3$ carbons (i.e., is fully saturated notwithstanding the radical carbon atoms) and in some aspects is unsubstituted.

"Carbocyclyl" as used herein, by itself of as part of another term, unless otherwise stated or implied by context, refers to a radical of a monocyclic, bicyclic, or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more $sp^3$ carbons). Thus, a carbocyclyl is a cyclic arrangement of saturated carbons but may also contain unsaturated carbon atom(s) and therefore its carbocyclic ring may be saturated or partially unsaturated but not fully unsaturated and in some aspects is fused with an aromatic ring system, wherein the points of fusion to the carbocyclic and aromatic ring systems are to adjacent carbons of each of these ring systems.

When carbocyclyl is used as a Markush group (i.e., a substituent) the carbocyclyl is attached to a Markush formula or another organic moiety with which it is associated through a carbon atom that is involved in the carbocyclic ring system of the carbocyclyl moiety provided that carbon atom is not aromatic. When an unsaturated carbon of an alkene moiety comprising the carbocyclyl substituent is present and is attached to a Markush formula with which it is associated that carbocyclyl is sometimes referred to as a cycloalkenyl substituent. The number of carbon atoms in a carbocyclyl moeity group or substituent is defined by the total number of skeletal atoms of its carbocyclic ring system. That number can vary and typically ranges from 3 to 50, 3 to 30, 3 to 20 or 3 to 12, and more typically from 3 to 8 or 3 to 6 skeletal carbon atoms unless otherwise specified, e.g., $C_3$-$C_8$ carbocyclyl means an carbocyclyl substituent, moiety or group containing 3, 4, 5, 6, 7, or 8 carbocyclic carbon atoms and $C_3$-$C_6$ carbocyclyl means a carbocyclyl substituent, moiety or group containing 3, 4, 5, or 6 carbocyclic carbon atoms. A carbocyclyl in some aspects is unsubstituted and in other aspects is derived by the removal of one hydrogen atom from a skeletal ring atom of a parent cycloalkane or cycloalkene. Representative $C_3$-$C_7$ carbocyclyls are cyclopropyl, cyclobutyl, cyclopentyl, cyclohexyl, cyclohexenyl, cycloheptyl and cyclooctyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share one (i.e., is a spiro ring system) or two carbon atoms and a tricyclic ring system may share a total of 2, 3, or 4 carbon atoms, typically 2 or 3. Thus, otherwise specified, a carbocyclyl is typically a $C_3$-$C_8$ carbocyclyl that may be substituted (i.e. optionally substituted) with moieties described herein for alkyl, alkenyl, alkynyl, aryl, arylalkyl, and alkylaryl and in some aspects is unsubstituted. In other aspects, a $C_3$-$C_8$ cycloalkyl moiety, group or substituent is selected from the group consisting of cyclopropyl, cyclopentyl and cyclohexyl, or is encompassed or further encompassed by other cyclic moieties that have no more than 8 carbon atoms in their cyclic ring systems. When the number of carbon atoms is not indicated, a carbocyclyl moiety, group or substituent has from 3 to 8 carbon atoms in its carboxcylic ring system.

"Carbocyclo," by itself or as part of another term, unless otherwise stated or implied by context, refers to an optionally substituted carbocyclyl as defined above wherein another hydrogen atom of its cycloalkyl ring system has been removed (i.e., it is divalent) and typically is a $C_3$-$C_{20}$ or $C_3$-$C_{12}$ carbocyclo, more typically a $C_3$-$C_8$ or $C_3$-$C_6$ carbocyclo and in some aspects is unsubstituted. When the number of carbon atoms is not indicated, a carbocyclo moiety, group or substituent has from 3 to 8 carbon atoms in its carboxcylic ring system. An carbocyclo moiety in some aspects is a carbocyclyl radical as described herein in which a hydrogen atom has been removed from another of its skeletal carbons or from the same radical sp$^3$ carbon atom of its skeletal radical, which provides a spiro ring system, to form a diradical. In other aspects, carbocyclo is or is further encompassed by a divalent moiety derived from removing two hydrogen atoms from a parent cycloalkane and are exemplified without limitation by $C_3$-$C_8$ carbocyclos cyclopentadienyl 1,3-cyclohexadienyl, 1,4-cyclohexadienyl, cycloheptyl, 1,3-cycloheptadienyl, 1,3,5-cycloheptatrienyl and cyclooctadienyl or from a parent cycloalkene.

"Alkenyl" as the terms are used herein, by itself or as part of another term, unless otherwise stated or implied by context, refers to an organic moiety, substituent or group that comprises one or more double bond functional groups (e.g., a —CH=CH— moiety) or 1, 2, 3, 4, 5, or 6 or more, typically 1, 2, or 3 of such functional groups, more typically one such functional group, and in some aspects may be substituted (i.e., is optionally substituted) with an aryl moiety or group such as phenyl, or linked normal, secondary, tertiary or cyclic carbon atoms, i.e., linear, branched, cyclic or any combination thereof unless the alkenyl substituent, moiety or group is a vinyl moiety (e.g., a —CH=CH$_2$ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

An alkenyl moiety, group or substituent contains at least one sp$^2$ carbon atom in which that carbon atom is doubly, or contains at least two sp$^2$ carbon atoms in conjugation to each other in which one of the sp$^2$ carbon atoms is singly bonded, to a Markush structure or another organic moeity to which it is associated. Typically, when alkenyl is used in a Markush grouping (i.e., is a substituent) the alkenyl is singly bonded to a Markush formula or another organic moiety with which it is associated through a double-bonded carbon (i.e., a sp$^2$ carbon) of one of its alkene functional groups. In some aspects when an alkenyl moiety, group or substituent is specified, species encompassed are any of the optionally substituted alkyl or carbocyclyl, groups moieties or substituents described herein that has one or more endo double bonds and monovalent moieties derived from removal of a hydrogen atom from a sp$^2$ carbon of a parent alkene compound. Such monovalent moieties are exemplified without limitation by vinyl (—CH=CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, and cyclohexenyl. In some aspects the term alkenyl encompasses those and/or other linear, cyclic and branched chained, all carbon-containing moieties containing at least one double bond functional group. The number of carbon atoms in an alkenyl substituent is defined by the number of sp$^2$ carbon atoms of the alkene functional group that defines it as an alkenyl substituent and the total number of contiguous non-aromatic carbon atoms appended to each of these sp$^2$ carbons not including any carbon atom of the other moiety or Markush structure for which the alkenyl moiety is a variable group. That number can vary ranging from 1 to 50, e.g., typically 1 to 30, 1 to 20, or 1 to 12, more typically, 1 to 8, 1 to 6, or 1 to 4 carbon atoms when the double bond functional group is doubly bonded to a Markush structure (e.g. =CH$_2$), or can vary ranging from 2 to 50, typically 2 to 30, 2 to 20, or 2 to 12, more typically 2 to 8, 2 to 6, or 2 to 4 carbon atoms, when the double bond functional group is singly bonded to the Markush structure (e.g., —CH=CH$_2$). For example, $C_2$-$C_8$ alkenyl or $C_2$-$C_8$ alkenyl means an alkenyl moiety containing 2, 3, 4, 5, 6, 7, or 8 carbon atoms in which at least two are sp$^2$ carbon atoms in conjugation with each other with one of these carbon atoms being monovalent, and $C_2$-$C_6$ alkenyl or $C_2$-$C_6$ alkenyl means an alkenyl moiety containing 2, 3, 4, 5, or 6 carbon atoms in which at least two are $sp^2$ carbons that are in conjugation with each other with one of these carbon atoms being monovalent. In some aspects, an alkenyl substituent or group is a $C_2$-$C_6$ or $C_2$-$C_4$ alkenyl moiety having two $sp^2$ carbons that are in conjugation with each other with one of these carbon atoms being monovalent, and in other aspects that alkenyl moeity is unsubstituted. When the number of carbon atoms is not indicated, an alkenyl moiety, group or substituent has from 2 to 8 carbon atoms.

"Alkenylene" as used herein, by itself of as part of another term, unless otherwise stated or implied by context, refers to an organic moiety, substituent or group that comprises one or more double bond moieties, as previously described for alkenyl, of the stated number of carbon atoms and has two radical centers derived by the removal of two hydrogen atoms from the same or two different $sp^2$ carbon atoms of an alkene functional group in a parent alkene. In some aspects an alkenylene moiety is that of an alkenyl radical as described herein in which a hydrogen atom has been removed from the same or different $sp^2$ carbon atom of a double bond functional group of the alkenyl radical, or from a $sp^2$ carbon from a different double bond moiety to provide a diradical. Typically, alkenylene moieties encompass diradicals containing the structure of —C=C— or —C=C—$X^1$—C=C— wherein $X^1$ is absent or is an optionally substituted saturated alkylene as defined herein, which is typically a $C_1$-$C_6$ alkylene, which is more typically unsubstituted. The number of carbon atoms in an alkenylene moiety is defined by the number of $sp^2$ carbon atoms of its alkene functional group(s) that defines it as an alkenylene moiety and the total number of contiguous non-aromatic carbon atoms appended to each of its $sp^2$ carbons not including any carbon atoms of the other moiety or Markush structure in which the alkenyl moiety is a present as a variable group. That number can vary and unless otherwise specified ranges from 2 to 50, typically 2 to 30, 2 to 20, or 2 to 12, more typically 2 to 8, 2 to 6, or 2 to 4. For example, $C_2$-$C_8$ alkenylene or $C_2$-$C_8$ alkenylene means an alkenylene moiety containing 2, 3, 4, 5, 6, 7, or 8 carbon atoms in which at least two are $sp^2$ carbons in conjugation with each other and $C_2$-$C_6$ alkenylene or $C_2$-$C_6$ alkenylene means an alkenyl moiety containing 2, 3, 4, 5, or 6 carbon atoms in which at least two are $sp^2$ carbons that are in conjugation with each other. Typically, an alkenylene substituent is a $C_2$-$C_6$ or $C_2$-$C_4$ alkenylene having two $sp^2$ carbons that are in conjugation with each other, which in some aspects is unsubstituted. When the number of carbon atoms is not indicated, an alkenylene moiety, group or substituent has from 2 to 8 carbon atoms.

"Alkynyl" as the terms are used herein, by itself or as part of another term, unless otherwise stated or implied by context, refers to an organic moiety, substituent or group that comprises one or more triple bond functional groups (e.g., a —C≡C— moiety) or 1, 2, 3, 4, 5, or 6 or more, typically 1, 2, or 3 of such functional groups, more typically one such functional group, and in some aspects may be substituted (i.e., is optionally substituted) with an aryl moiety such as phenyl, or by an alkenyl moiety or linked normal, secondary, tertiary or cyclic carbon atoms, i.e., linear, branched, cyclic or any combination thereof unless the alkynyl substituent, moiety or group is —C≡CH). An alkynyl moiety, group or substituent having multiple triple bonds may have the triple bonds arranged contiguously or non-contiguously with one or more intervening saturated or unsaturated carbon atoms or a combination thereof, provided that a cyclic, contiguous arrangement of triple bonds do not form a cyclic conjugated system of 4n+2 electrons (i.e., is not aromatic).

An alkynyl moiety, group or substituent contains at least two sp carbon atom in which the carbon atoms are in conjugation with each other and in which one of the sp carbon atoms is singly bonded to another organic moiety or Markush structure to which it is associated. When alkynyl is used in a Markush grouping (i.e., is a substituent) the alkynyl is singly bonded to a Markush formula or another organic moiety with which it is associated through a triple-bonded carbon (i.e., a sp carbon) of one of its alkyne functional groups. In some aspects when an alkynyl moiety, group or substituent is specified, species encompasses are any one of the optionally substituted alkyl moieties or substituents described herein having a terminal alkyne functional group, or any one of the carbocyclyl moieties or substituents described herein that has one or more endo triple bonds and monovalent moieties, derived from removal of a hydrogen atom from a sp carbon of a parent alkyne compound. Such optionally substituted monovalent moieties are exemplified without limitation by —C≡CH, —C≡C—$CH_3$, —C≡C-Ph and —C≡C—Cl.

The number of carbon atoms in an alkynyl substituent is defined by the number of sp carbon atoms of the alkyne functional group that defines it as an alkynyl substituent and the total number of contiguous non-aromatic carbon atoms appended to each of these sp carbons atoms not including any carbon atom of the other moiety or Markush structure for which the alkenyl moiety is a variable group. That number can vary ranging from 2 to 50, typically 2 to 30, 2 to 20, or 2 to 12, more typically 2 to 8, 2 to 6, or 2 to 4 carbon atoms, when the triple bond functional group is singly bonded to the Markush structure (e.g., —CH≡CH). For example, $C_2$-$C_8$ alkynyl or C2-C8 alkynyl means an alkynyl moiety containing 2, 3, 4, 5, 6, 7, or 8 carbon atoms in which at least two are sp carbon atoms in conjugation with each other with one of these carbon atoms being monovalent, and $C_2$-$C_6$ alkynyl or C2-C6 alkynyl means an alkynyl moiety containing 2, 3, 4, 5, or 6 carbon atoms in which at least two are sp carbon atoms that are in conjugation with each other with one of these carbon atoms being monovalent. In some aspects, an alkynyl substituent or group is a $C_2$-$C_6$ or $C_2$-$C_4$ alkynyl moiety having two sp carbons that are in conjugation with each other with one of these carbon atoms being monovalent, and in other aspects that alkynyl moeity is unsubstituted. When the number of carbon atoms is not indicated, an alkynyl moiety, group or substituent has from 2 to 8 carbon atoms.

"Aryl" as the terms are used herein, by itself or as part of another term, unless otherwise stated or implied by context, refers to an organic moiety, substituent or group having an aromatic or fused aromatic ring system with no ring heteroatoms comprising 1, 2, 3, or 4 to 6 aromatic rings, typically 1 to 3 aromatic rings, more typically 1 or 2 aromatic rings, wherein the rings are composed of only carbon atoms that participate in a cyclically conjugated system of 4n+2 electrons (Hückel rule), typically 6, 10, or 14 electrons, some of which may additionally participate in exocyclic conjugation with a heteroatom (cross-conjugated, e.g., quinone). Aryl substituents, moieties or groups are typically formed by six, eight, ten, or more aromatic carbon atoms up to 24 carbon atoms to include $C_6$-$C_{24}$ aryl. Aryl substituents, moieties or groups are optionally substituted and in some aspects are unsubstituted or are substituted with 1 or 2 independently selected substituents as defined herein for optional substituents. Exemplary aryls are $C_6$-$C_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Arylene" as used herein, by itself or as part of another term, unless otherwise stated or implied by context, is an aromatic diradical moiety in which all skeletal atoms are aromatic carbon atoms that forms two covalent bonds (i.e., it is divalent) within another moiety, which can be in the ortho, meta, or para configuration. Arylenes include divalent species by removal of a hydrogen atom from skeletal aromatic carbon atom of a parent aryl moiety, group or substituent as defined herein. Exemplary arylenes are, but not limited to, phenyl-1,2-ene, phenyl-1,3-ene, and phenyl-1,4-ene as shown in the following structures:

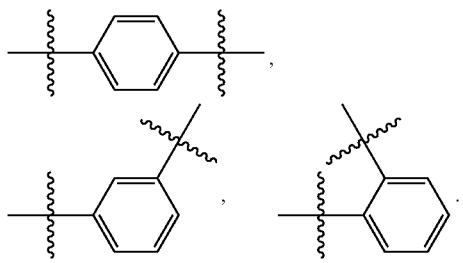

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. Typically an arylalkyl is a ($C_6$-$C_{24}$ aryl)-$C_1$-$C_{12}$ alkyl moiety, group or substituent, and heteroarylalkyl is a ($C_5$-$C_{24}$ heteroaryl)-$C_1$-$C_{12}$ alkyl moiety, group or substituent. When (hetero)arylalkyl is used as a Markush group (i.e., a substituent) the alkyl moiety of the (hetero)arylalkyl is attached to a Markush formula with which it is associated through a sp$^3$ carbon of its alkyl moiety. In some aspects an arylalkyl is a ($C_6$-$C_{10}$ aryl)-$C_1$-$C_{12}$ alkyl, more typically a ($C_6$-$C_{10}$ aryl)-$C_1$-$C_6$ exemplified without limitation, by $C_6H_5$—$CH_2$—, $C_6H_5$—$CH(CH_3)CH_2$— and $C_6H_5$—$CH_2$—$CH(CH_2CH_2CH_3)$—.

"Alkylaryl" or "alkylheteroaryl," as the terms are used herein, by itself or as part of another term, unless otherwise stated or implied by context, refers to an alkyl moiety bonded to an aryl or heteroaryl moiety, i.e., -(hetero)arylalkyl, where (hetero)aryl and alkyl groups are as described above. Typically, an alkylaryl is a ($C_1$-$C_{12}$ alkyl)-$C_6$-$C_{24}$ aryl-moeity, group or substituent, and alkylheteroaryl is a ($C_1$-$C_{12}$ alkyl)-$C_5$-$C_{24}$ heteroaryl-moeity, group or substituent. When alkyl(hetero)aryl is used as a Markush group (i.e., a substituent) the (hetero)aryl moiety of the alkyl(hetero)aryl is attached to a Markush formula with which it is associated through an aromatic carbon atom or heteroatom of its aryl or heteroaryl moiety. In some aspects, an alkylaryl is a ($C_1$-$C_{12}$ alkyl)-$C_6$-$C_{10}$ aryl- or a ($C_1$-$C_6$ alkyl)-$C_6$-$C_{10}$ aryl-exemplified without limitation, for example, by —$C_6H_4$—$CH_3$ or —$C_6H_4$—$CH_2CH(CH_3)_2$.

"Heterocyclyl," as the term is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms, optionally substituted where permitted, including without limitation N/NH, O, S, Se, B, Si, and P, wherein two or more heteroatoms may be adjacent to each other or separated by one or more carbon atoms within the same ring system, typically by 1 to 3 atoms. Those heteroatoms typically are N/NH, O, and S. A heterocyclyl typically contains a total of one to ten heteroatoms in the heterocyclic ring system provided that not all of the skeletal atoms of any one ring in the heterocyclic ring system are heteroatoms, wherein each heteroatom in the ring(s), optionally substituted where permitted, is independently selected from the group consisting of N/NH, O, and S, with the proviso that any one ring does not contain two adjacent O or S atoms. Exemplary heterocyclyls and heteroaryls are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 1960, 82:5545-5473 particularly 5566-5573).

When heterocyclyl is used as a Markush group (i.e., a substituent), a saturated or partially unsaturated heterocyclic ring of the heterocyclyl is attached to a Markush structure or other moiety with which it is associated through a carbon atom or a heteroatom of that heterocyclic ring, where such attachment does not result in an unstable or disallowed formal oxidation state of that carbon atom or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

Typically, a heterocyclyl is a $C_3$-$C_{20}$ carbocyclyl wherein 1, 2 or 3 carbons of its cycloalkyl ring system is replaced along with its attached hydrogens with a heteroatom selected from the group consisting of optionally substituted N/NH, O, and S and thus is a $C_3$-$C_{20}$ heterocyclyl, more typically a $C_3$-$C_{12}$ heterocyclyl, or a $C_5$-$C_{12}$, $C_3$-$C_6$, or $C_5$-$C_6$ heterocyclyl in which the subscript indicates the total number of skeletal atoms (inclusive of its carbon atoms and heteroatoms) of the heterocyclic ring system of the heterocyclyl. In some aspects a heterocyclyl contains 0 to 2 N atoms, 0 to 2 O atoms, or 0 to 1 S atoms or some combination thereof provided at least one of said heteroatoms is present in the cyclic ring system, which may be substituted at a carbon atom with an oxo (=O) moiety, as in pyrrolidin-2-one, or at a heteroatom with one or two oxo moieties so as to contain an oxidized heteroatom as exemplified, but not limited to, —N(=O), —S(=O)—, or —S(=O)$_2$—. More typically, heterocyclyl is selected from the group consisting of pyrrolidinyl, piperidinyl, morpholinyl and piperazinyl.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of the aryl is replaced by a heteroatom. A heteroaryl typically contains a total one to four heteroatoms in the ring(s) of the heteroaryl ring system, provided that not all of the skeletal atoms of any one ring system in the heteroaryl are heteroatoms, optionally substituted where permitted, and have 0 to 3 N atoms, 1 to 3 N atoms, or 0 to 3 N atoms, typically 0 to 1 O atoms and/or 0 to 1 S atoms, provided that at least one heteroatom is present. A heteroaryl may be monocyclic, bicyclic or polycyclic. A monocyclic heteroaryl typically is a $C_5$-$C_{24}$ heteroaryl, more typically a $C_5$-$C_{12}$ or $C_5$-$C_6$ heteroaryl, in which the subscript indicates the total number of skeletal atoms (inclusive of its carbon atoms and heteroatoms) of the aromatic ring system(s) of the heteroaryl. In some aspects a heteroaryl is an aryl moiety wherein one 1, 2, or 3 of the carbon atoms of the aromatic ring(s) and their attached hydrogen atoms of a parent aryl moiety are replaced by a heteroatom, optionally substituted where permitted, including N/NH, O and S, provided that not all of the skeletal atoms of any one aromatic ring system in the aryl moiety are replaced by heteroatoms and more typically are replaced by oxygen (—O—), sulfur (—S—) nitrogen (=N—) or —NR—, so that the aromatic nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a biaryl. In other aspects one 1, 2, or 3 of the carbon atoms of the aromatic ring(s) and their attached hydrogen atoms of a parent aryl moiety are replaced by nitrogen substituted with another organic moiety in a manner which retains the cyclic conjugated system. In some aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which its ring system has been aromatized.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of the aryl is replaced by a heteroatom. A heteroaryl typically contains a total one to four heteroatoms in the ring(s) of the heteroaryl ring system, provided that not all of the skeletal atoms of any one ring system in the heteroaryl are heteroatoms, optionally substituted where permitted, and have 0 to 3 N atoms, 1 to 3 N atoms, or 0 to 3 N atoms, typically 0 to 1 O atoms and/or 0 to 1 S atoms, provided that at least one heteroatom is present. A heteroaryl may be monocyclic, bicyclic or polycyclic. A monocyclic heteroaryl typically is a $C_5$-$C_{24}$ heteroaryl, more typically a $C_5$-$C_{12}$ or $C_5$-$C_6$ heteroaryl, in which the subscript indicates the total number of skeletal atoms (inclusive of its carbon atoms and heteroatoms) of the aromatic ring system(s) of the heteroaryl. In some aspects a heteroaryl is an aryl moiety wherein one 1, 2, or 3 of the carbon atoms of the aromatic ring(s) and their attached hydrogen atoms of a parent aryl moiety are replaced by a heteroatom, optionally substituted where permitted, including N/NH, 0 and S, provided that not all of the skeletal atoms of any one aromatic ring system in the aryl moiety are replaced by heteroatoms and more typically are replaced by oxygen (—O—), sulfur (—S—) nitrogen (=N—) or —NR—, so that the aromatic nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a biaryl. In other aspects one 1, 2, or 3 of the carbon atoms of the aromatic ring(s) and their attached hydrogen atoms of a parent aryl moiety are replaced by nitrogen substituted with another organic moiety in a manner which retains the cyclic conjugated system. In some aspects, the nitrogen, sulfur or oxygen heteroatom participates in the conjugated system either through pi-bonding with an adjacent atom in the ring system or through a lone pair of electrons on the heteroatom.

In still other aspects, a heteroaryl has the structure of a heterocyclyl as defined herein in which its ring system has been aromatized.

A "5-membered nitrogen-containing heteroaryl" as the terms is used herein, by itself or as part of another term, unless otherwise stated or implied by context, refers to a heteroaryl containing an optionally substituted 5-membered heteroaromatic ring that is monovalent and contains a skeletal aromatic nitrogen atom. In some aspects a 5-membered nitrogen-containing heteroaryl is a monocyclic heteroaryl and in other aspects contains one or more other independently selected heteroatoms selected from the group consisting of N/NH, O, and S, optionally substituted where permitted. Exemplary 5-membered nitrogen-containing heteroaryls that are monocyclic without limitation are thiazole, pyrrole, imidazole, oxazole, and triazole.

In some aspects a monovalent 5-membered nitrogen-containing heteroaromatic ring system is fused to an aryl ring system, or to a 6-membered heteroaromatic ring system that contains one or more independently selected heteroatoms selected from the group consisting of N/NH, O, and S, optionally substituted where permitted, to form a 6,5-fused ring system in which the monovalent 5-membered heteroaromatic ring is part of the 5-membered nitrogen-containing heteroaryl.

A "6-membered nitrogen-containing heteroaryl" as the term is used herein, by itself or as part of another term, unless otherwise stated or implied by context, refers to a heteroaryl containing an optionally substituted 6-membered heteroaromatic ring that is monovalent and contains a skeletal aromatic nitrogen atom. In some aspects a 6-membered nitrogen-containing heteroaryl is a monocyclic heteroaryl and in other aspects contains one or more other independently selected heteroatoms selected from the group consisting of N/NH, O, and S, optionally substituted where permitted. Exemplary 6-membered nitrogen-containing heteroaryls without limitation are pyridine, pyrimidine and pyrazine.

In some aspects a monovalent 6-membered nitrogen-containing heteroaromatic ring system is fused to an aryl ring system, or to a 5- or 6-membered heteroaromatic ring system that contains one or more independently selected heteroatoms selected from the group consisting of N/NH, O, and S, optionally substituted where permitted, to form a 6,5- or 6,6-fused ring system in which the monovalent 6-membered heteroaromatic ring system is part of the 6-membered nitrogen-containing heteroaryl.

"Heterocyclo", as the term is used herein, by itself or as part of another term, unless otherwise stated or implied by context, refers to a heterocyclyl moiety, group or substituent as defined above wherein a hydrogen atom or an electron, where permitted, from a different carbon atom or an electron or hydrogen atom from a skeletal nitrogen atom, if present, is removed to provide a divalent moeity.

"Heteroarylene", as the term is used herein, by itself or as part of another term, unless otherwise stated or implied by context refers a heteroaromatic diradical moiety that forms two covalent bonds (i.e., it is divalent) within another moiety, which can be in the ortho, meta, or para configurations. Heteroarylenes include divalent species by removal of a hydrogen atom from a skeletal aromatic carbon atom or a hydrogen atom or an electron from a skeletal heteroatom, where permitted, from a parent heteroaryl moiety, group or substituent as defined herein. Heteroarylene further include those in which heteroatom(s) replaces one or more but not all of the aromatic carbon atoms of a parent arylene as defined above and in which a hydrogen atom from a different aromatic carbon atom or an hydrogen atom or electron from a different skeletal aromatic nitrogen atom if present is removed to provide a divalent moiety. A "5-membered nitrogen-containing heteroarylene is a heteroarylene containing a heteroaromatic ring system having at least one aromatic nitrogen atom and is divalent and is similarly related in structure to a 5-membered nitrogen-containing heteroaryl as described above. Likewise, a "6-membered nitrogen-containing heteroarylene is divalent and is similarly related in structure to a 6-membered nitrogen heteroaryl as described above.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation and consisting of 1 to 12 carbon atom and 1 to 6 heteroatoms, typically 1 to 5 heteroatoms, more typically one or two heteroatoms, selected from the group consisting of O, N, Si and S, optionally substituted where permitted, which includes oxo (=O), so that each nitrogen and sulfur atom is independently optionally oxidized to an N-oxide, a sulfoxide or sulfone, and wherein one of the nitrogen atoms if present is optionally quaternized. The heteroatom(s) O, N, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and consists of 1 to 6 carbon atoms and 1 to 2 heteroatoms, and in other aspects that heteroalkyl is unsubstituted. Non-limiting examples are —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, as exemplified by —$CH_2$—NH—$OCH_3$ and —$CH_2$—O—Si($CH_3$)$_3$. A heteroalkyl is typically denoted by the number of its contiguous heteroatom(s) and non-aromatic carbon atoms of its alkyl moiety unless indicated otherwise or by context. Thus, —$CH_2$—$CH_2$—O—$CH_3$ and —$CH_2$—$CH_2$—S(O)—$CH_3$ are both $C_4$-heteroalkyls and —$CH_2$—CH=N—O—$CH_3$, and —CH=CH—N($CH_3$)—$CH_3$ are both $C_5$ heteroalkyls.

"Heteroalkylene" as used herein by itself or in combination with another term, unless otherwise stated or implied by context, means a divalent group derived from heteroalkyl (as discussed above), by removal of a hydrogen atom or an heteroatom electron form a parent heteroalkyl to provide a divalent moiety exemplified by, but not limited to —$CH_2$—$CH_2$—S—$CH_2$—$CH_2$— and —$CH_2$—S—$CH_2$—$CH_2$—NH—$CH_2$—. For a heteroalkylene, heteroatom(s) thereof may be interior to or may occupy either or both termini of its optionally substituted alkylene chain.

"Aminoalkyl" as used herein by itself or in combination with another term, unless otherwise stated or implied by context, refers to a moiety, group or substituent having a basic nitrogen bonded to a radical terminus of an alkylene moiety as defined above to provide a primary amine in which the basic nitrogen is not further substituted, or to provide a secondary or tertiary amine in which the basic amine is further substituted by one or two independent selected optional substituted $C_1$-$C_{12}$ alkyl moieties, respectively, as described above. In some aspects the optionally substituted "alkyl" moiety of an aminoalkyl is a $C_1$-$C_8$ alkylene or $C_1$-$C_6$ alkylene and in other aspects that alkylene is otherwise unsubstituted. In still other aspects, the basic nitrogen together with its substituents defines a $C_3$-$C_8$ heterocyclyl containing the basic nitrogen as a skeletal atom, typically in the form of a nitrogen-containing $C_3$-$C_6$ or $C_5$-$C_6$ heterocyclyl. When aminoalkyl is used as a variable group to a Markush structure, the "alkyl" moiety of the aminoalkyl is attached to a Markush formula with which it is associated through the sp$^3$ carbon of a radical terminus of the aforementioned alkylene, which may be the same or a different carbon atom to which the basic nitrogen atom is attached. An aminoalkyl is typically denoted by the number of contiguous carbon atoms of its alkylene moiety. Thus, a $C_1$ aminoalkyl is exemplified without limitation by —$CH_2NH_2$, —$CH_2NHCH_3$ and —$CH_2N(CH_3)_2$ and a $C_2$ amino alkyl is exemplified without limitation by —$CH_2CH_2NH_2$, —$CH_2CH_2NHCH_3$ and —$CH_2CH_2N(CH_3)_2$.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and like terms refer to an alkyl, alkenyl, alkynyl, alkylaryl, arylalkyl heterocycle, aryl, heteroaryl, alkylheteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects an alkene functional group replaces two contiguous sp$^3$ carbon atoms of an alkyl substituent, provided that the radical carbon of the alkyl moiety is not replaced, so that the optionally substituted alkyl becomes an unsaturated alkyl substituent.

Optional substituent replacing hydrogen(s) in any one of the foregoing substituents, moieties, or groups is independently selected from the group consisting of $C_6$-$C_{24}$ aryl, $C_5$-$C_{24}$ heteroaryl, hydroxyl, $C_1$-$C_{20}$ alkoxy, $C_6$-$C_{24}$ aryloxy, cyano, halogen, nitro, $C_1$-$C_{20}$ fluoroalkoxy, and amino, which encompasses —$NH_2$ and mono-, di-, and tri-substituted amino groups, and the protected derivatives thereof, or is selected from the group consisting of —X, —OR', —SR', —$NH_2$, —N(R')(R$^{op}$), —N(R$^{op}$)$_3$, =NR', —$CX_3$, —CN, —$NO_2$, —NR'C(=O)H, —NR'C(=O)R$^{op}$, —NR'C(=O)R$^{op}$, —C(=O)R', —C(=O)$NH_2$, —C(=O)N(R')R$^{op}$, —S(=O)R$^{op}$, —S(=O)$_2NH_2$, —S(=O)$_2$N(R')R$^{op}$, —S(=O)$_2NH_2$, —S(=O)$_2$N(R')R$^{op}$, —S(=O)$_2$OR', —S(=O)R$^{op}$, —OP(=O)(OR')(OR$^{op}$), —OP(OH)$_3$, —P(=O)(OR')(OR$^{op}$), —PO$_3H_2$, —C(=O)R', —C(=S)R$^{op}$, —CO$_2$R', —C(=S)OR$^{op}$, —C(=O)SR', —C(=S)SR', —C(=S)$NH_2$, —C(=S)N(R')(R$^{op}$)$_2$, —C(=NR')$NH_2$, —C(=NR')N(R')R$^{op}$, and salts thereof, wherein each X is independently selected from the group consisting of halogens: —F, —Cl, —Br, and —I; and wherein each R$^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of R$^{op}$ together with the heteroatom to which they are attached defines a $C_3$-$C_{24}$ heterocyclyl; and R' is hydrogen or R$^{op}$, wherein R$^{op}$ is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

Typically, optional substituents that are present are selected from the group consisting of —X, —OH, —OR$^{op}$, —SH, —SR$^{op}$, —NH$_2$, —NH(R$^{op}$), —NR'(R$^{op}$)$_2$, —N(R$^{op}$)$_3$, =NH, =NR$^{op}$, —NR'C(=O)H, —CX$_3$, —CN, —NO$_2$, —NR'C(=O)H, NR'C(=O)R$^{op}$, —CO$_2$H, —C(=O)H, —C(=O)R$^{op}$, —C(=O)NH$_2$, —C(=O)NR'R$^{op}$, —S(=O)$_2$R$^{op}$, —S(=O)$_2$NH$_2$, —S(=O)$_2$N(R')R$^{op}$, —S(=O)$_2$NH$_2$, —S(=O)$_2$N(R')(R$^{op}$), —S(=O)$_2$OR', —S(=O)R$^{op}$, —C(=S)R$^{op}$, —C(=S)NH$_2$, —C(=S)N(R')R$^{op}$, —C(=NR')N(R$^{op}$)$_2$, and salts thereof, wherein each X is independently selected from the group consisting of —F and —Cl, R$^{op}$ is typically selected from the group consisting of C$_1$-C$_6$ alkyl, C$_6$-C$_{10}$ aryl, C$_3$-C$_{10}$ heterocyclyl, C$_5$-C$_{10}$ heteroaryl, and a protecting group; and R' is independently selected from the group typically consisting of hydrogen, C$_1$-C$_6$ alkyl, C$_6$-C$_{10}$ aryl, C$_3$-C$_{10}$ heterocyclyl, C$_5$-C$_{10}$ heteroaryl, and a protecting group, independently selected from R$^{op}$.

More typically, optional substituents that are present are selected from the group consisting of —X, —R$^{op}$, —OH, —OR$^{op}$, —NH$_2$, —NH(R$^{op}$), —N(R$^{op}$)$_2$, —N(R$^{op}$)$_3$, —CX$_3$, —NO$_2$, —NHC(=O)H, —NHC(=O)R$^{op}$, —C(=O)NH$_2$, —C(=O)NHR$^{op}$, —C(=O)N(R$^{op}$)$_2$, —CO$_2$H, —CO$_2$R$^{op}$, —C(=O)H, —C(=O)R$^{op}$, —C(=O)NH$_2$, —C(=O)NH(R$^{op}$), —C(=O)N(R$^{op}$)$_2$, —C(=NR')NH$_2$, —C(=NR')NH(R$^{op}$), —C(=NR')N(R$^{op}$)$_2$, a protecting group and salts thereof, wherein each X is —F; R$^{op}$ is independently selected from the group consisting of C$_1$-C$_6$ alkyl, C$_6$-C$_{10}$ aryl, C$_5$-C$_{10}$ heteroaryl and a protecting group; and R' is selected from the group consisting of hydrogen, C$_1$-C$_6$ alkyl and a protecting group, independently selected from R$^{op}$.

In some aspects, an optional alkyl substituent that is present is selected from the group consisting —NH$_2$, —NH(R$^{op}$), —N(RP)$_2$, —N(R$^{op}$)$_3$, —C(=NR')NH$_2$, —C(=NR')NH(R$^{op}$), and —C(=NR')N(RP)$_2$, wherein R' and R$^{op}$ is as defined for any one of the R' or R$^{op}$ groups above. In some of those aspects, the R' and/or R$^{op}$ substituents together with the nitrogen atom to which they are attached provide for the basic functional group of a Basic Unit (BU), as when R$^{op}$ is independently selected from the group consisting of hydrogen and C$_1$-C$_6$ alkyl. Alkylene, carbocyclyl, carbocyclo, aryl, arylene, heteroalkyl, heteroalkylene, heterocyclyl, heterocyclo, heteroaryl, and heteroarylene groups as described above are similarly substituted or are unsubstituted, with exceptions, if any, described in the definitions of these moieties.

"Optionally substituted heteroatom" as used herein, unless otherwise stated or implied by context, refers to a heteroatom within a functional group or other organic moiety in which the heteroatom is not further substituted or modified or is substituted by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is oxidized by substitution with one or two oxo (=O) substituents or refers to an —NH— moiety within a functional group or other organic moiety in which its hydrogen atom is optionally replaced by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is replaced by a =O moiety to form an N-oxide.

Therefore, in some aspects, an optional substituent of a nitrogen atom that is present is selected from the group consisting of optionally substituted C$_1$-C$_{20}$ alkyl, C$_2$-C$_{20}$ alkenyl, C$_2$-C$_{20}$ alkynyl, C$_6$-C$_{24}$ aryl, C$_5$-C$_{24}$ heteroaryl, (C$_6$-C$_{24}$ aryl)-C$_1$-C$_{20}$ alkyl-, and (C$_5$-C$_{24}$ heteroaryl)-C$_1$-C$_{20}$ alkyl-, as those terms are defined herein. In other aspects optional substituents of a nitrogen atom that is present is selected from the group consisting of optionally substituted C$_1$-C$_{12}$ alkyl, C$_2$-C$_{12}$ alkenyl, C$_2$-C$_{12}$ alkynyl, C$_6$-C$_{24}$ aryl, C$_5$-C$_{24}$ heteroaryl, (C$_6$-C$_{24}$ aryl)-C$_1$-C$_{12}$ alkyl-, and (C$_5$-C$_{24}$ heteroaryl)-C$_1$-C$_{12}$ alkyl-, from the group consisting of C$_1$-C$_8$ alkyl, C$_2$-C$_8$ alkenyl, C$_2$-C$_8$ alkynyl, C$_6$-C$_{10}$ aryl, C$_5$-C$_{10}$ heteroaryl, (C$_6$-C$_{10}$ aryl)-C$_1$-C$_8$ alkyl-, and (C$_5$-C$_{10}$ heteroaryl)-C$_1$-C$_8$ alkyl, or from the group consisting of C$_1$-C$_6$ alkyl, C$_2$-C$_6$ alkenyl, C$_2$-C$_6$ alkynyl, C$_6$-C$_{10}$ aryl, C$_5$-C$_{10}$ heteroaryl, (C$_6$-C$_{10}$ aryl)-C$_1$-C$_6$ alkyl-, and (C$_5$-C$_{10}$ heteroaryl)-C$_1$-C$_6$ alkyl-.

In some aspects, an optional substituent that is present replaces a carbon atom in the acyclic carbon chain of an alkyl or alkylene moeity, group or substituent to provide for a C$_3$-C$_{12}$ heteroalkyl or C$_3$-C$_{12}$ heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, in which —NH— is an optionally substituted heteroatom by replacement of its hydrogen atom by an independently selected substituent from a group previously described for an —NH— optional substituent.

"O-linked moiety", "O-linked substituent" and like terms as used herein, unless otherwise stated or implied by context, refers to a moeity, group or substituent that is attached to a Markush structure or other organic moiety with which it is associated directly through an oxygen atom of the O-linked moiety or substituent. A monovalent O-linked moiety or substituent in some aspects is —OH or an ester such as —OC(=O)R$^b$ (acyloxy), wherein R$^b$ is —H, optionally substituted C$_1$-C$_{20}$ alkyl, optionally substituted C$_3$-C$_{20}$ cycloalkyl, optionally substituted C$_3$-C$_{20}$ alkenyl, optionally substituted C$_2$-C$_{20}$ alkynyl, optionally substituted C$_6$-C$_{24}$ aryl, optionally substituted C$_5$-C$_{24}$ heteroaryl or optionally substituted C$_3$-C$_{24}$ heterocyclyl, or R$^b$ is optionally substituted C$_1$-C$_{12}$ alkyl, optionally substituted C$_3$-C$_{12}$ cycloalkyl, optionally substituted C$_3$-C$_{12}$ alkenyl or optionally substituted C$_2$-C$_{12}$ alkynyl, and in other aspects a monovalent O-linked moeity is or further encompasses ether groups as defined herein. In other aspects, a monovalent O-linked moeity, group or substituent is selected from the group consisting of optionally substituted phenoxy, optionally substituted ether, such as C$_1$-C$_8$ alkyloxy, and optionally substituted ester, such as —OC(=O)R$^b$, wherein R$^b$ is optionally substituted C$_1$-C$_8$ alkyl, which is typically saturated or is an unsaturated C$_3$-C$_8$ alkyl.

In other aspects, a O-linked substituent is a monovalent moiety selected from the group consisting of —OH, saturated C$_1$-C$_6$ alkyl ether, unsaturated C$_3$-C$_6$ alkyl ether, phenoxy and —OC(=O)R$^b$, wherein R$^b$ is typically C$_1$-C$_6$ saturated alkyl, C$_3$-C$_6$ unsaturated alkyl, C$_3$-C$_6$ cycloalkyl, C$_2$-C$_6$ alkenyl, or phenyl, optionally substituted, or is selected from that group excluding —OH and/or wherein saturated C$_1$-C$_6$ alkyl ether and phenoxy are unsubstituted and R$^b$ is saturated C$_1$-C$_6$ alkyl or unsaturated C$_3$-C$_6$ alkyl.

Other exemplary O-linked substituents are provided by definitions for carbamate, ester, ether and carbonate as disclosed herein in which the monovalent oxygen atom of the carbamate, ester, ether or carbonate functional group is bonded to the Markush structure or other organic moiety with which it is associated.

In other aspects, an O-linked moiety to carbon is divalent and encompasses =O and —X—(CH$_2$)$_n$—Y—, wherein X and Y independently are S and O and subscript n is 2 or 3, to form a spiro ring system with the carbon to which X and Y are both attached.

"Halogen" as used herein, unless otherwise stated or implied by context, refers to fluorine, chlorine, bromine, or iodine and is typically —F or —Cl.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, $3^{rd}$ ed.", Wiley Interscience. Protecting groups for heteroatoms such as oxygen, sulfur and nitrogen are sometimes used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$, wherein least one of R$^{PR}$ is a nitrogen atom protecting group or both R$^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of an acyclic or cyclic basic group is an acid-labile carbamate protecting group such as t-butyloxycarbonyl (BOC).

"Ester" as used herein, unless otherwise stated or implied by context, refers to a substituent, moiety or group having the structure of —C(=O)—O— so as to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety at a different carbon atom to provide a lactone or to some other organic moiety. Typically, esters in addition to the ester functional group comprise or consist of an organic moiety containing 1 to 50 carbon atoms, typically 1 to 20 carbon atoms or more typically 1 to 8, 1 to 6 or 1 to 4 carbon atoms and 0 to 10 independently selected heteroatoms (e.g., O, S, N, P, Si, but usually O, S and N), typically 0 to 2 heteroatoms where the organic moieties are bonded through the —C(=O)—O— structure (i.e., through the ester functional group).

When an ester is a substituent or variable group of a Markush structure or other organic moiety with which it is associated, that substituent is bonded to the structure or other organic moiety through the monovalent oxygen atom of the ester functional group so that it is a monovalent O-linked substituent, which sometimes referred to as an acyloxy. In such instances, the organic moiety attached to the carbonyl carbon of the ester functional group typically is a $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl or $C_3$-$C_{24}$ heterocyclyl or is a substituted derivative of any one of these, e.g., having 1, 2, 3 or 4 substituents, more typically is a $C_1$-$C_{12}$ alkyl, $C_2$-$C_{12}$ alkenyl, $C_2$-$C_{12}$ alkynyl, $C_6$-$C_{10}$ aryl, $C_5$-$C_{10}$ heteroaryl or $C_3$-$C_{10}$ heterocyclyl or a substituted derivative of one any of these, e.g., having 1, 2, or 3 substituents or is a $C_1$-$C_8$ alkyl, $C_2$-$C_8$ alkenyl, $C_2$-$C_8$ alkynyl, or phenyl or a substituted derivative of any one of these, e.g., having 1 or 2 substituents, wherein each independently selected substituent is as defined herein for optional alkyl substituents, or is unsubstituted $C_1$-$C_6$ alkyl or unsubstituted $C_2$-$C_6$ alkenyl.

Exemplary esters, by way of example and not limitation, are acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)R$^b$ in which R$^b$ is as defined for acyloxy O-linked substituents and is typically selected from the group consisting of methyl, ethyl, propyl, iso-propyl, 2-methyl-prop-1-yl, 2,2-dimethyl-prop-1-yl, prop-2-ene-1-yl, and vinyl.

"Ether" as used herein, unless otherwise stated or implied by context, refers to an organic moiety, group or substituent that comprises 1, 2, 3, 4 or more —O— (i.e., oxy) moieties that are not bonded to carbonyl moiety(ies), typically 1 or 2, wherein no two —O— moieties are immediately adjacent (i.e., directly attached) to each other. Typically, an ether contains the formula of —O-organic moiety wherein organic moiety is as described for an organic moiety bonded to an ester functional group or is as described herein for an optionally substituted alkyl group. When ether is recited as a substituent or variable group of a Markush structure or other organic moiety with which it is associated, the oxygen of the ether functional group is attached to a Markush formula with which it is associated and is sometimes designated as an "alkoxy" group, which is an exemplary O-linked substituent. In some aspects an ether O-linked substituent is a $C_1$-$C_{20}$ alkoxy or a $C_1$-$C_{12}$ alkoxy, optionally substituted with 1, 2, 3 or 4 substituents, typically 1, 2 or 3, wherein the "alkyl" moiety is saturated or is a $C_3$-$C_{12}$ alkyloxy in which the "alkyl" moiety is unsaturated, and in other aspects is a $C_1$-$C_8$ alkoxy or $C_1$-$C_6$ alkoxy, optionally substituted with 1 or 2 substituents, wherein the "alkyl" moiety is saturated or is a $C_3$-$C_8$ alkyloxy in which the "alkyl" moiety is unsaturated, and wherein each independently selected substituent is as defined herein for optional alkyl substituents. Unless otherwise indicated or required by context term such as "$C_1$-$C_{12}$ alkyloxy", "$C_1$-$C_8$ alkyloxy" and "$C_1$-$C_6$ alkyloxy" refers to O-linked aliphatic ethers having either type of "alkyl" moiety. In still other aspects an ether O-linked substituent is an unsubstituted, saturated $C_1$-$C_4$ alkoxy or unsaturated $C_2$-$C_4$ alkoxy such as, by way of example and not limitation, methoxy, ethoxy, propoxy, iso-propoxy, butoxy and allyloxy (i.e., —OCH$_2$CH=CH$_2$).

"Amide" as used herein, unless otherwise stated or implied by context, refers to a moiety having an optionally substituted functional group having the structure of R—C(=O)N(R$^c$)— or —C(=O)N(R$^c$)$_2$ to which no other heteroatom is directly attached to the carbonyl carbon and wherein each R is independently hydrogen, a protecting group or an organic moiety and R is hydrogen or an organic moeity wherein organic moiety, independently selected, is as described herein for an organic moiety bonded to an ester functional group or is as described herein for an optionally substituted alkyl group. When an amide is recited as a substituent or variable group of a Markush structure or other organic moeity with which it is associated, the amide nitrogen atom or carbonyl carbon atom of the amide functional group is bonded to that structure or other organic moeity. Amides are typically prepared by condensing an acid halide, such an acid chloride, with a molecule containing a primary or secondary amine. Alternatively, amide coupling reactions well-known in the art of peptide synthesis, which oftentimes proceed through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

"Carbonate" as used here means a substituent, moiety or group that contains a functional group having the structure —O—C(=O)—O— which defines a carbonate functional group. Typically, carbonate groups as used herein are comprised of an organic moiety bonded to the —O—C(=O)—O— structure, wherein the organic moiety is as described herein for an organic moiety bonded to an ester functional group, e.g., organic moiety-O—C(=O)—O—. When carbonate is recited as a substituent or variable group of a Markush structure or other organic moiety with which it is associated, one of the monovalent oxygen atoms of the carbonate functional group is attached to that structure or organic moiety and the other is bonded to a carbon atom of another organic moiety as previously described for an organic moiety bonded to an ester functional group or is as described herein for an optionally substituted alkyl group. In such instances, carbonate is an exemplary O-linked substituent.

"Carbamate" as used here means a substituent, moiety or group that contains a optionally substituted carbamate functional group structure represented by —O—C(=O)N(R$^c$)— or —O—C(=O)N(R$^c$)$_2$, or —O—C(=O)NH (optionally substituted alkyl) or —O—C(=O)N (optionally substituted alkyl)$_2$ in which the optionally substituted alkyl(s) are exemplary carbamate functional group substituents, wherein R$^c$ and optionally substituted alkyl are independently selected, wherein independently selected R$^c$ is hydrogen, a protecting group or an organic moiety, wherein the organic moiety is as described herein for an organic moiety bonded to an ester functional group or is as described herein for an optionally substituted alkyl group. Typically, carbamate groups are additionally comprised of an organic moiety, independently selected from R$^c$, wherein the organic moiety is as described herein for an organic moiety bonded to an ester functional group, bonded through the —O—C(=O)—N(R$^c$)— structure, wherein the resulting structure has the formula of organic moiety-O—C(=O)—N(R$^c$)— or —O—C(=O)—N(R$^c$)-organic moiety. When carbamate is recited as a substituent or variable group of a Markush structure or other organic moeity with which it is associated, the monovalent oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents.

"Salt thereof" as the phrase is used herein, unless otherwise stated or implied by context, refers to a salt form of a compound (e.g., a Drug, a Drug Linker compound or a HMW LDC compound). A salt form of a compound is of one or more internal salt forms and/or involves the inclusion of another molecule such as an acetate ion, a succinate ion or other counterion. The counterion in a salt form of a compound is typically an organic or inorganic moiety that stabilizes the charge on the parent compound. A salt form of a compound has one or more than one charged atoms in its structure. In instances where multiple charged atoms are part of the salt form, multiple counter ions and/or multiple charged counter ions are present. Hence, a salt form of a compound typically has one or more charged atoms corresponding to those of the non-salt form of the compound and one or more counterions. In some aspects, the non-salt form of a compound contains at least one amino group or other basic moiety, and accordingly in the presence of an acid, an acid addition salt with the basic moiety is obtained. In other aspects, the non-salt form of a compound contains at least one carboxylic acid group or other acidic moiety, and accordingly in the presence of a base, a carboxylate or other anionic moiety is obtained.

Exemplary counteranion and countercations in compound salt forms include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2-hydroxy-3-naphthoate)) salts.

Selection of a salt form of a compound is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

A "pharmaceutically acceptable salt" is a salt form of a compound that is suitable for administration to a subject as described herein and in some aspects includes countercations or counteranions as described by P. H. Stahl and C. G. Wermuth, editors, *Handbook of Pharmaceutical Salts: Properties, Selection and Use*, Weinheim/Zürich: Wiley-VCH/VHCA, 2002.

"PEG Unit" as used herein is an organic moiety comprised of one or multiple polyethylene glycol chains, each of which is comprised of one or more ethyleneoxy subunits, covalently attached to each other.

The polyethylene glycol chains can be linked together, for example, in a linear, branched or star shaped configuration. PEGs include polydisperse PEGs, monodisperse PEGs and discrete PEGs. Polydisperse PEGs are a heterogeneous mixture of sizes and molecular weights. whereas monodisperse PEGs are typically purified from heterogeneous mixtures and are therefore provide a single chain length and molecular weight.

In some aspects, a PEG Unit is derived from a discrete PEG compound synthesized in step-wise fashion and not via a polymerization process. PEG Units derived in that manner have a defined and specified chain length and are exemplified by the structures of:

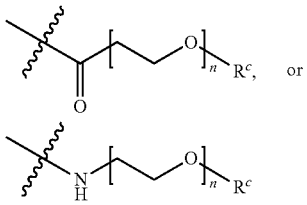

wherein $R^C$ is hydrogen or a PEG Capping Unit ($R^{PEG}$), and n is an integer ranging from 8 to 12, 8 to 24, or 12 to 38.

A preferred PEG Unit has a single polyethylene glycol chain with 8 to 24 —$CH_2CH_2O$— subunits covalently attached in series and terminated at one end with a PEG Capping Unit.

"PEG Capping Unit" as used herein is an organic moiety or functional group that terminates the free and untethered end of a PEG Unit, and in some aspects provides for a terminal methoxy, ethoxy, or other $C_1$-$C_6$ ether, or is —$CH_2$—$CO_2H$, —$CH_2CH_2$—$CO_2H$ or other suitable moeity. The ether, —$CH_2$—$CO_2H$, $CH_2CH_2$—$CO_2H$, or other suitable functional group thus acts as a cap for the terminal PEG subunit of the PEG Unit. A PEG Capping Unit is preferably —$CH_3$ or —$CH_2CH_2CO_2H$, "Antibody" as used herein, unless otherwise stated or implied by context, refers to is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment has the requisite number of sites for covalent attachment to the requisite number of drug-linker moieties. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., (2001), "Immunol. Biology, 5th ed.", Garland Publishing, New York). An antibody can be of any type (e.g., IgG, IgE, IgM, IgD, and IgA), class (e.g., $IgG_1$, $IgG_2$, $IgG_3$, $IgG_4$, $IgA_1$ and $IgA_2$) or subclass. The antibody can be derived from any suitable species. In some embodiments, the antibody is of human or murine origin. An antibody can be, for example, human, humanized or chimeric. An antibody or antibody fragment thereof, is an exemplary targeting agent that is incorporated as a Ligand Unit into an LDC of the present invention and in these instances is sometimes referred to as an antibody Ligand Unit.

In some aspects an antibody selectively and specifically binds to an epitope on hyper-proliferating or hyper-stimulated mammalian cells (i.e., abnormal cells), wherein the epitope is preferentially displayed by or is more characteristic the abnormal cells in contrast to normal cells, or is preferentially displayed within and is peculiar to the vicinity of the abnormal cells or is more characteristic of normal cells in the vicinity of abnormal cells in contrast to normal cells not localized to the abnormal cells. In those aspects the mammalian cells are typically human cells.

"Monoclonal antibody" as used herein, unless otherwise stated or implied by context, refers to an antibody obtained from a population of substantially homogeneous antibodies, i.e., the individual antibodies comprising the population are identical except for possible naturally-occurring mutations that may be present in minor amounts or differences in glycosylation patterns. A monoclonal antibody (mAb) is highly specific, being directed against a single antigenic site. The modifier "monoclonal" indicates the character of the antibody as being obtained from a substantially homogeneous population of antibodies, and is not to be construed as requiring production of the antibody by any particular method.

"Antibody fragment" as used herein, unless otherwise stated or implied by context, refers to a portion of an intact antibody that is comprised of the antigen-binding site or variable region of the intact antibody and remains capable of binding to the cognate antigen of the intact antibody. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically binds to a target antigen (e.g., a cancer cell antigen, an immune cell antigen, a viral antigen or a microbial antigen).

"Cytotoxic activity" as used herein, unless otherwise stated or implied by context, refers to a cell-killing effect or anti-survival effect of a cytotoxic compound or derivative thereof, or refers to a Ligand-Drug Conjugate, or an intracellular metabolite of a Ligand Drug Conjugate, having a cytotoxic Drug Unit. Cytotoxic activity may be expressed as an $IC_{50}$ value, which is the concentration (molar or mass) per unit volume at which half the cells survive after incubation of the cells for a defined time period in the presence of the cytotoxic compound or its derivative or in the presence of a Ligand-Drug Conjugate having a cytotoxic Drug Unit.

"Cytostatic activity" as used herein, unless otherwise stated or implied by context, refers to an anti-proliferative effect of a cytotoxic compound, a Ligand-Drug Conjugate, or an intracellular metabolite of a Ligand-Drug Conjugate having a cytotoxic Drug Unit whose biological effectiveness is not dependent on cell killing but whose effect is due to inhibition of cell division of hyper-proliferating cells, hyperstimulated immune cells or other abnormal or unwanted cells.

"Specific binding" and "specifically binds" as the terms are used herein, unless otherwise stated or implied by context, refers to an antibody, a fragment thereof, or antibody Ligand Unit as the targeting moiety in an Ligand Drug Conjugate that is capable of binding in a immunologically selective manner with its corresponding targeted antigen and not with a multitude of other antigens. Typically, the antibody or fragment thereof binds its targeted antigen with an affinity of at least about $1 \times 10^{-7}$ M, and preferably about $1 \times 10^{-8}$ M to $1 \times 10^{-9}$ M, $1 \times 10^{-10}$ M, or $1 \times 10^{-11}$ M and binds to that predetermined antigen with an affinity that is at least two-fold greater than its affinity for binding to a non-specific antigen (e.g., BSA, casein) other than for a closely-related antigen, wherein said affinities are substantially retained when incorporated into a Ligand Drug Conjugate as an antibody Ligand Unit.

"Drug Linker Compound," as used herein, unless otherwise stated or implied by context, is a compound containing a Drug Unit (-D) and a Linker Unit, which typically has functional group capable of reacting with a targeting agent to provide a Ligand Drug Conjugate. Drug-Linker compounds are therefore useful as discrete entities, or can be conjugated to a targeting agent, which results in a covalent bond between a Ligand Unit (L), which in some aspects is an antibody, and Linker Unit. Thus, a Linker Unit in a Drug Linker compound may in some instance be considered a Linker Unit precursor (LU') for a Linker Unit in a Ligand Drug Conjugate. In those aspects the Linker Unit (LU) operates to provide suitable targeted release of free drug from the Drug Unit(s) attached thereto. When LU/LU' is comprised of a Glucuronide unit, such moieties are referred to as a glucuronide-based Linker Unit.

Generally, as used herein, a Linker Unit is comprised of a Stretcher Unit precursor (Z') capable of forming a covalent bond to a targeting agent that provides for a Ligand Unit, a Glucuronide Unit comprising a β-glucuronidase-activateable self-immolative moiety covalently linked to a β-glucuronic acid moiety, wherein a β-glucuronidase cleavage of a β-glucuronic acid moiety from the self-immolative moiety in either the Drug-Linker compound or Conjugate compound derived therefrom results in release of its Drug Unit as free drug by self-immolation.

Generally, a Drug Linker Compound has the formula:

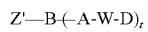

wherein:
B is an optional Branching Unit and is present when subscript t is greater than 1 and is absent when subscripts t is 1;
A is an optional Connector Unit;
W is a Glucuronide Unit,
Z' is a Stretcher Unit precursor to a Stretcher Unit (Z) and is comprised of a functional group that provides for covalent attachment of a Ligand Unit to Z;
D is a Drug Unit incorporating a therapeutic agent, which includes DNA minor groove binders, DNA damaging agents and DNA replication inhibitors, wherein the therapeutic agent has a functional group, which in some aspects is a hydroxyl, thiol or amine functional group capable of providing covalent attachment with the Glucuronide Unit; and
subscript t is 0, 1, 2, 3, or 4.

The Glucuronidase Cleavable Unit (W) includes a site that can be cleaved by a glucuronidase, which in some aspects is a mammalian β-glucuronidase enzyme. Generally, the Glucuronide Unit comprises a carbohydrate moiety (Su) linked via a glycosidic bonded oxygen atom (—O'—) to a Self-Immolative Spacer Unit (S*), wherein S* is comprised of a self-immolative group of the formula:

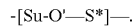

In some aspects, the therapeutic agent is incorporated as a prodrug into a Drug Unit, wherein the prodrug moiety thereof provides the functional group for providing covalent attachment with the Glucuronide Unit. The glycosidic bonded oxygen atom (—O'—) typically provides a β-glucuronidase-cleavage site, such that the glycosidic bond is cleavable by a glycosidase, which in some aspects is a human, lysosomal β-glucuronidase.

In the context of a Glucuronide Unit, the term "self-immolative group" refers to a di-or tri-functional chemical moiety that is capable of covalently linking together two or three spaced chemical moieties (i.e., the sugar moiety (via a glycosidic bond), a Drug Unit (directly or indirectly via a self-immolative Spacer Unit), and, in some embodiments, a Ligand Unit (directly or indirectly via a Stretcher Unit) into a stable molecule. The self-immolative group will spontaneously separate from the first chemical moiety (e.g., the Drug Unit) if the glycosidic bond to the Sugar moiety is cleaved.

Typically, the carbohydrate moiety (Su) is a residue of a cyclic hexose, such as a pyranose, or a cyclic pentose, such as a furanose, usually in the β-D conformation, of related structure to glucuronic acid. Preferably, the pyranose residue is a β-D-glucuronide moiety (i.e., β-D-glucuronic acid moiety linked to the self-immolative group —S*— via a glycosidic bond that is cleavable by β-glucuronidase). The carbohydrate moiety may be unsubstituted (e.g., a naturally occurring cyclic hexose or cyclic pentose residue), or may be a substituted β-D-glucuronide (e.g., a glucuronic acid residue in which a hydroxyl group is replaced with another O-linked group or a halogen).

Non-limiting examples of the self-immolative group S* are a p-aminobenzyl alcohol (PAB) residue and an o-aminobenzyl alcohol residue. Other suitable self immolative groups are known in the art can be used, such as those described by WO 2003/026577 and WO 2005/082023, the structures of which are specifically incorporated by reference herein.

As used herein, Stretcher Unit (Z), Stretcher Unit precursor (Z'), Connector Unit (A), and Branching Unit (B) are as defined, along with exemplary structures, in International Publication No. WO 2015/095755, which are specifically incorporated herein by reference for such disclosure.

"Drug Unit" (D) as used herein, unless otherwise stated or implied by context, is a therapeutic agent, such as a cytotoxic, cytostatic, or immunomodulatory drug in conjugated form in which an atom of the therapeutic agent participates in a covalent bond to the Self-Immolating Unit. In some aspects, a nitrogen atom from the therapeutic agent participates in the bond to the Self-Immolating Unit, typically through a carbamate functional group. As used herein, the terms "Drug Unit" and "Drug moiety" are synonymous and used interchangeably. Although a therapeutic agent is incorporated into a Drug Linker compound or Ligand Drug Conjugate as a Drug Unit, the manner in which that is accomplished varies. For example, the entire therapeutic agent may be used for conjugation or an intermediate thereof is used, which is further elaborated to complete the structure of the Drug Unit.

Useful classes of cytotoxic or immunomodulatory agents include, for example, DNA minor groove binders, DNA replication inhibitors and DNA damaging agents, including topoisomerase inhibitors, such as camptothecin and irinotecan, anthracyclins, such as doxorubicin, idarubicin, daunorubicin, doxorubicin propyloxazoline (DPO) and cyanomorpholino-doxorubicin and cyclopropyl-benzimidazole compounds, such as duocarmycin and CC-1065 and pyrrolobenzodiazepine dimer compound (PBD) such as those described in U.S. Pat. No. 9,242,013, the structures of which are specifically incorporated by reference herein.

EMBODIMENTS

A number of embodiments of the invention are described below followed by a more detailed discussion of the components, e.g., groups, reagents, and steps, that are useful in the processes of the present invention. Any of the selected embodiments for the components of the processes can apply to each and every aspect of the invention as described herein or they may relate to a single aspect. The selected embodiments may be combined together in any combination appropriate for preparing a Drug Linker compound or Intermediate thereof.

In one group of embodiments, provided herein are methods for preparing a Drug Linker intermediate compound of Formula VID:

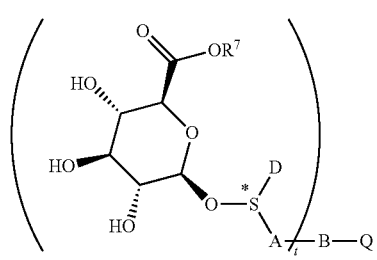
(VID)

or a salt thereof, wherein

Q is an optionally protected functional group, preferably, hydroxyl, thiol, amide or amine functional group;

A is a an optional Connector Unit;

B is a an optional Branching Unit and is present when subscript t is greater than 1 and is absent when subscript t is 1;

S* is a Self-Immolating Unit, preferably having the structure of Formula XV or Formula XVI:

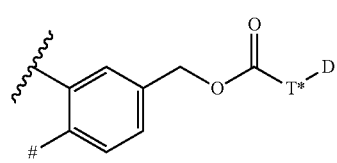
(XV)

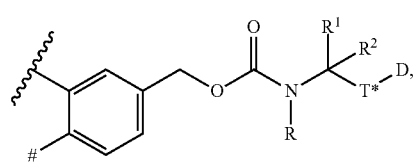
(XVI)

wherein the wavy line indicates the point of attachment to A, and # indicates the point of attachment to the glycosidic oxygen atom of the glucuronic acid moiety;

D is a Drug Unit incorporating a DNA minor groove binder, DNA damaging agent or DNA replication inhibitor;

$R^7$ is $C_1$-$C_8$ alkyl or optionally substituted phenyl so that —$OR^7$ provides for an ester functional group that is a suitable carboxylic acid protecting group; and Subscript t is 0, 1, 2, 3, or 4;

the method comprising the step of:
(c) contacting a compound of Formula VIC with either a Grignard reagent or an alkoxy magnesium halide in a suitable alcohol-containing solvent, wherein the Formula VIC compound has the structure of:

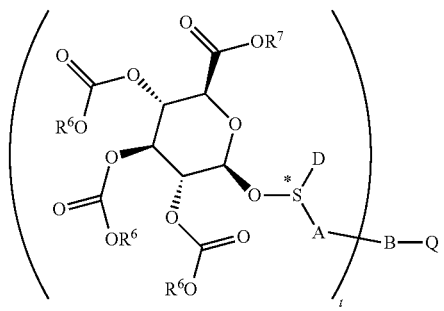
(VIC)

or a salt thereof, wherein each of $R^6$ is independently $C_1$-$C_8$ alkyl or optionally substituted phenyl so that $R^{6C}$(=O)— provides for an ester functional group that is a suitable hydroxyl protecting group; and the remaining variable groups are as previously defined, wherein said Grignard reagent or alkoxy magnesium halide contacting selectively removes the hydroxyl protecting groups whereby the Formula VID compound or its salt is obtained.

In another group of embodiments, provided herein are methods for preparing a Drug Linker intermediate compound of Formula VIIE:

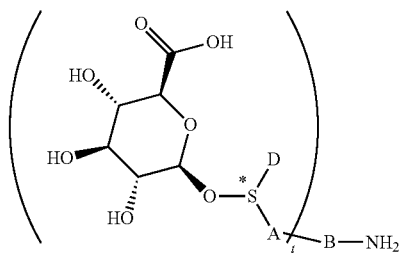
(VIIE)

or a salt thereof, wherein

S*, D, A, and B are as previously defined for Formula VID, and the method comprising the steps of:
(c) contacting a compound of Formula VIIC with either a Grignard reagent or an alkoxy magnesium halide in a suitable an alcohol-containing solvent, wherein the Formula VIIC compound has the structure of:

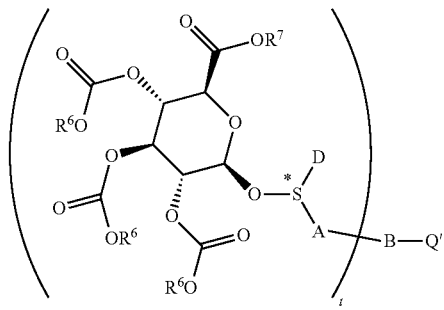
(VIIC)

or a salt thereof, wherein

S*, D, A, and B are as defined for Formula VIIE;

Q' is a suitably protected amino group;

each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable groups are as previously defined, wherein said Grignard reagent or alkoxy magnesium halide contacting selectively removes the hydroxyl protecting groups to provide a compound of Formula VIID:

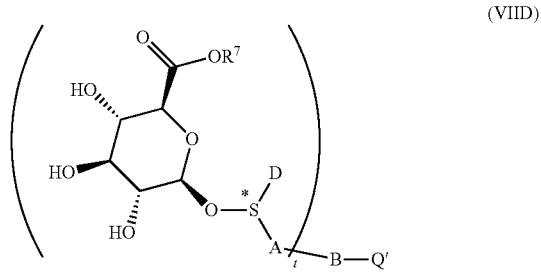

(VIID)

or a salt thereof, wherein the variable groups are as previously defined; and (d) contacting the Formula VIID compound with a deprotecting agent, wherein said deprotecting agent contacting removes the amine and carboxylic acid protecting groups whereby the Formula VIIE compound or its salt is obtained.

In another group of embodiments, provided herein are methods for preparing a Drug Linker intermediate compound of Formula ID:

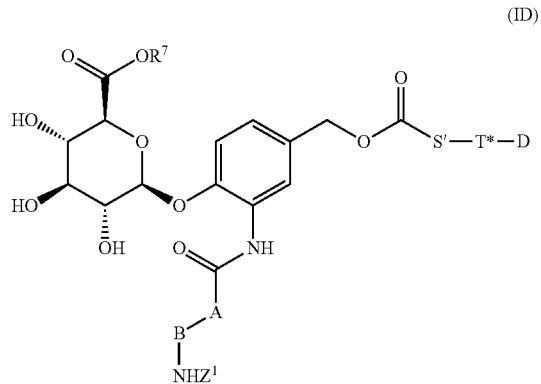

(ID)

or a salt thereof, wherein

S' is absent or —$NR^N$—$C(R^1)(R^2)$—, wherein $R^N$, $R^1$ and $R^2$ independently are hydrogen, optionally substituted $C_1$-$C_6$ alkyl, optionally substituted $C_6$-$C_{14}$ aryl, or optionally substituted C-linked $C_5$-$C_8$ heteroaryl, or $R^N$ and $R^1$ together with the nitrogen and carbon atoms to which they are attached comprise an azetidinyl, pyrrolodinyl, piperidinyl or homopiperidinyl moiety, and $R^2$ is hydrogen;

D is a Drug Unit incorporating a DNA minor groove binder, DNA damaging agent or DNA replication inhibitor having a functional group, in particular, hydroxyl, thiol or amine functional group, that forms a covalent bond with S';

T* is a heteroatom from said functional group, preferably, oxygen, sulfur, or optionally substituted nitrogen;

Z' is a first suitable amine protecting group; and $R^7$ is $C_1$-$C_8$ alkyl or optionally substituted phenyl so that —$OR^7$ provides for an ester functional group that is a suitable carboxylic acid protecting group; and the remaining variable groups are as defined for Formula VID, the method comprising the step of:

(c) contacting a compound of Formula IC with either a Grignard reagent or an alkoxy magnesium halide in a suitable alcohol-containing solvent, wherein the Formula IC compound has the structure of:

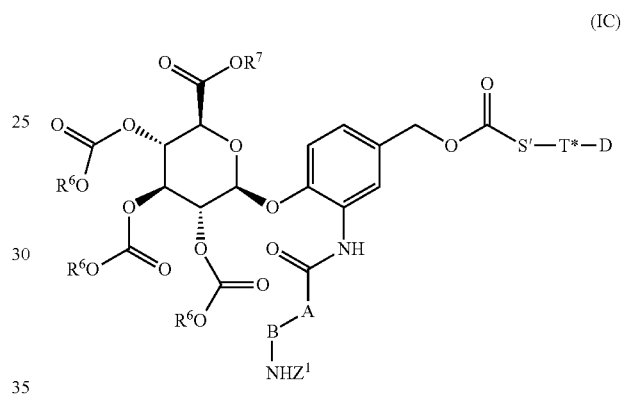

(IC)

or a salt thereof, wherein each of $R^6$ is independently $C_1$-$C_8$ alkyl or optionally substituted phenyl so that $R^6C(=O)$— provides for an ester functional group that is a suitable hydroxyl protecting group; and the remaining variable groups are as previously defined, wherein said Grignard reagent or alkoxy magnesium halide contacting selectively removes the hydroxyl protecting groups whereby the Formula ID compound or its salt is obtained.

In another group of embodiments, provided herein are methods for preparing a Drug Linker intermediate compound of Formula IE:

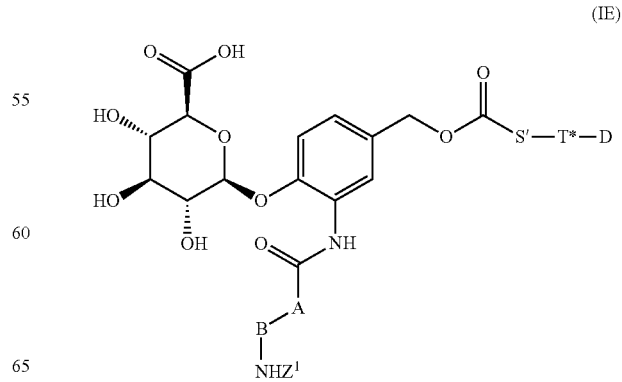

(IE)

or a salt thereof, wherein
S', D, T, B, and A are as previously defined for Formula VID,
the method comprising the steps of:
(c) contacting a compound of Formula IC with either a Grignard reagent or an alkoxy magnesium halide in a suitable alcohol-containing solvent, wherein the Formula IC compound has the structure of:

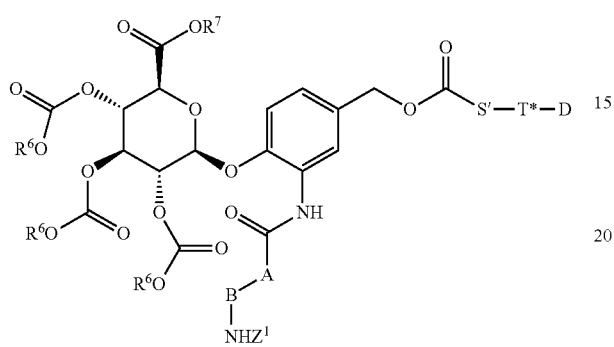

(IC)

or a salt thereof, wherein
$Z^1$ is a first suitable amine protecting group; and
each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable groups are as previously defined,
wherein said Grignard reagent or alkoxy magnesium halide contacting selectively removes the hydroxyl protecting groups to provide a compound of Formula ID:

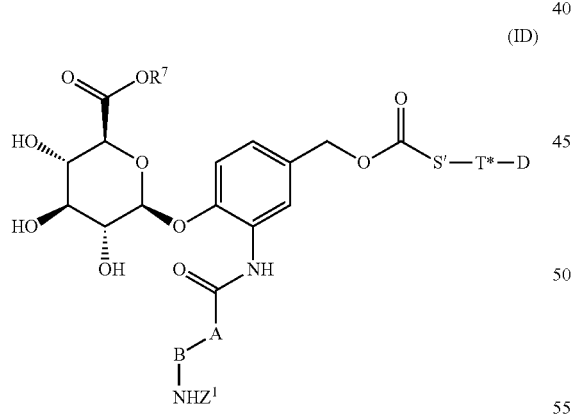

(ID)

or a salt thereof, wherein the variable groups are as previously defined; and
(d) contacting the Formula ID compound with a first deprotecting agent,
wherein said first deprotecting agent contacting removes the amine and carboxylic acid protecting groups whereby the Formula IE compound or its salt is obtained.

In another group of embodiments, provided herein are methods for preparing a Drug Linker intermediate compound of Formula IID:

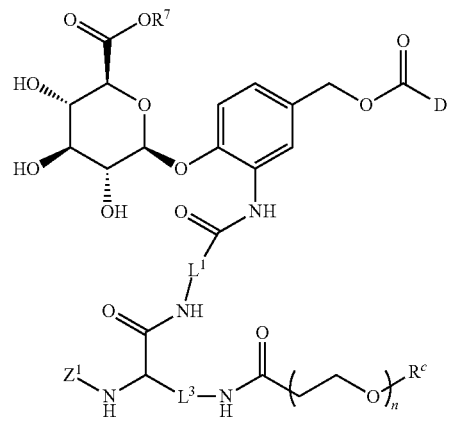

(IID)

or a salt thereof, wherein
D is a Drug Unit incorporating a DNA minor groove binder, DNA damaging agent or DNA replication inhibitor having a amine functional group that forms a carbamate functional group;
$R^c$ is hydrogen or a PEG Capping Unit;
$Z^1$ is a first suitable amine protecting group;
each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo;
$R^7$ is $C_1$-$C_8$ alkyl or optionally substituted phenyl so that —$OR^7$ provides for an ester functional group that is a suitable carboxylic acid protecting group; and
subscript n is an integer ranging from 2 to 24,
the method comprising the steps of:
(a) contacting a compound of Formula IIA with a second deprotecting agent, wherein the Formula IIA compound has the structure of:

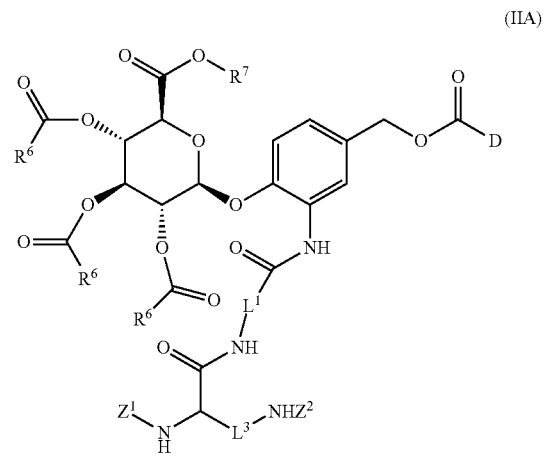

(IIA)

or a salt thereof, wherein
$Z^2$ is a second suitable amino protecting group;
each of $R^6$ is independently $C_1$-$C_8$ alkyl or optionally substituted phenyl so that $R^6C(=O)$— provides for an ester functional group that is a suitable hydroxyl protecting group; and the remaining variable groups are as defined for Formula IID.

wherein said second deprotecting agent contacting selectively removes the $Z^2$ amino protecting group to provide a compound of Formula IIB:

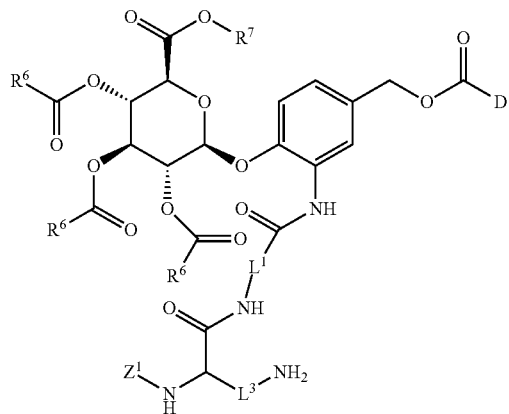

(IIB)

or a salt thereof, wherein the variable groups are as previously defined by Formula IIA;
(b) contacting the Formula IIB compound in a suitable solvent with a compound of Formula iv:

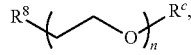

(iv)

wherein $R^8$ is an activated ester, $R^c$ is hydrogen or a PEG Capping Unit, and
subscript n is a integer ranging from 2 to 24, or
(b') contacting the Formula IIB compound in a suitable solvent with a Formula iv compound in which $R^8$ is —COOH in the presence of a first activating agent; and
subscript n is an integer ranging from 2 to 24,
wherein said contacting of step (b) or (b') provides a compound of Formula IIC:

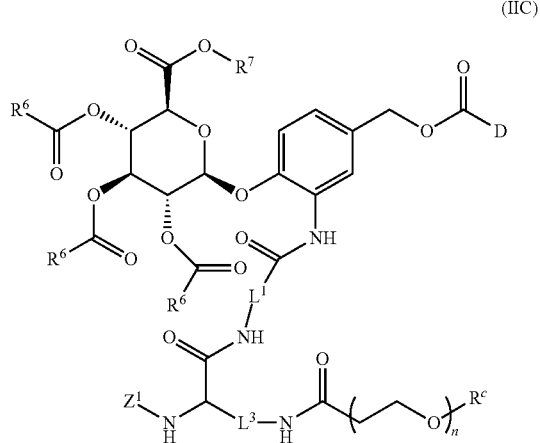

(IIC)

or a salt thereof, wherein the variable groups are as previously defined by Formula IIA; and (c) contacting the Formula IIC compound with either a Grignard reagent or an alkoxy magnesium halide in a suitable alcohol-containing solvent,
wherein said Grignard reagent or alkoxy magnesium halide contacting selectively removes the hydroxyl protecting groups to provide the Formula IID compound or its salt.

In another group of embodiments is provided herein are methods for preparing a Drug Linker intermediate compound of Formula IIE:

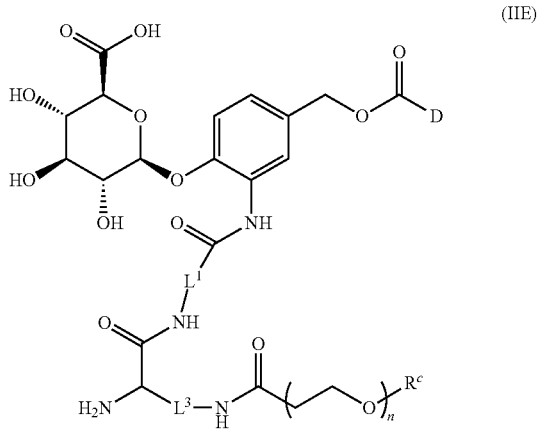

(IIE)

or a salt thereof, wherein
D is a Drug Unit incorporating a DNA minor groove binder, DNA damaging agent or DNA replication inhibitor having a amine functional group that forms a carbamate functional group;
$R^c$ is a PEG Capping Unit;
each of $L^1$ and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and
subscript n is an integer ranging from 2 to 24;
the method comprising the steps of:
(a) contacting a compound of Formula IIA with a second deprotecting agent, wherein the Formula IIA compound has the structure of:

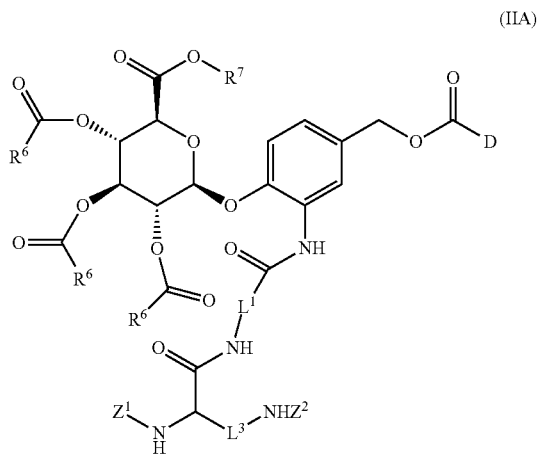

(IIA)

or a salt thereof, wherein each of $R^6$ is independently $C_1$-$C_8$ alkyl or optionally substituted phenyl so that $R^6C(=O)$— provides for an ester functional group that is a suitable hydroxyl protecting group;

each of $Z^1$ and $Z^2$ is independently a first and second suitable amino protecting group, respectively; and the remaining variable groups are as previously defined by Formula IIE, wherein said second deprotecting agent contacting selectively removes the $Z^2$ amino protecting group to provide a compound of Formula IIB:

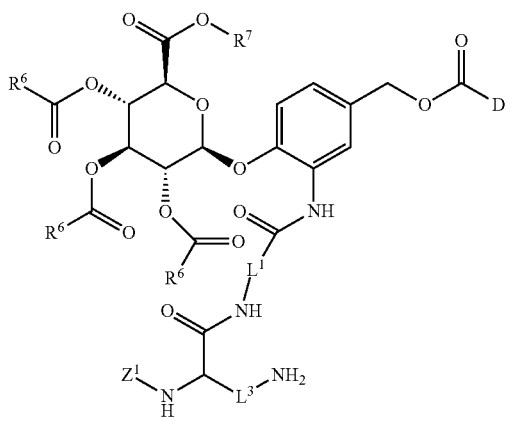

(IIB)

or a salt thereof, wherein the variable groups are as previously described by Formula IIA;

(b) contacting the Formula IIB compound in a suitable solvent with a compound of Formula iv:

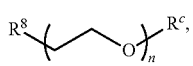

(iv)

wherein $R^8$ is an activated ester, $R^c$ is hydrogen or a PEG Capping Unit; and subscript n is an integer ranging from 2 to 24, or (b') contacting the Formula IIB compound with a Formula iv compound in which $R^8$ is —COOH and subscript n is an integer ranging from 2 to 24 in the presence of a first activating agent in a suitable solvent; and wherein said contacting of step (b) or (b') provides a compound of Formula IIC:

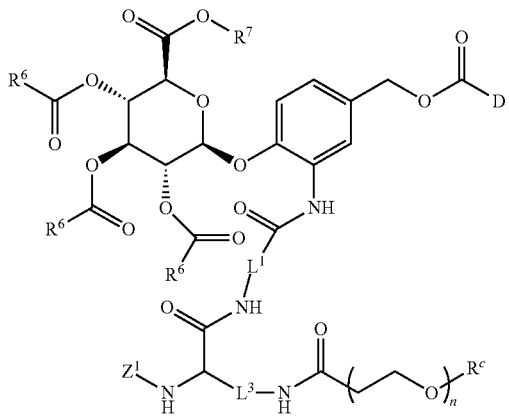

(IIC)

or a salt thereof, wherein the variable groups are as previously defined by Formula IIA and Formula iv;

(c) contacting the Formula IIC compound with either a Grignard reagent or an alkoxy magnesium halide in a suitable alcohol-containing solvent, wherein said Grignard reagent or alkoxy magnesium halide contacting selectively removes the hydroxyl protecting groups to provide a compound of Formula IID:

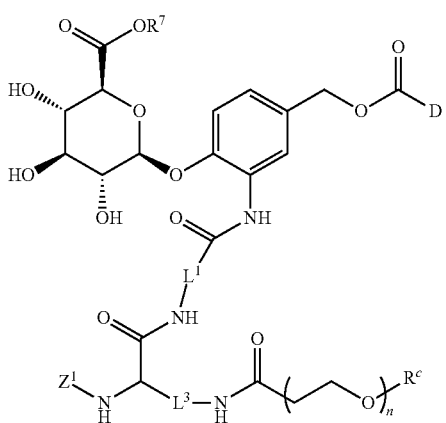

(IID)

or a salt thereof, wherein the variable groups are as previously fined by Formula IIC; and (d) contacting the Formula IID compound with a first deprotection agent, wherein said first deprotection agent contacting removes the amine and carboxylic acid protecting groups whereby the Formula IIE compound or its salt is obtained.

In another group of embodiments, provided herein are methods for preparing a Drug Linker compound of Formula II:

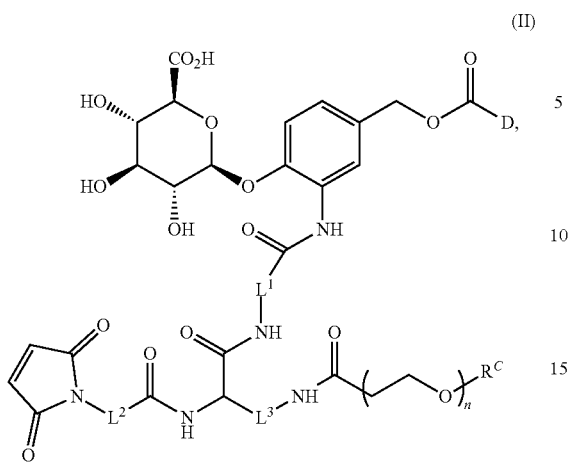

(II)

or a salt thereof, wherein
D is a Drug Unit incorporating a DNA minor groove binder, DNA damaging agent or DNA replication inhibitor having a amine functional group that forms a carbamate functional group;
$R^c$ is hydrogen or a PEG Capping Unit;
each of $L^1$, $L^2$, and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and
subscript n is an integer ranging from 2 to 24,
the method comprising the steps of:
(c) contacting a compound of Formula IIC with either a Grignard reagent or an alkoxy magnesium halide in a suitable alcohol-containing solvent, wherein the Formula IIC compound has the structure of:

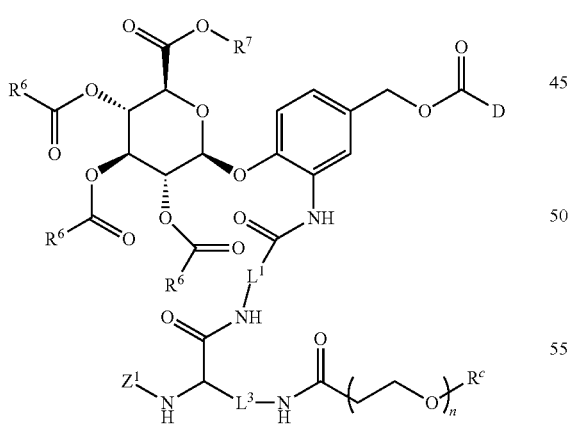

(IIC)

or a salt thereof, wherein
$Z^1$ is a first suitable amino protecting group; and
the remaining variable groups are as previously defined by Formula II,
wherein said Grignard reagent or alkoxy magnesium halide contacting selectively removes the hydroxyl protecting groups to provide a compound of Formula IID:

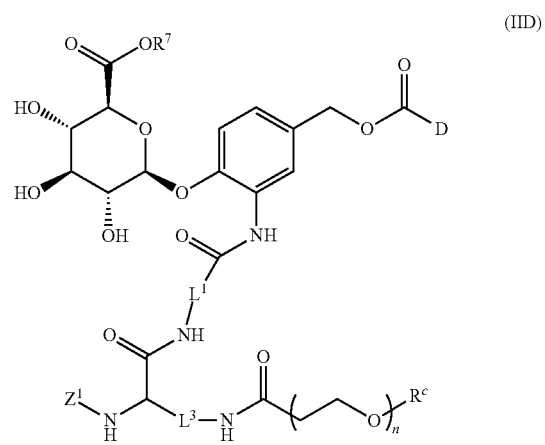

(IID)

or a salt thereof, wherein the variable groups are as previously defined by Formula II;
(b) contacting the Formula IID compound with a first deprotecting agent,
wherein said first deprotecting agent contacting removes the amine and carboxylic acid protecting groups to provide a compound of Formula IIE:

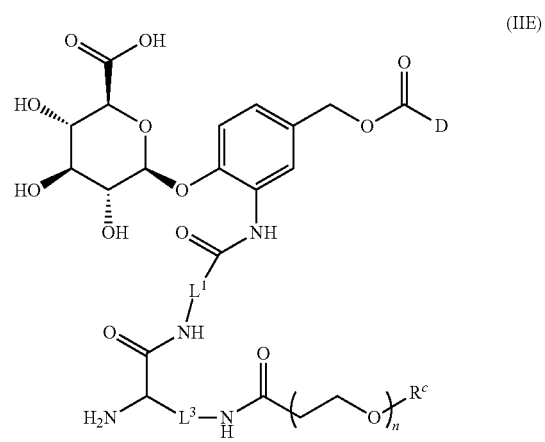

(IIE)

or a salt thereof, wherein the variable groups are as previously defined by Formula II;
(c) contacting the Formula IIE compound in a suitable solvent with a compound of Formula v:

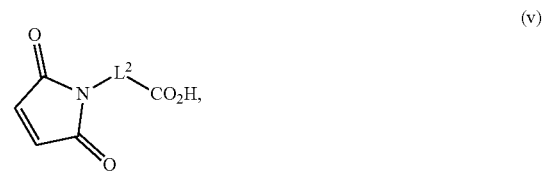

(v)

or a salt thereof, wherein $L^2$ is as previously defined by Formula II, in the presence of an second activating agent,
wherein said Formula v contacting provides the Formula II compound.
In another group of embodiments, provided herein are methods for preparing a Drug Linker compound of Formula II:

(II)

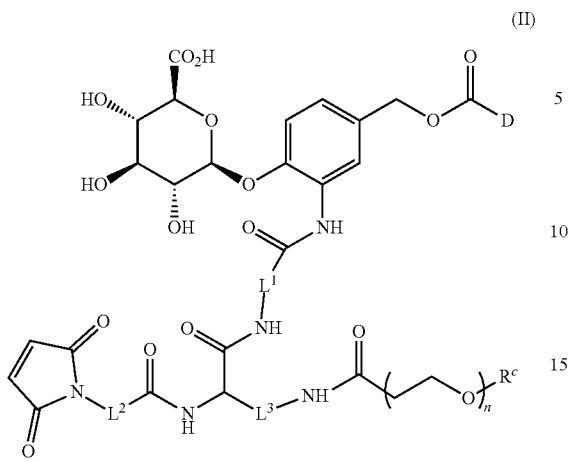

or a salt thereof, wherein
D is a Drug Unit incorporating a DNA minor groove binder, DNA damaging agent or DNA replication inhibitor having a amine functional group that forms a carbamate functional group;
each of $L^1$, $L^2$, and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and
subscript n is an integer ranging from 2 to 24,
the method comprising the steps of:
(a) contacting a compound of Formula IIA with a second deprotecting agent, wherein the Formula IIA compound has the structure of:

(IIA)

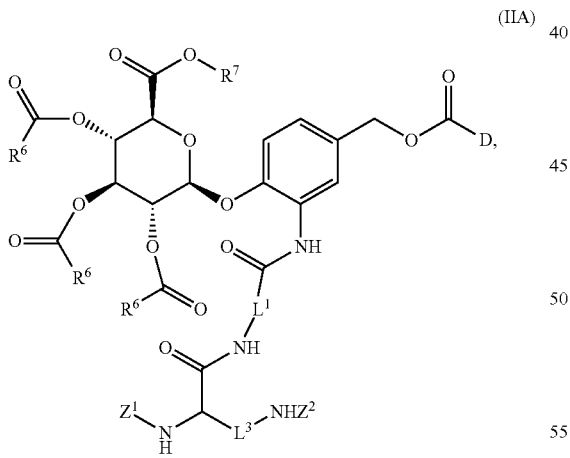

or a salt thereof, wherein
each of $R^6$ and $R^7$ is independently $C_1$-$C_8$ alkyl or optionally substituted phenyl so that $R^6C(\!=\!O)$— provides for an ester functional group that is a suitable hydroxyl protecting group and —$OR^7$ provides for an ester functional group that is a suitable carboxylic acid protecting group,
each of $Z^1$ and $Z^2$ is independently a first and second suitable amino protecting group, respectively;
subscript n is an integer ranging from 2 to 24; and the remaining variable groups are as previously defined by Formula II,
wherein said second deprotecting agent contacting selectively removes the $Z^2$ amino protecting group to provide a compound of Formula IIB:

(IIB)

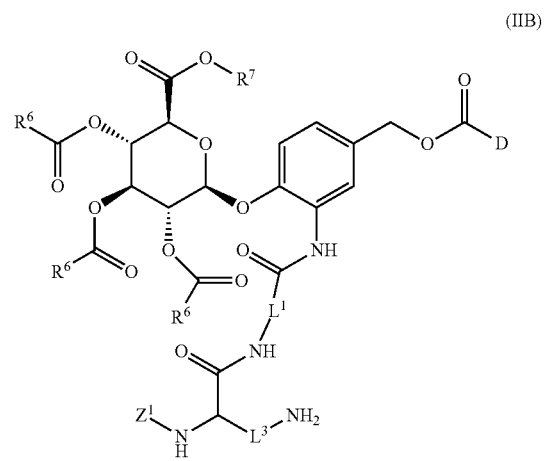

or a salt thereof, wherein the variable groups are as previously defined by Formula IIA;
(b) contacting the Formula IIB compound in a suitable solvent with a compound of Formula iv:

(iv)

wherein $R^8$ is an activated ester, $R^c$ is hydrogen or a PEG Capping Unit, and subscript n is an integer ranging from 2 to 24, or
(b') contacting the Formula IIB compound with a compound of Formula iv in which $R^8$ is —COOH in the presence of a first activating agent, and subscript n is an integer ranging from 2 to 24,
wherein said contacting of step (b) or (b') provides a compound of Formula IIC:

(IIC)

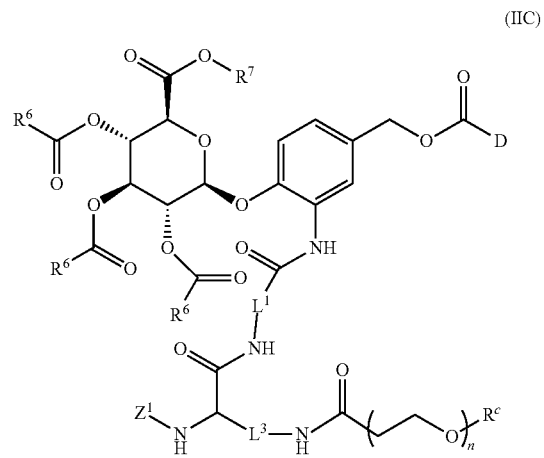

or a salt thereof, wherein the variable groups are as previously defined by Formula IIA and Formula iv;

(c) contacting the Formula IIC compound with either a Grignard reagent or an alkoxy magnesium halide in a suitable alcohol-containing solvent, wherein said Grignard reagent or alkoxy magnesium halide contacting selectively removes the hydroxyl protecting groups to provide a compound of Formula IID:

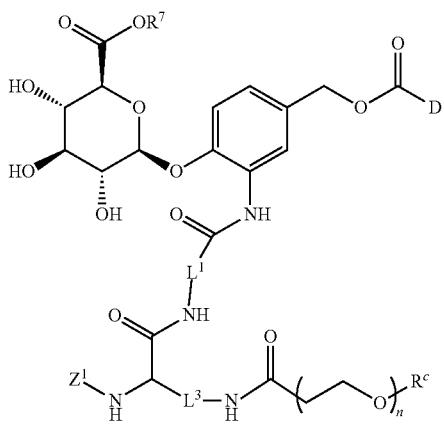

(IID)

or a salt thereof, wherein the variable groups are as previously defined by Formula IIC;

(d) contacting the Formula IID compound with a first deprotecting agent, wherein said first deprotecting agent contacting removes the amine and carboxylic acid protecting groups to provide a compound of Formula IIE:

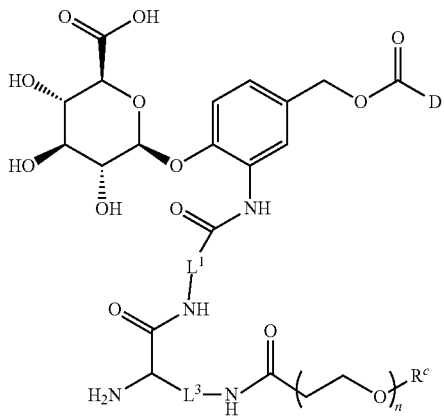

(IIE)

or a salt thereof, wherein the variable groups are as previously defined by Formula IID; and (e) contacting the Formula IIE compound with a compound of Formula v:

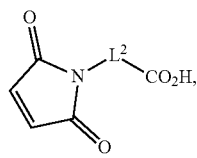

(v)

or a salt thereof, wherein $L^2$ is as previously defined by Formula II, in the presence of a second activating agent, wherein said Formula v contacting provides the Formula II compound.

In another group of embodiments, provided herein are methods for preparing a Drug Linker compound of Formula II:

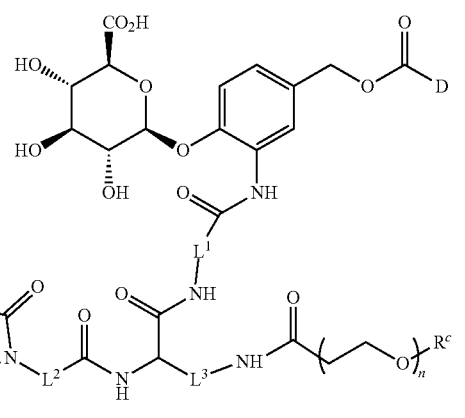

(II)

or a salt thereof, wherein

D is a Drug Unit incorporating a DNA minor groove binder, DNA damaging agent or DNA replication inhibitor having a amine functional group that forms a carbamate functional group;

$R^c$ is hydrogen or a PEG Capping Unit;

each of $L^1$, $L^2$, and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, and optionally substituted $C_3$-$C_8$ heterocyclo; and subscript n is an integer ranging from 2 to 24, the method comprising the steps of:

(b) contacting a compound of Formula IIB in a suitable solvent with a compound of Formula iv:

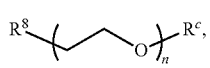

(iv)

wherein $R^8$ is an activated ester, $R^c$ is hydrogen or a PEG Capping Unit, and subscript n is an integer ranging from 2 to 24, or (b') contacting the Formula IIB compound in a suitable solvent with a compound of Formula iv in which $R^8$ is —COOH in the presence of a first activating agent, and subscript n is an integer ranging from 2 to 24, wherein the Formula IIB compound has the structure of:

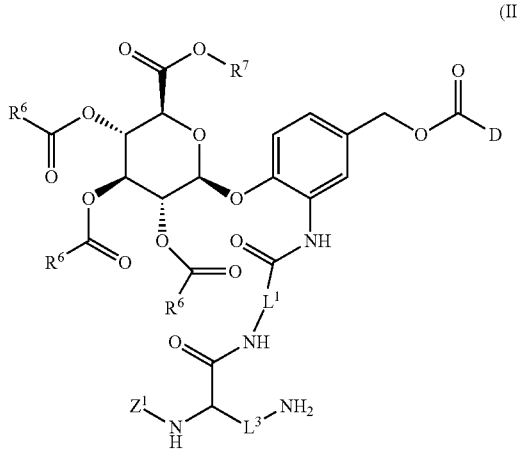

(IIB)

or a salt thereof, wherein $Z^1$ is a first suitable amino protecting group;

each of $R^6$ and $R^7$ is independently $C_1$-$C_8$ alkyl or optionally substituted phenyl so that $R^6C(=O)-$ provides for an ester functional group that is a suitable hydroxyl protecting group and $-OR^7$ provides for an ester functional group that is a suitable carboxylic acid protecting group;

subscript n is an integer ranging from 2 to 24; and the remaining variable groups are as previously defined by Formula II, wherein said contacting of step (b) or (b') provides a compound of Formula IIC:

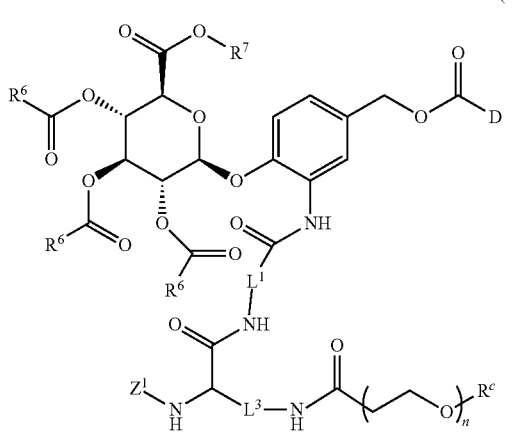

(IIC)

or a salt thereof, wherein the variable groups are as previously defined;

(c) contacting the Formula IIC compound with either a Grignard reagent or an alkoxy magnesium halide in a suitable alcohol-containing solvent, wherein said Grignard reagent or alkoxy magnesium halide contacting selectively removes the hydroxyl protecting groups to provide a compound of Formula IID:

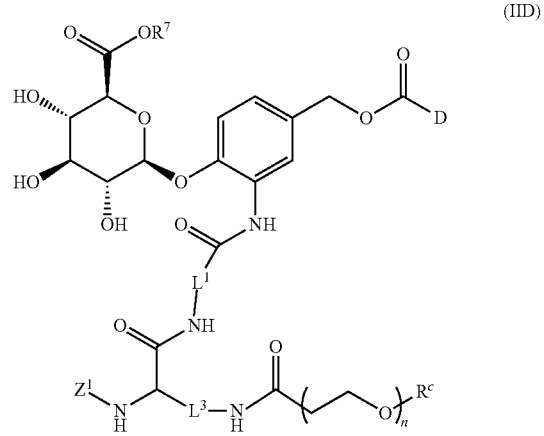

(IID)

or a salt thereof, wherein the variable groups are as previously defined by Formula IIB and Formula iv;

(d) contacting the Formula IID compound with a first deprotecting agent, wherein said first deprotecting agent contacting removes the amine and carboxylic acid protecting groups to provide a compound of Formula IIE:

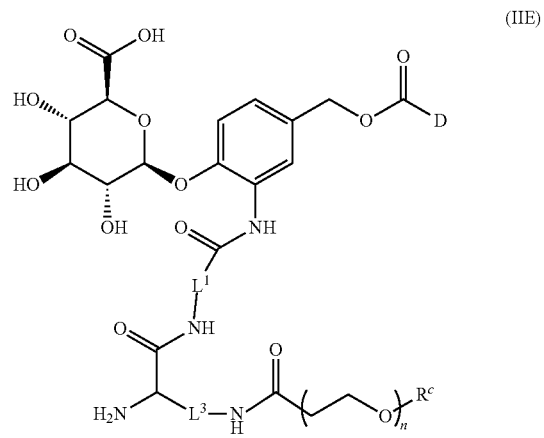

(IIE)

or a salt thereof, wherein the variable groups are as previously defined for Formula II; and (d) contacting the Formula IIE compound with a compound of Formula v:

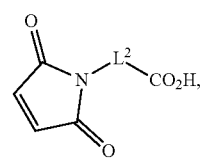

(v)

or a salt thereof, wherein $L^2$ is as previously defined by Formula II, in the presence of a second activating agent, wherein said Formula v contacting provides the Formula II compound or its salt.

In other embodiments, provided herein are methods for preparing a Drug Linker intermediate compound of Formula IIID:

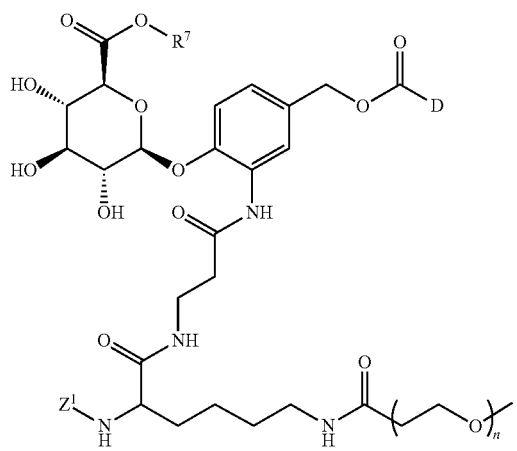

(IIID)

or a salt thereof, wherein
D is a Drug Unit incorporating a DNA minor groove binder, DNA damaging agent or DNA replication inhibitor having a amine functional group that forms a carbamate functional group;
$Z^1$ is a suitable amino protecting group;
$R^7$ is $C_1$-$C_8$ alkyl or optionally substituted phenyl so that —$OR^7$ provides for an ester functional group that is a suitable carboxylic acid protecting group; and
subscript n is an integer ranging from 2 to 24,
the method comprising the step of:
(c) contacting a compound of Formula IIIC with either a Grignard reagent or an alkoxy magnesium halide in a suitable alcohol-containing solvent, wherein the Formula IIC compound has the structure of:

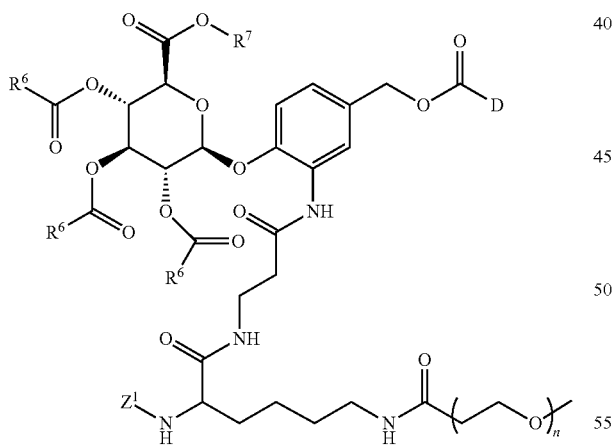

(IIIC)

or a salt thereof, wherein
each of $R^6$ is independently $C_1$-$C_8$ alkyl or optionally substituted phenyl so that $R^6C(=O)$— provides for an ester functional group that is a suitable hydroxyl protecting group;
and the remaining variable groups are as previously defined by Formula IIID,
wherein said Grignard reagent or an alkoxy magnesium halide contacting provides the Formula IIIC compound or its salt.

In other embodiments, provided herein are methods for preparing a Drug Linker intermediate compound of Formula IIID:

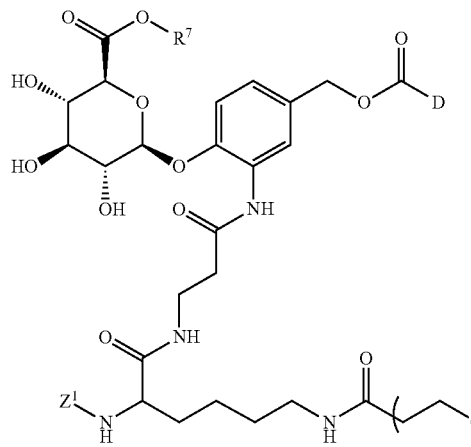

(IIID)

or a salt thereof, wherein
D is a Drug Unit incorporating a DNA minor groove binder, DNA damaging agent or DNA replication inhibitor having a amine functional group that forms a carbamate functional group;
$Z^1$ is a first suitable amino protecting group;
$R^7$ is $C_1$-$C_8$ alkyl or optionally substituted phenyl so that -$OR^7$ provides for an ester functional group that is a suitable carboxylic acid protecting group; and
subscript n is an integer ranging from 2 to 24,
the method comprising the steps of:
a) contacting a compound of Formula IIIA with a second deprotecting agent, wherein the Formula IIIA compound has the structure of:

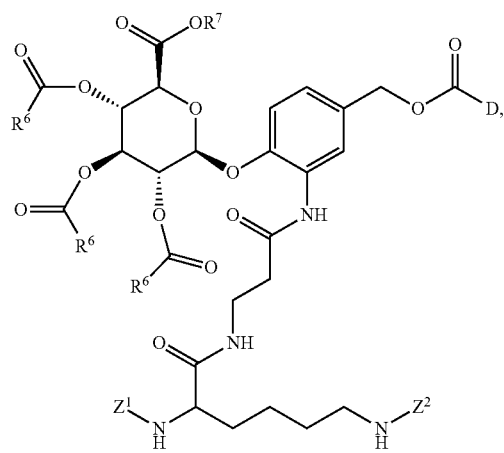

(IIIA)

or a salt thereof, wherein
$Z^2$ is a second suitable amino protecting group,
each of $R^6$ is independently $C_1$-$C_8$ alkyl or optionally substituted phenyl so that $R^6C(=O)$— provides for an ester functional group that is a suitable hydroxyl protecting group, wherein said second deprotecting agent contacting selectively removes the $Z^2$ amino protecting group to provide a compound of Formula IIIB:

(IIIB)

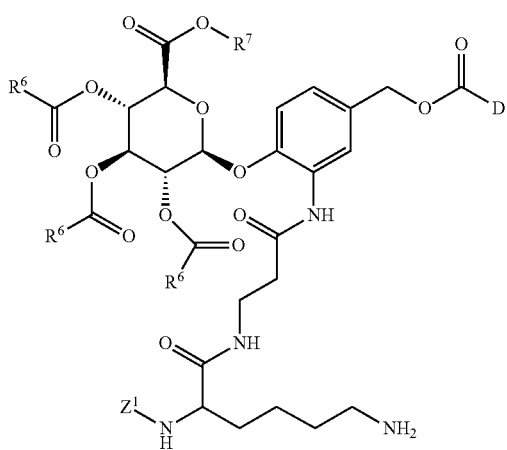

or a salt thereof, wherein the variable groups are as previously defined by Formula IIIA;

(b) contacting the compound of Formula IIIB in a suitable solvent with a compound of Formula iv:

(iv)

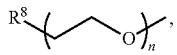

wherein $R^8$ is an activated ester, and subscript n is an integer ranging from 2 to 24, or (b') contacting the Formula IIIB compound with a compound of Formula iv in which $R^8$ is —COOH and subscript n is an integer ranging from 2 to 24 in the presence of an activating agent; and wherein said contacting of step (b) or (b') provides a compound of Formula IIIC:

(IIIC)

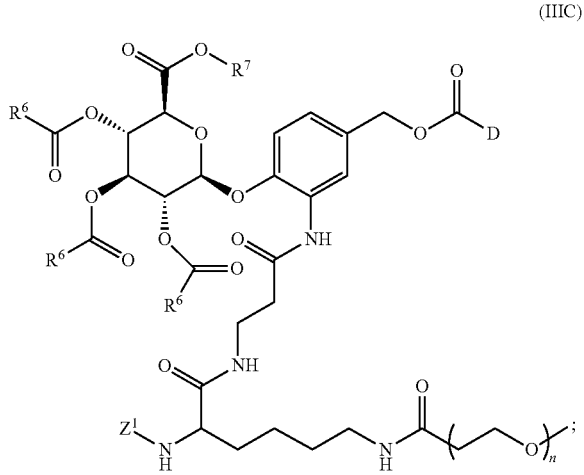

or a salt thereof, wherein the variable groups are as previously defined by Formula IIIA and Formula iv;

(c) contacting the Formula IIIC compound with either a Grignard reagent or an alkoxy magnesium halide in a suitable alcohol-containing solvent, wherein said Grignard reagent or an alkoxy magnesium halide contacting provides the Formula IIID compound or its salt.

In other embodiments, provided herein are methods for preparing a Drug Linker intermediate compound of Formula IIID:

(IIID)

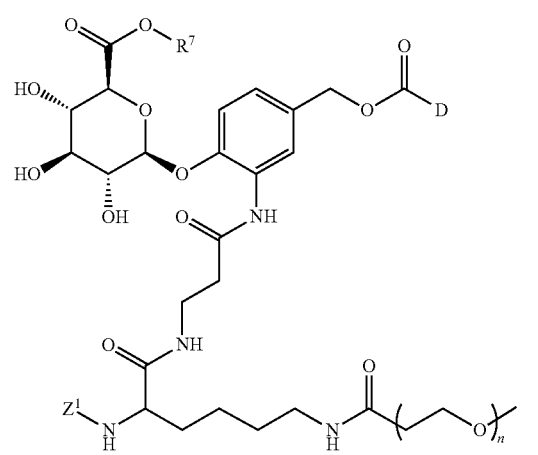

or a salt thereof, wherein

D is a Drug Unit incorporating a DNA minor groove binder, DNA damaging agent or DNA replication inhibitor having an amine functional group that forms a carbamate functional group;

$Z^1$ is a first suitable amino protecting group;

$R^7$ is $C_1$-$C_8$ alkyl or optionally substituted phenyl so that -$OR^7$ provides for an ester functional group that is a suitable carboxylic acid protecting group; and subscript n is an integer ranging from 2 to 24, the method comprising the steps of:

(b) contacting a compound of Formula IIIB in a suitable solvent with a compound of Formula iv:

(iv)

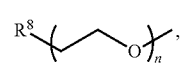

wherein $R^8$ is an activated ester, and subscript n is an integer ranging from 2 to 24, or (b') contacting the Formula IIIB compound with a compound of Formula iv in which $R^8$ is —COOH and n is an integer ranging from 2 to 24 in the presence of a first activating agent, wherein the Formula IIIB compound has the structure of:

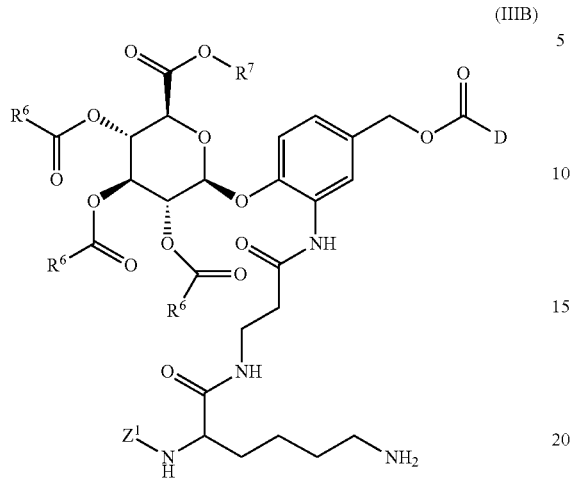

(IIIB)

or a salt thereof, wherein each of $R_6$ is independently $C_1$-$C_8$ alkyl or optionally substituted phenyl so that $R^6C(=O)$— provides for an ester functional group that is a suitable hydroxyl protecting group; and the remaining variable groups are as previously defined by Formula IIID; and wherein said contacting of step (b) or (b') provides a compound of Formula IIIC:

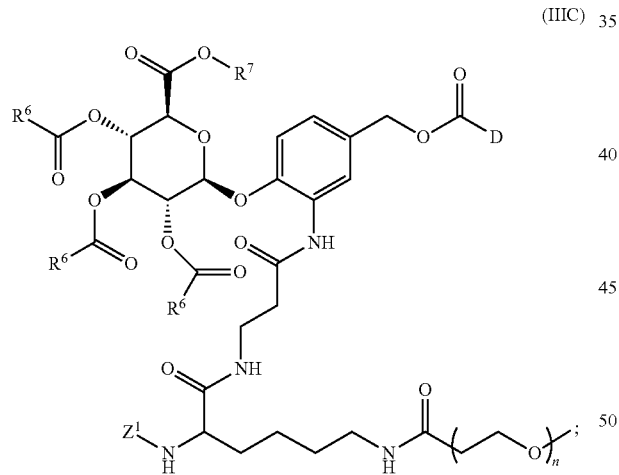

(IIIC)

or a salt thereof, wherein the variable groups are as previously defined by Formula IIIB and Formula iv; and (b) contacting the Formula IIC compound with either a Grignard reagent or an alkoxy magnesium halide in a suitable alcohol-containing solvent, wherein said Grignard reagent or an alkoxy magnesium halide contacting provides the Formula IIID compound or its salt.

In other embodiments, provided herein are methods for preparing a Drug Linker intermediate compound of Formula IIIE:

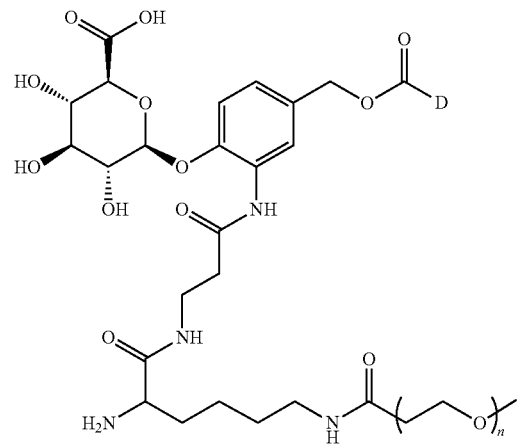

(IIIE)

or a salt thereof, wherein

D is a Drug Unit incorporating a DNA minor groove binder, DNA damaging agent or DNA replication inhibitor having an amine functional group that forms a carbamate functional group; and subscript n is an integer ranging from 2 to 24, the method comprising the step of:

(c) contacting a compound of Formula IIIC with either a Grignard reagent or an alkoxy magnesium halide in a suitable alcohol-containing solvent; and (d) contacting the product of step (c) with a first deprotecting agent wherein the first deprotecting agent is an aqueous-containing solution of a suitable base, wherein the Formula IIIC compound has the structure of:

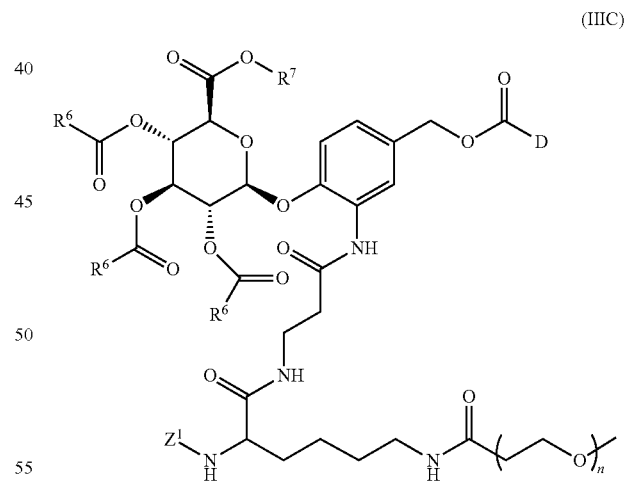

(IIIC)

or a salt thereof, wherein $Z^1$ is a suitable amino protecting group;

each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable groups are as previously defined by Formula IIIE, and wherein said contacting of steps (c) and (b) provide the Formula IIIE compound or its salt.

In other embodiments, provided herein are methods for preparing a Drug Linker intermediate compound of Formula IIIE:

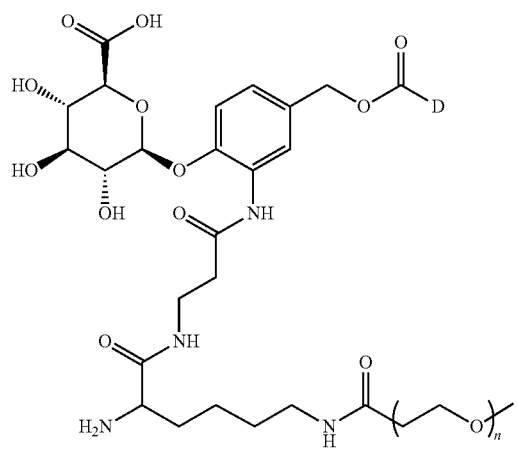

(IIIE)

or a salt thereof, wherein

D is a Drug Unit incorporating a DNA minor groove binder, DNA damaging agent or DNA replication inhibitor having a amine functional group that forms a carbamate functional group; and subscript n is an integer ranging from 2 to 24, the method comprising the steps of:

(b) contacting a compound of Formula IIIB in a suitable solvent with a compound of Formula iv:

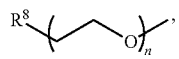

(iv)

wherein $R^8$ is an activated ester, and subscript n is an integer ranging from 2 to 24, or (b') contacting the Formula IIIB compound with a compound of Formula iv in which $R^8$ is —COOH and subscript n is an integer ranging from 2 to 24 in the presence of a first activating agent, wherein the Formula IIIB compound has the structure of:

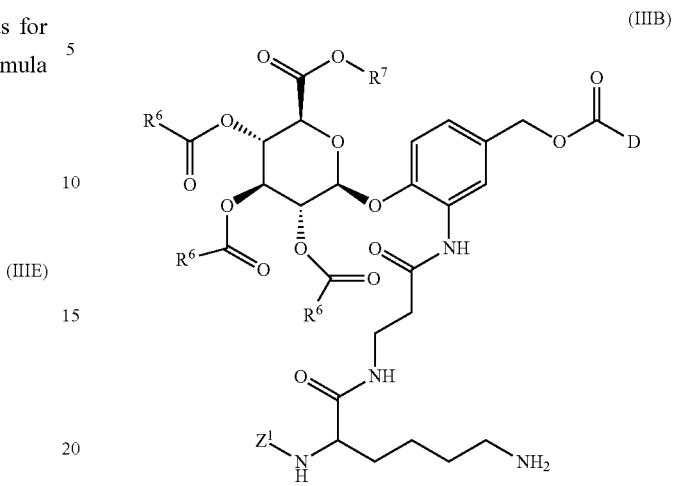

(IIIB)

or a salt thereof, wherein $Z^1$ is a suitable amino protecting group;

each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable group are as previously defined by Formula IIIE said contacting of step (b) or (b') provides a compound of Formula IIIC

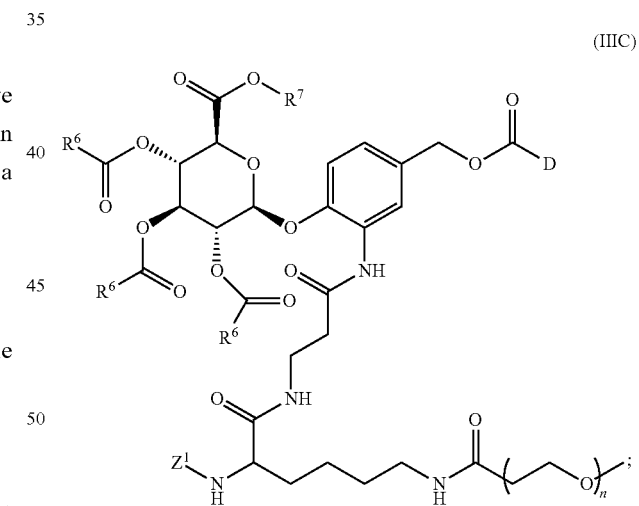

(IIIC)

or a salt thereof, wherein the variable groups are as previously defined by Formula IIIB and Formula iv;

(c) contacting the Formula IIIC compound with either a Grignard reagent or an alkoxy magnesium halide in a suitable alcohol-containing solvent; and (c) contacting the product of step (b) with a first deprotecting agent wherein the first deprotecting agent is an aqueous-containing solution of a suitable base, wherein said contacting of steps (b) and (c) provide the Formula IIIE compound.

In other embodiments, provided herein are methods for preparing a Drug Linker compound or intermediate thereof of Formula IIIE:

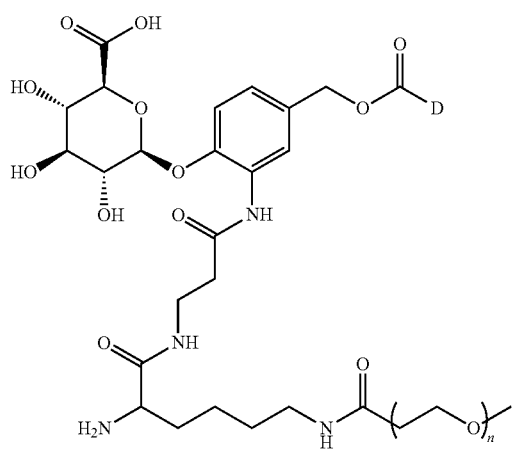

(IIIE)

or a salt thereof, wherein

D is a Drug Unit incorporating a DNA minor groove binder, DNA damaging agent or DNA replication inhibitor having an amine functional group that forms a carbamate functional group; and subscript n is an integer ranging from 2 to 24, the method comprising the steps of:

(a) contacting a compound of Formula IIIA with a second deprotecting agent, wherein the Formula IIIA compound has the structure of:

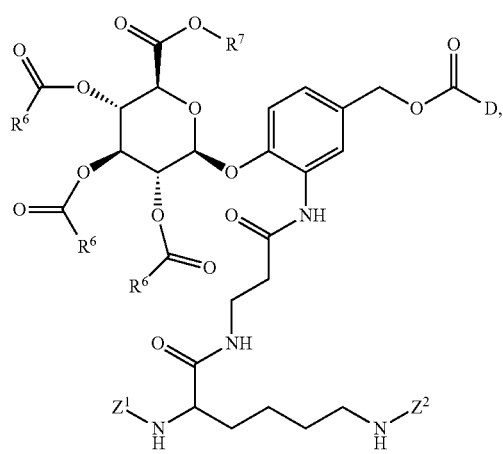

(IIIA)

or a salt thereof, wherein $Z^1$ and $Z^2$ are independently a first and second suitable amino protecting group, respectively;

each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and wherein said first deprotecting agent contacting selectively removes the $Z^2$ amino protecting group to provide a compound of Formula IIIB:

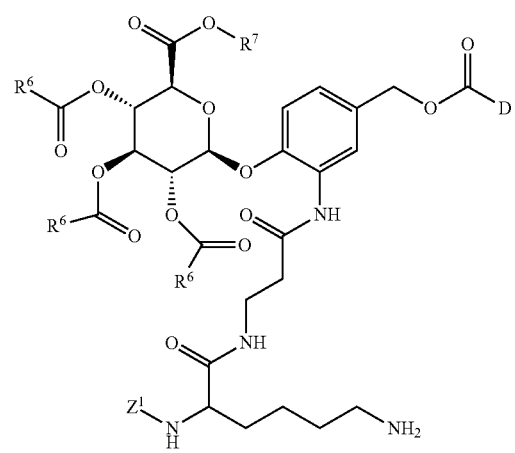

(IIIB)

or a salt thereof, wherein the variable groups are as previously defined by Formula IIIA;

(b) contacting the Formula IIIB compound in a suitable solvent with a compound of Formula iv:

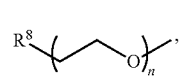

(iv)

wherein $R^8$ is an activated ester, and subscript n is an integer ranging from 2 to 24, or (b') contacting the Formula IIIB compound with a compound of Formula iv in which $R^8$ is —COOH and subscript n is an integer ranging from 2 to 24 in the presence of a first activating agent; and wherein said contacting of step (b) or (b') provides a compound of Formula IIIC:

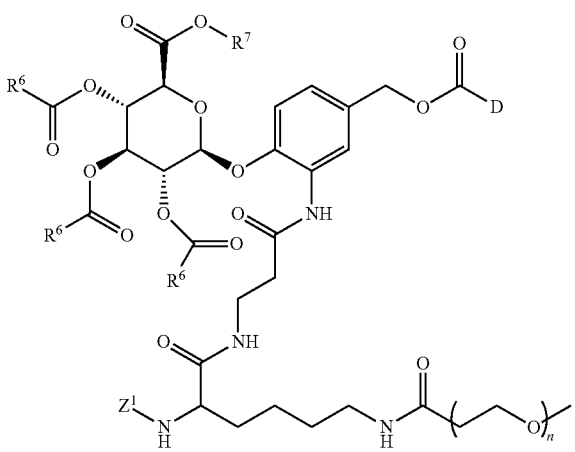

(IIIC)

or a salt thereof, wherein the variable groups are as previously defined by Formula IIA and Formula iv;

(c) contacting the Formula IIIC compound with either a Grignard reagent or an alkoxy magnesium halide in a suitable alcohol-containing solvent; and (d) contacting the product of step (c) with a first deprotecting agent, wherein the first deprotecting agent is an aqueous-containing solution of a suitable base, wherein said contacting of steps (c) and (d) provide the Formula IIIE compound or its salt.

In other embodiments, provided herein are methods for preparing a Drug Linker compound or intermediate thereof of Formula IIIF:

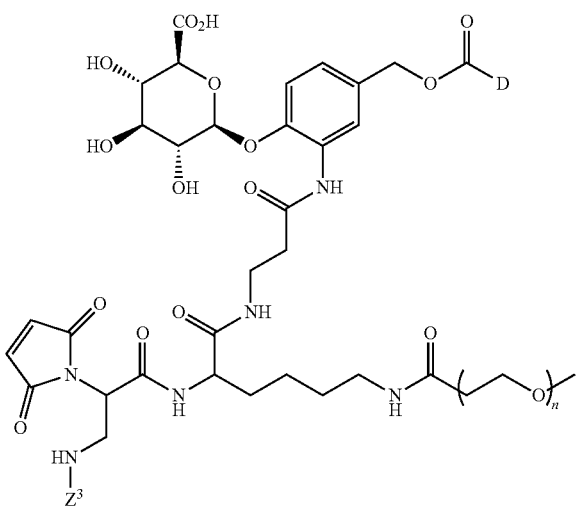

(IIIF)

or a salt thereof, wherein

D is a Drug Unit incorporating a DNA minor groove binder, DNA damaging agent or DNA replication inhibitor having an amine functional group that forms a carbamate functional group;

$Z^3$ is a third suitable amino protecting group that is acid-labile; and subscript n is an integer ranging from 2 to 24, the method comprising the steps of:

(c) contacting a compound of Formula IIIC with either a Grignard reagent or an alkoxy magnesium halide in a suitable alcohol-containing solvent; and (d) contacting the product of step (a) with a second deprotecting agent, wherein the second deprotecting agent is an aqueous-containing solution of a suitable base, wherein the Formula IIIC compound has the structure of:

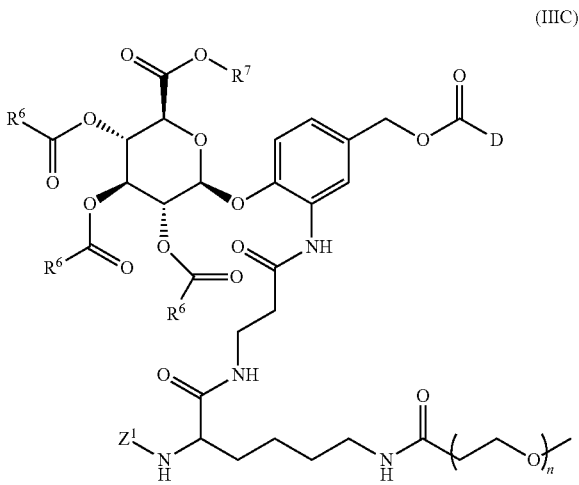

(IIIC)

or a salt thereof, wherein $Z^1$ is a first suitable amino protecting group;

each of $R^6$ and $R^7$ is independently $C_1$-$C_8$ alkyl or optionally substituted phenyl so that $R^6C(=O)-$ provides for an ester functional group that is a suitable hydroxyl protecting group and $-OR^7$ provides for an ester functional group that is a suitable carboxylic acid protecting group; and and the remaining variable groups are as previously defined by Formula IIIF, wherein said contacting of steps (c) and (d) provide a compound of Formula IIIE, wherein the Formula IIIE compound has the structure of:

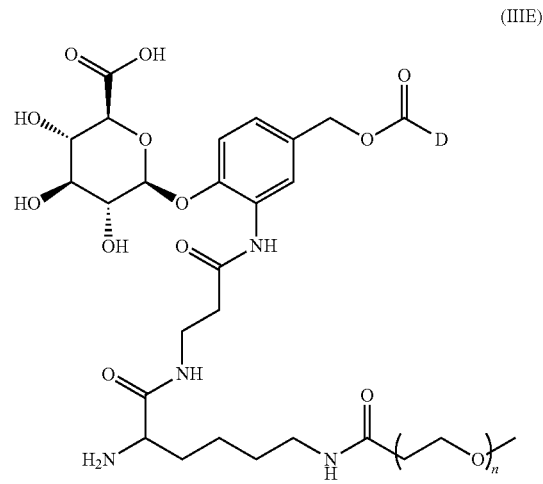

(IIIE)

or a salt thereof, wherein the variable groups are as previously defined by Formula IIIC; and contacting the compound of Formula IIIE in a suitable solvent with a compound of Formula v:

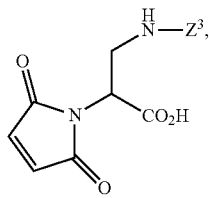

(v)

or a salt thereof, in e presence of a second activating agent, wherein said Formula v contacting provides the Formula IIIF compound or its salt.

In other embodiments, provided herein are methods for preparing Drug Linker compound or intermediate thereof of Formula IIIF:

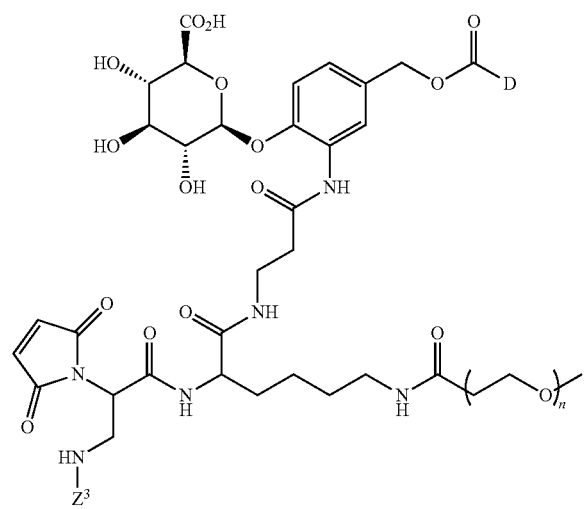

(IIIF)

or a salt thereof, wherein

D is a Drug Unit incorporating a DNA minor groove binder, DNA damaging agent or DNA replication inhibitor having an amine functional group that forms a carbamate functional group;

$Z^3$ is a third suitable amino protecting group that is acid-labile; and subscript n is an integer ranging from 2 to 24, the method comprising the steps of:

(b) contacting a compound of Formula IIIB in a suitable solvent with a compound of Formula iv:

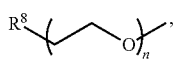

(iv)

wherein $R^8$ is an activated ester, and n is an integer ranging from 2 to 24, or (b') contacting a compound of Formula IIIB with a compound of Formula iv in which $R^8$ is —COOH and subscript n is an integer ranging from 2 to 24 in the presence of first activating agent;

wherein the Formula IIIB compound has the structure of:

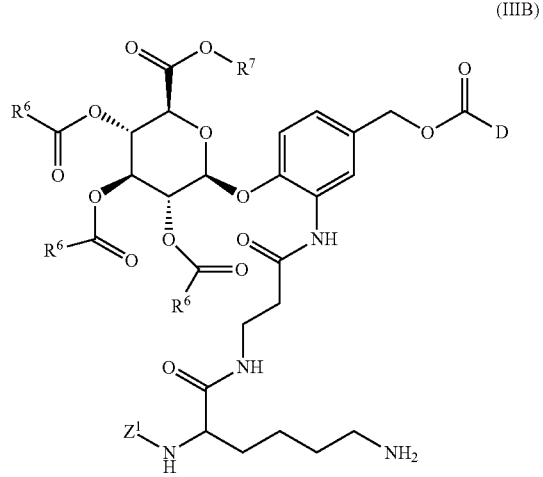

(IIIB)

wherein $Z^1$ is a first suitable amino protecting group;

each of $R^6$ and $R^7$ is independently $C_1$-$C_8$ alkyl or optionally substituted phenyl so that $R^6C(\!\!=\!\!O)$— provides for an ester functional group that is a suitable hydroxyl protecting group and —$OR^7$ provides for an ester functional group that is a suitable carboxylic acid protecting group; and the remaining variable group is as previously defined by Formula IIIF, wherein said contacting of step (b) or (b') provides a compound of Formula IIIC:

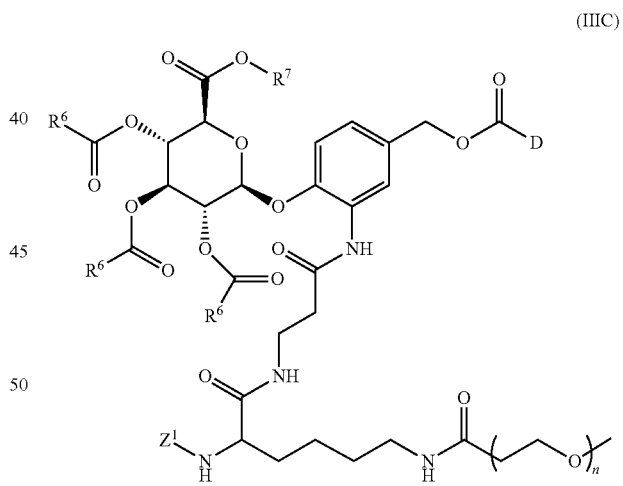

(IIIC)

or a salt thereof, wherein the variable groups are as previously defined by Formula IIIB and Formula iv;

(c) contacting the Formula IIC compound with either a Grignard reagent or an alkoxy magnesium halide in a suitable alcohol-containing solvent; and (d) contacting the product of step (c) with a second deprotecting agent, wherein the second deprotecting agent is an aqueous-containing solution of a suitable base, wherein said contacting of steps (c) and (d) provide a compound of Formula IIIE:

wherein the Formula IIIE compound has the structure of:

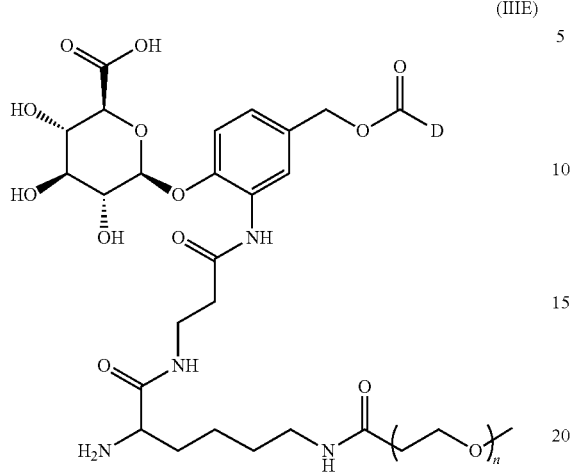

(IIIE)

or a salt thereof, wherein the variable groups are as previously defined by Formula IIIF; and
(e) contacting the Formula IIIE compound with a compound of Formula v:

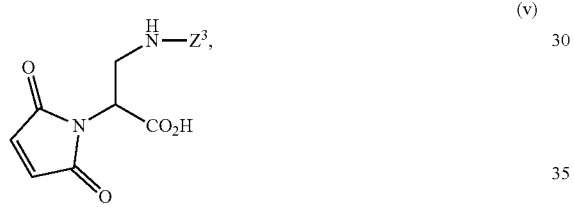

(v)

or a salt thereof, wherein $Z^3$ is as previously defined by Formula IIIF, in the presence of a second activating agent,
wherein said Formula v contacting provides the Formula IIIF compound or its salt In other embodiments, provided herein are methods for preparing compounds of Formula IIIF:

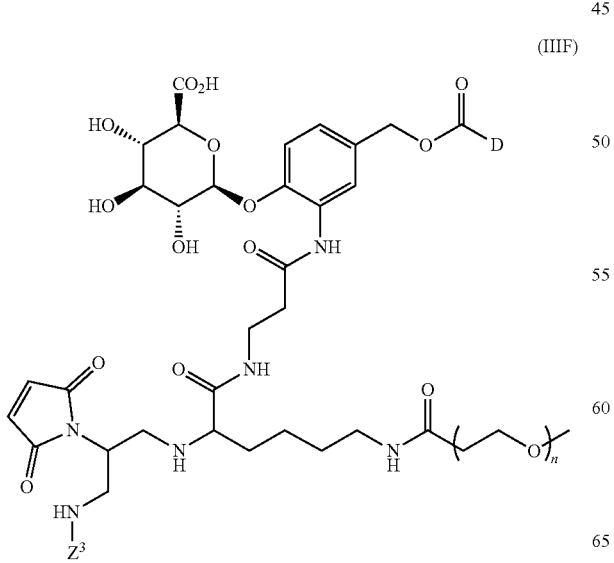

(IIIF)

or a salt thereof, wherein

D is a Drug Unit incorporating a DNA minor groove binder, DNA damaging agent or DNA replication inhibitor having an amine functional group that forms a carbamate functional group;
$Z^3$ is a third suitable amino protecting group that is acid-labile; and
subscript n is an integer ranging from 2 to 24,
the method comprising the steps of:
(a) contacting a compound of Formula IIIA with a second deprotecting agent, wherein the Formula IIIA compound has the structure of:

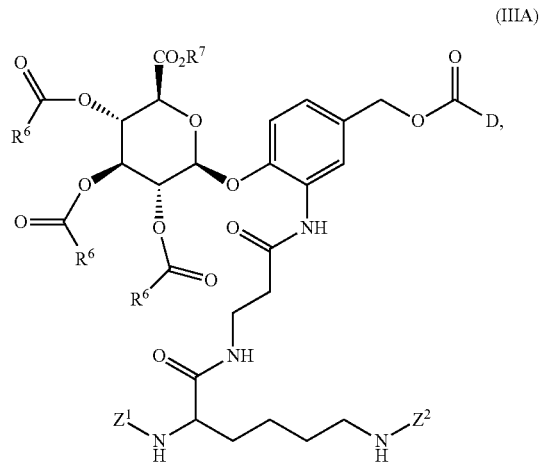

(IIIA)

or a salt thereof, wherein
$Z^1$ is a first suitable amino protecting group;
$Z^2$ is a second suitable amino protecting group;
each of $R^6$ and $R^7$ is independently $C_1$-$C_8$ alkyl or optionally substituted phenyl so that $R^6C(=O)$— provides for an ester functional group that is a suitable hydroxyl protecting group, and —$OR^7$ provides for an ester functional group that is a suitable carboxylic acid protecting group; and wherein the remaining variable groups are as previously defined by Formula IIIF,
wherein the second deprotecting agent contacting selectively removes the $Z^2$ amino protecting group to provide a compound of Formula IIB:

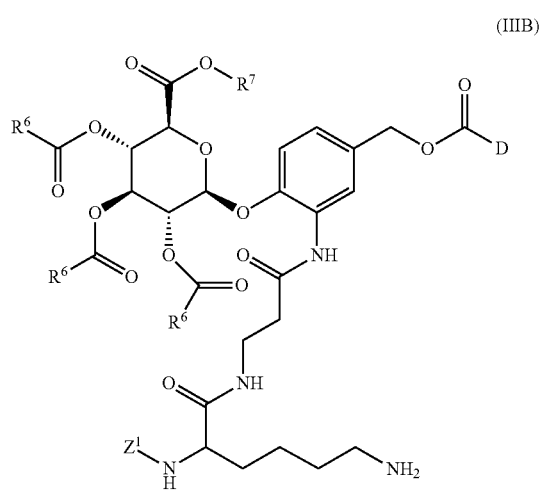

(IIIB)

or a salt thereof, wherein the variable groups are as previously defined by Formula IIIA;

(b) contacting the Formula IIIB compound in a suitable solvent with a compound of Formula iv:

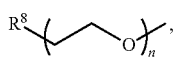

wherein $R^8$ is an activated ester, and subscript n is an integer ranging from 2 to 24, or (b') contacting the Formula IIIB compound with a compound of Formula iv in which $R^8$ is —COOH and subscript n is an integer ranging from 2 to 24 in the presence of a first activating agent;

wherein said contacting of step (b) or (b') provides a compound of Formula IIIC:

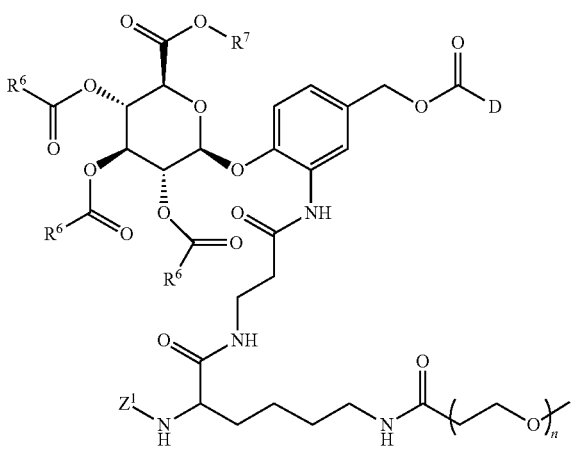

or a salt thereof, wherein the variable groups are as previously defined by Formula IIA and Formula iv;

(c) contacting the Formula WIC compound with either a Grignard reagent or an alkoxy magnesium halide in a suitable alcohol-containing solvent; and (d) contacting the product of step (c) with a first deprotecting agent wherein the first deprotecting agent is an aqueous-containing solution of a suitable base, wherein said contacting of steps (c) and (d) provide a compound of Formula IIIE

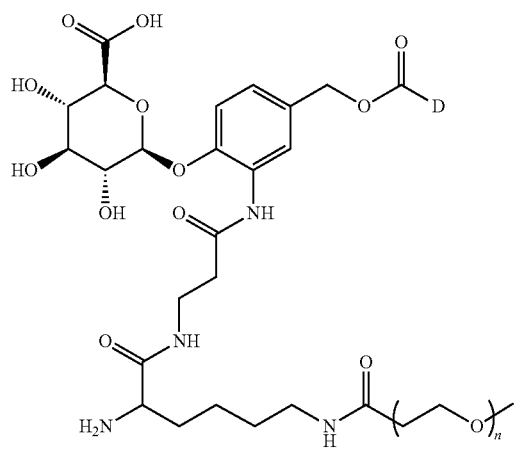

or a salt thereof, wherein the variable groups are as previously defined by Formula IIIF;

(e) contacting the compound of Formula IIIE with a compound of Formula v:

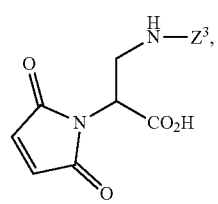

wherein $Z^3$ is as previously defined by Formula IIIF, in the presence of a second activating agent to form the Formula IIIF compound or its salt.

In other embodiments, provided herein are methods for preparing a Drug Linker compound or intermediate thereof of Formula III:

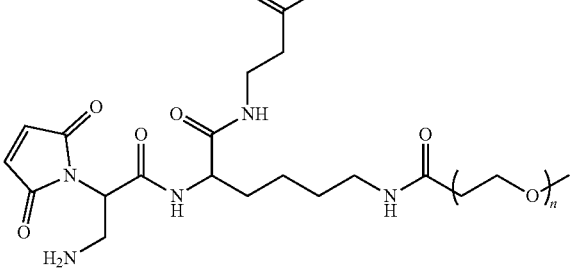

or a salt thereof, wherein
D is a Drug Unit incorporating a DNA minor groove binder, DNA damaging agent or DNA replication inhibitor having an amine functional group that forms a carbamate functional group; and subscript n is an integer ranging from 2 to 24, the method comprising the step of:

contacting a compound of Formula IIIF, with an acidic aqueous-containing solvent, wherein the Formula IIIF compound has the structure of:

(IIIF)

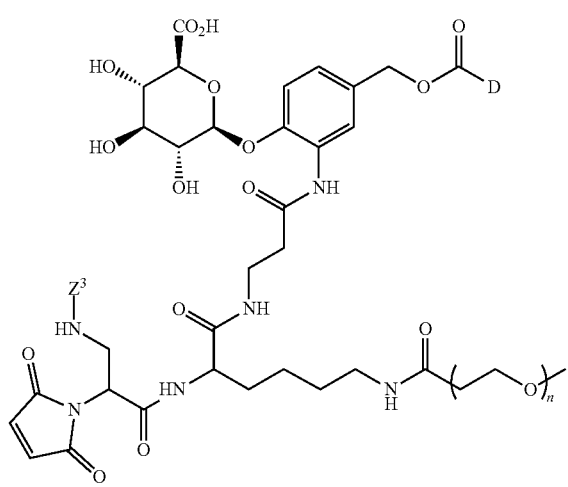

or a salt thereof, wherein $Z^3$ is a third suitable amino activating agent that is acid-labile; and the remaining variable group are as previously defined by Formula III; and wherein the Formula IIIF compound is prepared according to any one of the preceding methods providing that compound.

In some embodiments of the methods of preparing a compound of Formula IIIF, the compound of Formula v has the following chemical structure:

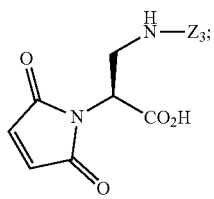

and the compound of Formula IIIF has the following chemical structure:

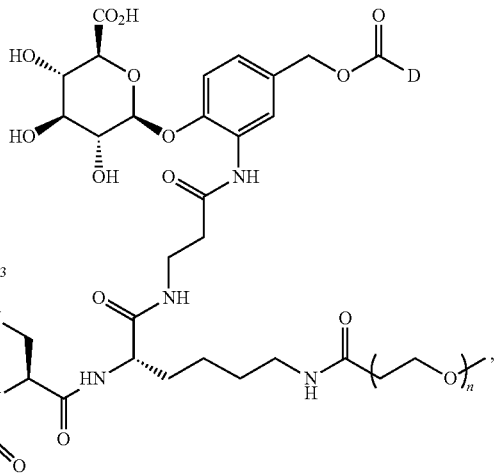

wherein D is a Drug Unit incorporating a DNA minor groove binder, DNA damaging agent or DNA replication inhibitor having an amine functional group that forms a carbamate functional group subscript n is an integer ranging from 2 to 34; and $Z^3$ is a third suitable amino protecting group that is acid-labile.

In some embodiments of the methods of preparing a compound of Formula IIIF, the compound of Formula v has the following chemical structure:

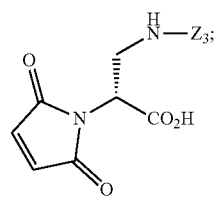

and the compound of Formula IIIF has the following chemical structure

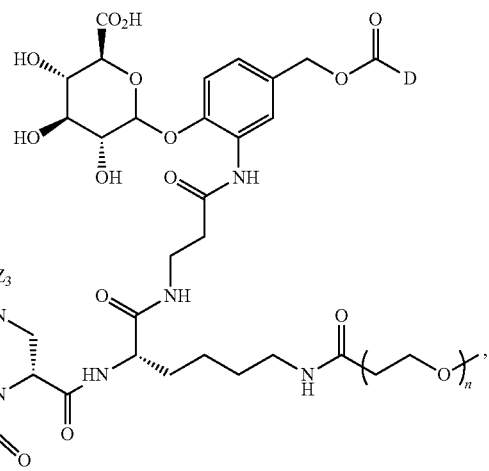

wherein D is a Drug Unit incorporating a DNA minor groove binder, DNA damaging agent or DNA replication inhibitor having a amine functional group that forms a carbamate functional group subscript n is an integer ranging from 2 to 34; and $Z^3$ is a third suitable amino protecting group that is acid-labile.

In certain embodiments of any one of the preceding methods, $R^6$ group of compounds of Formula IA, Formula IB, Formula IC, Formula ID, Formula IIA, Formula IIB, Formula IIC, Formula IID, Formula IIIA, Formula IIIB, Formula IIIC, Formula IIID, Formula VIC, and/or Formula VIIC is $C_1$-$C_4$ alkyl. More preferably, $R^6$ is methyl.

In certain embodiments of any one of the preceding methods, $R^7$ group of Drug Linker intermediate compounds of Formula IA, Formula IB, Formula IC, Formula ID, Formula IIA, Formula IIB, Formula IIC, Formula IID, Formula IIA, Formula IIIB, Formula IIIC, Formula IIID, Formula VIC, Formula VIIC, Formula VID, and/or Formula VIID is $C_1$-$C_4$ alkyl. More preferably, $R^7$ is methyl.

In particularly preferred embodiments, each of $R^6$ and $R^7$ of Drug Linker intermediate compounds of Formula IA, Formula IB, Formula IC, Formula ID, Formula IIA, Formula IIB, Formula IIC, Formula IID, Formula IIIA, Formula IIIB, Formula IIIC, Formula IIID, Formula VIC, and/or Formula VIIC is $C_1$-$C_4$ alkyl. In those embodiments each of $R^6$ and $R^7$ is methyl is especially preferred.

In selected embodiments of the methods of the present invention, $L^1$ of compounds of Formula IIA, Formula IIB, Formula IIC, Formula IIE, Formula IID, and/or Formula II is an optionally substituted $C_1$-$C_6$ alkylene or optionally substituted $C_4$-$C_{10}$ heteroalkylene, preferably, $L^1$ is a $C_1$-$C_6$ alkylene, and more preferably, $L^1$ is an unsubstituted $C_2$ alkylene.

In other selected embodiments of the methods of the present invention, $L^2$ of compounds of Formula II and/or Formula v is an optionally substituted $C_1$-$C_6$ alkylene or optionally substituted $C_4$-$C_{10}$ heteroalkylene. Preferably, $L^2$ is a substituted $C_1$-$C_6$ alkylene, and more preferably, $L^2$ is a methylene substituted with —$CH_2NH_2$ or $CH_2NH$—$Z^3$, wherein $Z^3$ is an amino protecting group. In some preferred embodiments, $L^2$ is CH—$CH_2$—NHBOC.

In certain embodiments of the methods of the present invention, $L^3$ in compounds of Formula IIA, Formula IIB, Formula IIC, Formula IIE, Formula IID, and/or Formula II is an optionally substituted $C_1$-$C_6$ alkylene or optionally substituted $C_4$-$C_{10}$ heteroalkylene. Preferably, $L^3$ is a $C_1$-$C_6$ alkylene, and more preferably, $L^3$ is unsubstituted $C_4$ alkylene, and even more preferably, $L^3$ is n-butylene.

In some embodiments of the methods of the present invention, amino protecting group $Z^1$ of Drug Linker intermediate compounds of Formula IIA, Formula IIB, Formula IIC, Formula IID, Formula IIA, Formula IIB, Formula IIC, and/or Formula IID is an amino protecting group that can be selectively removed by contacting the compound with a base. In some preferred embodiments, $Z^1$ is an FMOC. Preferably, $Z^1$ can be removed by contacting the compound with an aqueous solution of a base. A variety of bases can be used for removal of $Z^1$. Preferred bases include NaOH, KOH, NaHCO$_3$, and LiOH. Most preferably, the base is LiOH.

In selected embodiments of the methods of the present invention, $Z^2$ in compounds of Formula IIIA is an acid-labile amine protecting group. In certain preferred embodiments of these methods, $Z^2$ has the formula

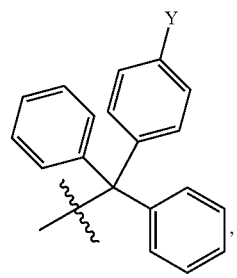

wherein Y is a H or OMe. Most preferably, $Z^2$ is MMTr.

Removal of the $Z^2$ amino protecting group can be carried out in any suitable manner. In some embodiments of the presently claimed methods, removal of $Z^2$ is achieved by contacting with an acid. Any suitable acid can be used, preferably having a pKa of between about 0 and about 3. Preferably, the acid is trichloroacetic acid or trifluoroacetic acid.

In certain embodiments of the methods of the present invention, wherein $R^C$ is present in the structure, $R^c$ is selected from H and $C_1$-$C_{10}$ alkyl. Preferably, $R^c$ is a $C_1$-$C_5$ alkyl, and more preferably, $R^c$ is methyl.

In selected embodiments of the methods of the present invention, $R^8$ of compound of Formula iv is an activated ester group.

An activated ester group, as used herein, is an ester group that can spontaneously react with an amino group to form an amide. In some embodiments, the activated ester group is selected from p-nitrophenyl, pentafluorophenyl, tetrafluorophenyl, and succinimido. In more preferred embodiments, the compound of Formula iv has the structure:

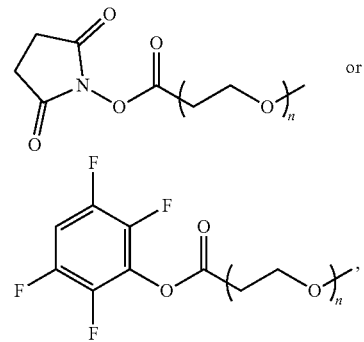

wherein subscript n ranges from 2 to 24, or is an integer ranging from 2 to 24, preferably ranging from 8 to 16. In particularly preferred embodiments subscript n is 12.

In some embodiments of the presently claimed methods, when $R^8$ of compound iv is COOH, contacting of compound iv with compound of Formula IB, Formula IIB, or Formula IIIB is done in the presence of a first suitable activating agent. Preferably, such first activating agent is selected from N-(3-Dimethylaminopropyl)-N'-ethylcarbodiimide hydrochloride (EDC.HCl), 2-ethoxy-1-ethoxycarbonyl-1,2-dihydroquinoline (EEDQ), (1-Cyano-2-ethoxy-2-oxoethylidenaminooxy)dimethylamino-morpholino-carbenium hexafluorophosphate (COMU), N-(3-Dimethylaminopropyl)-N'-ethylcarbodiimide hydrochloride/N-Hydroxysuccinimide, O-(7-Azabenzotriazol-1-yl)-N,N,N',N'-tetramethyluronium hexafluorophosphate (HATU), Diphenyl phosphoryl azide (DPPA), Chloro-N,N,N',N'-bis(tetramethylene)formamidinium tetrafluoroborate, Fluoro-N,N,N',N'-bis(tetramethylene)formamidinium hexafluorophosphate, N,N'-Dicyclohexylcarbodiimide, N-(3-Dimethylaminopropyl)-N'-ethylcarbodiimide hydrochloride, 1,1'-Carbonyldiimidazole, 2-Chloro-1,3-dimethylimidazolidinium tetrafluoroborate, (Benzotriazol-1-yloxy)tripyrrolidinophosphonium hexafluorophosphate, O-(7-Azabenzotriazol-1-yl)-N,N,N',N'-tetramethyluronium hexafluorophosphate, 2-Chloro-1-methylpyridinium iodide, and Propylphosphonic anhydride.

Any suitable solvent or a mixture of solvents can be used for contacting compound of Formula iv with a Drug Linker intermediate compound of Formula IB, Formula IIB, or Formula IIIB. In some embodiments, the solvent is an aprotic solvent, which includes those selected from the group consisting of acetonitrile, THF, 2-methyl-THF, dichloromethane, dioxane, DMF, NMP, and mixtures thereof. Preferably, the solvent comprises dichloromethane.

In selected embodiments of any of the preceding methods, the Grignard reagent has the formula of $R^gMgX$, wherein Re is $C_1$-$C_8$ alkyl or phenyl and X is I, Br, or Cl. In preferred embodiments, the Grignard reagent is MeMgI.

In certain embodiments of any of the preceding methods, the alkoxy magnesium halide has the formula of $R^gOMgX$, wherein $R^g$ is $C_1$-$C_5$ alkyl or phenyl and X is I, Br, or Cl. In preferred embodiments, the alkoxy magnesium halide is MeOMgCl.

In certain embodiments of the preceding methods said Grignard reagent or alkoxy magnesium halide contacting with a Drug Linker intermediate compound of Formula IC, Formula IIC, Formula IIIC, Formula VIC, and/or Formula VIC is done in a suitable alcohol-containing solvent. Preferably, the alcohol is comprised of a $C_1$-$C_4$ alcohol, more preferably, methanol or ethanol, and most preferably, methanol. In some embodiments, the suitable alcohol-containing solvent is a mixture of a $C_1$-$C_4$ alcohol with one or more other solvents other than an alcohol. Preferably, the other solvent is THF or 2-methyl-THF.

In some embodiments, said Grignard reagent or alkoxy magnesium halide contacting with a Drug Linker intermediate compound of Formula IC, Formula IIC, Formula IIIC, Formula VIC, and/or Formula VIIC is done in a 1:1 (v/v) mixture of methanol and 2-methyl-THF. In some embodiments, the Drug Linker intermediate compound of Formula IC, Formula IIC, Formula IIIC, Formula VIC, and/or Formula VIIC is dissolved in a 1:1 (v/v) mixture of methanol and 2-methyl-THF or 1:1 (v/v) mixture of methanol and THF, and the Formula IC, Formula IIC, Formula IIIC, Formula VIC, and/or Formula VIIC Drug Linker intermediate compound solution is contacted with a Grignard reagent or alkoxy magnesium halide. In preferred embodiments, the alcohol-containing alkoxy magnesium halide solution is formed in situ by contacting a Grignard reagent in an alcohol-containing solvent, which is then contacted with the Formula IC, Formula IIC, Formula IIIC, Formula VIC, and/or Formula VIIC Drug Linker intermediate compound solution.

In method embodiments reciting step (c), contacting of a Drug Linker intermediate compound of Formula IC, Formula IIC, Formula IIIC, Formula VIC, or Formula VIIC with an alcohol-containing solution of a Grignard reagent or alkoxy magnesium halide produces a deprotected Drug Linker intermediate product of Formula ID, Formula IID, Formula IIID, Formula VID, or Formula VIID in which the $R^6C(=O)$— hydroxyl protecting groups are removed by transesterification that produces a deprotected product that contains less than about wt. 10%, less than about wt. 7%, less than about wt 6%, less than about wt. 5%, less than about wt. 4%, less than about wt. 3%, of an impurity comprising a beta-eliminated glucuronic acid moiety of structure:

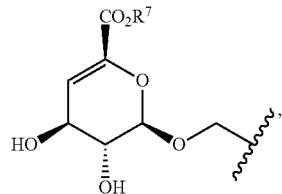

wherein the wavy line indicates the site of attachment to the phenyl moeity of a PAB (p-aminobenzyl) Self-Immolative Unit of a Drug Linker Intermediate compound of Formula ID, Formula IID, or Formula IIID, or the S* moiety of Compound VID or Compound VIID, or the S' moiety of Compound ID.

In certain embodiments of the preceding methods, the product of contacting of Drug Linker intermediate compound of Formula IC, Formula IIC, or Formula IIIC with a Grignard reagent or alkoxy magnesium halide is greater than about 90% pure, greater than about 93% pure, greater than about 94% pure, greater than about 95% pure, greater than about 96% pure, greater than about 97% pure as determined by HPLC.

In some embodiments of the preceding methods, the product of contacting of compound of Formula IC, Formula IIC, Formula IIIC, Formula VIC, or Formula VIIC with an alcohol-containing Grignard reagent or alkoxy magnesium halide is contacted with a first deprotecting agent wherein the first deprotecting agent removes the amine protecting group $Z^1$ and the carboxylic acid protecting group, wherein $Z^1$ and $R^7$ are as previously defined. Preferably, said second deprotecting agent contacting is done without isolation of the Drug Linker intermediate product of Formula ID, Formula IID, Formula IIID, Formula VID, or Formula VIID of said Grignard reagent or alkoxy magnesium halide contacting. In some preferred embodiments, said Grignard reagent or alkoxy magnesium halide contacting and said second deprotecting agent contacting are done sequentially in one pot. In some preferred embodiments, the second deprotecting agent is an aqueous-containing solution of a base. Preferably, the base is LiOH. In less preferred embodiments the alkoxy magnesium halide contacting and said second deprotecting agent contacting are done as separate and distinct steps with isolation of the intermediate product of Formula ID, Formula IID, Formula IIID, Formula VID, or Formula VIID.

Without being bound by theory, it is believed that the magnesium (II) species of the alkoxy magnesium halide, through complexation with the $R^6$—$C(=O)$ acyl protecting groups, which protects each hydroxyl groups in the form of an ester, preferentially promotes transesterification with the alcohol solvent or the alkoxy group that is also coordinated with magnesium (II) species to remove these acyl protecting groups over β-elimination of the C4-acyloxy substituent by that alkoxy group acting as a base. Preferably, the alkoxy component of the alkoxy magnesium halide reagent is derived from the same alcohol solvent in the acyl deprotection step so that transesterification with the ester that protects the C5-carboxylic acid functional group does not result in a mixture of deacylated intermediates differing at that position. According, in more preferred embodiments, the alcohol solvent used in the selective deprotection of the acyl protecting groups is the same as the alcohol component of the C5-carboxylic acid ester so that transesterification at that position does not alter the identity of that ester that would otherwise result in a mixture of deacylated intermediates. Based upon the same reasoning, in particularly preferred embodiments, acyl deprotection is conducted in the same alcohol solvent used to generate the alkoxy magnesium halide reagent and is the same as the alcohol component of the ester protecting the C5-carboxylic acid functional group.

In some embodiments of the preceding methods, the Drug Unit may be suitably protected with one or more protecting groups to prevent decomposition of D and/or side reactions during one or more steps of the presently claimed methods.

In some embodiments the Drug Unit in any one of the preceding methods incorporates a DNA damaging agent or a DNA minor groove binder.

Preferred DNA damaging agents in any one of Formulae IC, ID, IE, II, IIA, IIB, IIC, IID, IIE, III, IIIA, IIIB, IIIC, IIID, IIIE, IIIF, VIC, VID, VIIC and VIID are pyrrolobenzodiazepine (PBD) compounds, which are comprised of the following core structure:

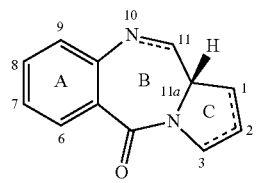

Thus, in some embodiments a preferred PBD Drug Unit of any one IC-E, II, IIA-E, III, IIIA-F, VIC, VID, VIIC and VIID that incorporates a Drug PBD dimer that is a DNA minor groove binder has the general structure of Formula X:

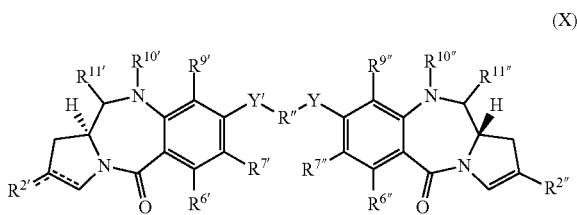

(X)

or a salt thereof, wherein: the dotted lines represent a tautomeric double bond; $R^{2''}$ is of formula XI:

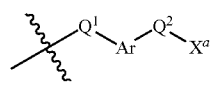

(XI)

wherein the wavy line indicates the site of covalent attachment to the remainder of the Formula X structure; Ar is an optionally substituted $C_{5-7}$ arylene; $X^a$ is a from a reactive or activateable group for conjugation to a Linker Unit, wherein X is selected from the group comprising: —O—, —S—, —C(O)O—, —C(O)—, —NHC(O)—, and —N($R^N$)—, wherein $R^N$ is H or $C_1$-$C_4$ alkyl, and $(C_2H_4O)_m$ $CH_3$, where subscript m is 1, 2 or 3; and either:
(i) $Q^1$ is a single bond; and $Q^2$ is a single bond or —Z—$(CH_2)_n$—, wherein Z is selected from the group consisting of a single bond, O, S, and NH; and subscript n is 1, 2 or 3, or (ii) $Q^1$ is —CH=CH—, and $Q^2$ is a single bond; and $R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent, wherein the dotted lines indicate a single bond to $R^{2'}$, or $R^{2'}$ an optionally substituted $C_1$-$C_4$ alkenylene, wherein the dotted lines indicate a double bond to $R^{2'}$; $R^{6''}$ and $R^{9'''}$ are independently selected from the group consisting of H, R, OH, OR, SH, SR, $NH_2$, NHR, NRR', nitro, $Me_3Sn$ and halo; $R^{7''}$ is selected from the group consisting of H, R, OH, OR, SH, SR, $NH_2$, NHR, NRR', nitro, $Me_3Sn$ and halo; and R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl; either:

(a) $R^{10'''}$ is H, and $R^{11'''}$ is OH or $OR^A$, wherein $R^A$ is $C_1$-$C_4$ alkyl, (b) $R^{10'''}$ and $R^{11'''}$ form a nitrogen-carbon double bond between the nitrogen and carbon atoms to which they are bound, or (c) $R^{10'''}$ is H and $R^{11'''}$ is $SO_zM$, wherein subscript z is 2 or 3 and M is a monovalent pharmaceutically acceptable cation, or (d) $R^{10'''}$, $R^{11'}$ and $R^{10'''}$ are each H and $R^{11'''}$ is $SO_zM$, or $R^{10'}$ and $R^{11'}$ are each H and $R^{10'''}$ and $R^{11'''}$ form a nitrogen-carbon double bond between the nitrogen and carbon atoms to which they are bound, or $R^{10'''}$, $R^{11'''}$ and $R^{10'}$ are each H and $R^{11'}$ is $SO_zM$, or $R^{10'''}$ and $R^{11'''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and R'' is a $C_{3-12}$ alkylene group, the carbon chain of which is optionally interrupted by one or more heteroatoms, in particular by one of O, S or $NR^{N2}$ (where $R^{N2}$ is H or $C_1$-$C_4$ alkyl), and/or by aromatic rings, in particular by one of benzene or pyridine; Y and Y' are selected from the group consisting of O, S, and NH; $R^{6'}$, $R^{7'}$, $R^{9'}$ are selected from the same groups as $R^{6''}$, $R^{7''}$ and $R^{9'''}$, respectively, and $R^{10'}$ and $R^{11'}$ are the same as $R^{10'''}$ and $R^{11'''}$, respectively, wherein if $R^{11'''}$ and $R^{11'}$ are $SO_zM$, each M is either a monovalent pharmaceutically acceptable cation or together represent a divalent pharmaceutically acceptable cation.

In other embodiments a preferred PBD Drug Unit of any one of Formula IC-E, II, IIA-E, III, IIIA-F, VIC, VID, VIIC and VIID that incorporates a PBD dimer that is a DNA minor groove binder has the general structure of Formula XI or XII:

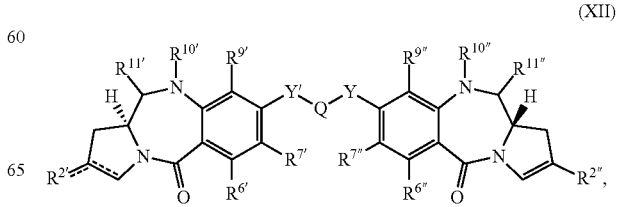

(XII)

-continued

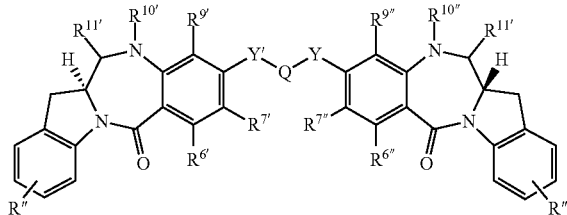

(XIII)

or a salt thereof, wherein: the dotted lines indicate a tautomeric double bond; Q is of formula XIV:

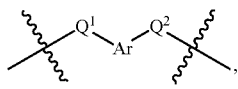

(XIV)

wherein the wavy lines indicate the sites of covalent attachment to Y' and Y in either orientation; Ar is a $C_{5-7}$ arylene group substituted by $X^a$ and is otherwise optionally substituted, wherein $X^a$ is from an activateable group for conjugation to a Linker Unit, wherein $X^a$ is selected from the group comprising: —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3; and either:

(i) $Q^1$ is a single bond; and $Q^2$ is a single bond or —(CH$_2$)$_n$—, wherein subscript n is 1, 2 or 3, or (ii) $Q^1$ is —CH=CH—, and $Q^2$ is a single bond or —CH=CH—; and $R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent, wherein the dotted lines indicate a single bond to $R^{2'}$, or $R^{2'}$ an optionally substituted $C_1$-$C_4$ alkenylene wherein the dotted lines indicate a double bond to $R^{2'}$; and $R^{2''}$ is an optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent; $R^{6''}$ and $R^{9''}$ are independently selected from the group consisting of H, R, OH, OR, SH, SR, NH$_2$, NHR, NRR', nitro, Me$_3$Sn and halo; $R^{7''}$ is selected from the group consisting of H, R, OH, OR, SH, SR, NH$_2$, NHR, NRR', nitro, Me$_3$Sn and halo; and R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl; and either:

(a) $R^{10''}$ is H, and $R^{11''}$ is OH or $OR^A$, wherein $R^A$ is $C_1$-$C_4$ alkyl, or (b) $R^{10''}$ and $R^{11''}$ form a nitrogen-carbon double bond between the nitrogen and carbon atoms to which they are bound, or (c) $R^{10''}$ is H and $R^{11''}$ is $SO_zM$, wherein subscript z is 2 or 3 and M is a monovalent pharmaceutically acceptable cation, or (d) $R^{10'}$, $R^{11'}$ and $R^{10''}$ are each H and $R^{11''}$ is $SO_zM$, or $R^{10'}$ and $R^{11'}$ are each H and $R^{10''}$ and $R^{11''}$ form a nitrogen-carbon double bond between the nitrogen and carbon atoms to which they are bound, or $R^{10''}$, $R^{11''}$ and $R^{10'}$ are each H and $R^{11'}$ is $SO_zM$, or $R^{10''}$ and $R^{11''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and Y and Y' are selected from the group consisting of O, S, and NH; R'' represents one or more optional substituents; and $R^{6'}$, $R^{7'}$, $R^{9'}$ are selected from the same groups as $R^{6''}$, $R^{7''}$ and $R^{9''}$, respectively, and $R^{10'}$ and $R^{11'}$ are the same as $R^{10''}$ and $R^{11''}$, respectively, wherein if $R^{11''}$ and $R^{11'}$ are $SO_zM$, each M is either a monovalent pharmaceutically acceptable cation or together represent a divalent pharmaceutically acceptable cation.

In more preferred embodiments of any one of Formula IC-E, II, IIA-E, III, IIIA-F, VIC, VID, VIIC and VIID the PBD dimer has the general structure of Formula X, Formula XI or Formula XIII in which one, $R^7$ is selected from the group consisting of H, OH and OR, wherein R is a previously defined for each of the formula, or is a $C_{1-4}$ alkyloxy group, in particular $R^{7''}$ is —OCH$_3$. In other more preferred embodiments, Y and Y' are O, $R^{9''}$ is H, or $R^{6''}$ is selected from the group consisting of H and halo.

In other more preferred embodiments of any one of Formula IC-E, II, IIA-E, III, IIIA-F, VIC, VID, VIIC and VIID the PBD dimer has the general structure of Formula X in which Ar is phenylene; $X^a$ is selected from the group consisting of —O—, —S— and —NH—; and $Q^1$ is a single bond, and in more preferred embodiments of Formula XII Ar is phenylene, X is selected from the group consisting of —O—, —S—, and —NH—, $Q^1$ —CH$_2$— and $Q_2$ is —CH$_2$—.

In particularly preferred embodiments of any one of Formula IC-E, II, IIA-E, III, IIA-F, VIC, VID, VIIC and VIID, the PBD dimer has the general structure of Formula X in which $X^a$ is NH, and other particularly preferred PBD Drug Units are of Formula X in which $Q^1$ is a single bond and $Q^2$ is a single bond.

In other particularly preferred embodiments of any one of Formula IC-E, II, IIA-E, III, IIIA-F, VIC, VID, VIIC and VIID, the PBD dimer has the general structure of Formula X, Formula XII or Formula XIII in which $R^{2'}$ is an optionally substituted $C_{5-7}$ aryl group so that the dotted lines indicate a single bond to $R^{2'}$ and the substituents when present are independently selected from the group consisting of halo, nitro, cyano, $C_{1-7}$ alkoxy, $C_{5-20}$ aryloxy, $C_{3-20}$ heterocyclyloxy, $C_{1-7}$ alkyl, $C_{3-7}$ heterocyclyl and bis-oxy-$C_{1-3}$ alkylene wherein the $C_{1-7}$ alkoxy group is optionally substituted by an amino group, and if the $C_{3-7}$ heterocyclyl group is a $C_6$ nitrogen containing heterocyclyl group, it is optionally substituted by a $C_{1-4}$ alkyl group.

In more particularly preferred embodiments of any one of Formula IC-E, II, IIA-E, III, IIIA-F, VIC, VID, VIIC and VIID, the PBD dimer has the general structure of Formula X, Formula XI or Formula XII in which Ar is an optionally substituted phenyl that has one to three such substituents when substituted.

In other more particularly preferred embodiments of any one of Formula IC-E, II, IIA-E, III, IIA-F, VIC, VID, VIIC and VIID, the PBD dimer has the general structure of Formula X, Formula XI or Formula XII in which $R^{10''}$ and $R^{11''}$ form a nitrogen-carbon double bond and/or $R^{6'}$, $R^{7'}$, $R^{9'}$, and Y' are the same as $R^{6''}$, $R^{7''}$, $R^{9''}$, and Y respectively.

In especially preferred embodiments of any one of Formula IC-E, II, IIA-E, III, IIIA-F, VIC, VID, VIIC and VIID, the PBD Drug Unit has the structure of:

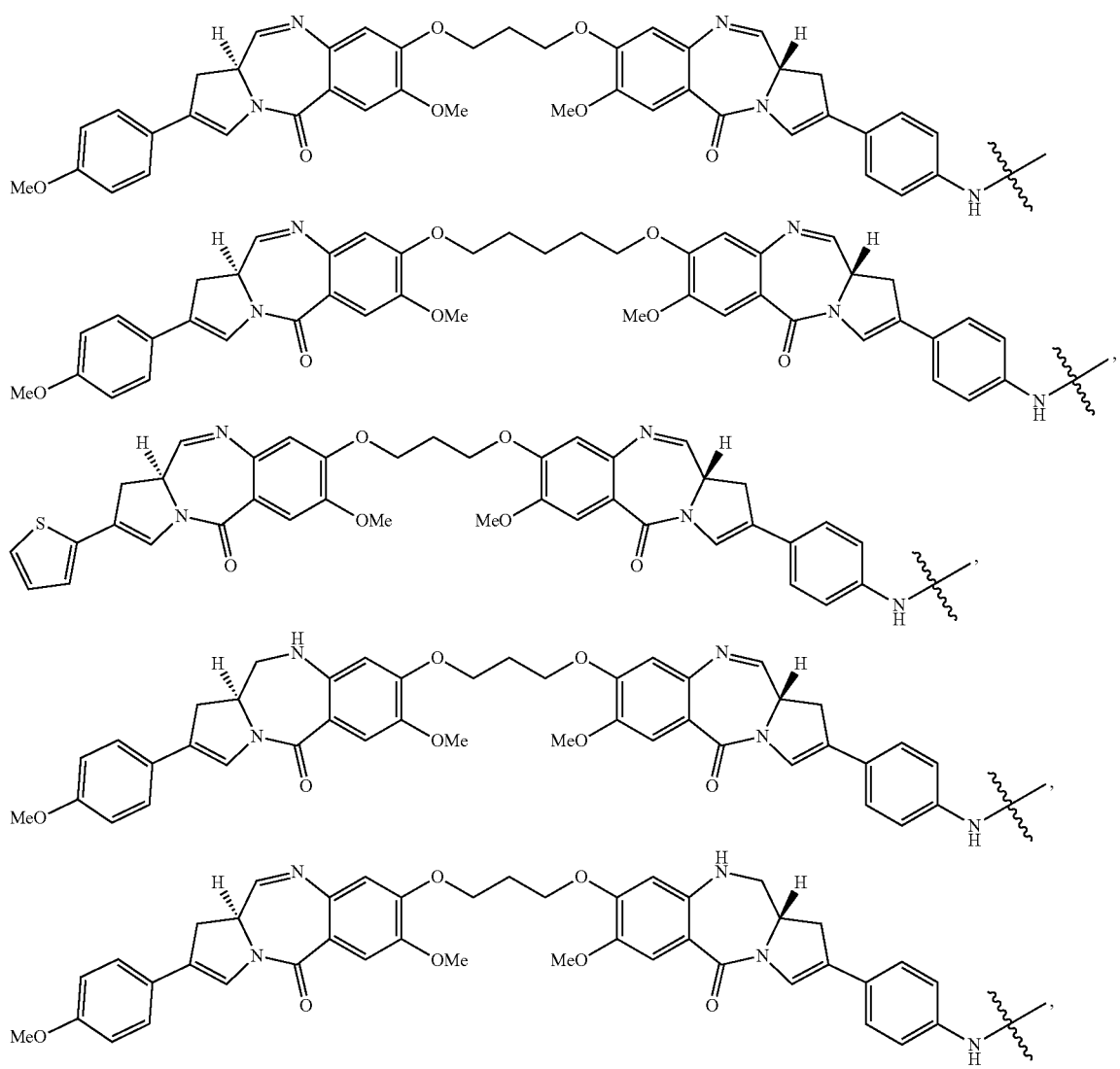
or a salt thereof, wherein the wavy line indicates the point of covalent attachment to S* in the form of a carbamate functional group.
In especially preferred embodiments of any one of Formula IC-E, H, IIA-E, III, IIIA-F, VIC, VID, VIIC and VIID, the PBD Drug Unit has the structure of:
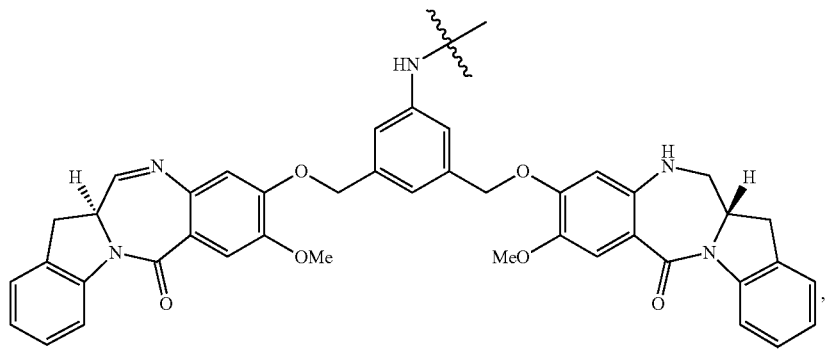 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

or a salt thereof, wherein the wavy line indicates the point of covalent attachment to S* in the form of a carbamate functional group.

In other especially preferred embodiments a Drug Linker compound intermediate of Formula IE or Formula VIIE in which D is a PBD Drug Unit has the structure of:

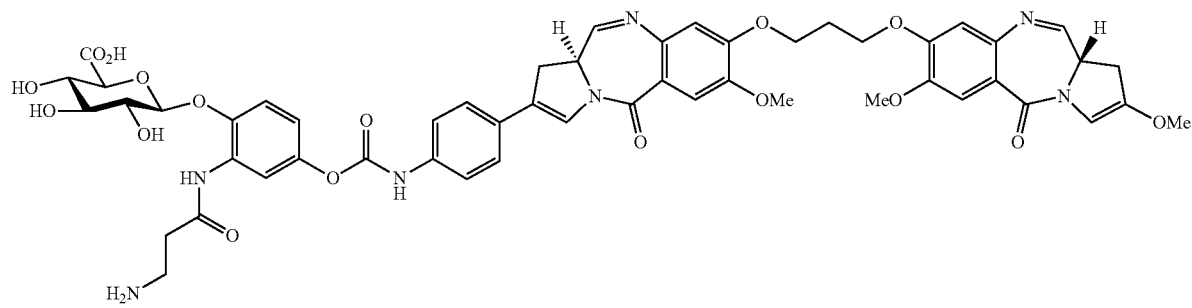

or a salt thereof.

In some instances during the transesterification step for selectively removing the glucuronide acyl protecting groups in any one of the methods for preparing a glucuronide-based Drug Linker compound having PBD Drug Unit, alcohol solvent or the alkoxy moiety of an alkoxy magnesium halide reagent used for that purpose adds across the imine bond of the PBD dimer incorporated therein to form a carbinolamine ether. In other instances, water may also add across that imine bond during the subsequent removal of the FMOC and C5 ester protecting groups to form a carbinolamine and/or water may displace the alcohol of the carbinolamine ether, if formed during the acyl deprotection, also forming the carbinolamine. Those reactions, which are reversible, are illustrated below for a PBD monomer where the solvent is water or an alcohol ($R^4$OH, wherein $R^4$ is $C_1$-$C_4$ alkyl):

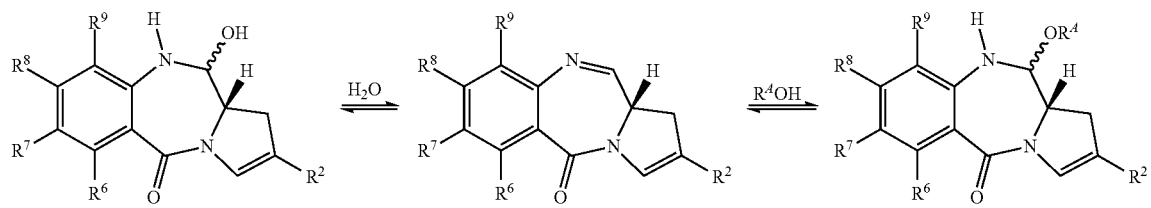

Other preferred DNA damaging agents are anthracyclins, whose cytotoxicity to some extent may also be due topoisomerase inhibition. Accordingly, other preferred embodiments of any one of Formula IC-E, II, IIA-E, III, IIIA-F, VIC, VID, VIC and VIID have a anthracyclin Drug Unit that incorporates an anthracyclin compound. In some of those embodiments a preferred anthracyclin has a structure disclosed in Minotti, G., et al., "Anthracyclins: molecular advances and pharmacologic developments in antitumor activity and cardiotoxicity" *Pharmacol Rev.* (2004) 56(2): 185-229. In more preferred embodiments, an anthracyclin that is incorporated into an anthracyclin Drug Unit for any one of Formula IC-E, II, IIA-E, III, IIIA-F, VIC, VID, VIIC and VIID is doxorubicin, idarubicin, daunorubicin, doxorubicin propyloxazoline (DPO) or cyanomorpholino-doxorubicin.

In particularly preferred embodiments a Drug Linker compound intermediate of Formula IE or Formula VIIE in which D is an anthracyclin Drug Unit has the structure of:

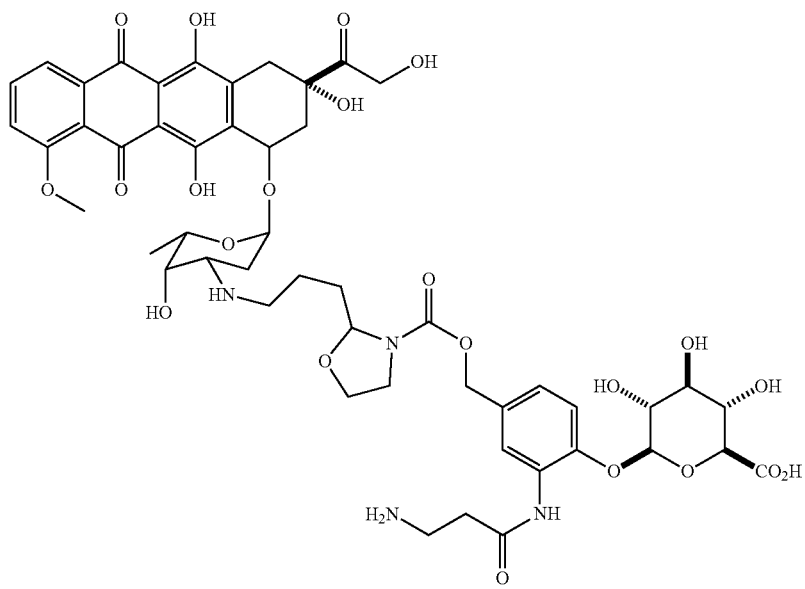

or a salt thereof.

Other preferred DNA minor groove binders that are topoisomerase inhibitors are camptothecin compounds. Accordingly, other preferred embodiments of any one of Formula IC-E, II, IIA-E, III, IIIA-F, VIC, VID, VIIC and VIID have camptothecin Drug Unit that incorporates an camptothecin compound. In some of those embodiments a preferred camptothecin has a structure disclosed in Zunino, F. et al. "Current status and perspectives in the development of camptothecins" Curr. Pharm. Des. (2002) 8(27): 2505-2520 in which there is a primary or secondary amine substituent as the reactive functional group $X^a$ that provides the site of attachment for its incorporation into a camptothecin Drug Unit.

In more preferred embodiments, an camptothecin compound that is incorporated into an camptothecin Drug Unit for any one of Formula IC-E, II, IIA-E, III, IIIA-F, VIC, VID, VIIC and VIID has the general structure of:

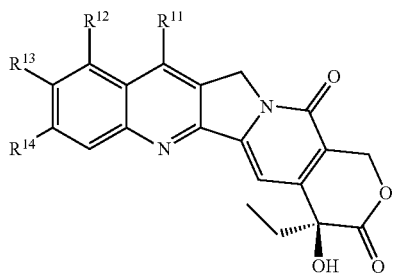

wherein one of $R^{11}$ is n-butyl and one of $R^{12}$-$R^{14}$ is —$NH_2$ and the other are hydrogen, or $R^{12}$ is —$NH_2$ and $R^{13}$ and $R^{14}$ together are —$OCH_2O$—.

In particularly preferred embodiments a Drug Linker compound intermediate of Formula IE or Formula VIIE in which D is an camptothecin Drug Unit has the structure of:

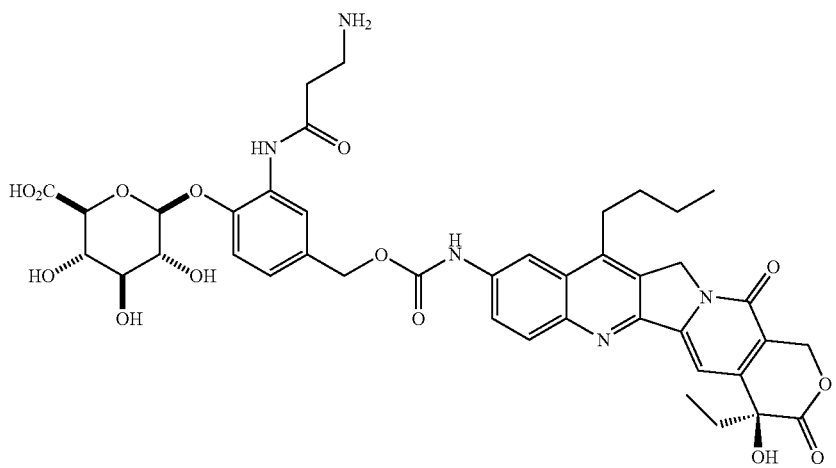

Still other preferred DNA damaging agents are CPI compounds, which have the core structure of 1,2,8,8a-tetrahydrocyclopropa[c]pyrrolo[3,2-e]indoi-4(5H)-one, CBI compounds, which have the core structure of 1,2,9,9a-tetrahydrocyclopropa-[c]benz[e]indol-4-one, and seco analogs thereof in which the alkylating cyclopropyl moiety of the CPT or CBI pharmacophore is in nascent ring opened form and is convertible to the DNA damaging species through an intramolecular cyclization as described by Ghosh, N. et al. "Chemical and biological evaluations of the family of CC-1065 and the duocarmycin natural products" Curr. Topics in Med. Chem. (2009) 9: 1494-152. As those compounds are related in structure to the natural product duocarmycin, Drug Units incorporating such compounds are collectively referred to as duocarmycin Drug Units. In preferred embodiments of any one of Formula IC-E, II, IIA-E, III, IIIA-F, VIC, VID, VIIC and VIID a duocarmycin Drug Unit incorporates a CBI compound having a hydroxyl or amine substituent on its benzoid aromatic ring, which is the reactive functional group $X^a$ that allows for that incorporation.

In particularly preferred embodiments a Drug Linker compound intermediate of Formula IE or Formula VIIE in which D is an duocarmycin Drug Unit has the structure of:

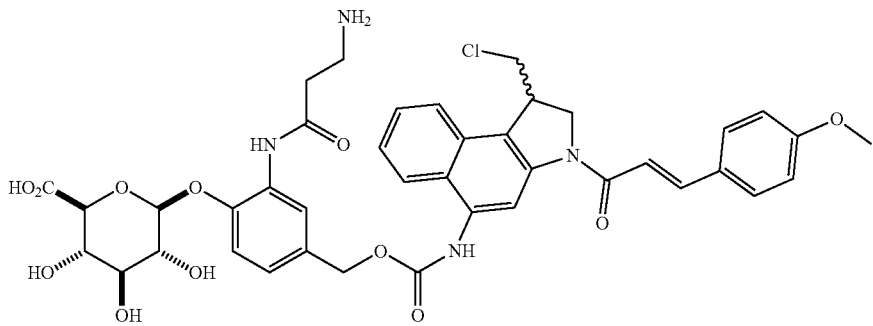

In certain embodiments of the preceding methods, the Self-Immolating Unit S* comprises a methylene carbamate as when S' of Formula IC, Formula ID or Formula IE has the structure of —$NR^N$—$C(R^1)(R^2)$—, wherein $R^N$, $R^1$ and $R^2$ independently are hydrogen, optionally substituted $C_1$-$C_6$ alkyl, optionally substituted $C_6$-$C_{14}$ aryl, or optionally substituted C-linked $C_5$-$C_8$ heteroaryl, or $R^N$ and $R^1$ together with the nitrogen and carbon atoms to which they are attached comprise an azetidinyl, pyrrolodinyl, piperidinyl or homopiperidinyl moiety, and $R^2$ is hydrogen. In preferred embodiments S' has the structure of —$NR^N$—$CH_2$— wherein $R^N$ is hydrogen or —$CH_2CH_2$-EWG, wherein EWG is an electron withdrawing group.

Those and other aspects of the present invention may be more fully understood by reference to the following detailed, non-limiting examples of specific embodiments. Particular materials used, protocols and conditions are intended to be further illustrative of the inventions and should not be construed to limit the reasonable scope thereof.

Numbered Embodiments

The following numbered embodiments further illustrate various aspects of the invention and are not intended to limit the invention in any way.

1. A method for preparing a Drug Linker intermediate compound of Formula IID:

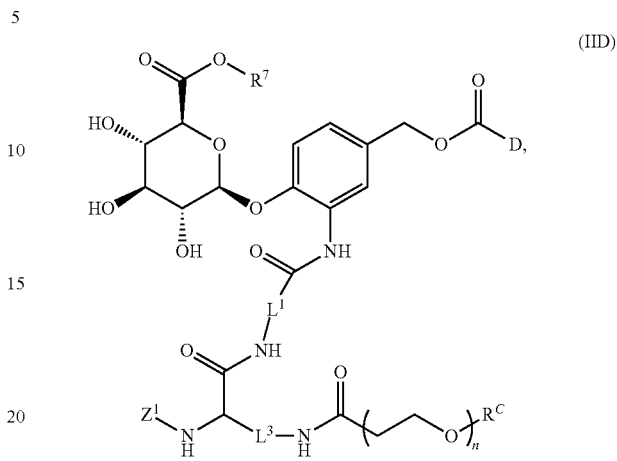

or a salt thereof, wherein D is a Drug Unit incorporating a DNA minor groove binder, DNA damaging agent or DNA replication inhibitor having an amine functional group capable of forming a carbamate functional group; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene such that —$OR^7$ provides for an ester functional group that is a suitable carboxylic acid protecting group; $Z^1$ is a first suitable amino protecting group; $R^C$ is hydrogen or a PEG Capping Unit; and subscript n ranges from 2 to 24, the method comprising the step of:

(c) contacting a compound of Formula IIC with a Grignard reagent or an alkoxy magnesium halide with either in a suitable alcohol-containing solvent, wherein the Formula IIC compound has the structure of:

(IIC)

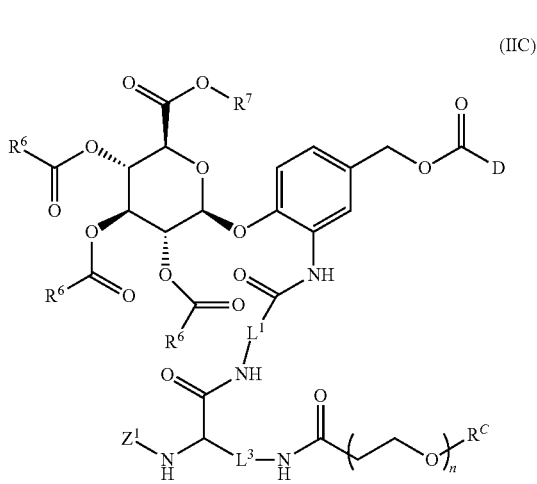

or a salt thereof, wherein each of $R^6$ is independently optionally substituted $C_1$-$C_8$ alkyl, optionally substituted $C_6$-$C_{10}$ arylene or optionally substituted $C_5$-$C_{10}$ heteroarylene so that $R^6C$(=O)— provides for an ester functional group that is a suitable hydroxyl protecting group; and the remaining variable groups are as previously described by Formula IID; and wherein said Grignard reagent or an alkoxy magnesium halide contacting selectively removes the hydroxyl protecting groups to provide the Formula IIC compound.

2. A method for preparing a Drug Linker intermediate compound of Formula IIIE:

(IIE)

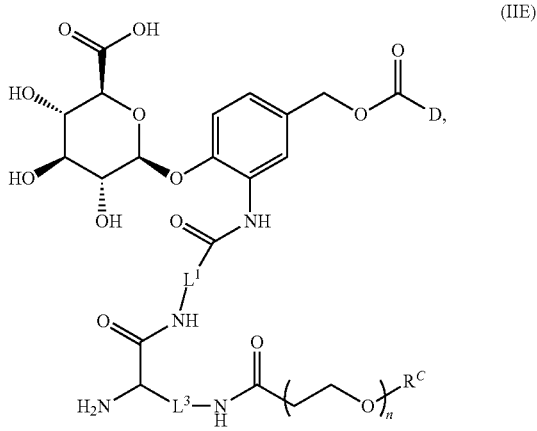

or a salt thereof, wherein D is a Drug Unit incorporating a DNA minor groove binder, DNA damaging agent or DNA replication inhibitor having an amine functional group capable of forming a carbamate functional group; each of $L^1$ and $L^2$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^7$ is optionally substituted $C_1$-$C_8$ alkyl, optionally substituted $C_6$-$C_{10}$ arylene or optionally substituted $C_5$-$C_{10}$ heteroarylene such that —$OR^7$ provides for ester functional group that is a suitable carboxylic acid protecting group; $R^C$ is hydrogen or a PEG Capping Unit; and subscript n ranges from 2 to 24, the method comprising the steps of:

(c) contacting a Drug Linker intermediate compound of Formula IIC with a Grignard reagent or an alkoxy magnesium halide with either in a suitable alcohol-containing solvent, wherein the Formula IIC Drug Linker intermediate compound has the structure of:

(IIC)

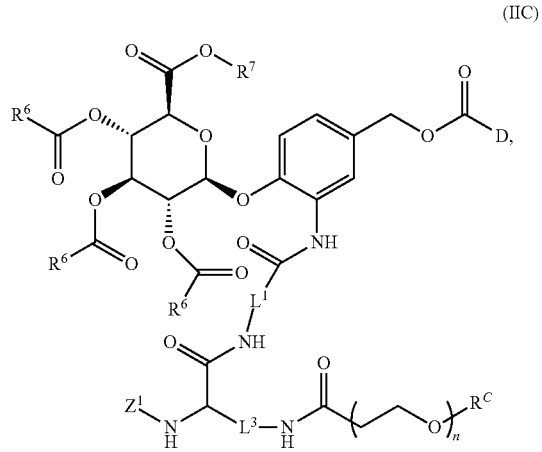

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene such that $R^6C$(=O)— provides for an ester functional group that is a suitable hydroxyl protecting group and —$OR^7$ provides an ester functional group that is a suitable carboxylic acid protecting group; $Z^1$ is a first suitable amino protecting group; and the remaining variable groups are as previously defined for Formula IIE, wherein said Grignard reagent or alkoxy magnesium halide contacting selectively removes the hydroxyl protecting groups; and (d) contacting the product of step (a) with a first deprotecting agent, wherein said first deprotecting agent contacting removes the amine and carboxylic acid protecting groups to provide the Formula IIE Drug Linker intermediate compound.

3. The method of embodiment 1 or 2, wherein each of $L^1$ and $L^3$ is independently $C_1$-$C_4$ alkylene.

4. The method of embodiment 1, wherein the Formula IIC and Formula IID Drug Linker intermediate compounds, optionally in salt form, have the structures of:

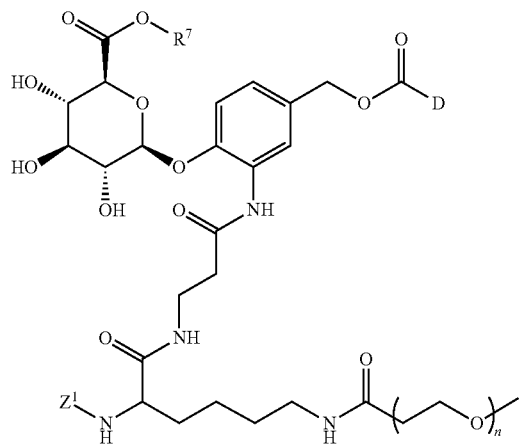

-continued and

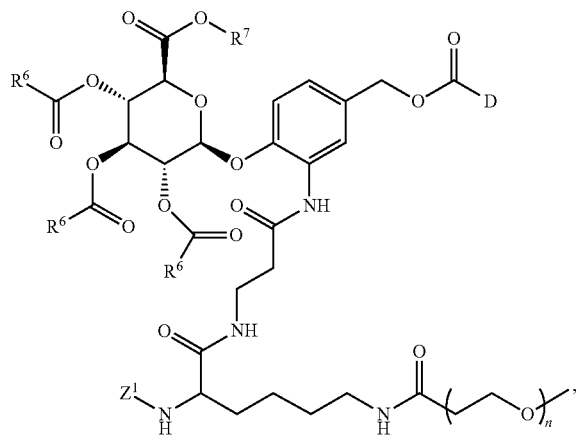

5. The method of embodiment 2, wherein the Formula IIC and Formula IIE Drug Linker intermediate compounds, optionally in salt form have the structures of:

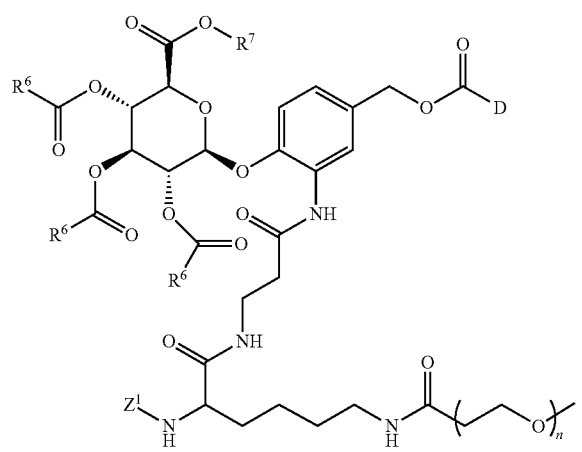

and

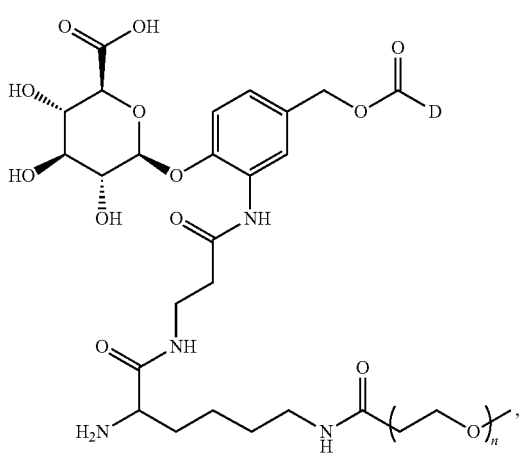

6. A method for preparing a Drug Linker compound of Formula II

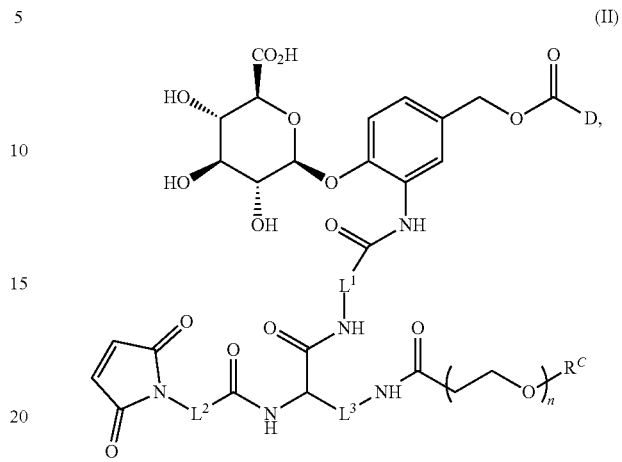

or a salt thereof, wherein D is a Drug Unit incorporating a DNA minor groove binder, DNA damaging agent or DNA replication inhibitor having an amine functional group capable of forming a carbamate functional group; each of $L^1$, $L^2$, and $L^3$ is independently selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; and subscript n ranges from 2 to 24, the method comprising the steps of:

(a) contacting a Drug Linker intermediate compound of Formula IIA with a second deprotecting agent, wherein the Formula IIA Drug Linker intermediate compound has the structure of:

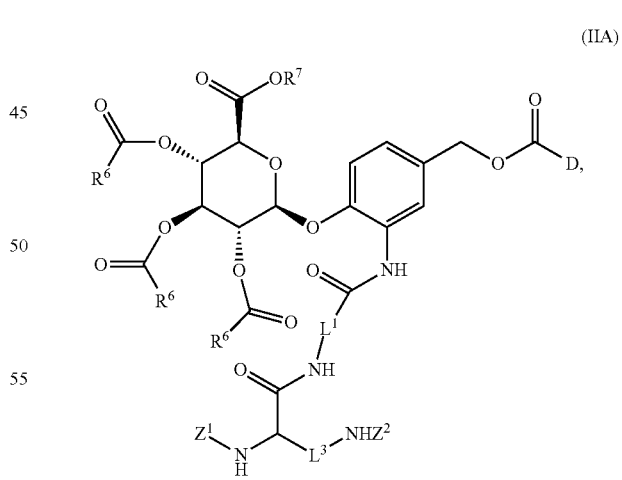

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene such that $R^6C(=O)$— provides for an ester functional group that is a suitable hydroxyl protecting group and —$OR^7$ provides an ester functional group that is a suitable carboxylic acid protecting group; $Z^1$ and $Z^2$ is independently a first and second suitable amino protecting group, respectively; and the remaining variable groups as previously defined by Formula II, wherein said second deprotecting agent contacting selectively removes the $Z^2$ amino protecting group to provide a Drug Linker intermediate compound of Formula IIB:

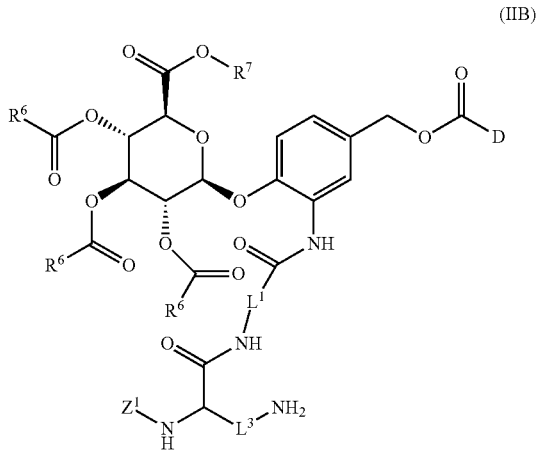

(IIB)

or a salt thereof, wherein the variable groups are as previously defined;

(b) contacting the Formula IIB compound in a suitable solvent with a compound of Formula iv:

(iv)

wherein $R^8$ is an activated ester group; and the remaining variable groups are as previously defined by Formula II, or (b') contacting the Formula IIB Drug Linker intermediate compound in a suitable solvent with a compound of Formula iv in which $R^8$ is —COOH and the remaining variable groups are as previously defined by Formula II in the presence of a first activating agent, wherein said contacting of step (b) or (b') provides a Drug Linker intermediate compound of Formula IIC:

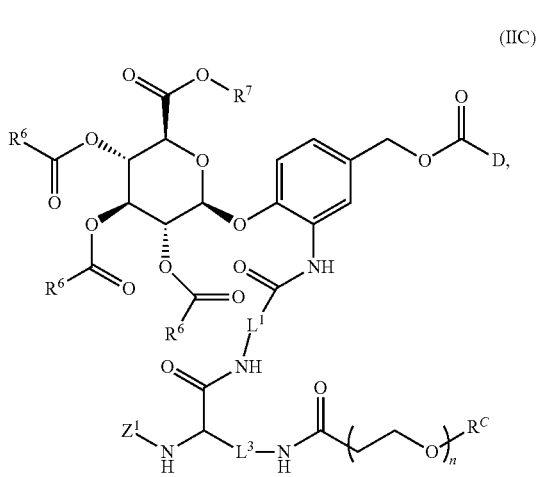

(IIC)

or a salt thereof, wherein the variable groups are as previously defined by Formula IIB and Formula iv;

(c) contacting the Formula IIC Drug Linker intermediate compound with either a Grignard reagent or an alkoxy magnesium halide with either in a suitable alcohol-containing solvent, wherein said Grignard reagent or an alkoxy magnesium halide contacting selectively removes the hydroxyl protecting groups to provide a Drug Linker intermediate compound of Formula IID:

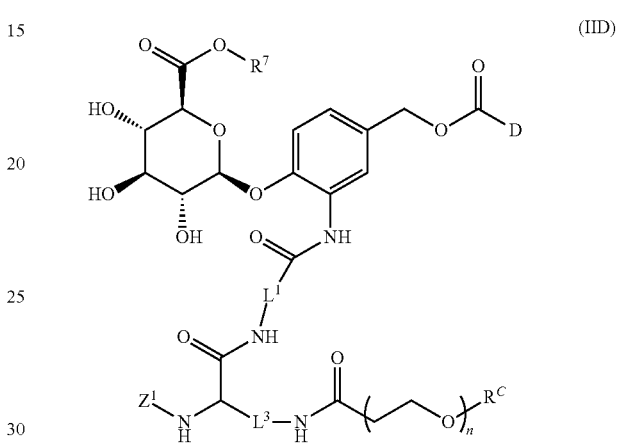

(IID)

or a salt thereof, wherein the variable groups are as previously defined by Formula IIB and Formula iv;

(d) contacting the Formula IID Drug Linker intermediate compound with a first deprotecting agent, wherein said deprotecting agent contacting removes the amine and carboxylic acid protecting groups to provide a Drug Linker intermediate compound of Formula IIE:

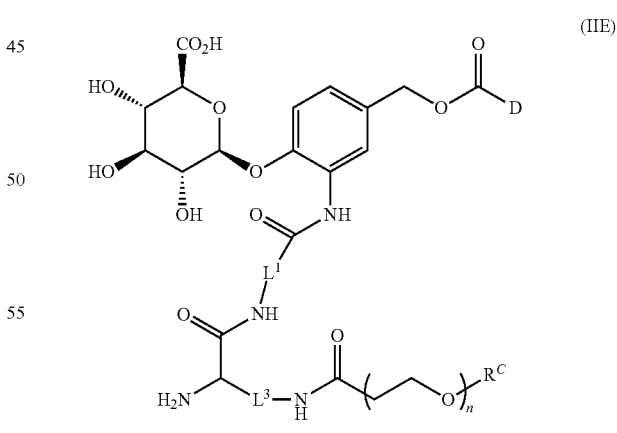

(IIE)

or a salt thereof, wherein the variable groups are as previously defined by Formula IIB and Formula iv; and (e) contacting the Formula IIE Drug Linker intermediate compound in a suitable solvent with a compound of Formula v:

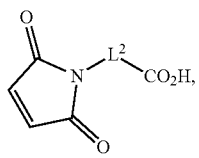

or a salt thereof, wherein $L^2$ is as previously defined by Formula II, in the presence of a second activating agent; and wherein said Formula v contacting provides the Formula II Drug Linker compound or salt thereof.

7. The method of embodiment 6, wherein each of $L^1$ and $L^3$ is independently $C_1$-$C_4$ alkylene and $L^2$ is independently optionally substituted $C_1$-$C_4$ alkylene.

8. A method for preparing a Drug Linker compound of Formula III:

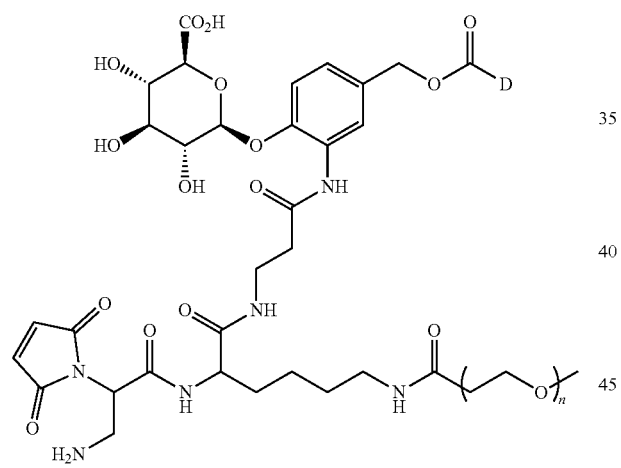

(III)

or a salt thereof, wherein D is a Drug Unit incorporating a DNA minor groove binder, DNA damaging agent or DNA replication inhibitor having an amine functional group capable of forming a carbamate functional group; and subscript n ranges from 2 to 24, the method comprising the steps of:

(a) contacting a Drug Linker intermediate compound of Formula IIIA with a second deprotecting agent wherein the Formula IIIA Drug Linker intermediate compound has the structure of:

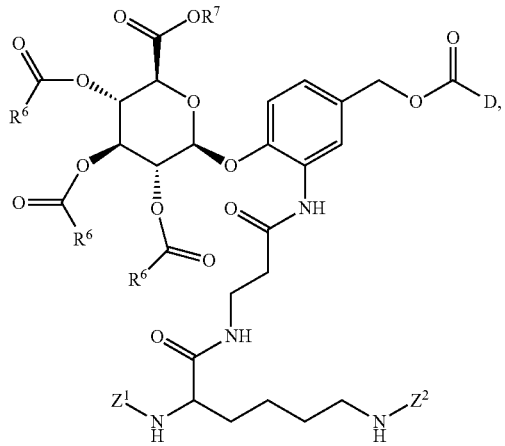

(IIIA)

or a salt thereof, wherein each of $R^6$ and $R^7$ is independently optionally substituted $C_1$-$C_8$ alkyl, optionally substituted $C_6$-$C_{10}$ arylene or optionally substituted $C_5$-$C_{10}$ heteroarylene such that $R^6C(=O)$— provides for an ester functional group that is a suitable hydroxyl protecting group and —$OR^7$ provides an ester functional group that is a suitable carboxylic acid protecting group; each of $Z^1$ and $Z^2$ is independently a first and second suitable amino protecting group, respectively, wherein said second deprotecting agent contacting provides a Drug Linker intermediate compound of Formula IIIB:

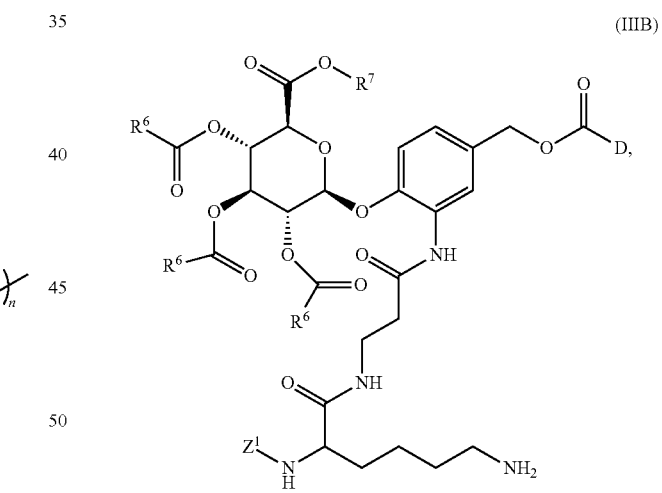

(IIIB)

or a salt thereof, wherein the variable groups are as previously defined;

(b) contacting the Formula IIIB Drug Linker intermediate compound in a suitable solvent with a compound of Formula iv:

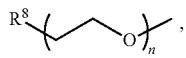

(iv)

wherein $R^8$ is an activated ester; and subscript n is as previously defined by Formula III, or (b') contacting the Formula IIIB Drug Linker intermediate compound in a suitable solvent in which $R^8$ is —COOH and subscript n is a previously defined by Formula III in the presence of a first activating agent, wherein said contacting of step (b) or (b') provides a Drug Linker intermediate compound of Formula IIIC:

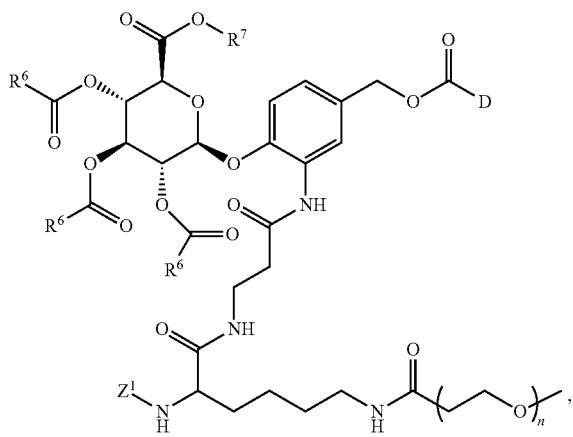
(IIIC)

or a salt thereof, wherein the variable groups are as previously defined by Formula IIIB;

(c) contacting the Formula IIIC Drug Linker intermediate compound with a Grignard reagent or an alkoxy magnesium halide with either in a suitable alcohol-containing solvent, wherein said Grignard reagent or an alkoxy magnesium halide contacting selectively removes the hydroxyl protecting groups to provide a Drug Linker intermediate compound of Formula IIID:

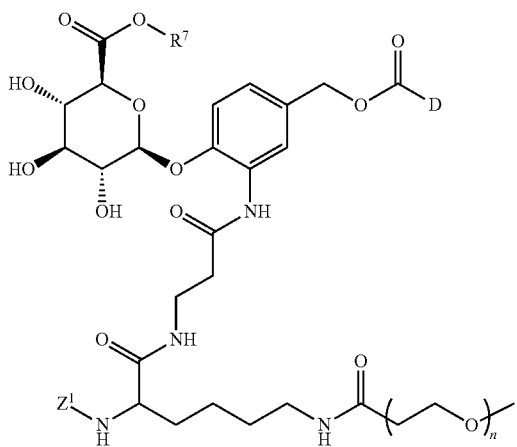
(IIID)

or a salt thereof, wherein the variable groups are as previously defined;

(d) contacting the Formula IIID Drug Linker intermediate compound with a first deprotecting agent, wherein said first deprotecting agent contacting removes the amine and carboxylic acid protecting groups to provide a Drug Linker intermediate compound of Formula IIIE:

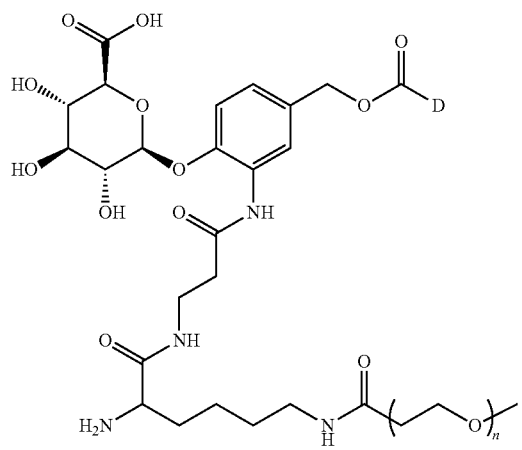
(IIIE)

or a salt thereof, wherein the variable groups are as previously defined by Formula I;

(e) contacting the Formula IIIE Drug Linker intermediate compound with a compound of Formula v:

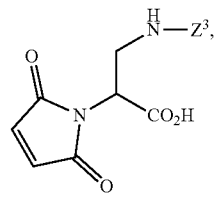
(v)

or a salt thereof, wherein $Z^3$ is a third suitable amino protecting group, in the presence of a third activating agent to form a Drug Linker intermediate compound of Formula IIIF:

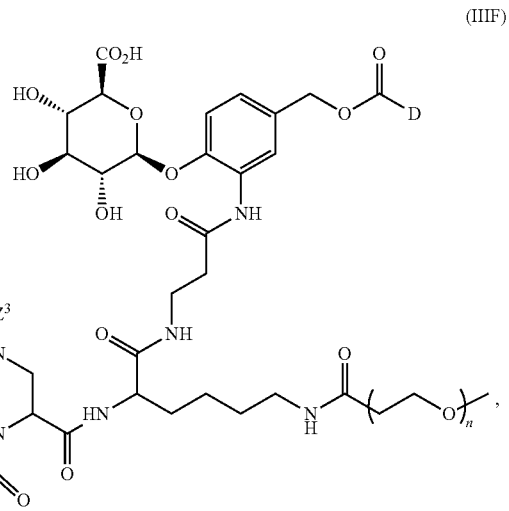
(IIIF)

or a salt thereof, wherein the variable groups are as previously defined by Formula III and Formula v; and (d) contacting the Formula IIIF Drug Linker intermediate compound of with a third deprotecting agent, wherein said third deprotecting reagent contacting removes the $Z^3$ amino protecting group whereby the Formula III Drug Linker compound or salt thereof is provided.

9. The method of embodiment 8, wherein $Z^3$ is an acid-labile amino protecting group, in particular —C(═O)O-t-Bu.

10. The method of any one of embodiments 1 to 9, wherein $Z^1$ has the formula:

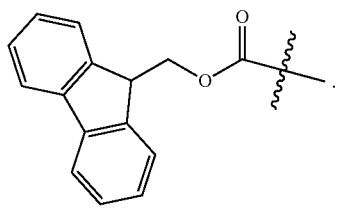 [SMILES: *C(=O)OCC1c2ccccc2-c2ccccc21]

11. The method of any one of embodiments 1 to 10, wherein $Z^2$ has the formula:

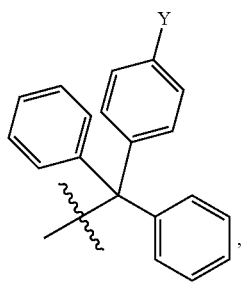

wherein Y is a H or OMe.

12. The method of embodiment 11, wherein Y is OMe.

13. The method of any one of embodiments 6 to 12, wherein the Formula iv compound has the structure of:

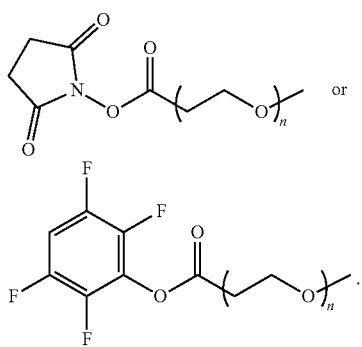

14. The method of any one of embodiments 1 to 13, wherein subscript n ranges from 8 to 16.

15. The method of embodiment 14, wherein subscript n is 12.

16. The method of any one of embodiments 6 to 15, wherein $Z^3$ of the Formula v compound is BOC, which is —C(═O)—O-t-Bu.

17. The method of any one of embodiment 6 to 16, wherein the second or third deprotecting agent for removal of $Z^2$ or $Z^3$, respectively, is an aqueous-containing acid solution having a pKa ranging from about 0 to about 3.

18. The method of embodiments 17, wherein the acid of the aqueous-containing acid solution is trifluoroacetic acid or trichloroacetic acid.

19. The method of any one of embodiments 1 to 18, wherein the Grignard reagent has the formula of $R^gMgX$ and the alkoxy magnesium halide has the formula of $R^gOMgX$, wherein Re is $C_1$-$C_5$ alkyl and X is I, Br, or Cl.

20. The method of embodiment 19, wherein the Grignard reagent is MeMgI or MeMgCl.

21. The method of embodiment 19, wherein the alkoxy magnesium halide is MeOMgI or MeOMgCl.

22. The method of any one of embodiments 1 to 21, wherein the alcohol-containing solvent comprises a $C_1$-$C_4$ alcohol.

23. The method of embodiment 22, wherein the alcohol-containing solvent further comprises THF.

24. The method of embodiment 23, wherein the solvent is a 1:1 (v/v) mixture of methanol and THF.

25. The method any one of embodiments 1 to 24, wherein the deprotecting agent for removal of $Z^1$ is an aqueous-containing solution of LiOH.

26. The method of any one of embodiments 6 to 25, wherein said Grignard reagent or alkoxy magnesium halide contacting and said deprotecting agent contacting to remove $Z^1$ are done sequentially in one pot.

27. The method of any one of embodiments 6 to 26, wherein the first activating agent for said Formula iv contacting is a solution of: N-(3-dimethylaminopropyl)-N'-ethylcarbodiimide hydrochloride (EDC.HCl), 2-ethoxy-1-ethoxycarbonyl-1,2-dihydroquinoline (EEDQ), (1-cyano-2-ethoxy-2-oxoethylidenaminooxy)dimethylamino-morpholino-carbenium hexafluorophosphate (COMU), N-(3-dimethylaminopropyl)-N'-ethylcarbodiimide hydrochloride/N-Hydroxysuccinimide, O-(7-azabenzotriazol-1-yl)-N,N,N',N'-tetramethyluronium hexafluorophosphate (HATU), diphenyl phosphoryl azide (DPPA), chloro-N,N,N',N'-bis(tetramethylene)formamidinium tetrafluoroborate, fluoro-N,N,N',N'-bis(tetramethylene)formamidinium hexafluorophosphate, N,N'-dicyclohexylcarbodiimide, N-(3-dimethylaminopropyl)-N'-ethylcarbodiimide hydrochloride, 1,1'-carbonyldiimidazole, 2-chloro-1,3-dimethyl-imidazolidinium tetrafluoroborate, (benzotriazol-1-yloxy)tripyrrolidinophosphonium hexafluorophosphate, O-(7-azabenzotriazol-1-yl)-N,N,N',N'-tetramethyluronium hexafluorophosphate, 2-chloro-1-methylpyridinium iodide, or propylphosphonic anhydride.

28. The method of embodiment 27, wherein the first activating agent for said Formula iv contacting is a solution of EDC. HCl, EEDQ or COMU.

29. The method of embodiment 28, wherein the first activating agent for said Formula iv contacting is a solution of COMU.

30. A Drug Linker intermediate compound or Drug Linker compound, wherein the Drug Linker intermediate compound or Drug Linker compound, has the structure of:

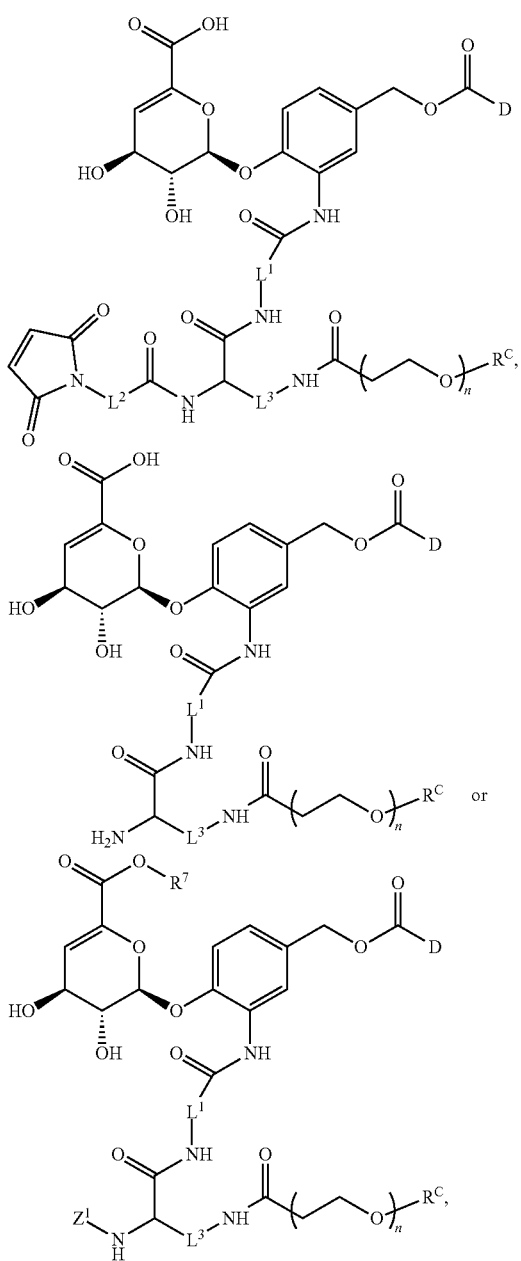

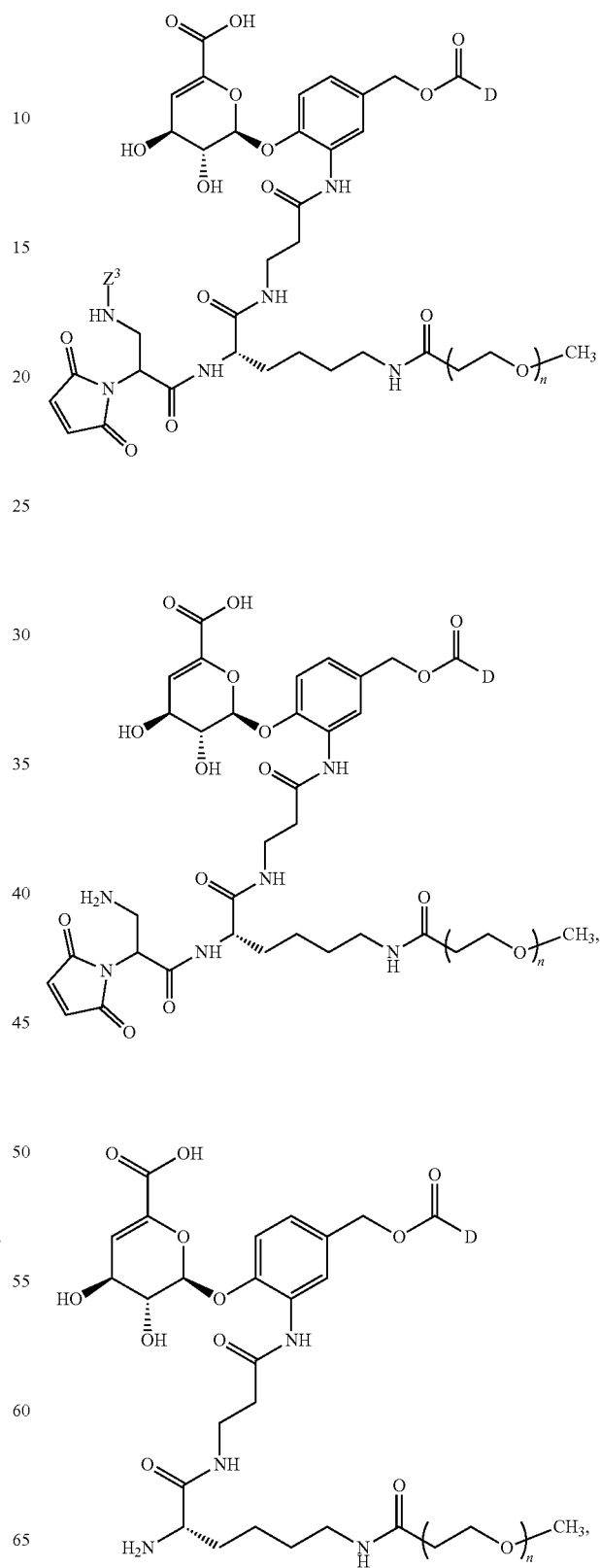

optionally in salt form, wherein D is a Drug Unit incorporating a DNA minor groove binder, DNA damaging agent or DNA replication inhibitor having an amine functional group capable of forming a carbamate functional group;

$L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo, in particular $L^1$, $L^2$ and $L^3$ are independently $C_1$-$C_4$ alkyl and $L^2$ is independently optionally substituted $C_1$-$C_4$ alkyl; $Z^1$ is a first suitable amino protecting group; $R^7$ is optionally substituted $C_1$-$C_8$ alkyl, optionally substituted $C_6$-$C_{10}$ arylene or optionally substituted $C_5$-$C_{10}$ heteroarylene; $R^C$ is hydrogen or a PEG Capping Unit; and subscript n ranges from 2 to 24, in particular, subscript n is 8 or 12 and/or the Drug Linker intermediate or Drug Linker compound has the structure selected from the group consisting of:

-continued

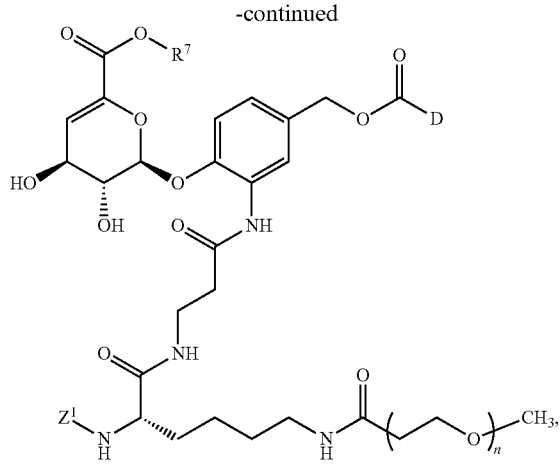

and salts thereof, wherein $Z^3$ is a third suitable amino protecting group that is acid-labile, particularly a carbamate having the structure of —C(=O)O—$R^8$, wherein $R^8$ is $C_1$-$C_4$ alkyl or optionally substituted phenyl; and $R_7$ is a $C_1$-$C_4$ alkyl, particularly methyl or ethyl.

31. A composition comprising Antibody Drug Conjugates represented by Formula 1 and Formula 1A, optionally in salt form, in particular in pharmaceutically acceptable salt form, having the structures of:

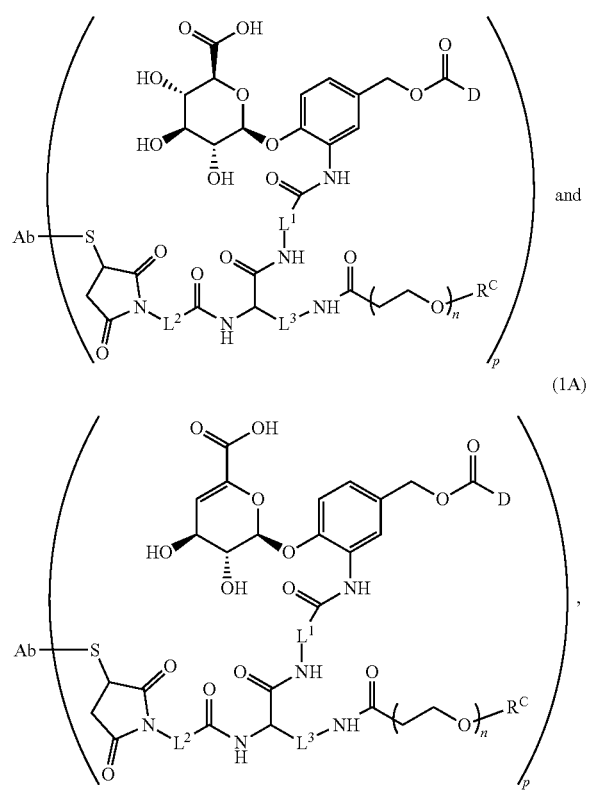

wherein Ab is an antibody; S is a sulfur atom from the antibody; D is a Drug Unit incorporating a DNA minor groove binder, DNA damaging agent or DNA replication inhibitor having an amine functional group capable of forming a carbamate functional group;

$L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; subscript n ranges from 2 to 24; and subscript p ranges from about 1 to about 16, wherein the composition contains no more than 10 wt. %, in particular no more than 5 wt. %, of Formula 1A Antibody Drug Conjugate.

32. A composition comprising Antibody Drug Conjugates represented by Formula 2 and Formula 2A, optionally in salt form, in particular in pharmaceutically acceptable salt form, having the structures of:

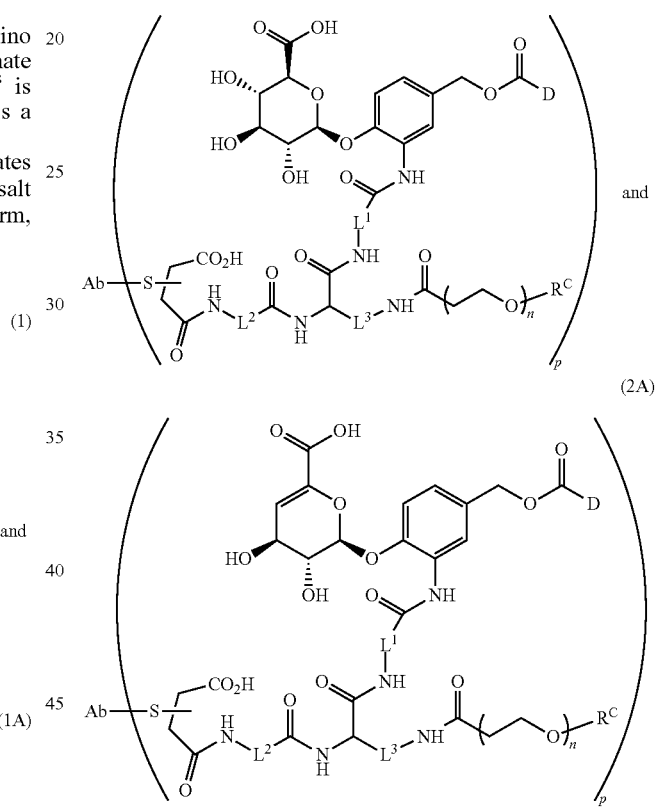

wherein Ab is an antibody; S is a sulfur atom from the antibody; the Ab-S-moeity is attached to the carbon atom a or 3 to the carboxylic acid functional group;

D is a Drug Unit incorporating a DNA minor groove binder, DNA damaging agent or DNA replication inhibitor having an amine functional group capable of forming a carbamate functional group;

$L^1$, $L^2$ and $L^3$, independently are selected from the group consisting of optionally substituted $C_1$-$C_{20}$ alkylene, optionally substituted $C_4$-$C_{20}$ heteroalkylene, optionally substituted $C_3$-$C_8$ carbocyclo, optionally substituted $C_6$-$C_{10}$ arylene, optionally substituted $C_5$-$C_{10}$ heteroarylene and optionally substituted $C_3$-$C_8$ heterocyclo; $R^C$ is hydrogen or a PEG Capping Unit; subscript n ranges from 2 to 24; and subscript p ranges from about 1 to about 16, wherein the composition contains no more than 10 wt. % Formula 2A Antibody Drug Conjugate, in particular, the Formula 2 and Formula 2A Antibody drug Conjugates, optionally in salt form, in particular in pharmaceutically acceptable salt form, have the structures of:

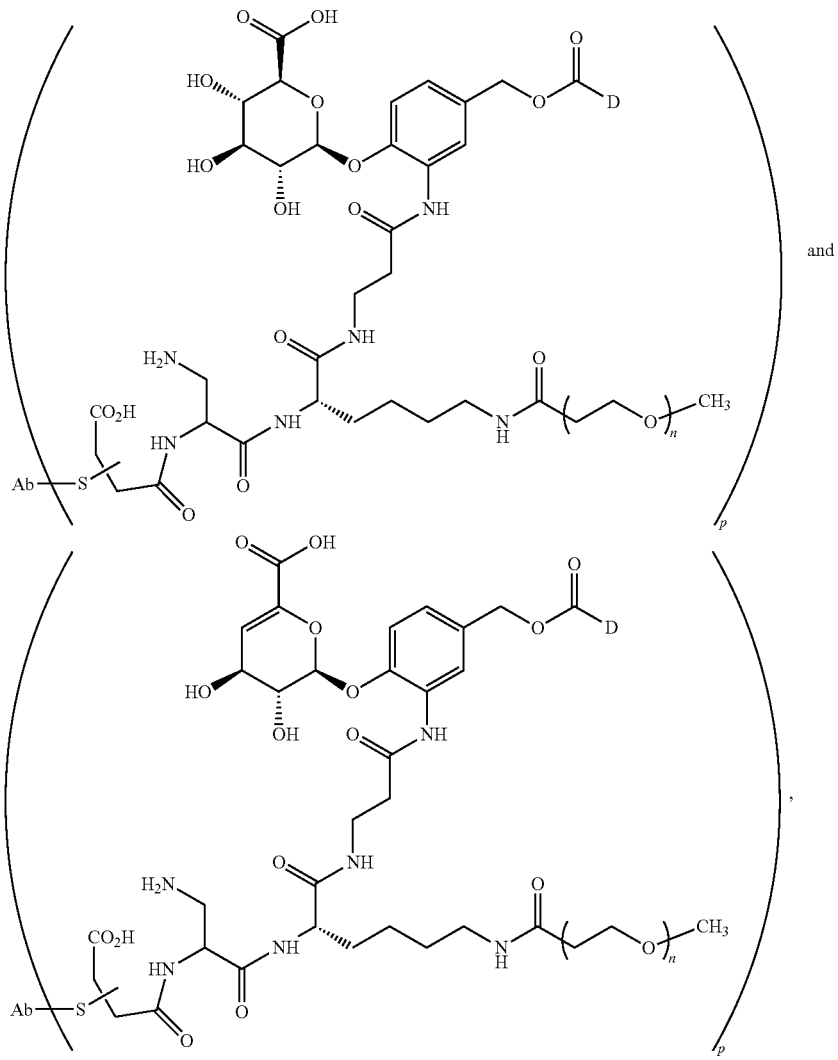

33. The composition of embodiment 31 or 32, wherein the antibody is capable of selectively binding to a tumor associated antigen.

34. The composition of embodiment 33, wherein the tumor associated antigen is comprised of an extracellular domain of a cell-surface protein or glycoprotein to which the antibody is capable of binding, particularly wherein the cell-surface protein or glycoprotein is that of an abnormal cell, more particularly one that is capable of internalization upon binding by an Antibody Drug Conjugate compound of the composition.

35. A method of treating a subject having a haematological malignancy, comprising administering an effective amount of a composition of any one of embodiments 31 to 34, particularly a leukemia or lymphoma, more particularly a B-cell malignancy.

1A. A method for preparing a Drug Linker intermediate compound of Formula VID:

or a salt thereof,

Wherein Q is an optionally protected functional group, preferably, hydroxyl, thiol or amine functional group; A is a an optional Connector Unit; B is a an optional Branching Unit and is present when subscript t is greater than 1 and is absent when subscript t is 1;

S* is a Self-Immolating Unit, in particular having the structure of Formula XV or Formula XVI:

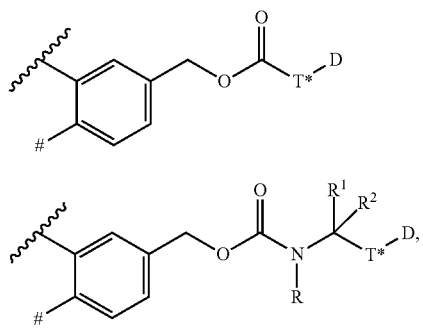

(XV)

(XVI)

wherein the wavy line indicates the point of attachment to A, and # indicates the point of attachment to the glycosidic oxygen atom of the glucuronic acid moiety;

D is a Drug Unit incorporating a DNA minor groove binder, DNA damaging agent or DNA replication inhibitor having a functional group comprising heteroatom T*, wherein T* is oxygen, sulfur, or optionally substituted nitrogen, in particular D having an amine functional group capable of forming a carbamate functional group in Formula XV or a methylene carbamate functional group in Formula XVI;

R, $R^1$, and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or both R and R' together with the nitrogen and carbon atoms to which they are attached comprise an azetidinyl, pyrrolodinyl, piperidinyl, or homopiperidinyl moiety, in particular a pyrrolodinyl or piperidinyl moiety and $R^2$ is hydrogen; $R^7$ is $C_1$-$C_8$ alkyl or optionally substituted phenyl so that —$OR^7$ provides for an ester functional group that is a suitable carboxylic acid protecting group; and subscript t is 0, 1, 2, 3, or 4, the method comprising the step of:

(c) contacting a compound of Formula VIC with Grignard reagent or an alkoxy magnesium halide with either in a suitable alcohol-containing solvent, wherein the Formula VIC compound has the structure of:

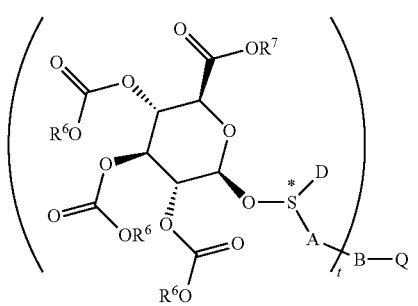

(VIC)

or a salt thereof, wherein each of $R^6$ is independently $C_1$-$C_8$ alkyl or optionally substituted phenyl such that $R^6C(=O)$— provides for an ester functional group that is a suitable hydroxyl protecting group; and the remaining variable groups are as previously defined, wherein said Grignard reagent or alkoxy magnesium halide contacting selectively removes the hydroxyl protecting groups whereby the Formula VID compound or its salt is obtained.

2A. A method for preparing a Drug Linker intermediate compound of Formula VIIE:

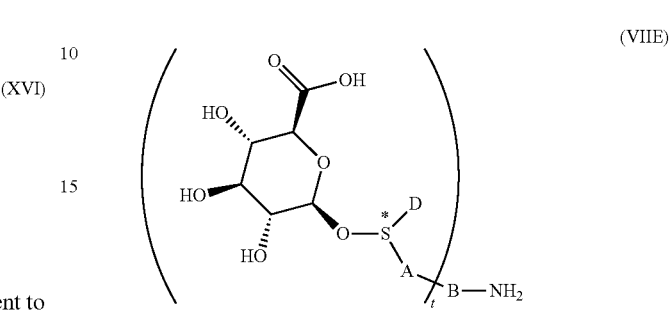

(VIIE)

or a salt thereof,

Wherein A is a an optional Connector Unit; B is a an optional Branching Unit and is present when subscript t is greater than 1 and is absent when subscript t is 1;

S* is a Self-Immolating Unit, in particular having the structure of Formula XII or Formula XIV:

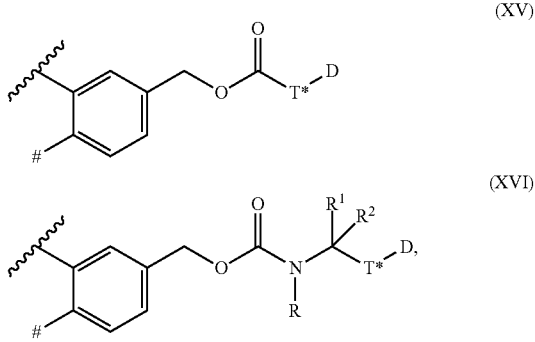

(XV)

(XVI)

wherein the wavy line indicates the point of attachment to A, and # indicates the point of attachment to the glycosidic oxygen atom of the glucuronic acid moiety;

D is a Drug Unit incorporating a DNA minor groove binder, DNA damaging agent or DNA replication inhibitor having a functional group comprising heteroatom T*, wherein T* is oxygen, sulfur, or optionally substituted nitrogen, in particular D having an amine functional group capable of forming a carbamate functional group in Formula XIII or a methylene carbamate functional group in Formula XIV, the method comprising the steps of:

(c) contacting a compound of Formula VIIC with a Grignard reagent or an alkoxy magnesium halide with either in a suitable an alcohol-containing solvent, wherein the Formula VIIC compound has the structure of:

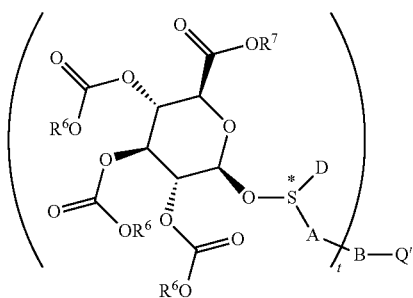

(VIIC)

or a salt thereof, wherein S*, D, A, B and subscript t are as defined for Formula VIIE of claim 2; Q' is a suitably protected amino group; each of $R^6$ and $R^7$ is independently $C_1$-$C_8$ alkyl or optionally substituted phenyl such that $R^6C(=O)$— provides for an ester functional group that is a suitable hydroxyl protecting group and —$OR^7$ provides for an ester functional group that is a suitable carboxylic acid protecting group; and the remaining variable groups are as previously defined, wherein said Grignard reagent or alkoxy magnesium halide contacting selectively removes the hydroxyl protecting groups to provide a compound of Formula VIID:

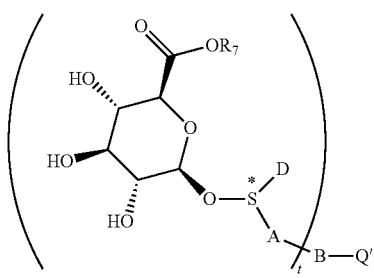

(VIID)

or a salt thereof, wherein the variable groups are as previously defined by Formula VIIC; and (d) contacting the Formula VIID compound with a first deprotecting agent, wherein said first deprotecting agent contacting removes the amine and carboxylic acid protecting groups whereby the Formula VIIE compound or its salt is obtained.

3A. A method for preparing a Drug Linker intermediate compound of Formula IE:

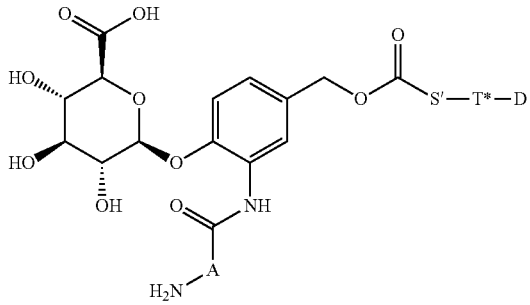

(IE)

or a salt thereof, wherein A is a an optional Connector Unit; S' is absent or —$NR^N$—$C(R^1)(R^2)$—, wherein $R^N$, $R^1$ and $R^2$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^N$ and $R^1$ together with the nitrogen and carbon atoms to which they are attached comprise an azetidinyl, pyrrolodinyl, piperidinyl or homopiperidinyl moiety, and $R^2$ is hydrogen;

D is a Drug Unit incorporating a DNA minor groove binder, DNA damaging agent or DNA replication inhibitor having a functional group, preferably, hydroxyl, thiol or amine functional group, wherein the functional group forms a covalent bond with S';

T* is a heteroatom from said functional group, in particular oxygen, sulfur, or optionally substituted nitrogen; $Z^1$ is a first suitable amine protecting group; and $R^7$ is $C_1$-$C_8$ alkyl or optionally substituted phenyl so that —$OR^7$ provides for an ester functional group that is a suitable carboxylic acid protecting group; the method comprising the steps of:

(c) contacting a compound of Formula IC with Grignard reagent or an alkoxy magnesium halide with either in a suitable an alcohol-containing solvent, wherein the Formula IC compound has the structure of:

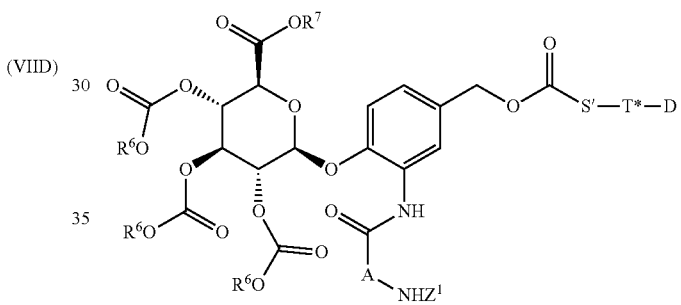

(IC)

or a salt thereof, wherein $Z^1$ is a first suitable amine protecting group; and each of $R^6$ and $R^7$ is independently $C_1$-$C_8$ alkyl or optionally substituted phenyl so that $R^6C(=O)$— provides for an ester functional group that is a suitable hydroxyl protecting group and —$OR^7$ provides for an ester functional group that is a suitable carboxylic acid protecting group; and the remaining variable groups are as previously defined by Formula IE, wherein said Grignard reagent or alkoxy magnesium halide contacting selectively removes the hydroxyl protecting groups to provide a compound of Formula ID:

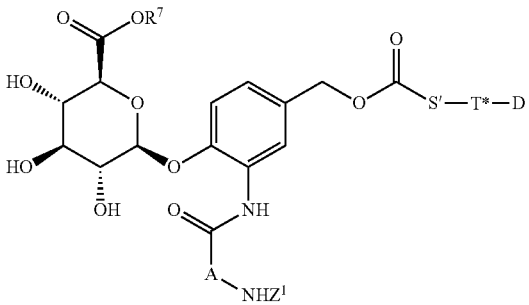

(ID)

or a salt thereof, wherein the variable groups are as previously defined by Formula IC; and (d) contacting the Formula ID compound with a first deprotecting agent, wherein said deprotecting agent contacting removes the amine and carboxylic acid protecting groups whereby the Formula IE compound or its salt is obtained.

4A. The method of embodiment 1A, 2A or 3A, wherein the Grignard reagent has the formula of $R^gMgX$ and the alkoxy magnesium halide has the formula of $R^gOMgX$, wherein Re is $C_1$-$C_8$ alkyl and X is I, Br, or Cl.

5A. The method of embodiment 4A, wherein the Grignard reagent is MeMgI or MeMgCl.

6A. The method of embodiment 5A, wherein the alkoxy magnesium halide is MeOMgI or MeOMgCl.

7A. The method of any one of embodiments 1A to 6A, wherein the alcohol-containing solvent comprises a $C_1$-$C_4$ alcohol.

8A. The method of embodiment 7A, wherein the alcohol-containing solvent further comprises THF.

9A. The method of embodiment 8A, wherein the solvent is a 1:1 (v/v) mixture of methanol and THF.

10A. The method of embodiment 2A, wherein the first deprotecting agent for removal of $Z^1$ is an aqueous-containing solution of LiOH.

11A. The method of any one of embodiments 2A to 10A, wherein $Z^1$ has the formula:

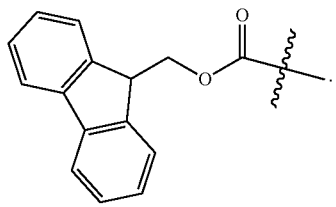 [SMILES: *C(=O)OCC1c2ccccc2-c2ccccc21]

12A. The method of any one of embodiments 1A to 11A, wherein said Grignard reagent or alkoxy magnesium halide contacting and said deprotecting agent contacting to remove $Z^1$ are done sequentially in one pot.

13A. The method of any one of embodiments 1 to 35 and 1A to 12A, wherein D is a PBD Drug Unit.

14A. The method of embodiment 13A, wherein the PBD Drug Unit has the structure of Formula IV:

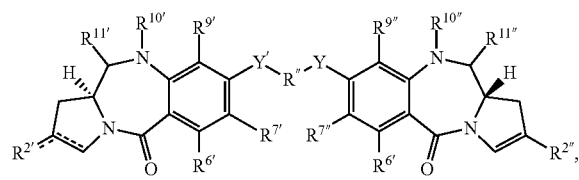

(X)

or a salt thereof, wherein: the dotted lines represent a tautomeric double bond;
$R^{2''}$ is of formula XI:

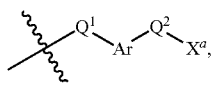

(XI)

wherein the wavy line indicates the site of covalent attachment to the Formula X structure; Ar is an optionally substituted $C_{5-7}$ arylene; $X^a$ is from a reactive or activateable group for covalent attachment to a Linker Unit or precursor thereof, wherein $X^a$ is selected from the group comprising: —O—, —S—, —C(O)O—, —C(O)—, —NHC(O)—, and —N($R^N$)—, wherein $R^N$ is H or $C_1$-$C_4$ alkyl, and $(C_2H_4O)_m$ $CH_3$, Where subscript m is 1, 2 or 3; and either:

(i) $Q^1$ is a single bond; and $Q^2$ is a single bond or —Z—$(CH_2)_n$—, wherein Z is selected from the group consisting of a single bond, O, S, and NH; and subscript n is 1, 2 or 3, or (ii) $Q^1$ is —CH=CH—, and $Q^2$ is a single bond; and $R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent, wherein the dotted lines indicate a single bond to $R^{2'}$, or $R^{2'}$ an optionally substituted $C_1$-$C_4$ alkenylene, wherein the dotted lines indicate a double bond to $R^{2'}$;

$R^{6''}$ and $R^{9''}$ are independently selected from the group consisting of H, R, OH, OR, SH, SR, $NH_2$, NHR, NRR', nitro, $Me_3Sn$ and halo; $R^{7''}$ is selected from the group consisting of H, R, OH, OR, SH, SR, $NH_2$, NHR, NRR', nitro, $Me_3Sn$ and halo, wherein R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl; and either:

(a) $R^{10''}$ is H, and $R^{11''}$ is OH or $OR^A$, wherein $R^A$ is $C_1$-$C_4$ alkyl, or (b) $R^{10''}$ and $R^{11''}$ form a nitrogen-carbon double bond between the nitrogen and carbon atoms to which they are bound, or (c) $R^{10''}$ is H and $R^{11''}$ is $SO_zM$, wherein subscript z is 2 or 3 and M is a monovalent pharmaceutically acceptable cation, or (d) $R^{10'}$, $R_{11'}$ and $R^{10''}$ are each H and $R^{11''}$ is $SO_zM$, or $R^{10'}$ and $R^{11'}$ are each H and $R^{10''}$ and $R^{11''}$ form a nitrogen-carbon double bond between the nitrogen and carbon atoms to which they are bound, or $R^{10''}$, $R^{11''}$ and $R^{10'}$ are each H and $R^{11'}$ is $SO_zM$, or $R^{10''}$ and $R^{11''}$ are each H and $R^{10'}$ and $R^{11'}$ form a nitrogen-carbon double bond between the nitrogen and carbon atoms to which they are bound, wherein subscript z is 2 or 3 and M is a monovalent pharmaceutically acceptable cation; and R" is a $C_{3-12}$ alkylene group, the carbon chain of which is optionally interrupted by one or more heteroatoms, in particular by one of O, S or $NR^{N2}$ (where $R^{N2}$ is H or $C_1$-$C_4$ alkyl), and/or by aromatic rings, in particular by one of benzene or pyridine; Y and Y' are selected from the group consisting of O, S, and NH; $R^{6'}$, $R^{7'}$, $R^{9'}$ are selected from the same groups as $R^{6''}$, $R^{7''}$ and $R^{9''}$, respectively, and for (a), (b) and (c) $R^{10'}$ and $R^{11'}$ are the same as $R^{10''}$ and $R^{11''}$, respectively, and if $R^{11''}$ and $R^{11'}$ are $SO_zM$, each M is either a monovalent pharmaceutically acceptable cation or together represent a divalent pharmaceutically acceptable cation.

15A. The method of embodiment 13A, wherein the PBD Drug Unit has the structure of Formula XII or Formula XIII:

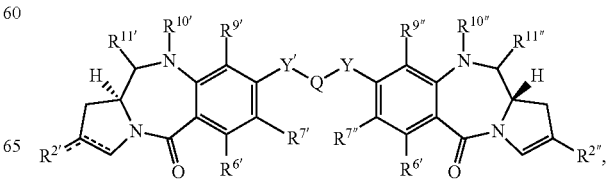

(XII)

-continued

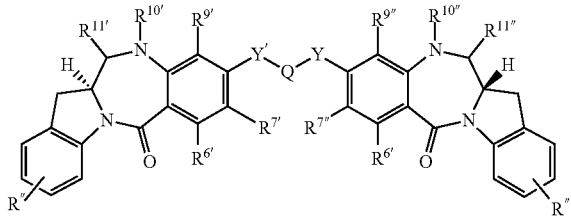

(XIII)

or a salt thereof, wherein: the dotted lines indicate a tautomeric double bond;
Q is of formula VIII:

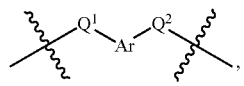

(XIV)

wherein the wavy lines indicate the sites of covalent attachment to Y' and Y in either orientation; Ar is a $C_{5-7}$ arylene group substituted by $X^a$ and is otherwise optionally substituted, wherein $X^a$ is from a reactive or activateable group for covalent attachment to a Linker Unit or precursor thereof, wherein $X^a$ is selected from the group comprising —O—, —S—, —C(O)O—, —C(O), —NHC(O)—, and —N($R^N$)—, wherein $R^N$ is H or $C_1$-$C_4$ alkyl, and $(C_2H_4O)_m$$CH_3$, wherein subscript m is 1, 2 or 3; and either:
(i) $Q^1$ is a single bond; and $Q^2$ is a single bond or —$(CH_2)_n$—, wherein subscript n is 1, 2 or 3, or (ii) $Q^1$ is —CH=CH—, and $Q^2$ is a single bond or —CH=CH—; and
$R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent, wherein the dotted lines indicate a single bond to $R^{2'}$, or $R^{2'}$ an optionally substituted $C_1$-$C_4$ alkenylene wherein the dotted lines indicate a double bond to $R^{2'}$;
$R^{2''}$ is an optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent;
$R^{6''}$ and $R^{9''}$ are independently selected from the group consisting of H, R, OH, OR, SH, SR, $NH_2$, NHR, NRR', nitro, $Me_3Sn$ and halo; $R^{7''}$ is selected from the group consisting of H, R, OH, OR, SH, SR, $NH_2$, NHR, NRR', nitro, $Me_3Sn$ and halo, wherein R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl; and either:
(a) $R^{10'''}$ is H, and $R^{11'''}$ is OH or $OR^A$, wherein $R^A$ is $C_1$-$C_4$ alkyl, or (b) $R^{10'''}$ and $R^{11'''}$ form a nitrogen-carbon double bond between the nitrogen and carbon atoms to which they are bound, or (c) $R^{10'''}$ is H and $R^{11'''}$ is $SO_zM$, wherein subscript z is 2 or 3 and M is a monovalent pharmaceutically acceptable cation, or (d) $R^{10'}$, $R^{11'}$ and $R^{10'''}$ are each H and $R^{11'''}$ is $SO_zM$, or $R^{10'}$ and $R^{11'}$ are each H and $R^{10'''}$ and $R^{11'''}$ form a nitrogen-carbon double bond between the nitrogen and carbon atoms to which they are bound, or $R^{10'''}$, $R^{11'''}$ and $R^{10'}$ are each H and $R^{11'}$ is $SO_zM$, or $R^{10'}$ and $R^{11'}$ are each H and $R^{10'''}$ and $R^{11'''}$ form a nitrogen-carbon double bond between the nitrogen and carbon atoms to which they are bound; wherein subscript z is 2 or 3 and M is a monovalent pharmaceutically acceptable cation; and Y and Y' are selected from the group consisting of O, S, and NH; R" represents one or more optional substituents; and $R^{6'}$, $R^{7'}$, $R^{9'}$ are selected from the same groups as $R^{6'''}$, $R^{7'''}$ and $R^{9'''}$, respectively, and for (a), (b) and (c) $R^{10'}$ and $R^{11'}$ are the same as $R^{10'''}$ and $R^{11'''}$, respectively, and if $R^{11''}$ and $R^{11'}$ are $SO_zM$, each M is either a monovalent pharmaceutically acceptable cation or together represent a divalent pharmaceutically acceptable cation.

16A. The method of embodiment 14A or 15A, wherein $R^{7'''}$ is selected from the group consisting of H, OH and OR.

17A. The method of embodiment 14A or 15A, wherein $R^{7'''}$ is a $C_{1-4}$ alkyloxy group.

18A. The method of embodiment 14A or 15A, wherein $R^{7'''}$ is —$OCH_3$.

19A. The method of any one of embodiments 14A to 18A, wherein Y and Y' are O.

20A. The method of any one of embodiments 14A to 19A, wherein $R^{9'''}$ is H.

21A. The method of any one of embodiments 14A to 20A, wherein $R^{6'''}$ is selected from the group consisting of H and halo.

22A. The method of embodiment 14A, wherein Ar is phenylene; $X^a$ is selected from the group consisting of —O—, —S— and —NH—; and $Q^1$ is a single bond 23A. The method of embodiment 15A, wherein Ar is phenylene, $X^a$ is selected from the group consisting of —O—, —S—, and —NH—, $Q^1$ —$CH_2$— and $Q_2$ is —$CH_2$—.

24A. The method of embodiment 22A or 23A, wherein $X^a$ is NH

25A. The method of embodiment 14A, wherein $Q^1$ is a single bond and $Q^2$ is a single bond.

26A. The method of any one of embodiments 14A to 25A, wherein the dotted lines indicate a single bond to $R^{2'}$, wherein $R^{2'}$ is a $C_{5-7}$ aryl group optionally substituted by one or more substituents selected from the group consisting of halo, nitro, cyano, $C_{1-7}$ alkoxy, $C_{5-20}$ aryloxy, $C_{3-20}$ heterocyclyoxy, $C_{1-7}$ alkyl, $C_{3-7}$ heterocyclyl and bis-oxy-$C_{1-3}$ alkylene wherein the $C_{1-7}$ alkoxy group is optionally substituted by an amino group, and if the $C_{3-7}$ heterocyclyl group is a $C_6$ nitrogen containing heterocyclyl group, it is optionally substituted by a $C_{1-4}$ alkyl group.

27A. The method of embodiment 26A, wherein the optionally substituted $C_{5-7}$ aryl is optionally substituted phenyl.

28A. The method of embodiment 26A, wherein the optionally substituted $C_{5-7}$ aryl is phenyl having one to three substituents.

29A. The method of any one of embodiments 14A to 28A, wherein $R^{10'''}$ and $R^{11'''}$ form a nitrogen-carbon double bond.

30A. The method of any one of embodiments 14A to 29A, wherein $R^{6'}$, $R^{7'}$, $R^{9'}$, and Y' are the same as $R^{6'''}$, $R^{7'''}$, $R^{9'''}$, and Y respectively.

31A. The method of embodiment 14A, wherein the PBD Drug Unit is:

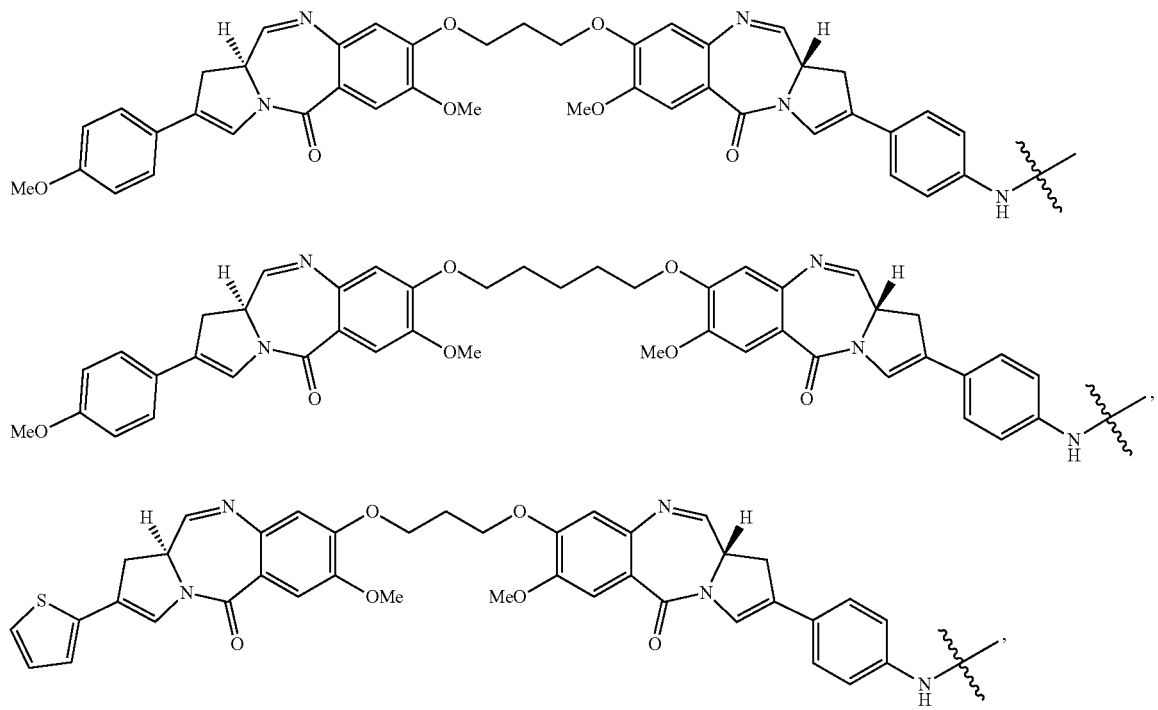

or a salt thereof, wherein the wavy line indicates the point of covalent attachment to the remainder of the Drug Linker intermediate compound or the remainder of the Drug Linker compound in the form of a carbamate functional group.

32A. The method of embodiment 14A, wherein the PBD Drug Unit is:

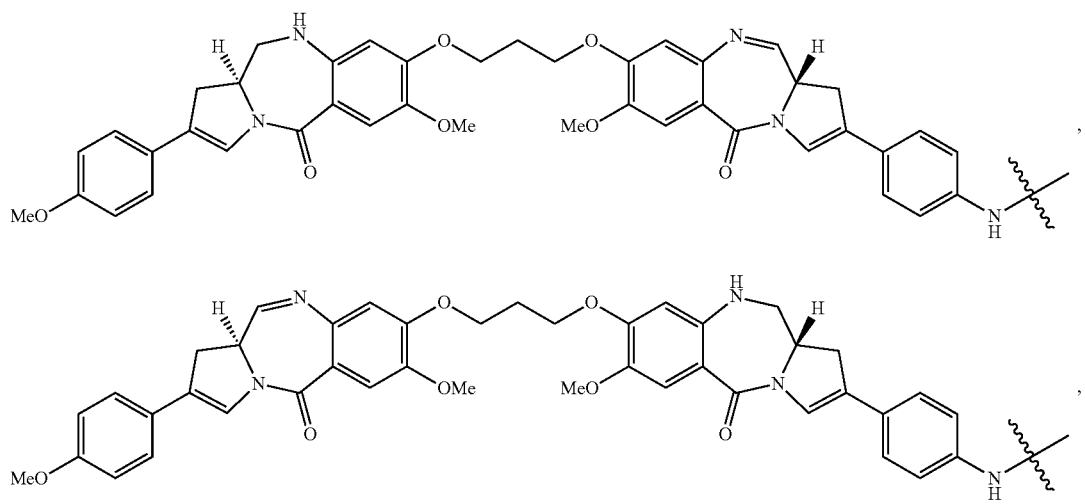

or a salt thereof, wherein the wavy line indicates the point of covalent attachment to the remainder of the Drug Linker intermediate compound or the remainder of the Drug Linker compound in the form of a carbamate functional group.

33A. The method of embodiment 15A, wherein the PBD Drug Unit is:

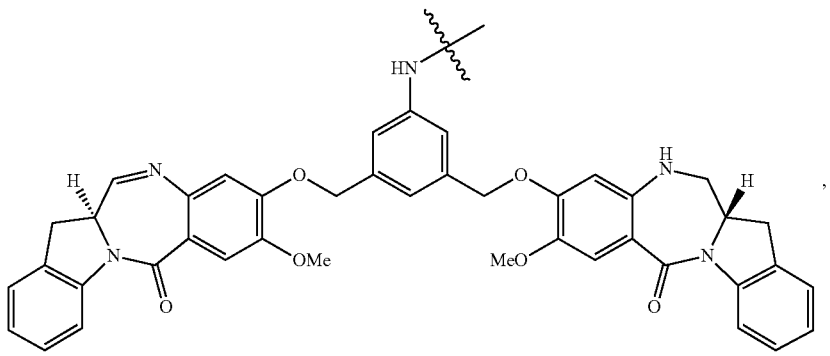 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

or a salt thereof, wherein the wavy line indicates the point of covalent attachment to the remainder of the Drug Linker intermediate compound or the remainder of the Drug Linker compound in the form of a carbamate functional group.

35A. The method of any one of embodiments 1 to 35 and 1A to 12A, wherein D is an anthracyclin Drug Unit.

36A. The method of embodiment 35A, wherein the anthracyclin Drug Unit incorporates doxorubicin, idarubicin, daunorubicin, doxorubicin propyloxazoline (DPO) or cyanomorpholino-doxorubicin.

38A. The method of any one of embodiments 1A to 12A, wherein D is an camptothecin Drug Unit.

39A. The method of embodiment 38A, wherein the camptothecin Drug Unit incorporates a camptothecin compound having the structure of:

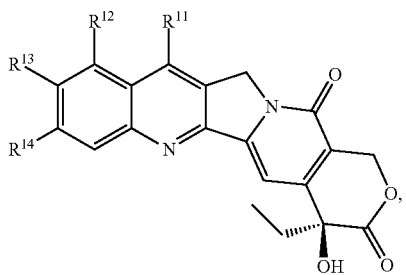

or a lactone ring-opened form thereof, optionally in salt form, wherein one of $R^{11}$ is n-butyl; and one of $R^{12}$-$R^{14}$ is —$NH_2$ that is the site of covalent attachment in the form of a carbamate functional group to the remainder of the Drug Linker intermediate compound or the remainder of the Drug Linker compound; and the other are hydrogen, or $R^{12}$ is —$NH_2$ that is the site of covalent attachment in the form of a carbamate functional group to the remainder of the Drug Linker intermediate compound or the remainder of the Drug Linker compound; and the other are hydrogen; and $R^{13}$ and $R^{14}$ together are —$OCH_2O$—.

41A. The method of any one of embodiments 1 to 35 and 1A to 12A, wherein D is an duocarmycin Drug Unit.

1C. The method of embodiment 3, wherein D is an anthracyclin Drug Unit in which the Drug Linker intermediate compound of Formula IE, optionally in salt form, has the structure of:

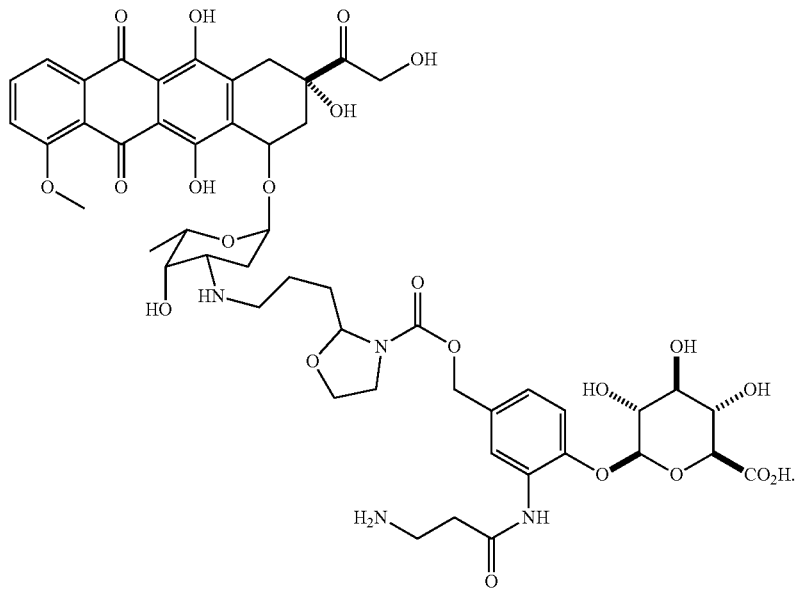

2C. The method of embodiment 3, wherein D is an camptothecin Drug Unit in which the Drug Linker intermediate compound of Formula IE has the structure of

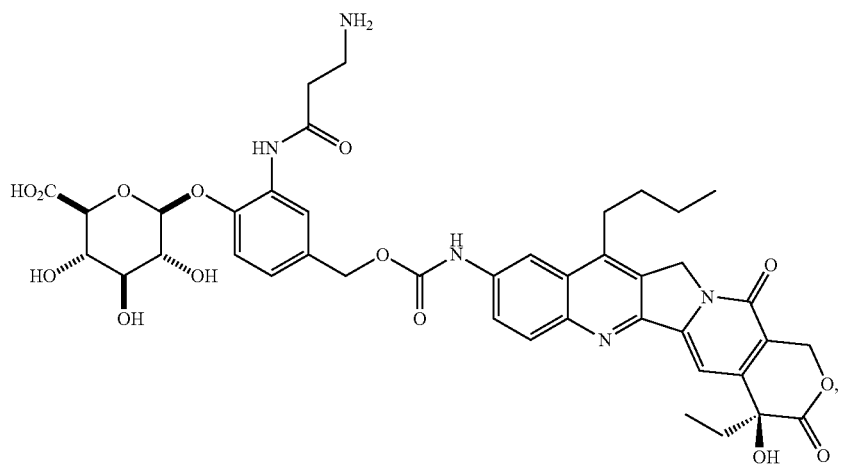

25 or a lactone ring-opened form thereof, optionally in salt form.

3C. The method of embodiment 3, wherein D is a PBD Drug Unit, in which the Drug Linker intermediate compound of Formula IE, optionally in salt form, has the structure of:

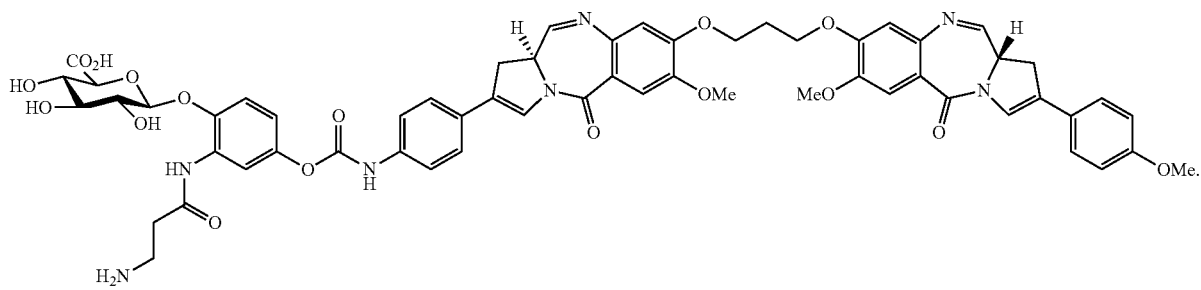

4C. The method of embodiment 3, wherein D is an duocarmycin Drug Unit in which the Drug Linker intermediate compound of Formula IE, optionally in salt form has the structure of:

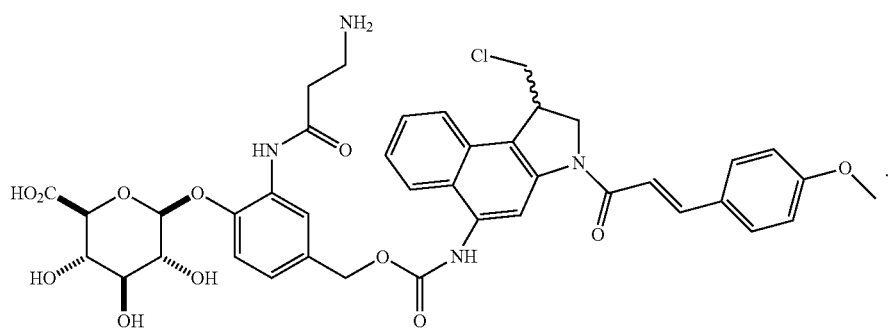

EXAMPLES

General Information.

All commercially available anhydrous solvents were used without further purification. Analytical thin layer chromatography was performed on silica gel MF254 (Agela Technologies). Column chromatography was performed on a Biotage SNAP ultra 340 g HP—sphere 25 μm. Radial chromatography was performed on a Chromatotron instrument (Harrison Research, Palo Alto, Calif.) on normal phase silica plates (Analtech, Newark, Del.). Thin Layer Chromatography (TLC) was performed on silica gel aluminum plates (Merck 60, $F_{254}$). Whatman 60 Å 230-400 mesh silica gel was used for flash chromatographic purification. Preparative and analytical HPLC methods for compounds of each Drug Unit type are as follows, unless indicated otherwise.

Anthracyclin Drug Unit:

Compounds were eluted on a C12 Phenomenex Synergi 2.0×150 mm, 4 μm, 80 Å MAX reverse phase column using a linear gradient of phase B ($CH_3CN$ with 0.05% formic acid) in A (0.05% aqueous formic acid) at 0.4 mL/min. Reported retention times ($t_R$) are from LC-MS. High-resolution mass spectral data obtained on a Bruker APEXIII 47e [FT(ICR)]MS. Analytical HPLC was conducted on a Waters 2695 instrument using a Waters 2996 PDA and Millennium software and a C12 Phenomenex Synergi 4.6×150 mm, 4 μm, 80 Å MAX reverse phase column. Compounds were eluted with either acidic (A) linear gradients of mobile phase B ($CH_3$—CN with 0.05% formic acid; 10% to 95% over 8 min) in A (0.05% aqueous TFA) (Gradient 1), or neutral (N) linear gradients of mobile phase B (CH3CN; 10% to 90% over 10 min, then hold at 90% for 5 min) in A (5.0 mM $NH_4H_2PO_4$) at a flow rate of 1.0 mL/min (Gradient 2). Preparative HPLC purifications were performed on a Varian instrument equipped with C12 Phenomenex Synergy MAX-RP 4 μm 250×21.2 mm reversed phase column, eluting with 0.05% formic acid in a water and acetonitrile gradient at a flow rate of 4.6 mL/min (gradient 1: 10% organic for 5 min followed by a ramp up to 70% organic over 25 min; gradient 2: 10% organic for 3 min followed by a ramp up to 50% organic over 50 min).

PBD Drug Unit:

Mass spectroscopy (MS) data were collected using a Waters Micromass ZQ instrument coupled to a Waters 2695/2996 PDA HPLC system eluting with water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 ml/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm. Waters Micromass ZQ parameters used were: Capillary (kV), 3.38; Cone (V), 35; Extractor (V), 3.0; Source temperature CC), 1 00; Desolvation Temperature (0 C), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument.

Camptothecin Drug Unit: Analytical HPLC was performed on two different HPLC systems. Data collected by "gradient A" were obtained on an HP Agilent 1100 HPLC equipped with a C12 Phenomenex Synergi 2.0×150 mm, 4 μm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). Data collected by "gradient B" were obtained on a Waters 2690 HPLC interfaced with a Waters 996 PDA and Millennium[32] software. Samples were eluted over a C12 Phenomenex Synergi 2.0×150 mm, 4 μm, 80 Å reverse phase column. The neutral eluent consisted of a linear gradient of acetonitrile from 10% to 90% in 5 mM ammonium phosphate pH 7 over 10 min, followed by isocratic 90% acetonitrile for 5 min (flow rate=1.0 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 μm, 80 Å reverse phase column eluting with 0.05% TFA in water (solvent A) and 0.05% TFA in acetonitrile (solvent B). Purification "Method A" consisted of the following gradient of solvent A to solvent B: 90:10 from 0 to 5 min; 90:10 to 40:60 from 5 min to 45 min; 40:60 to 10:90 from 45 to 50 min; followed by isocratic 10:90 for 5 min. The flow rate was 4.6 mL/min with monitoring at 254 nm. Purification "Method B" consisted of the following gradient of solvent A to solvent B: isocratic 90:10 from 0 to 5 min; 90:10 to 60:40 from 5 min to 45 min; 60:40 to 10:90 from 45 to 50 min; followed by isocratic 10:90 for 5 min. The flowrate was 4.6 mL/min with monitoring at 254 nm.

Auristatin Drug Unit:

Analytical HPLC was performed on a Varian ProStar 210™ solvent delivery system configured with a Varian ProStar 330™ PDA detector. Samples were eluted over a C12 Phenomenex Synergi™ 2.0×150 mm, 4 μm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass™ mass spectrometer interfaced to an HP Agilent 1100™ HPLC instrument equipped with a C12 Phenomenex Synergi 2.0×150 mm, 4 μm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2™ Tof mass spectrometer interfaced to a Waters 2695 Separations Module™ with a Waters 2996 Photodiode Array Detector™; the column, mobile phases, gradient, and flow rate were same as for LC-MS system 1. UPLC-MS was performed by a Waters Xevo G2 ToF mass spectrometer interfaced to a Waters Acquity H-Class Ultra Performance LC™ equipped with an Acquity UPLC BEH™ C18 2.1×50 mm, 1.7 μm reverse phase column (Milford, Mass.). The acidic mobile phase (0.1% formic acid) consisted of a gradient of 3% acetonitrile/97% water to 100% acetonitrile (flow rate=0.7 mL/min). Preparative HPLC was carried out on a Waters 2545 Binary Gradient Module with a Waters 2998 Photodiode Array Detector. Products were purified over a C12 Phenomenex Synergi 250×10.0 mm, 4 μm, 80 Å reverse phase column (Column 1) or a C12 Phenomenex Synergi 250×50 mm, 10 μm, 80 Å reverse phase column (Column 2) eluting with 0.1% trifluoroacetic acid in water (solvent A) and 0.1% trifluoroacetic acid in acetonitrile (solvent B). The purification methods generally consisted of linear gradients of solvent A to solvent B, ramping from 90% aqueous solvent A to 10% solvent A. The flow rate was 4.6 mL/min with monitoring at 254 nm.

Example 1. Synthesis of an Anthracyclin β-Glucuronide-Based Drug Linker Compound Scheme 1. Preparation of a glucuronide-based Drug Linker compound having an anthracyclin Drug Unit.
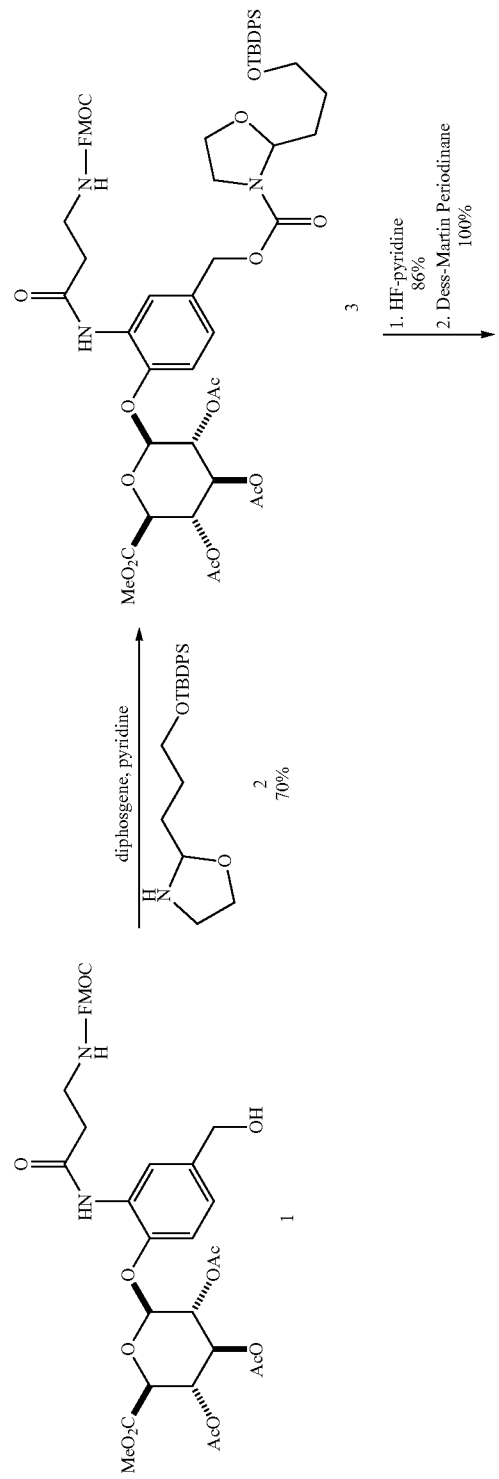

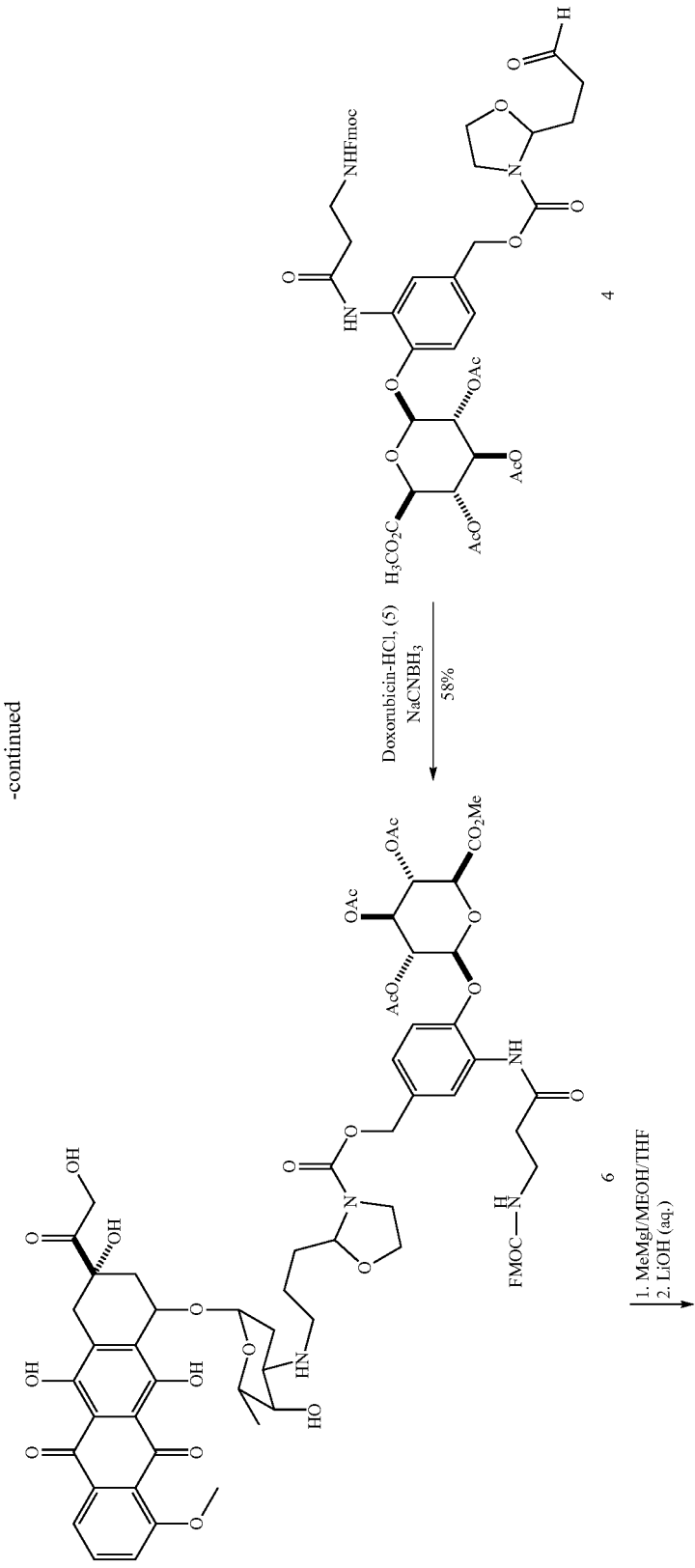

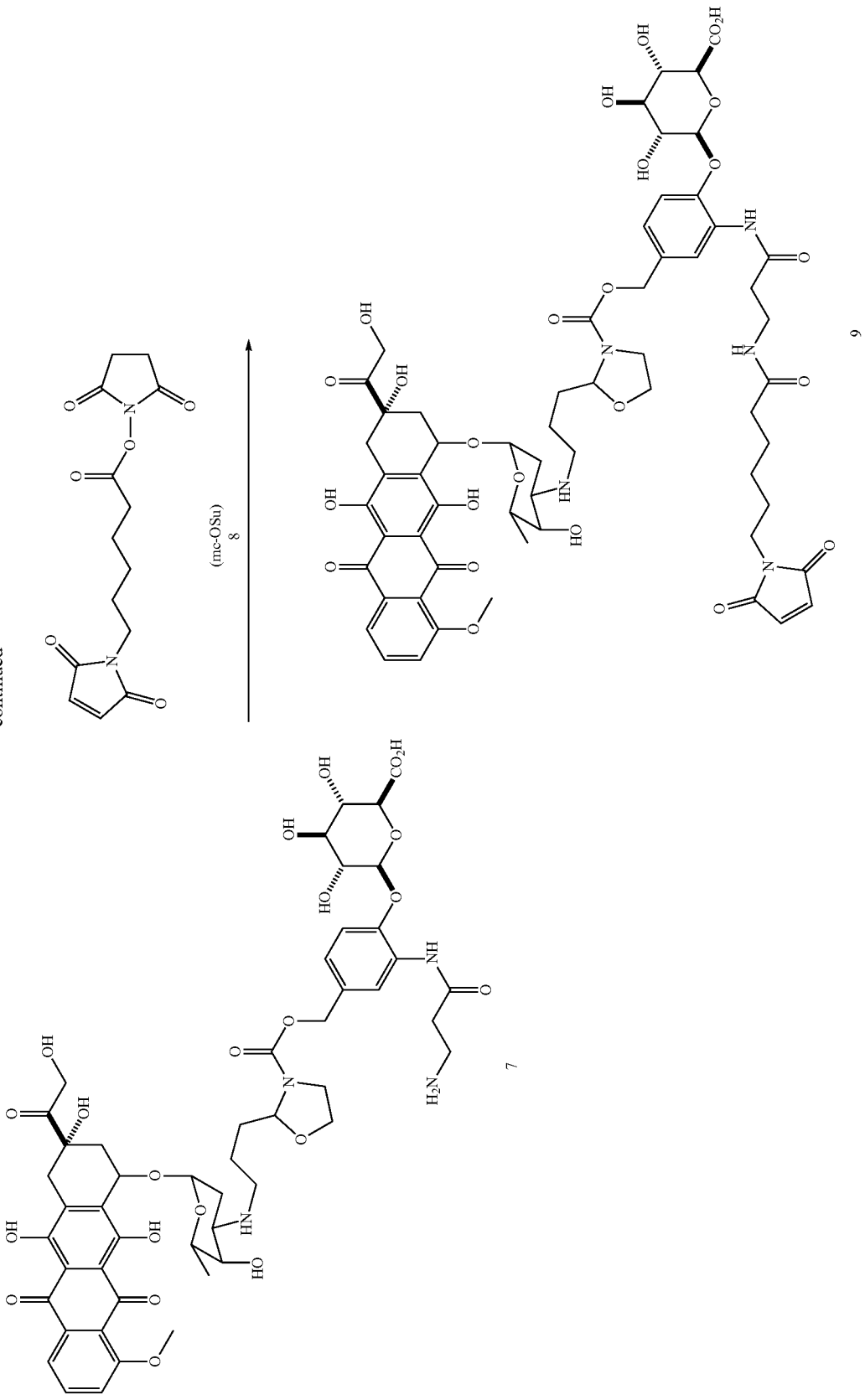

Drug linker compound intermediate 6 was prepared according to the methods described in International Publication No. WO 2007/011968, which is incorporated herein by reference for such disclosure. Stepwise deprotection of compound 6 by a method of the present invention to provide compound 7, which reduces the amount of impurities from β-elimination of the C-4 acetate within the glucuronic acid residue, is achieved in the following manner. Compound 6 is added to a round bottle flask and then equal volumes of THF and MeOH are added. After complete dissolution of the solids, the solution is cooled in ice bath. Methylmagnesium iodide solution (3 M in $Et_2O$)(5 eq.)(Sigma-Aldrich, cat #254363) is added dropwise, and the temperature is controlled to remain below 5° C. (internal). The reaction mixture is the allowed to reach RT and stirred overnight to complete the transesterification reaction, which deprotects the acetate functional groups, but retains the methyl ester protection of the carboxylic acid functional group. The reaction mixture is then cooled in ice bath again and lithium hydroxide (12 eq.) in water is added slowly to remove the FMOC and methyl ester protecting groups. The temperature is allowed to increase gradually to room temperature. The reaction mixture is filtered through celite to remove FMOC related by-product. Purity of compound 7 product may be assessed by analytical HPLC to determine the amount of β-elimination impurity, or that determination may be delayed until the Drug Linker compound (9) is obtained by condensing the fully deprotected compound 7 with 2,5-dioxopyrrolidin-1-yl 6-(2,5-dioxo-2,5-dihydro-1H-pyrrol-1-yl)hexanoate (mc-OSu, 8) in DMF in the presence of di-isopropyldiethylamine (DIPEA) as follows:

To a mixture of the compound 7 (6.1 mg, 5.7 μmol) in DMF (0.2 mL) was added mc-OSu (8; 4 mg, 14 μmol) followed by DIPEA (3 μL, 17 μmol). The reaction mixture was concentrated under reduced pressure and then dissolved in a mixture of water and DMSO (1:1, 2 mL). The mixture was purified via reverse-phase preparative HPLC (gradient 2) to yield 2.1 mg (26%) of compound 9 as a red solid: $^1$H NMR ($CD_3OD$); δ 1.1-1.25 (b, 2H), 1.29 (d, 3H, J=6.6 Hz), 1.35-1.62 (b, 3H), 1.65-1.90 (b, 3H), 2.02-2.13 (m, 4H), 2.67 (s, 4H, N-hydroxysuccinimide impurity), 3.00-3.10 (m, 4H), 3.41-3.57 (m, 3H), 3.57-3.70 (m, 3H), 3.81 (m, 2H), 3.94 (d, 1H, J=9.6 Hz), 4.02 (b, 1H), 4.05 (s, 3H), 4.29 (q, 1H, J=7.0 Hz), 4.71 (s, 3H), 4.73 (m, 1H), 5.06 (m, 1H), 5.12 (b, 1H), 5.49 (s, 1H), 6.78 (s, 2H), 6.82-7.09 (b, 2H), 7.57 (d, 1H, J=6.4 Hz), 7.84 (t, 1H), J=7.4 Hz), 7.95 (sd, 1H, J=7.4 Hz), 8.08 (bs, 1H); LC-MS m/z ($ES^-$), 1260.24 $(M-H)^-$, $t_R$=6.49 min.

Example 2. Synthesis of a Pyrrolobenzodiazepine (PBD) β-Glucuronide-Based Drug Linker Compound

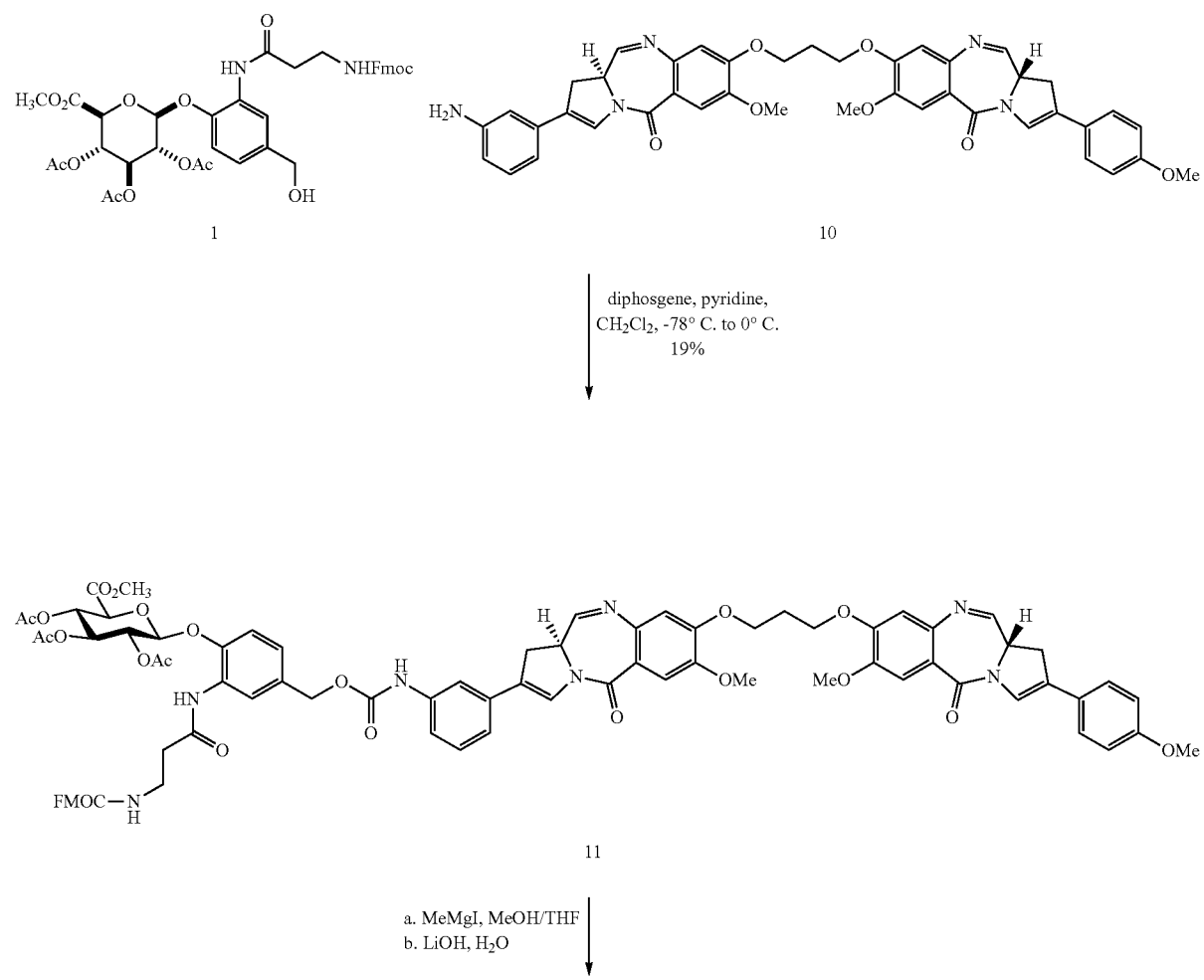

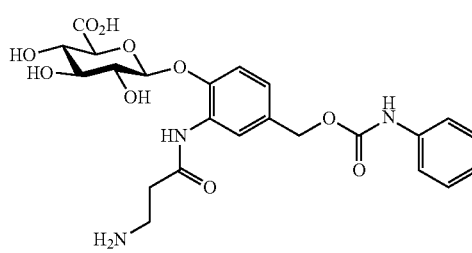

125

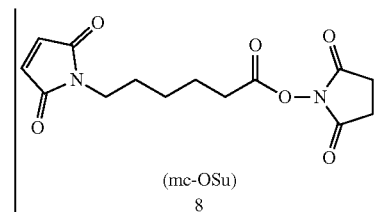

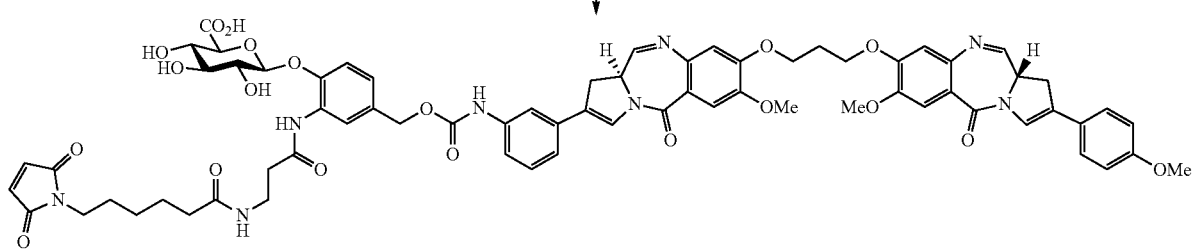

Compound I was prepared according to the methods described in International Publication No. WO 2007/011968, which is incorporated herein by reference for such disclosure and compounds 10 and 11 were prepared as previously described by International Publication No WO 2011/130613, which is incorporated herein by reference for such disclosure. Stepwise deprotection of compound 11 is achieved in the manner as described for Example 1 to provide the Drug linker intermediate compound 12 having reduced amounts of impurities from β-elimination of the C-4 acetate within the glucuronic acid residue compared to global deprotection with aqueous base. In addition to compound 12 varying amounts of carbinol and carbinol methyl ether derivative(s) may also be obtained. Compound 12 is further elaborated to provide the Drug Linker compound 13 by condensing fully deprotected compound 12 with 2,5-dioxopyrrolidin-1-yl 6-(2,5-dioxo-2,5-dihydro-1H-pyrrol-1-yl)hexanoate (mc-OSu, 8) in DMF in the presence of diisopropyldiethylamine (DIPEA) as follows:

To a solution of 12 (4.3 mg, 3.8 µmol) dissolved in 0.38 mL anhydrous DMF was added mc-OSu (8, 1.2 mg, 3.8 µmol), followed by diisopropylethylamine (4.0 µl, 22.8 µmol). The reaction was stirred at RT under nitrogen for 2 h, at which time LC-MS revealed conversion to product. The reaction was diluted with a mixture of acetonitrile (0.5 mL), DMSO (1 mL), water (0.5 mL), and then purified by preparative HPLC. The mobile phase consisted of A=water and B=acetonitrile, both containing 0.1% formic acid. A linear elution gradient of 90:10 A:B to 10:90 A:B over 75 minutes was employed and fractions containing the desired product were lyophilized to provide glucuronide-based drug linker compound 13 (1.2 mg). Analytical HPLC (0.1% formic acid): $t_R$=10.85 min. LC-MS: $t_R$=12.12 min, m/z (ES$^+$) found 1331.4 (M+H)$^+$, m/z (ES) found 1329.5 (M−H)$^−$ Example 3. Synthesis of a Camptothecin β-Glucuronide-Based Drug Linker Compound Scheme 3. Preparation of a glucuronide-based Drug Linker compound having a camptothecin Drug Unit
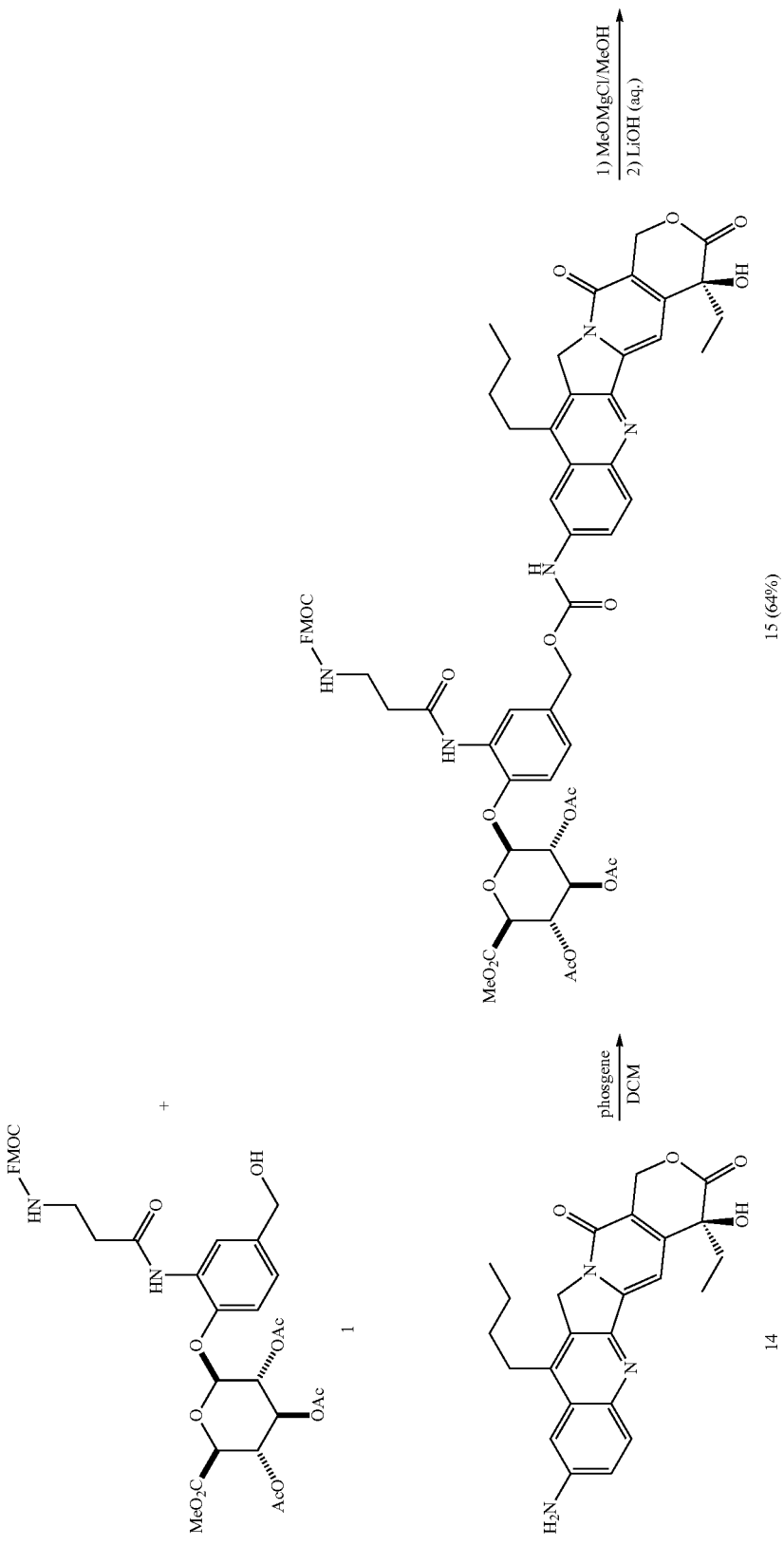

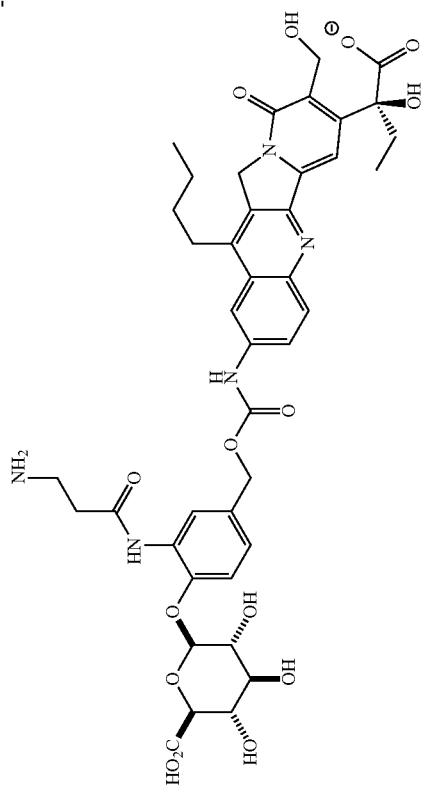
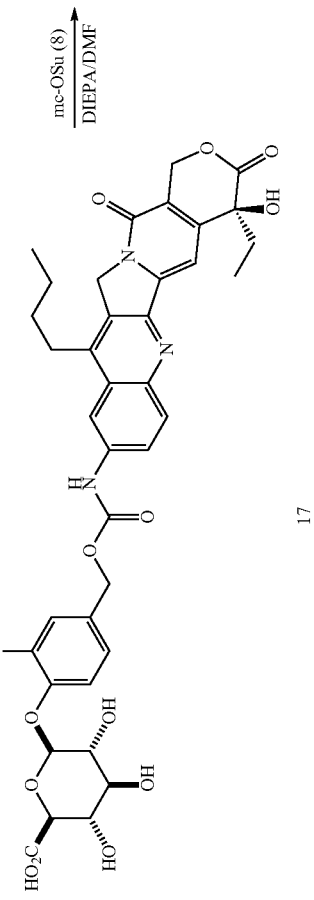
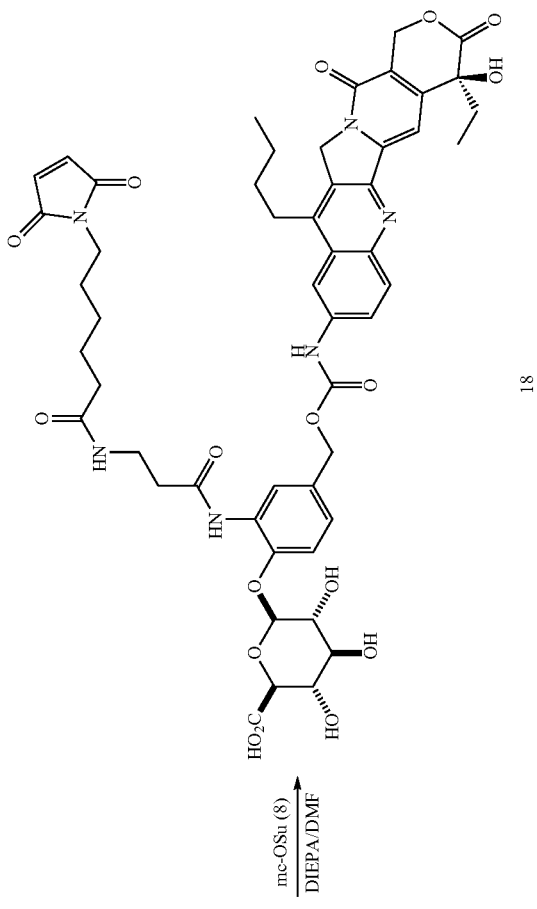

Compound 1 was prepared according to the methods described in International Publication No. WO 2007/011968, which is incorporated herein by reference for such disclosure and compounds 15 was prepared as previously described by Burke, P. J. et al. "Design, synthesis, and biological evaluation of antibody-drug conjugates comprised of potent camptothecin analogues" *Bioconj. Chem.* (2009) 20: 1242-1250 which is incorporated herein by reference for such disclosure. Stepwise deprotection of compound 15 by a method of the present invention, which reduces the amount of impurities from β-elimination of the C-4 acetate within the glucuronic acid residue as compared to global deprotection by aqueous base, is achieved in the manner as described for Example 1. Deprotection step (1) of Scheme 3 converts the lactone of compound 15 in variable amount to the methyl ester of its ring opened form during the transesterification for removing the acetate protecting groups. However, LiOH hydrolysis in deprotection step (2) will convert that ester and hydrolyze any remaining lactone to the carboxylate ring opened form, which provides the Drug linker intermediate compound 16 as the predominate reaction product. On recovery of the product, closure to reform the lactone ring occurs. Further elaboration of compound 17 is by condensing that fully deprotected compound with 2,5-dioxopyrrolidin-1-yl 6-(2,5-dioxo-2,5-dihydro-1H-pyrrol-1-yl)hexanoate (mc-OSu, 8) in DMF in the presence of di-isopropyldiethylamine (DIPEA) as follows:

To a solution of 17 (23.0 mg, 27.6 μmol) dissolved in 1.5 mL anhydrous DMF was added maleimidocaproyl NHS ester (8, 12.8 mg, 41.4 μmol), followed by DIPEA (14.4 μL, 82.8 μmol). The reaction was stirred at room temperature under nitrogen for 4 h, at which time LC-MS revealed conversion to product. The crude reaction was diluted in DMSO and purified by preparative HPLC (Method A) to give 10 (20.5 mg, 72%). $^1$H NMR (DMF-$d_7$) δ (ppm) 0.99 (m, 6H), 1.26 (p, J=8.4 Hz, 2H), 1.57 (m, 6H), 1.81 (p, J=7.2 Hz, 2H), 2.01 (m, 2H), 2.16 (t, J=7.2 Hz, 2H), 2.68 (t, J=6.8 Hz, 2H), 3.21 (t, J=8.0 Hz, 2H), 3.57 (m, 10H), 4.10 (d, J=9.6 Hz, 2H), 5.03 (m, 1H), 5.23 (s, 2H), 5.36 (s, 2H), 5.52 (d, J=2.4 Hz, 2H), 6.52 (bs, 1H), 7.01 (s, 2H), 7.19 (dd, J=8.4, 2.0 Hz, 1H), 7.27 (d, J=8.4 Hz, 1H), 7.43 (s, 1H), 7.94 (t, J=5.6 Hz, 1H), 8.09 (dd, J=9.2, 2.0 Hz, 1H), 8.18 (d, J=9.2 Hz, 1H), 8.48 (s, 1H), 8.57 (s, 1H), 9.36 (s, 1H), 10.37 (s, 1H). UV $\lambda_{max}$ 267 nm and 385 nm. Analytical HPLC: gradient A, $t_R$=11.93 min; gradient B, $t_R$=5.76 min. LC-MS: m/z (ES$^+$) found 1025.40 (M+H)$^+$, m/z (ES$^-$) found 1023.29 (M−H)$^-$.

Example 4. Synthesis of a Cyclopropyl-Benzimidazole β-Glucuronide-Based Drug Linker Compound

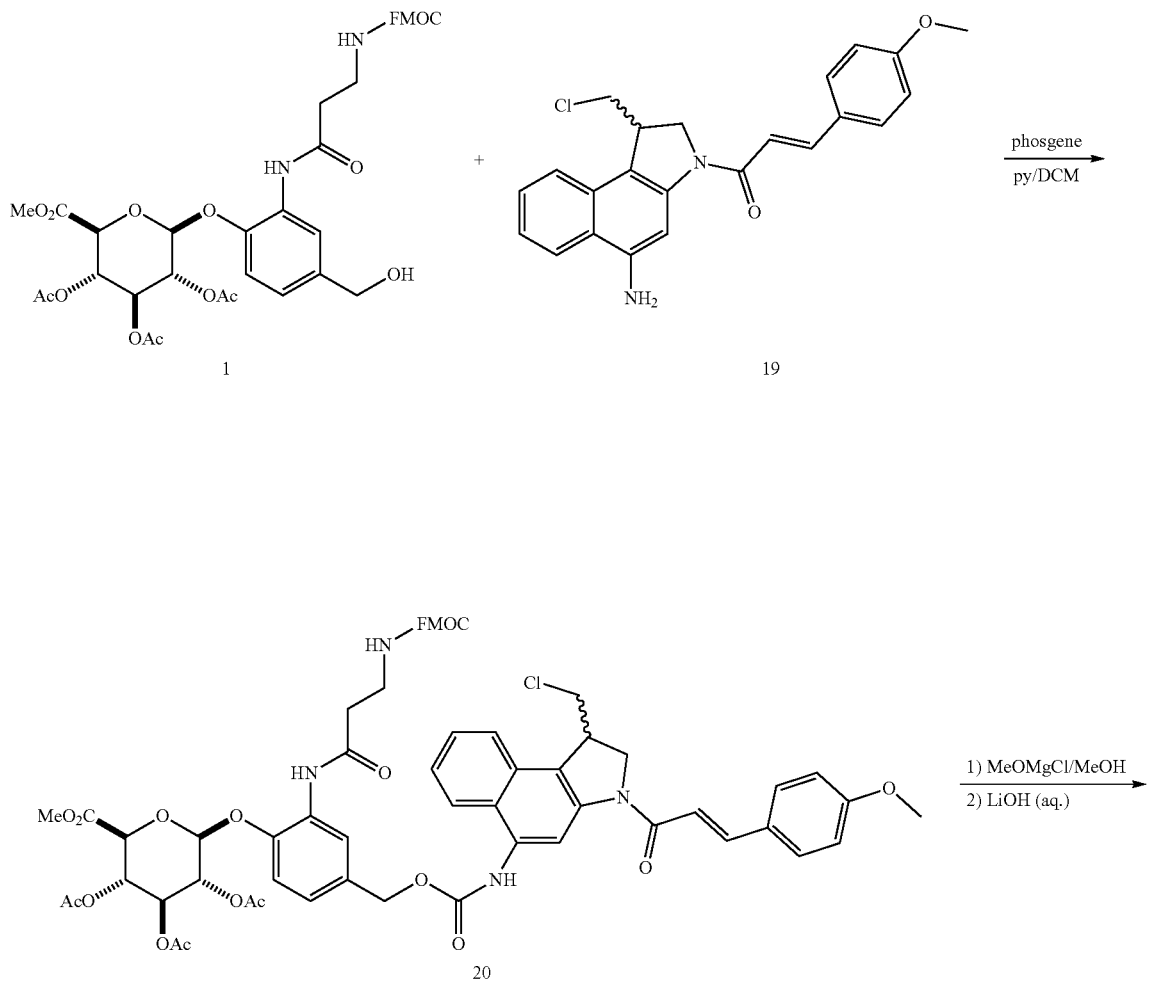

Scheme 4. Preparation of a glucuronide-based Drug Linker compound having a cyclopropyl-benzimidazole (CBI) Drug Unit

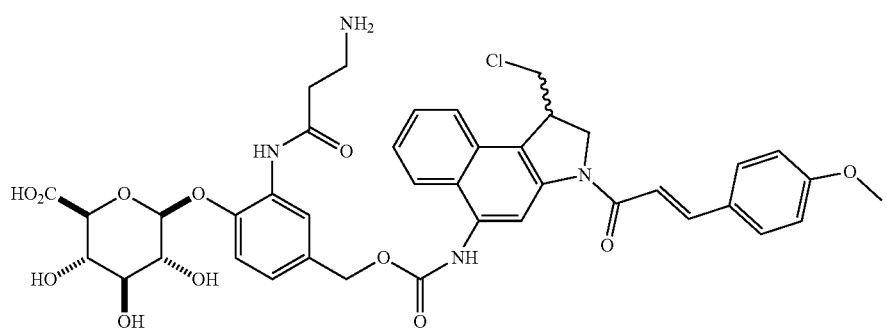 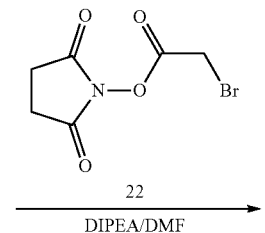

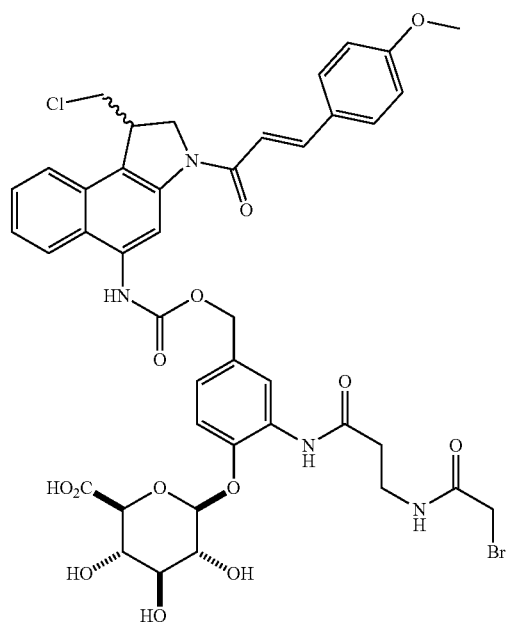

Compound 1 was prepared according to the methods described in International Publication No. WO 2007/011968, which is incorporated herein by reference for such disclosure and compounds 20 was prepared as previously described by Jeffrey, S. C., et al. "Minor groove binder antibody conjugates employing a water soluble β-glucuronide linker" Bioorg. Med Chem. Lett. (2007) 17: 2278-2280, which is incorporated herein by reference for such disclosure. Stepwise deprotection of compound 20 by a method of the present invention, to provides the Drug linker intermediate compound 21, which reduces the amount of impurities from β-elimination of the C-4 acetate within the glucuronic acid residue compared to global deprotection using aqueous base, is achieved in the manner as described for Example 1. Further elaboration of compound 21 using the activated α-bromo ester 2,5-dioxopyrrolidin-1-yl 2-bromoacetate (22) is conducted as follows to provide Drug Linker compound 23.

To a mixture of compound 21 as it acetate salt (20 mg, 23 μmol) in DMF (0.5 mL) was added compound 22 (5 mg, 23 μmol) followed by DIPEA (9 mg, 69 μmol). After 20 min at RT, consumption of compound 21 was deemed to be complete. The reaction mixture was then diluted with water (1 mL) and filtered through a syringe prior to purification by HPLC, which provided 4.6 mg of compound 23 (22% yield).

Example 5. Synthesis of an Auristatin
β-Glucuronide-Based Drug Linker Compound
Scheme 5. Preparation of a glucuronide-based Drug Linker compound having a MMAE Drug Unit
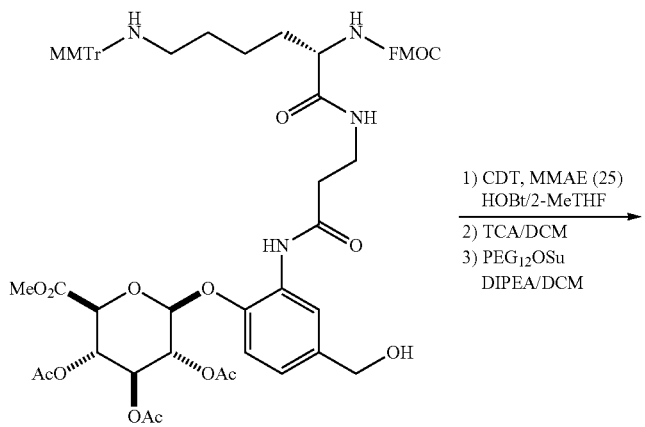
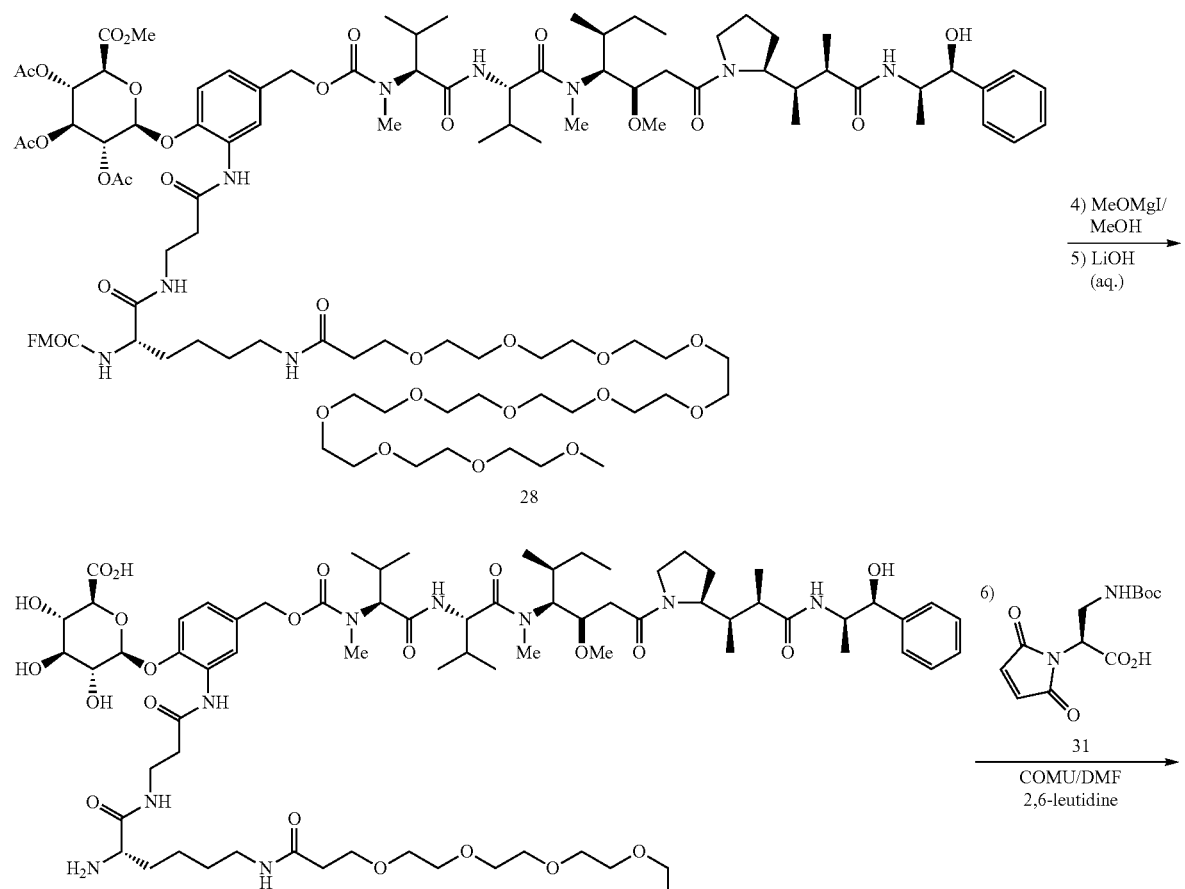

-continued

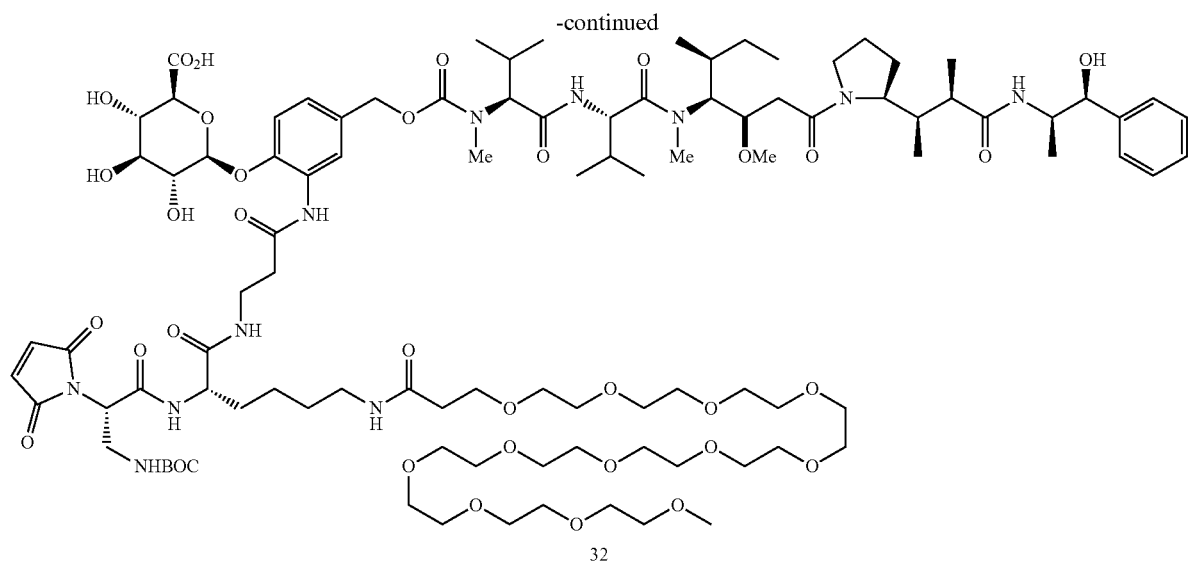

32

Step 1: To compound 24 (4.86 g) in 2-MeTHF (194 mL) was added 1,1'-Carbonyl-di-(1,2,4-triazole) (CDT) (Sigma-Aldrich, Cat #21861) 2.084 g (3 eq.). The reaction mixture was stirred at room temperature for 5 hrs with LC-MS showing completeness of the reaction. The reaction mixture was then washed with water (49 mL×3) (a little NaCl is needed for phase separation), (note: the wet solution is stable overnight) dried over anhydrous sodium sulfate. Evaporated of the solvent yielded a solid (5.833 g). That solid and MMAE (25) 3.646 g (1.3 eq.) were dissolved in 2-MeTHF (29 mL). 1-Hydroxybenzotriazole hydrate (HOBt) (0.15 g, 0.2 eq.) (Sigma-Aldrich, Cat #711489) in 4 mL 2-MeTHF was evaporated to reduce the volume by about ½. The concentrated HOBt solution was then added to the reaction mixture, which was stirred at 55° C. for 60 hours. The reaction was washed with water (29 mL×4) to remove excess MMAE and HOBt and dried over anhydrous sodium sulfate. Solvent was exchanged with EtOAc and the resulting solution was loaded on Biotage column. 5% MeOH in EtOAc was used to elute the product to provide 4.914 g (62% yield) of compound 26. Analytical LC-MS: $t_R$=2.22 min, m/z (ES$^+$) found 1894.1.

Step 2: Compound 26 (4.40 g) was dissolved in 44 mL DCM; and 8.8 g trichloroacetic acid (TCA) was dissolved in 440 mL DCM. The TCA solution is cooled in ice bath to ~5° C. and then the compound 26 solution was added in 5 minutes. Upon addition the reaction mixture immediately turned orange. The ice bath was removed and the temperature increased slowly to 15° C. The reaction was complete in 1 h, and was then cooled again in ice bath to ~10° C. whereupon 6.0 g of KHCO$_3$ in 100 mL water is added in 5 min to quench the reaction mixture, which resulted in disappearance of the color. The organic phase was separated and washed with brine and dried over anhydrous sodium sulfate. The solvent was evaporated with addition of heptane to form compound 27 as a white solid. The white solid was collected by vacuum filtration, which was used in step 3 without further purification.

Step 3: To the DCM solution of compound 27 was added PEG$_{12}$-OSu (27, 1.756 g, 1.1 eq.) (Quanta BioDesign, cat #10262) and then N,N-Diisopropylethylamine (DIPEA) (0.24 mL, 0.60 eq.). The reaction mixture was stirred at room temperature for 4 h, then was loaded on to silica gel (88 g) and eluted with 5% MeOH/EtOAc to remove excess amount of PEG-OSu, MMTr related by-product and N-hydroxysuccimide, followed by elution with 5% MeOH/DCM to obtain compound 28 (3.335 g, 66% yield). Analytical UPLC-MS: $t_R$=1.53 min, m/z (ES$^+$) found 2191.3.

Step 4: Compound 28 (2.73 g) was added to a round bottle flask and then 9 mL THF and 9 mL MeOH were added. The solid dissolved and the solution so obtained was cooled in ice bath. Methylmagnesium iodide solution (3 M in Et$_2$O) (2.08 mL, 5 eq.)(Sigma-Aldrich, cat #254363) was added dropwise with control of the internal temperature to below 5° C. to provide a methanolic solution of MeOMgI. Afterwards, the reaction mixture was stirred at room temperature overnight to effect the transesterification reaction for selective removal of the acetate protecting groups by MeOMgI formed in situ, resulting in intermediate compound 29, which is then further deprotected, without requiring its purification, with LiOH (aq.) as follows.

Step 5: The reaction mixture resulting from step 4 was again cooled in ice bath and lithium hydroxide (358 mg, 12 eq.) in water (9 mL) was added slowly. The temperature increased gradually to room temperature. After 3 hours removal of the FMOC protecting group was complete. The reaction mixture was then filtered through celite to remove FMOC related by-product. The pH of the filtrate, which contained the desired product, was adjusted to 7 by acetic acid. Purified Compound 30 (~1.8 g, 78% yield), as assessed by analytical HPLC, was obtained by reverse phase chromatography of the filtrate. Analytical LC-MS: $t_R$=1.53 min, m/z (ES$^+$) found 1828.8.

The ratio of desired compound 30 to its β-elimination impurity using MeOMgI prepared in situ in stepwise deprotection of compound 28 is 21:1, whereas that ratio from global deprotection with LiOH is 3.5:1. Use of MeOMgCl prepared in situ in stepwise deprotection of compound 28 also results in a 21:1 ratio of compound 30 to its β-elimination impurity.

As the Drug Unit is essentially sterically and electronically isolated from the protected glucuronic acid residue in a glucuronide-based Linker Unit, a reasonable basis of prediction exists that similar improvements in the product to impurity ratios are to be expected in preparation of Drug Linker compounds in which the MMAE Drug Unit is replaced by a cyclopropyl-benzimidazole Drug Unit, as in Example 4, a camptothecin Drug Unit, as in Example 3, a PBD Drug Unit, as in Example 2, or a anthracyclin Drug Unit as in Example 1.

Step 6: A 4 mL vial was charged with compound 31 (46.6 mg, 0.16 mmol), prepared as described in PCT Publication No. WO2015057699, the method of which is specifically incorporated by reference herein, COMU (46.8 mg, 0.11 mmol)(Sigma-Aldrich, cat #712191) and DMF (0.5 mL). The mixture was cooled to 0° C. and 2,6-lutidine (38.2 µL, 0.33 mmol))(Sigma-Aldrich, cat #336106) was added slowly and the reaction was stirred for 30 min. In a separate vial compound 30 (100.0 mg, 0.06 mmol) was dissolved in DMF (1.0 mL). After cooling to 0° C., the DMF solution of compound 30 was added to the DMF solution of compound 31 and stirred for 30 min. DMSO (0.5 mL) was added to the reaction, then 0.1% TFA in water (2.0 mL) was slowly added to the reaction keeping the temperature at 0° C. The crude material was purified by preparative HPLC and the fractions were lyophilized to afford compound 32 (28.0 mg, 24% yield). Analytical UPLC-MS: $t_R$=1.32 min, m/z (ES$^+$) found 2096.44.

What is claimed is:
1. A method for preparing a Drug Linker compound intermediate of Formula VID:

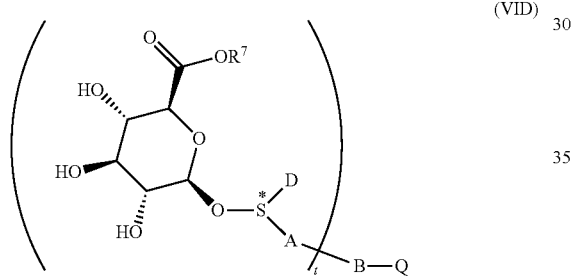

(VID)

or a salt thereof, wherein
Q is a suitably protected hydroxyl, thiol or amine functional group;
A is an optional Connector Unit;
B is absent;
S* is a Self-Immolating Unit of Formula XV or Formula XVI:

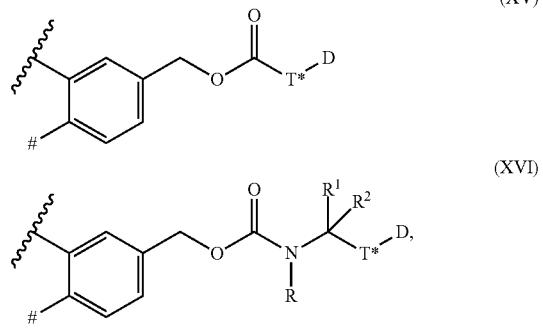

(XV)

(XVI)

wherein the wavy line indicates the point of attachment to A, and # indicates the point of attachment to the glycosidic oxygen atom of the glucuronic acid moiety;

D is a Drug Unit incorporating a DNA minor groove binder, DNA damaging agent or DNA replication inhibitor having a functional group comprising heteroatom T*, wherein T* is oxygen or sulfur, or an optionally substituted nitrogen;

R is hydrogen or optionally substituted $C_1$-$C_6$ alkyl, and one of $R^1$ and $R^2$ is hydrogen and the other is hydrogen, or optionally substituted $C_1$-$C_6$ alkyl or both R and $R^1$ together with the nitrogen and carbon atoms to which they are attached form a pyrrolodinyl or piperidinyl moiety and $R^2$ is hydrogen;

$R^7$ is $C_1$-$C_8$ alkyl or optionally substituted phenyl so that —$OR^7$ provides for an ester functional group that is a suitable carboxylic acid protecting group; and subscript t is 1, the method comprising the step of:
(c) contacting a compound of Formula VIC with a Grignard reagent or an alkoxy magnesium halide with either in a suitable alcohol-containing solvent, wherein the Formula VIC compound has the structure of:

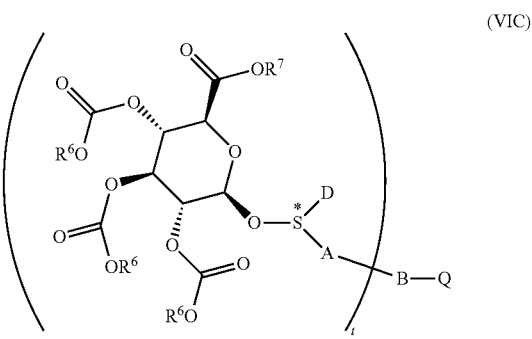

(VIC)

or a salt thereof, wherein
each of $R^6$ is independently $C_1$-$C_8$ alkyl or optionally substituted phenyl such that $R^6C(\!=\!O)$— provides for an ester functional group that is a suitable hydroxyl protecting group; and the remaining variable groups are as previously defined for Formula VID, wherein said contacting with the Grignard reagent or alkoxy magnesium halide selectively removes the hydroxyl protecting groups whereby the Formula VID compound or its salt is obtained.

2. The method of claim 1, wherein the Grignard reagent has the formula of $R^gMgX$ and the alkoxy magnesium halide has the formula of $R^gOMgX$, wherein $R^g$ is $C_1$-$C_5$ alkyl and X is I, Br, or Cl.

3. The method of claim 2, wherein the Grignard reagent is MeMgI or MeMgCl and the alkoxy magnesium halide is MeOMgI or MeOMgCl.

4. The method of claim 1, wherein the Grignard reagent is MeMgI or MeMgCl, the alkoxy magnesium halide is MeOMgI or MeOMgCl and the alcohol-containing solvent comprises a $C_1$-$C_4$ alcohol.

5. The method of claim 4, wherein the alcohol-containing solvent further comprises THF.

6. The method of claim 5, wherein the alcohol-containing solvent is a 1:1 (v/v) mixture of methanol and THF.

7. The method of claim 1, wherein D is a pyrrolobenzodiazepine (PBD) Drug Unit.

8. The method of claim 7, wherein the PBD Drug Unit is of Formula X:

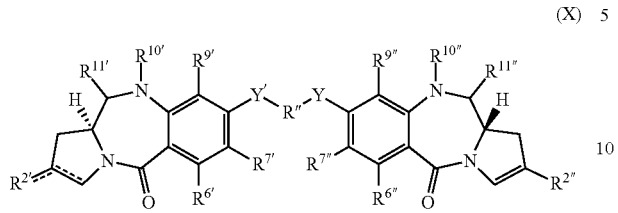

(X)

or a salt thereof,
wherein:
the dotted lines represent a tautomeric double bond;
$R^{2''}$ is of formula XI:

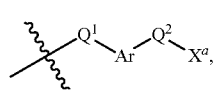

(XI)

wherein the wavy line indicates the site of covalent attachment to the Formula X structure;
Ar is an optionally substituted $C_{5-7}$ arylene;
$X^a$ is from a reactive or activateable group for covalent attachment to a Linker Unit or precursor thereof, wherein $X^a$ is selected from the group consisting of —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3;
and either:
(i) $Q^1$ is a single bond; and $Q^2$ is a single bond or —Z—$(CH_2)_n$—, wherein Z is selected from the group consisting of a single bond, O, S, and NH; and subscript n is 1, 2 or 3, or
(ii) $Q^1$ is —CH=CH—, and $Q^2$ is a single bond; and
$R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, wherein the dotted lines indicate a single bond to $R^{2'}$, or
$R^{2'}$ an optionally substituted $C_1$-$C_4$ alkenylene, wherein the dotted lines indicate a double bond to $R^{2'}$;
$R^{6''}$ and $R^{9''}$ are independently selected from the group consisting of H, R, OH, OR, SH, SR, $NH_2$, NHR, NRR', nitro, $Me_3Sn$ and halo;
$R^{7''}$ is selected from the group consisting of H, R, OH, OR, SH, SR, $NH_2$, NHR, NRR', nitro, $Me_3Sn$ and halo; and
R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl;
and either:
(a) $R^{10''}$ is H, and $R^{11''}$ is OH or $OR^A$, wherein $R^A$ is $C_1$-$C_4$ alkyl, or
(b) $R^{10''}$ and $R^{11''}$ form a nitrogen-carbon double bond between the nitrogen and carbon atoms to which they are bound, or
(c) $R^{10''}$ is H and $R^{11''}$ is $SO_zM$, wherein subscript z is 2 or 3 and M is a monovalent pharmaceutically acceptable cation, or (d) $R^{10'}$, $R^{11'}$ and $R^{10'''}$ are each H and $R^{11'''}$ is $SO_zM$, or $R^{10'}$ and $R^{11'}$ are each H and $R^{10'''}$ and $R^{11'''}$ form a nitrogen-carbon double bond between the nitrogen and carbon atoms to which they are bound, or $R^{10'''}$, $R^{11'''}$ and $R^{10'}$ are each H and $R^{11'}$ is $SO_zM$, or $R^{10'''}$ and $R^{11'''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and R" is a $C_{3-12}$ alkylene group, the carbon chain of which is optionally interrupted by one or more heteroatoms and/or by aromatic rings;
Y and Y' are selected from the group consisting of O, S, and NH;
$R^{6'}$, $R^{7'}$, $R^{9'}$ are selected from the same groups as $R^{6''}$, $R^{7''}$ and $R^{9''}$, respectively, and for (a), (b) and (c) $R^{10'}$ and $R^{11'}$ are the same as $R^{10'''}$ and $R^{11'''}$, respectively, and if $R^{11'''}$ and $R^{11'}$ are $SO_zM$, each M is either a monovalent pharmaceutically acceptable cation or together represent a divalent pharmaceutically acceptable cation.

9. The method of claim 7, wherein the PBD Drug Unit is of Formula XII or Formula XIII:

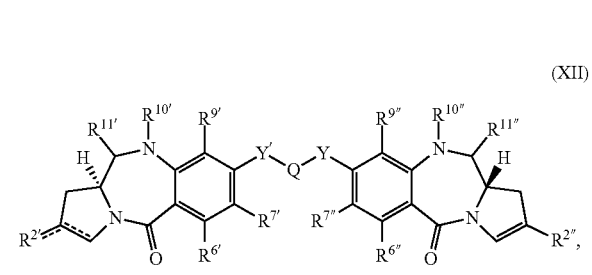

(XII)

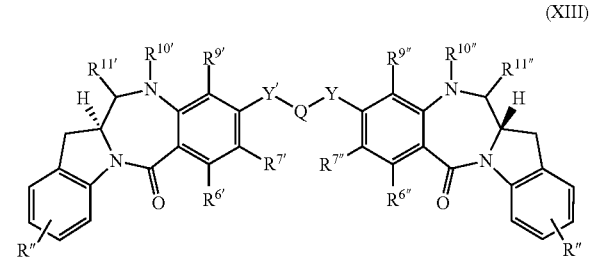

(XIII)

or a salt thereof,
wherein:
the dotted lines indicate a tautomeric double bond;
Q is of formula XIV:

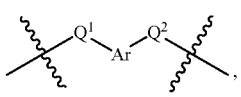

(XIV)

wherein the wavy lines indicate the sites of covalent attachment to Y' and Y in either orientation;
Ar is a $C_{5-7}$ arylene group substituted by $X^a$ and is otherwise optionally substituted, wherein $X^a$ is from a reactive or activateable group for covalent attachment to a Linker Unit or precursor thereof, wherein $X^a$ is selected from the group consisting of —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3;

and either:
(i) $Q^1$ is a single bond; and $Q^2$ is a single bond or —$(CH_2)_n$—, wherein subscript n is 1, 2 or 3, or
(ii) $Q^1$ is —CH=CH—, and $Q^2$ is a single bond or —CH=CH—; and $R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, wherein the dotted lines indicate a single bond to $R^{2'}$, or $R^{2'}$ an optionally substituted $C_1$-$C_4$ alkenylene wherein the dotted lines indicate a double bond to $R^{2'}$;

$R^{2''}$ is an optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene;

$R^{6''}$ and $R^{9''}$ are independently selected from the group consisting of H, R, OH, OR, SH, SR, $NH_2$, NHR, NRR', nitro, $Me_3Sn$ and halo;

$R^{7''}$ is selected from the group consisting of H, R, OH, OR, SH, SR, $NH_2$, NHR, NRR', nitro, $Me_3Sn$ and halo; and R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl;

and either:
(a) $R^{10''}$ is H, and $R^{11''}$ is OH or $OR^A$, wherein $R^A$ is $C_1$-$C_4$ alkyl, or
(b) $R^{10''}$ and $R^{11''}$ form a nitrogen-carbon double bond between the nitrogen and carbon atoms to which they are bound, or
(c) $R^{10'''}$ is H and $R^{11'''}$ is $SO_zM$, wherein subscript z is 2 or 3 and M is a monovalent pharmaceutically acceptable cation, or
(d) $R^{10'''}$, $R^{11''}$ and $R^{10''}$ are each H and $R^{11'''}$ is $SO_zM$, or $R^{10'}$ and $R^{11'}$ are each H and $R^{10'''}$ and $R^{11'''}$ form a nitrogen-carbon double bond between the nitrogen and carbon atoms to which they are bound, or $R^{10'''}$, $R^{11''}$ and $R^{10'}$ are each H and $R^{11'''}$ is $SO_zM$, or $R^{10'''}$ and $R^{11'''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and Y and Y' are selected from the group consisting of O, S, and NH;

R" represents one or more optional substituents; and $R^{6'}$, $R^{7'}$, $R^{9'}$ are selected from the same groups as $R^{6''}$, $R^{7''}$ and $R^{9''}$, respectively, and for (a), (b) and (c) $R^{10'}$ and $R^{11'}$ are the same as $R^{10''}$ and $R^{11''}$, respectively, and if $R^{11''}$ and $R^{11'}$ are $SO_zM$, each M is either a monovalent pharmaceutically acceptable cation or together represent a divalent pharmaceutically acceptable cation.

10. The method of claim 8, wherein the dotted lines indicate a single bond to $R^{2'}$, wherein $R^{2'}$ is a $C_{5-7}$ aryl group optionally substituted by one or more substituents selected from the group consisting of halo, nitro, cyano, $C_{1-7}$ alkoxy, $C_{5-20}$ aryloxy, $C_{3-20}$ heterocyclyoxy, $C_{1-7}$ alkyl, $C_{3-7}$ heterocyclyl and bis-oxy-$C_{1-3}$ alkylene wherein the $C_{1-7}$ alkoxy group is optionally substituted by an amino group, and if the $C_{3-7}$ heterocyclyl group is a $C_6$ nitrogen containing heterocyclyl group, it is optionally substituted by a $C_{1-4}$ alkyl group.

11. The method of claim 8, wherein the PBD Drug Unit is:

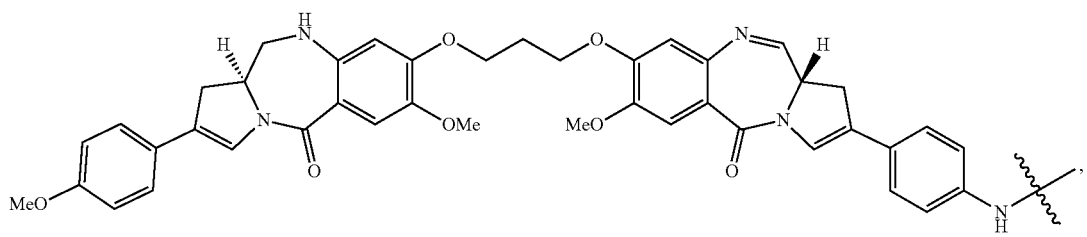

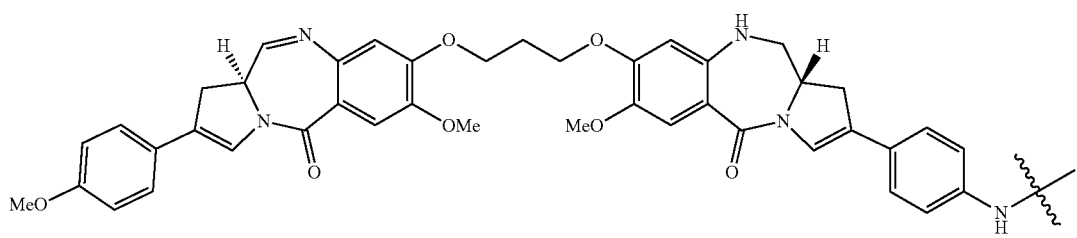

or a salt thereof, wherein the wavy line indicates the point of covalent attachment to S* in the form of a carbamate functional group.

12. The method of claim 9, wherein the PBD Drug Unit is:

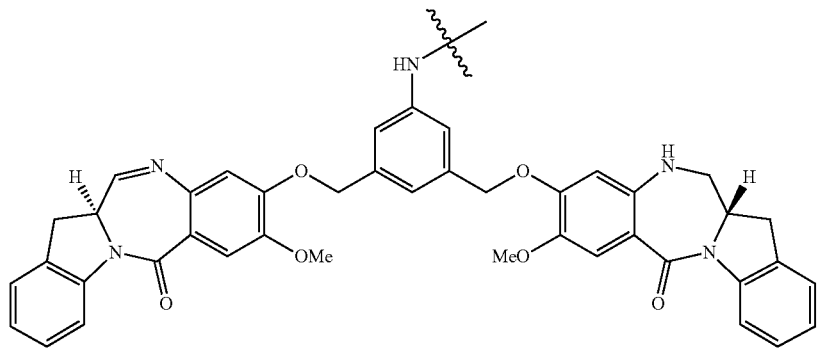 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

or a salt thereof, wherein the wavy line indicates the point of covalent attachment to S* in the form of a carbamate functional group.

13. The method of claim 1, wherein D is a PBD Drug Unit, in which the Drug Linker intermediate compound of Formula VID is:

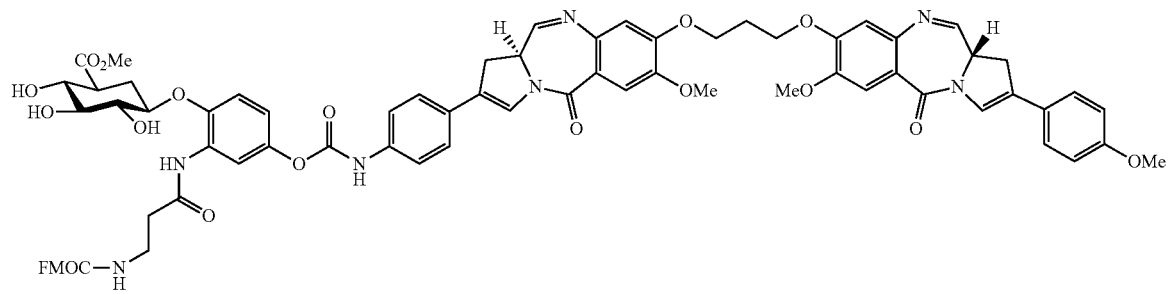

or a salt thereof.

14. The method of claim 1, wherein D is an anthracyclin Drug Unit.

15. The method of claim 14, wherein the anthracyclin Drug Unit is selected from the group consisting of doxorubicin, idarubicin, daunorubicin, doxorubicin propyloxazoline (DPO) or cyanomorpholino-doxorubicin.

16. The method of claim 1, wherein D is an anthracyclin Drug Unit in which the Drug Linker intermediate compound of Formula VID is:

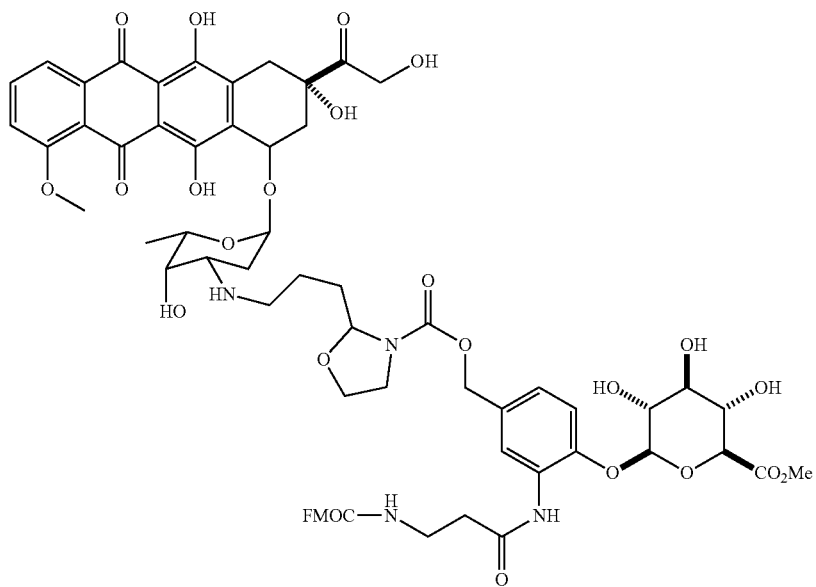

or a salt thereof.

17. The method of claim 1, wherein D is a camptothecin Drug Unit.

18. The method of claim 17, wherein the camptothecin Drug Unit has the structure of:

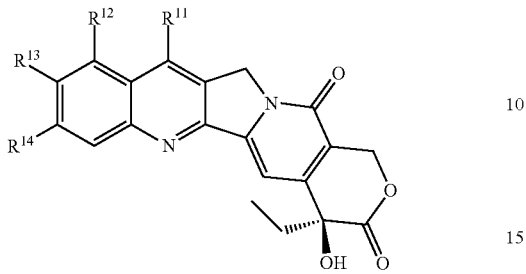

or a lactone ring-opened form thereof, or a salt of either of the foregoing, wherein
one of $R^{11}$ is n-butyl and one of $R^{12}$-$R^{14}$ is —$NH_2$ and the other are hydrogen, or $R^{12}$ is —$NH_2$ and $R^{13}$ and $R^{14}$ together are —$OCH_2O$—, wherein the camptothecin is attached via the —$NH_2$ group.

19. The method of claim 1, wherein D is a camptothecin Drug Unit in which the Drug Linker intermediate compound of Formula VID is:

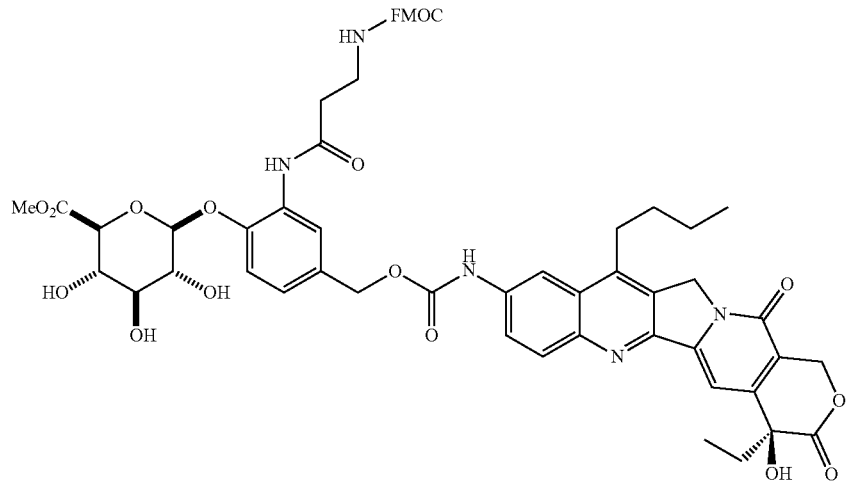

or a lactone ring-opened form thereof, or a salt of either of the foregoing.

20. The method of claim 1, wherein D is a duocarmycin Drug Unit.

21. The method of claim 1, wherein D is a duocarmycin Drug Unit in which the Drug Linker intermediate compound of Formula VID is:

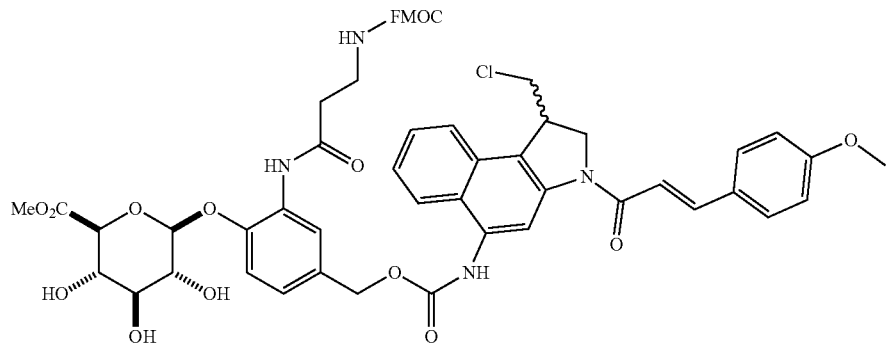

or a salt thereof.

22. A method for preparing a Drug Linker intermediate compound of Formula VIIE:

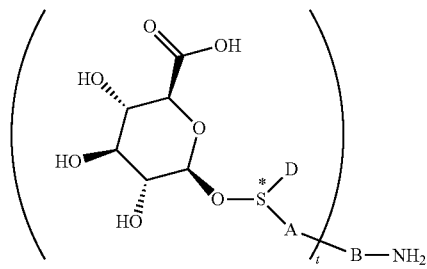

(VIIE)

or a salt thereof, wherein

A is an optional Connector Unit;

B is absent;

S* is a Self-Immolating Unit of Formula XIII or Formula XIV:

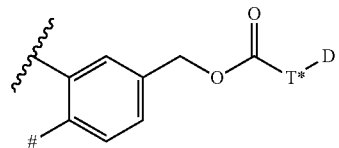

(XIII)

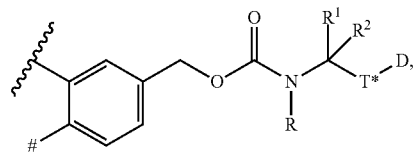

(XIV)

wherein the wavy line indicates the point of attachment to A, and # indicates the point of attachment to the glycosidic oxygen atom of the glucuronic acid moiety;

D is a Drug Unit incorporating a DNA minor groove binder, DNA damaging agent or DNA replication inhibitor having a functional group comprising heteroatom T*, wherein T* is oxygen, sulfur, or optionally substituted nitrogen; and t is 1, the method comprising the steps of:

(c) contacting a compound of Formula VIIC with a Grignard reagent or an alkoxy magnesium halide with either in a suitable an alcohol-containing solvent, wherein the Formula VIIC compound has the structure of:

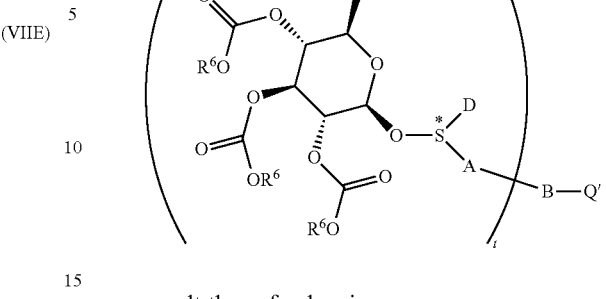

(VIIC)

or a salt thereof, wherein

S*, D, A, B and subscript t are as defined for Formula VIIE;

Q' is a suitably protected amino group;

each of $R^6$ and $R^7$ is independently $C_1$-$C_8$ alkyl or optionally substituted phenyl such that $R^6C(=O)$— provides for an ester functional group that is a suitable hydroxyl protecting group and —$OR^7$ provides for an ester functional group that is a suitable carboxylic acid protecting group; and the remaining variable groups are as previously defined, wherein said contacting with the Grignard reagent or alkoxy magnesium halide selectively removes the hydroxyl protecting groups to provide a compound of Formula VIID:

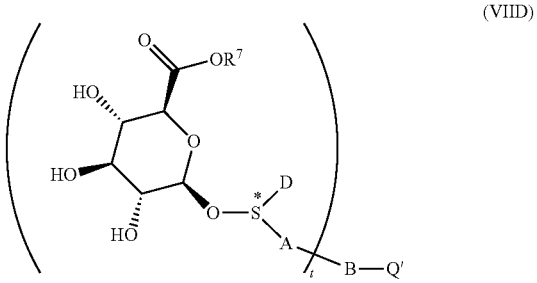

(VIID)

or a salt thereof, wherein the variable groups are as previously defined by Formula VIIC; and (d) contacting the Formula VIID compound with a first deprotecting agent, wherein said first deprotecting agent contacting removes the amine and carboxylic acid protecting groups whereby the Formula VIIE compound or its salt is obtained.

23. The method of claim 22, wherein the Grignard reagent has the formula of $R^gMgX$ and the alkoxy magnesium halide has the formula of $R^gOMgX$, wherein $R^g$ is $C_1$-$C_5$ alkyl and X is I, Br, or Cl.

24. The method of claim 23, wherein the Grignard reagent is MeMgI or MeMgCl and the alkoxy magnesium halide is MeOMgI or MeOMgCl.

25. The method of claim 22, wherein the Grignard reagent is MeMgI or MeMgCl, the alkoxy magnesium halide is MeOMgI or MeOMgCl and the alcohol-containing solvent comprises a $C_1$-$C_4$ alcohol.

26. The method of claim 25, wherein the alcohol-containing solvent further comprises THF.

27. The method of claim 26, wherein the alcohol-containing solvent is a 1:1 (v/v) mixture of methanol and THF.

28. The method of claim 22, wherein the first deprotecting agent for removal of the amino protecting group is an aqueous solution of LiOH.

29. The method of claim 28, wherein the amino protecting group has the formula:

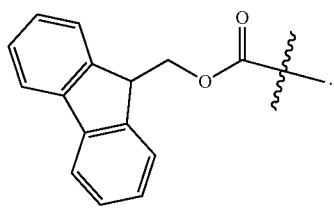 [SMILES: *C(=O)OCC1c2ccccc2-c2ccccc21]

30. The method of claim 22, wherein said Grignard reagent or alkoxy magnesium halide contacting and said deprotecting agent contacting to remove the amino protecting group are done sequentially in one pot.

31. The method of claim 22, wherein D is a pyrrolobenzodiazepine (PBD) Drug Unit.

32. The method of claim 31, wherein the PBD Drug Unit is of Formula X:

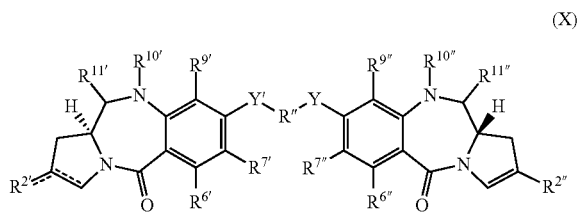

or a salt thereof,
wherein:
the dotted lines represent a tautomeric double bond;
$R^{2''}$ is of formula XI:

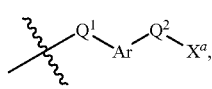

wherein the wavy line indicates the site of covalent attachment to the Formula X structure;
Ar is an optionally substituted $C_{5-7}$ arylene;
$X^a$ is from a reactive or activateable group for covalent attachment to a Linker Unit or precursor thereof, wherein $X^a$ is selected from the group consisting of —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3;
and either:
(i) $Q^1$ is a single bond; and $Q^2$ is a single bond or —Z—$(CH_2)_n$—, wherein Z is selected from the group consisting of a single bond, O, S, and NH; and subscript n is 1, 2 or 3, or
(ii) $Q^1$ is —CH=CH—, and $Q^2$ is a single bond; and
$R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, wherein the dotted lines indicate a single bond to $R^{2'}$, or
$R^{2'}$ an optionally substituted $C_1$-$C_4$ alkenylene, wherein the dotted lines indicate a double bond to $R^{2'}$;
$R^{6''}$ and $R^{9''}$ are independently selected from the group consisting of H, R, OH, OR, SH, SR, $NH_2$, NHR, NRR', nitro, $Me_3Sn$ and halo;
$R^{7''}$ is selected from the group consisting of H, R, OH, OR, SH, SR, $NH_2$, NHR, NRR', nitro, $Me_3Sn$ and halo; and
R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl;
and either:
(a) $R^{10''}$ is H, and $R^{11''}$ is OH or $OR^A$, wherein $R^A$ is $C_1$-$C_4$ alkyl, or
(b) $R^{10''}$ and $R^{11''}$ form a nitrogen-carbon double bond between the nitrogen and carbon atoms to which they are bound, or
(c) $R^{10''}$ is H and $R^{11''}$ is $SO_zM$, wherein subscript z is 2 or 3 and M is a monovalent pharmaceutically acceptable cation, or
(d) $R^{10'}$, $R^{11'}$ and $R^{10''}$ are each H and $R^{11''}$ is $SO_zM$, or $R^{10'}$ and $R^{11'}$ are each H and $R^{10''}$ and $R^{11''}$ form a nitrogen-carbon double bond between the nitrogen and carbon atoms to which they are bound, or $R^{10''}$, $R^{11''}$ and $R^{10'}$ are each H and $R^{11'}$ is $SO_zM$, or $R^{10''}$ and $R^{11''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and
R'' is a $C_{3-12}$ alkylene group, the carbon chain of which is optionally interrupted by one or more heteroatoms and/or by aromatic rings;
Y and Y' are selected from the group consisting of O, S, and NH;
$R^{6'}$, $R^{7'}$, $R^{9'}$ are selected from the same groups as $R^{6''}$, $R^{7''}$ and $R^{9''}$, respectively, and for (a), (b) and (c) $R^{10'}$ and $R^{11'}$ are the same as $R^{10''}$ and $R^{11''}$, respectively, and if $R^{11''}$ and $R^{11'}$ are $SO_zM$, each M is either a monovalent pharmaceutically acceptable cation or together represent a divalent pharmaceutically acceptable cation.

33. The method of claim 31, wherein the PBD Drug Unit is of Formula XII or Formula XIII:

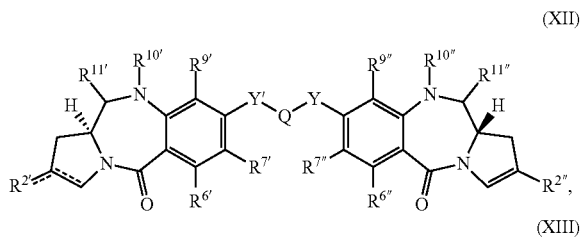

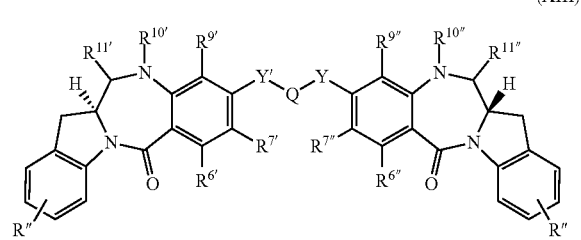

or a salt thereof, wherein:
the dotted lines indicate a tautomeric double bond;
Q is of formula XIV:

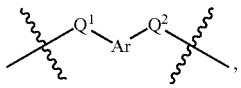

(XIV)

wherein the wavy lines indicate the sites of covalent attachment to Y' and Y in either orientation;
Ar is a $C_{5-7}$ arylene group substituted by $X^a$ and is otherwise optionally substituted, wherein $X^a$ is from a reactive or activateable group for covalent attachment to a Linker Unit or precursor thereof, wherein $X^a$ is selected from the group consisting of —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3;
and either:
(i) $Q^1$ is a single bond; and $Q^2$ is a single bond or —$(CH_2)_n$—, wherein subscript n is 1, 2 or 3, or
(ii) $Q^1$ is —CH=CH—, and $Q^2$ is a single bond or —CH=CH—; and
$R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, wherein the dotted lines indicate a single bond to $R^{2'}$, or
$R^{2'}$ an optionally substituted $C_1$-$C_4$ alkenylene wherein the dotted lines indicate a double bond to $R^{2'}$;
$R^{2''}$ is an optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene;
$R^{6''}$ and $R^{9''}$ are independently selected from the group consisting of H, R, OH, OR, SH, SR, $NH_2$, NHR, NRR', nitro, $Me_3Sn$ and halo;
$R^{7''}$ is selected from the group consisting of H, R, OH, OR, SH, SR, $NH_2$, NHR, NRR', nitro, $Me_3Sn$ and halo; and R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl;
and either:
(a) $R^{10'''}$ is H, and $R^{11'''}$ is OH or $OR^A$, wherein $R^A$ is $C_1$-$C_4$ alkyl, or
(b) $R^{10'''}$ and $R^{11'''}$ form a nitrogen-carbon double bond between the nitrogen and carbon atoms to which they are bound, or
(c) $R^{10'''}$ is H and $R^{11'''}$ is $SO_zM$, wherein subscript z is 2 or 3 and M is a monovalent pharmaceutically acceptable cation, or
(d) $R^{10'}$, $R^{11'}$ and $R^{10'''}$ are each H and $R^{11'''}$ is $SO_zM$, or $R^{10'}$ and $R^{11'}$ are each H and $R^{10'''}$ and $R^{11'''}$ form a nitrogen-carbon double bond between the nitrogen and carbon atoms to which they are bound, or $R^{10'''}$, $R^{11'''}$ and $R^{10'}$ are each H and $R^{11'}$ is $SO_zM$, or $R^{10'''}$ and $R^{11'''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and
Y and Y' are selected from the group consisting of O, S, and NH;
R'' represents one or more optional substituents; and
$R^{6'}$, $R^{7'}$, $R^{9'}$ are selected from the same groups as $R^{6''}$, $R^{7''}$ and $R^{9''}$, respectively, and for (a), (b) and (c) $R^{10'}$ and $R^{11'}$ are the same as $R^{10'''}$ and $R^{11'''}$, respectively, and if $R^{11'}$ and $R^{11'''}$ are $SO_zM$, each M is either a monovalent pharmaceutically acceptable cation or together represent a divalent pharmaceutically acceptable cation.

34. The method of claim 32, wherein the dotted lines indicate a single bond to $R^{2'}$, wherein $R^{2'}$ is a $C_{5-7}$ aryl group optionally substituted by one or more substituents selected from the group consisting of halo, nitro, cyano, $C_{1-7}$ alkoxy, $C_{5-20}$ aryloxy, $C_{3-20}$ heterocyclyoxy, $C_{1-7}$ alkyl, $C_{3-7}$ heterocyclyl and bis-oxy-$C_{1-3}$ alkylene wherein the $C_{1-7}$ alkoxy group is optionally substituted by an amino group, and if the $C_{3-7}$ heterocyclyl group is a $C_6$ nitrogen containing heterocyclyl group, it is optionally substituted by a $C_{1-4}$ alkyl group.

35. The method of claim 32, wherein the PBD Drug Unit is:

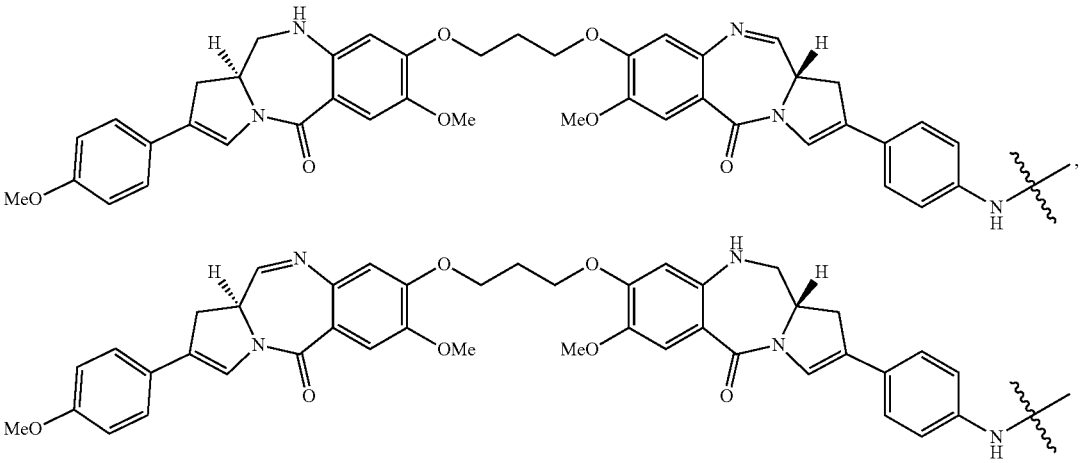

or a salt thereof, wherein the wavy line indicates the point of covalent attachment to S* in the form of a carbamate functional group.

36. The method of claim 33, wherein the PBD Drug Unit is:

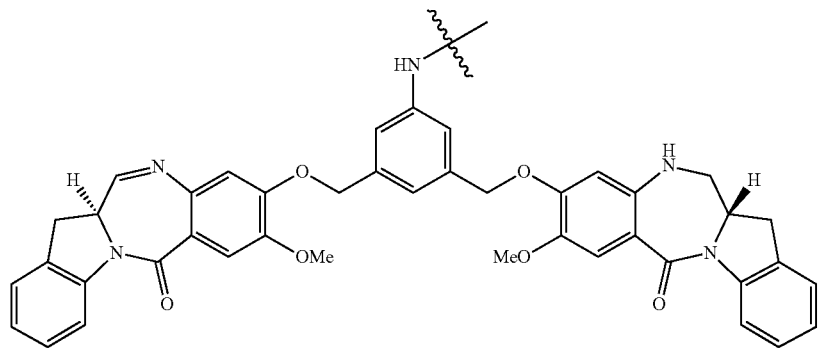 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

or a salt thereof, wherein the wavy line indicates the point of covalent attachment to S* in the form of a carbamate functional group.

37. The method of claim 22, wherein D is a PBD Drug Unit, in which the Drug Linker intermediate compound of Formula VIIE is:

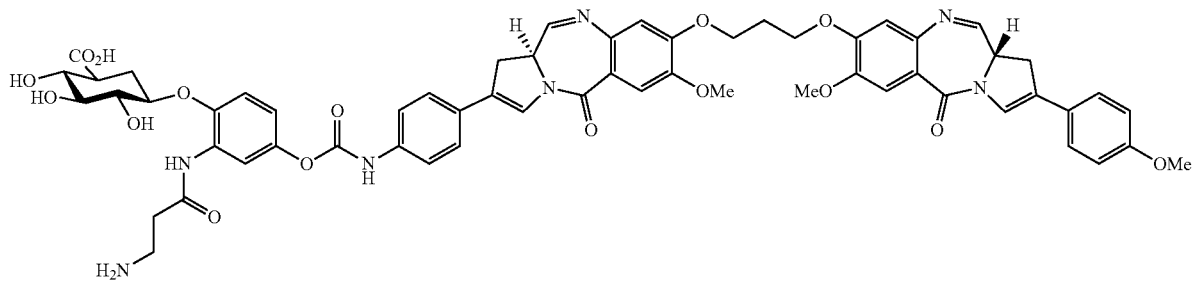

or a salt thereof.

38. The method of claim 22, wherein D is an anthracyclin Drug Unit.

39. The method of claim 38, wherein the anthracyclin Drug Unit is selected from the group consisting of doxorubicin, idarubicin, daunorubicin, doxorubicin propyloxazoline (DPO) or cyanomorpholino-doxorubicin.

40. The method of claim 22, wherein D is an anthracyclin Drug Unit in which the Drug Linker intermediate compound of Formula VIIE is:

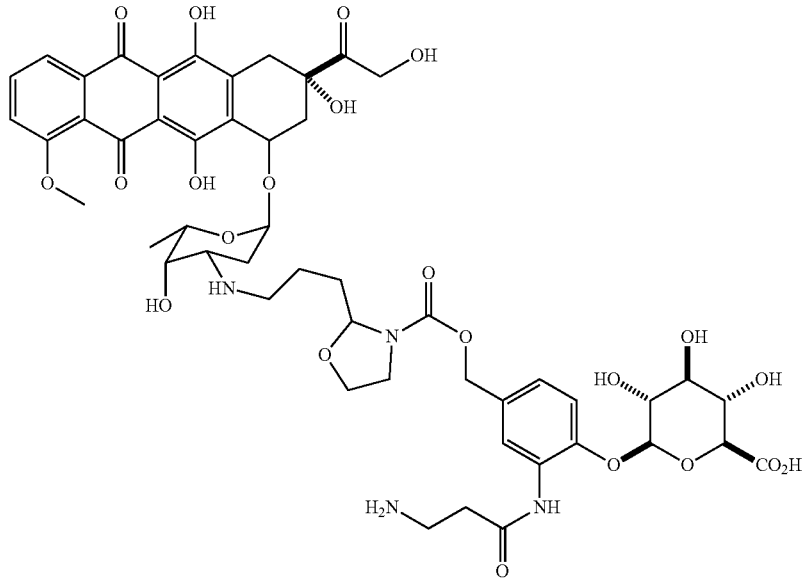

or a salt thereof.

41. The method of claim 22, wherein D is a camptothecin Drug Unit.

42. The method of claim 41, wherein the camptothecin Drug Unit has the structure of:

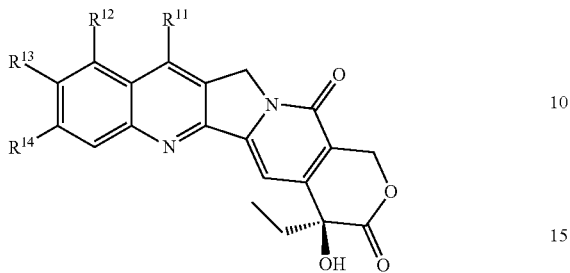

or a lactone ring-opened form thereof, or a salt of either of the foregoing, wherein
one of $R^{11}$ is n-butyl and one of $R^{12}$-$R^{14}$ is —$NH_2$ and the other are hydrogen, or $R^{12}$ is —$NH_2$ and $R^{13}$ and $R^{14}$ together are —$OCH_2O$—, wherein the camptothecin is attached via the —$NH_2$ group.

43. The method of claim 22, wherein D is a camptothecin Drug Unit in which the Drug Linker intermediate compound of Formula VIIE is:

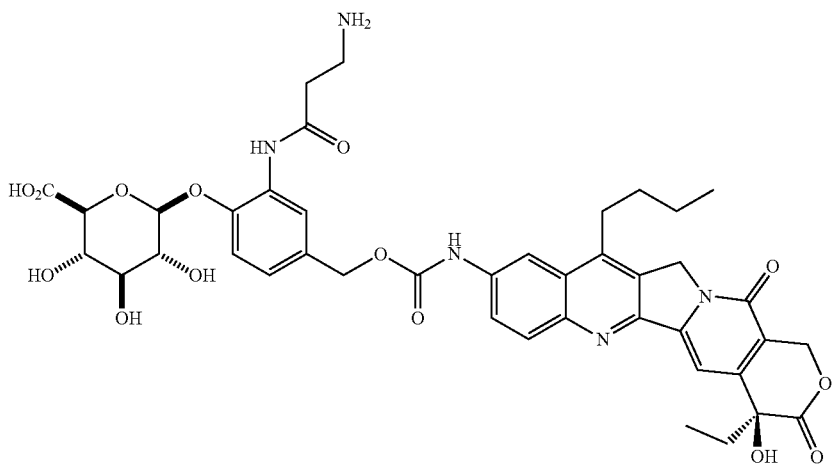

or a lactone ring-opened form thereof, or a salt of either of the foregoing.

44. The method of claim 22, wherein D is a duocarmycin Drug Unit.

45. The method of claim 22, wherein D is a duocarmycin Drug Unit in which the Drug Linker intermediate compound of Formula VIIE is:

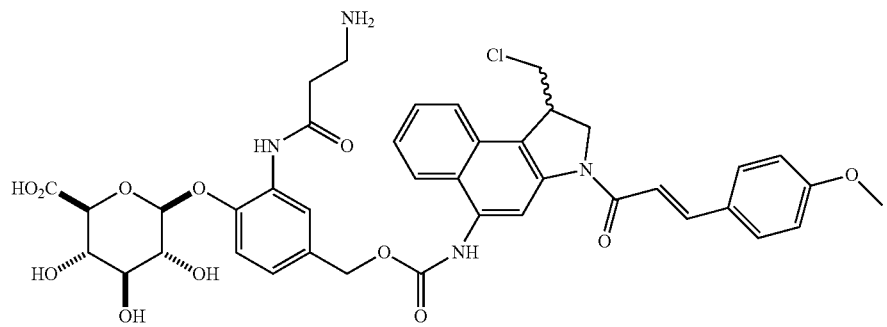

or a salt thereof.

46. The method of claim 8, wherein R" is a $C_{3-12}$ alkylene group, the carbon chain of which is optionally interrupted by one or more of O, S or $NR^{N2}$ where $R^{N2}$ is H or $C_1$-$C_4$ alkyl, and/or by one of benzene or pyridine.

47. A method for preparing a Drug Linker intermediate compound of Formula IIID:

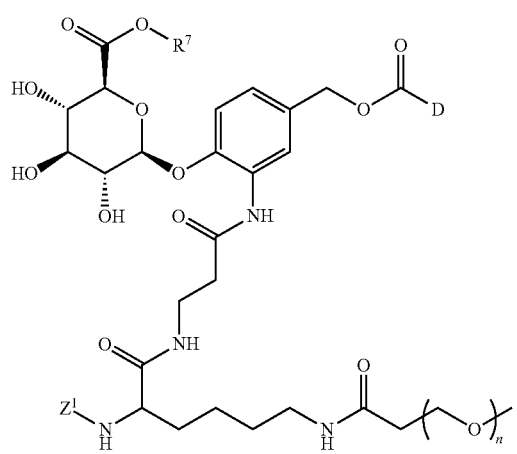

(IIID)

or a salt thereof, wherein

D is a Drug Unit incorporating a DNA minor groove bender, DNA damaging agent or DNA replication inhibitor having a amine functional group that forms a carbamate functional group;

$Z^1$ is a suitable amino protecting group;

$R^7$ is $C_1$-$C_8$ alkyl or optionally substituted phenyl so that —$OR^7$ provides for an ester functional group that is a suitable carboxylic acid protecting group; and subscript n is an integer ranging from 2 to 24, the method comprising the step of:

(c) contacting a compound of Formula IIIC with either a Grignard reagent or an alkoxy magnesium halide in a suitable alcohol-containing solvent, wherein the Formula IIIC compound is:

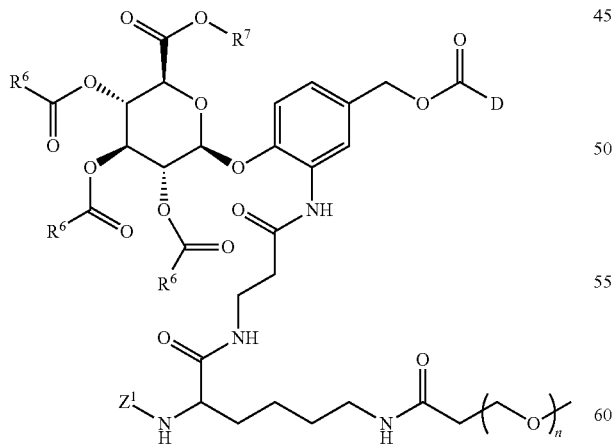

(IIIC)

or a salt thereof, wherein each of $R^6$ is independently $C_1$-$C_8$ alkyl or optionally substituted phenyl so that $R^6C(=O)$-provides for an ester functional group that is a suitable hydroxyl protecting group;

and the remaining variable groups are as previously defined by Formula IIID, wherein said Grignard reagent or alkoxy magnesium halide contacting provides the Formula IIIC compound or its salt.

48. A method for preparing a Drug Linker intermediate compound of Formula III:

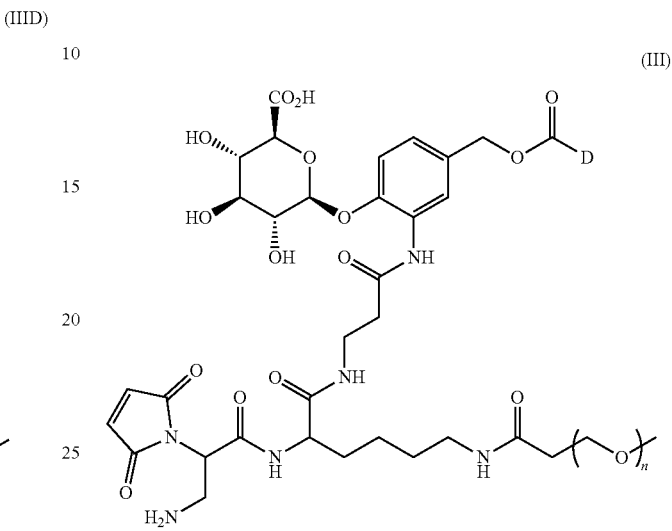

(III)

or a salt thereof, wherein

D is a Drug Unit incorporating a DNA minor groove bender, DNA damaging agent or DNA replication inhibitor having a amine functional group that forms a carbamate functional group; and subscript n is an integer ranging from 2 to 24, the method comprising the step of:

contacting a compound of Formula IIIF, with an acidic aqueous solvent, wherein the Formula IIIF compound is:

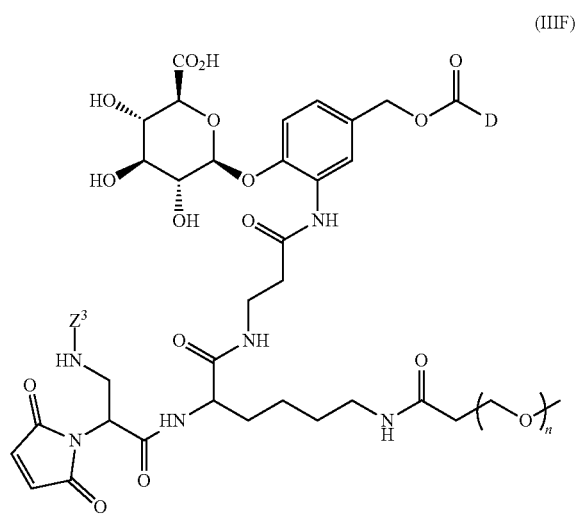

(IIIF)

or a salt thereof, wherein $Z^3$ is a suitable amino protecting agent that is acid-labile; and the remaining variable group are as previously defined by Formula III.

* * * * *

UNITED STATES PATENT AND TRADEMARK OFFICE
CERTIFICATE OF CORRECTION

Page 1 of 2

PATENT NO. : 11,730,822 B2
APPLICATION NO. : 16/497133
DATED : August 22, 2023
INVENTOR(S) : Yunyu Mao et al.

It is certified that error appears in the above-identified patent and that said Letters Patent is hereby corrected as shown below:

On the Title Page

Item (56) at Column 2, Line number 9, please replace "Lactonizatin" with -- Lactonization --.

In the Claims

At Column 140, Claim number 1, Line numbers 24-38 (Approx.), please replace

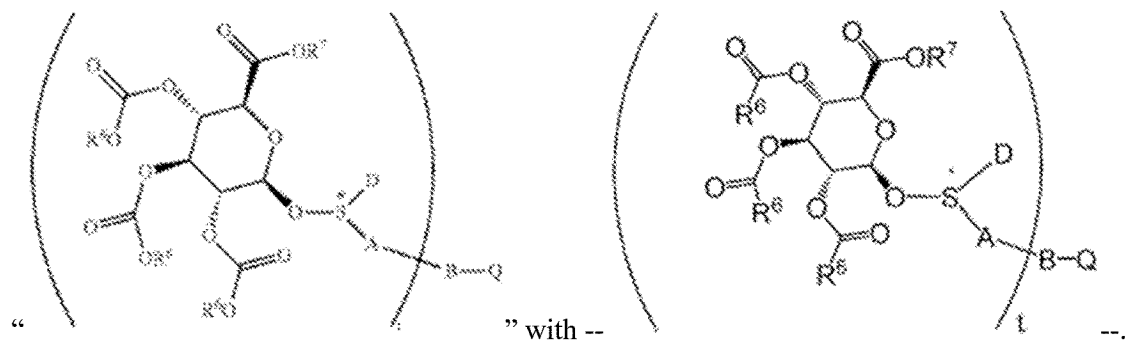

At Column 144, Claim number 10, Line number 27, please replace "heterocyclyoxy" with -- heterocyclyloxy, --.

Signed and Sealed this
Fifth Day of December, 2023

Katherine Kelly Vidal
*Director of the United States Patent and Trademark Office*

CERTIFICATE OF CORRECTION (continued)
U.S. Pat. No. 11,730,822 B2

At Column 150, Claim number 22, Line number 1-15 (Approx.), please replace

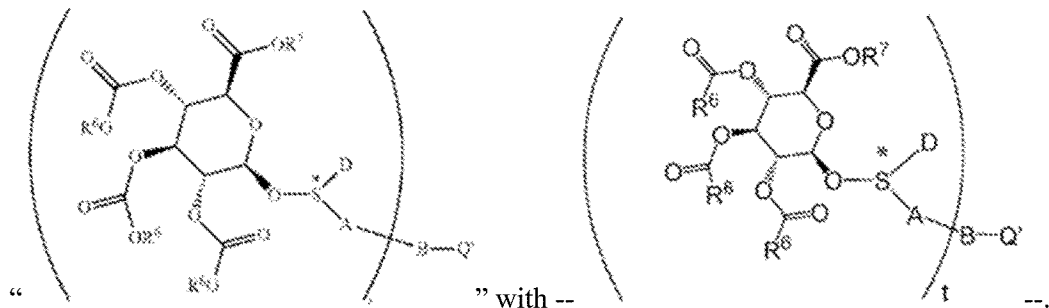

" " with -- --.

At Column 154, Claim number 34, Line number 37, please replace "heterocyclyoxy," with -- heterocyclyloxy, --.